(12) United States Patent
Spangenberg et al.

(10) Patent No.: US 9,840,695 B2
(45) Date of Patent: Dec. 12, 2017

(54) PLANT TECHNOLOGY

(75) Inventors: German Spangenberg, Bundoora (AU); Aidyn Mouradov, Mill Park (AU); Timothy Ivor Sawbridge, Collingwood (AU)

(73) Assignee: Agriculture Victoria Services Pty Ltd, Attwood (AU)

( * ) Notice: Subject to any disclaimer, the term of this patent is extended or adjusted under 35 U.S.C. 154(b) by 1468 days.

(21) Appl. No.: 12/722,878

(22) Filed: Mar. 12, 2010

(65) Prior Publication Data

US 2010/0275330 A1    Oct. 28, 2010

Related U.S. Application Data

(60) Provisional application No. 61/173,272, filed on Apr. 28, 2009.

(51) Int. Cl.
| | | |
|---|---|---|
| *A01H 5/10* | (2006.01) |
| *C12N 15/82* | (2006.01) |
| *C12N 15/54* | (2006.01) |
| *C12N 9/10* | (2006.01) |

(52) U.S. Cl.
CPC ......... *C12N 9/1055* (2013.01); *C12N 9/1051* (2013.01); *C12N 15/8222* (2013.01); *C12N 15/8246* (2013.01); *C12N 15/8266* (2013.01); *C12N 15/8273* (2013.01); *C12Y 204/01099* (2013.01)

(58) Field of Classification Search
CPC . C12N 9/1051; C12N 9/1055; C12N 15/8222
See application file for complete search history.

(56) References Cited

U.S. PATENT DOCUMENTS

| | | | | |
|---|---|---|---|---|
| 5,908,975 | A * | 6/1999 | Caimi et al. ................. | 800/298 |
| 5,986,173 | A * | 11/1999 | Smeekens et al. ........... | 800/284 |
| 7,227,055 | B2 * | 6/2007 | Spangenberg et al. ....... | 800/298 |
| 2003/0237108 | A1 * | 12/2003 | Demmer et al. ............. | 800/284 |
| 2004/0168215 | A1 * | 8/2004 | Jiang et al. .................. | 800/287 |

FOREIGN PATENT DOCUMENTS

| | | |
|---|---|---|
| WO | 94/14970 A1 | 7/1994 |
| WO | 2008128293 A1 | 10/2008 |
| WO | 2010/028456 A1 | 3/2010 |

OTHER PUBLICATIONS

Chalmers et al (Plant Biotechnology Journal (2005) 3 pp. 459-474).*
Schardi et al (Gene, 61 (1987) 1-11.*
Pilon-Smits et al Plant Physiol. Biochem., 1999, 37 (4), 313-317.*
Caimi et el (Plant Physio. (1996) 110: 355-363).*
Cairns (Journal of Experimental Botany,2003, vol. 54 No. 382).*
Vijn et al (Plant Physiology, Jun. 1999, vol. 120 pp. 351-359).*
Caimi et al (Plant Physiology (1996) 110: 355-636).*
Caimi, P.G. et al. "Cytosolic expression of the Bacillus amyloliquefaciens SacB protein inhibits tissue development in transgenic tobacco and potato." New Phytol., 1997, pp. 19-28, vol. 136.
Caimi, P.G. et al. "Fructan Accumulation and Sucrose Metabolism in Transgenic Maize Endosprem Expressing a Bacillus amyloliquefaciens SacB Gene." Plant Physiol., 1996, pp. 355-363, vol. 110.
Cairns, Andrew. "Fructan biosynthesis in transgenic plants." Journal of Experimental Botany, Jan. 2003, pp. 549-567, vol. 54, No. 382.
Ebskamp, Michel et al. "Accumulation of Fructose Polymers in Transgenic Tobacco." Nature Publishing Group, Mar. 1994, pp. 272-275, vol. 12.
Hattori, Tsukaho et al. "Molecular cloning and nucleotide sequence of cDNA for sporamin, the major soluble protein of sweet potato tuberous roots." Plant Molecular Biology, 1985, pp. 313-320, vol. 5.
Li, Song et al. "Cloning of Three MYB-like Genes from *Arabidopsis thaliana* (Accession No. U26933, AF048841, and U26934)." Plant Gene Register PGR99-138, Plant Physiol, 1999, p. 313, vol. 121.
Sasanuma, T. et al. "Characterization of the rbcS multigene family in wheat: subfamily classification, determination of chromosomal location and evolutionary analysis." Mol Genet Genomics, 2001, pp. 161-171, vol. 265.
Wei-Ke, Zeng et al. "PCR Amplification and Sequencing of a Whaet rbc S Gene Promotor." Acta Botanica Sinica, 1995, pp. 496-500, vol. 37, No. 6.
Ye, X.D. et al. "Altered fructan accumulation in transgenic Lolium multiflorum plants expressing a Bacillus subtilis sacB gene." Plant Cell Reports, 2001, pp. 205-212, vol. 20.
Perlak, F. J. et al., Modification of the Coding sequence Enhances Plant Expression of Insect Control Protein Genes, Proceedings of the National Academy of Sciences, US, 1991, pp. 3324-3328, vol. 88.
Gerrits, N. et al., Sucrose Metabolism in Plastids1, Plant Physiology, 2001, pp. 926-934.
Pilon-Smits, E. A. H. et al., Improved Performance of Transgenic Fructan-Accumulating Toabacco under Drought Stress1, Plant Physiol., 1995, pp. 125-130, vol. 107.

* cited by examiner

*Primary Examiner* — Lee A Visone
(74) *Attorney, Agent, or Firm* — Larson & Anderson, LLC

(57) ABSTRACT

Genetic constructs capable of manipulating fructan biosynthesis in photosynthetic cells of a plant, said genetic constructs include a promoter operatively linked to a nucleic acid encoding a bacterial FT enzyme. These constructs can be used in modification of fructan biosynthesis in plants and, more particularly, for manipulating fructan biosynthesis in photosynthetic cells. The constructs can also be used for increasing plant biomass and, more particularly, for enhancing biomass yield and/or yield stability, including shoot and/or root growth in a plant, and for enhancing the productivity of biochemical pathways.

15 Claims, 56 Drawing Sheets

FIGURE 2

ATGAACATCAAAAAGTTTGCAAAACAAGCAACAGTATTAACCTTTACTACCGCACTGCTGGCAGGAGGCGCAACTCA AGCGTTTGCGAAAGAAACGAACCAAAAGCCATATAAGGAAACATACGGCATTTCCCATATTACACGCCATGATATGC
TGCAAATCCCTGAACAGCAAAAAAATGAAAAATATCAAGTTCCTGAATTCGATTCGTCCACAATTAAAAATATCTCT
TCTGCAAAAGGCCTGGACGTTTGGGACAGCTGGCCATTACAAAACGCTGACGGCACTGTCGCAAACTATCACGGCTA
CCACATCGTCTTTGCATTAGCCGGAGATCCTAAAAATGCGGATGACACATCGATTTACATGTTCTATCAAAAGTCG
GCGAAACTTCTATTGACAGCTGGAAAAACGCTGGCCGCGTCTTTAAAGACAGCGACAAATTCGATGCAAATGATTCT
ATCCTAAAAGACCAAACACAAGAATGGTCAGGTTCAGCCACATTTACATCTGACGGAAAAATCCGTTTATTCTACAC
TGATTTCTCCGGTAAACATTACGGCAAACAAACACTGACAACTGCACAAGTTAACGTATCAGCATCAGACAGCTCTT
TGAACATCAACGGTGTAGAGGATTATAAATCAATCTTTGACGGTGACGGAAAAACGTATCAAAATGTACAGCAGTTC
ATCGATGAAGGCAACTACAGCTCAGGCGACAACCATACGCTGAGAGATCCTCACTACGTAGAAGATAAAGGCCACAA
ATACTTAGTATTTGAAGCAAACACTGGAACTGAAGATGGCTACCAAGGCGAAGAATCTTTATTTAACAAAGCATACT
ATGGCAAAAGCACATCATTCTTCCGTCAAGAAAGTCAAAAACTTCTGCAAAGCGATAAAAAACGCACGGCTGAGTTA
GCAAACGGCGCTCTCGGTATGATTGAGCTAAACGATGATTACACACTGAAAAAAGTGATGAAACCGCTGATTGCATC
TAACACAGTAACAGATGAAATTGAACGCGCGAACGTCTTTAAAATGAACGGCAAATGGTACCTGTTCACTGACTCCC
GCGGATCAAAAATGACGATTGACGGCATTACGTCTAACGATATTTACATGCTTGGTTATGTTTCTAATTCTTTAACT
GGCCCATACAAGCCGCTGAACAAAACTGGCCTTGTGTTAAAAATGGATCTTGATCCTAACGATGTAACCTTTACTTA
CTCACACTTCGCTGTACCTCAAGCGAAAGGAAACAATGTCGTGATTACAAGCTATATGACAAACAGAGGATTCTACG
CAGACAAACAATCAACGTTTGCGCCAAGCTTCCTGCTGAACATCAAAGGCAAGAAAACATCTGTTGTCAAAGACAGC
ATCCTTGAACAAGGACAATTAACAGTTAACAAATAA

FIGURE 3

MNIKKFAKQATVLTFTTALLAGGATQAFAKETNQKPYKETYGISHITRHDMLQIPEQQKNEKYQVPEFDSSTIKNIS
SAKGLDVWDSWPLQNADGTVANYHGYHIVFALAGDPKNADDTSIYMFYQKVGETSIDSWKNAGRVFKDSDKFDANDS
ILKDQTQEWSGSATFTSDGKIRLFYTDFSGKHYGKQTLTTAQVNVSASDSSLNINGVEDYKSIFDGDGKTYQNVQQF
IDEGNYSSGDNHTLRDPHYVEDKGHKYLVFEANTGTEDGYQGEESLFNKAYYGKSTSFFRQESQKLLQSDKKRTAEL
ANGALGMIELNDDYTLKKVMKPLIASNTVTDEIERANVFKMNGKWYLFTDSRGSKMTIDGITSNDIYMLGYVSNSLT
GPYKPLNKTGLVLKMDLDPNDVTFTYSHFAVPQAKGNNVVITSYMTNRGFYADKQSTFAPSFLLNIKGKKTSVVKDS
ILEQGQLTVNK

FIGURE 4

**ATGTTGGAAAATAAAAATCATAAAAAGATATCTTTAAGCGGAAAATCTTTGTTAATGGGAACCTTGTCAACAGCAGC
AATTGTATTAAGTGCATCAACTGCAAATGCTGCGA**CTATTAATGCAGACAATGTTAATGAAAATCAAACTGTAGAAG
TAACTGCTAGTTCAGTAAACAATGAAAATAATAAGCAAGTAACTGAAAAAGATAGTGCAGATAAAAGTACTAGTGAT
GTGGCTGAAGATGCTAACACCAAGAAATCAAACGAAAATACAGAAACTACAGAAAAGAATACTCAAACAGTTGTTAC
TAATGCGCCAGTAAGTGATGTGAAAAATACAAACACAGTTACCGCTGAAACACCTGTTGATAAAGTAGTAAATAATA
GTGATCAAAAGACAACTAATGCTGCAACTACTGATACTAAAAAAGATGATGTAAAACAAGTTGAAAAGAAAGACTCA
GTAGATAAAACAAATGCTGAGGAAAATAAAGATAGTTCAGTAAAGCCAGCTGAAAATGCTACTAAGGCTGAATTAAA
GGGCCAAGTTAAAGATATCGTTGAAGAATCTGGTGTTGATACTAGCAAGTTAACTAATGATCAAATTAATGAATTAA
ATAAAATTAATTTCTCCAAAGAAGCAAAAAGTGGTACTCAGTTAACTTACAACGACTTTAAAAAAATTGCTAAAACT
TTAATTGAACAAGATGCTCGTTATGCTATTCCATTCTTCAATGCAAGTAAAATTAAAAATATGCCTGCTGCTAAAAC
ACTTGATGCTCAAAGTGGAAAAGTAGAAGATTTGGAAATTTGGGATTCATGGCCTGTTCAAGATGCAAAAACTGGTT
ACGTATCTAACTGGAATGGCTACCAATTAGTGATTGGTATGATGGGAGTTCCAAACGTCAATGATAACCACATTTAT
CTTCTTTACAACAAGTATGGTGATAATGACTTTAATCATTGGAAGAATGCCGGTCCTATTTTCGGTCTAGGTACTCC
AGTTATTCAACAATGGTCTGGATCAGCAACTTTAAATAAAGATGGCTCAATTCAACTTTACTACACTAAGGTTGATA
CTAGTGATAATAATACTAACCACCAAAAACTCGCTAGTGCAACTGTTTACTTAAATCTTGAAAAAGATCAAGATAAG
ATTTCTATTGCTCATGTTGACAACGACCATATTGTCTTTGAAGGTGATGGTTACCACTACCAAACTTATGACCAATG
GAAAGAAACTAACAAGGGTGCTGACAATATCGCAATGCGTGATGCACACGTGATTGATGATGATAATGGTAATCGTT
ACCTTGTGTTTGAAGCAAGTACTGGAACCGAAAATTATCAAGGTGATGATCAAATTTATCAATGGTTAAATTACGGC
GGTACTAACAAGGATAATTTAGGTGATTTCTTCCAAATTTTATCTAACTCCGATATTAAAGATAGAGCTAAATGGTC
AAACGCTGCAATTGGTATCATTAAATTAAATGATGATGTTAAGAATCCAAGTGTTGCAAAGGTCTACAGCCCACTTA
TTAGTGCACCAATGGTAAGTGATGAAATTGAACGCCCTGATGTTGTTAAATTAGGTAATAAGTATTACTTATTTGCT
GCTACTAGATTAAACCGTGGTAGTAACGATGATGCTTGGATGGCAACTAACAAAGCAGTTGGTGATAACGTAGCTAT
GATTGGTTATGTTTCTGATAACTTAACTCATGGTTATGTTCCATTGAATGAATCTGGCGTTGTTTTAACTGCATCTG
TACCGGCTAACTGGCGTACTGCAACTTATTCATACTATGCAGTTCCAGTAGAAGGAAGAGATGATCAACTTTTAATT
ACTTCATACATCACTAATCGTGGTGAGGTTGCTGGAAAGGGTATGCATGCAACTTGGGCACCAAGTTTCTTGTTACA
AATTAATCCAGATAACACTACTACTGTTTTAGCTAAAATGACTAACCAAGGGGATTGGATTTGGGATGATAGTAGTG
AAAATCCAGATATGATGGGTGTACTTGAAAAAGATGCTCCAAATAGTGCTGCCCTTCCTGGAGAATGGGGAAAACCA
GTTGATTGGGATTTAATTGGTGGATACAACTTGAAGCACACCAACCTGTAACTCCTATTCCAAATGTACCAACTAC
TCCTGAAACCCCAACCACACCAGATAAGCCAGAGGTACCAACTACCCCTGAAGTTCCAACCACTCCAGAAACTCCAA
CTCCAGAAGCTCCAAAGAATCCAGTTAAGAAAACTAGTCAGTCTAAACTTCCAAAGGCTGGAGATAAAAATAGCTTT
GCAGCAGTTGTTTTAGGTGCTGTAAGTTCAATATTAGGTGCTGTTGGTTTAACAGGTGTTTCAAAACGTAAACGTAA
TAATTAA

FIGURE 5

MLENKNHKKISLSGKSLLMGTLSTAAIVLSASTANAATINADNVNENQTVEVTASSVNNENNKQVTEKDSADKSTSD
VAEDANTKKSNENTETTEKNTQTVVTNAPVSDVKNTNTVTAETPVDKVVNNSDQKTTNAATTDTKKDDVKQVEKKDS
VDKTNAEENKDSSVKPAENATKAELKGQVKDIVEESGVDTSKLTNDQINELNKINFSKEAKSGTQLTYNDFKKIAKT
LIEQDARYAIPFFNASKIKNMPAAKTLDAQSGKVEDLEIWDSWPVQDAKTGYVSNWNGYQLVIGMMGVPNVNDNHIY
LLYNKYGDNDFNHWKNAGPIFGLGTPVIQQWSGSATLNKDGSIQLYYTKVDTSDNNTNHQKLASATVYLNLEKDQDK
ISIAHVDNDHIVFEGDGYHYQTYDQWKETNKGADNIAMRDAHVIDDDNGNRYLVFEASTGTENYQGDDQIYQWLNYG
GTNKDNLGDFFQILSNSDIKDRAKWSNAAIGIIKLNDDVKNPSVAKVYSPLISAPMVSDEIERPDVVKLGNKYYLFA
ATRLNRGSNDDAWMATNKAVGDNVAMIGYVSDNLTHGYVPLNESGVVLTASVPANWRTATYSYYAVPVEGRDDQLLI
TSYITNRGEVAGKGMHATWAPSFLLQINPDNTTTVLAKMTNQGDWIWDDSSENPDMMGVLEKDAPNSAALPGEWGKP
VDWDLIGGYNLKPHQPVTPIPNVPTTPETPTTPDKPEVPTTPEVPTTPETPTPEAPKNPVKKTSQSKLPKAGDKNSF
AAVVLGAVSSILGAVGLTGVSKRKRNN

FIGURE 6

ATGAAAGCCTTCACACTCGCTCTCTTCTTAGCTCTTTTCCTCTATCTCCTGCCCAATCCAGCCCATTCCAGGTTCAA
TCCCATCCGCCTCCCCACCACACACGAACCCGCCTCCTCTGAAACTCCAGTACTCGACATCAACGGCGACGAGGTCC
GCGCCGGCGGGAACTACTACATGGTCTCCGCCATATGGGGAGCCGGCGGGGGAGGGCTAAGACTCGCCCACTTGGAC
ACGATGTCCAAATGCGCCAGCGACGTCATCGTATCCCCCAACGACTTAGACAACGGCGACCCCATCACCATCACGCC
GGCGACGGCCGACCCGGAATCCACCGTGGTCATGGCGTCGACCTACCAGACTTTCCGGTTCAATATCGCCAACAACA
AACTGTGCGTGAAGAACGTGAACTGGGGAATCCAGCACGACAGCGCGTCCGGGCAGTATTTCCTGAAAGACGGCGAG
TTTGTCTCCGACAATAGCAACCAGTTCAAGATTGAGGTGGTGGATGCCAACCTTAACTTCTACAAACTCACTTACTG
TCAGTTCGGCTCCGACAAATGCTACAACTGCGGCAGATTCCACGACCCCATGTTGAGGACCACGCGCTTGGCTCTCT
CCAATTCTCCCTTCGTTTTTGTCATCAAACCTACCGATGTG

FIGURE 7

MKAFTLALFLALFLYLLPNPAHSRFNPIRLPTTHEPASSETPVLDINGDEVRAGGNYYMVSAIWGAGGGGLRLAHLD
TMSKCASDVIVSPNDLDNGDPITITPATADPESTVVMASTYQTFRFNIANNKLCVKNVNWGIQHDSASGQYFLKDGE
FVSDNSNQFKIEVVDANLNFYKLTYCQFGSDKCYNCGRFHDPMLRTTRLALSNSPFVFVIKPTDV

FIGURE 8

ATGAAAGCCTTCACACTCGCTCTCTTCTTAGCTCTTTTCCTCTATCTCCTGCCCAATCCAGCCCATTCCACGAACCA
AAAGCCATATAAGGAAACATACGGCATTTCCCATATTACACGCCATGATATGCTGCAAATCCCTGAACAGCAAAAAA
ATGAAAAATATCAAGTTCCTGAATTCGATTCGTCCACAATTAAAAATATCTCTTCTGCAAAAGGCCTGGACGTTTGG
GACAGCTGGCCATTACAAAACGCTGACGGCACTGTCGCAAACTATCACGGCTACCACATCGTCTTTGCATTAGCCGG
AGATCCTAAAAATGCGGATGACACATCGATTTACATGTTCTATCAAAAAGTCGGCGAAACTTCTATTGACAGCTGGA
AAAACGCTGGCCGCGTCTTTAAAGACAGCGACAAATTCGATGCAAATGATTCTATCCTAAAAGACCAAACACAAGAA
TGGTCAGGTTCAGCCACATTTACATCTGACGGAAAAATCCGTTTATTCTACACTGATTTCTCCGGTAAACATTACGG
CAAACAAACACTGACAACTGCACAAGTTAACGTATCAGCATCAGACAGCTCTTTGAACATCAACGGTGTAGAGGATT
ATAAATCAATCTTTGACGGTGACGGAAAAACGTATCAAAATGTACAGCAGTTCATCGATGAAGGCAACTACAGCTCA
GGCGACAACCATACGCTGAGAGATCCTCACTACGTAGAAGATAAAGGCCACAAATACTTAGTATTTGAAGCAAACAC
TGGAACTGAAGATGGCTACCAAGGCGAAGAATCTTTATTTAACAAAGCATACTATGGCAAAAGCACATCATTCTTCC
GTCAAGAAAGTCAAAAACTTCTGCAAAGCGATAAAAAACGCACGGCTGAGTTAGCAAACGGCGCTCTCGGTATGATT
GAGCTAAACGATGATTACACACTGAAAAAAGTGATGAAACCGCTGATTGCATCTAACACAGTAACAGATGAAATTGA
ACGCGCGAACGTCTTTAAAATGAACGGCAAATGGTACCTGTTCACTGACTCCCGCGGATCAAAAATGACGATTGACG
GCATTACGTCTAACGATATTTACATGCTTGGTTATGTTTCTAATTCTTTAACTGGCCCATACAAGCCGCTGAACAAA
ACTGGCCTTGTGTTAAAAATGGATCTTGATCCTAACGATGTAACCTTTACTTACTCACACTTCGCTGTACCTCAAGC
GAAAGGAAACAATGTCGTGATTACAAGCTATATGACAAACAGAGGATTCTACGCAGACAAACAATCAACGTTTGCGC
CAAGCTTCCTGCTGAACATCAAAGGCAAGAAAACATCTGTTGTCAAAGACAGCATCCTTGAACAAGGACAATTAACA
GTTAACAAATAA

FIGURE 9

MKAFTLALFLALFLYLLPNPAHSTNQKPYKETYGISHITRHDMLQIPEQQKNEKYQVPEFDSSTIKNISSAKGLDVW
DSWPLQNADGTVANYHGYHIVFALAGDPKNADDTSIYMFYQKVGETSIDSWKNAGRVFKDSDKFDANDSILKDQTQE
WSGSATFTSDGKIRLFYTDFSGKHYGKQTLTTAQVNVSASDSSLNINGVEDYKSIFDGDGKTYQNVQQFIDEGNYSS
GDNHTLRDPHYVEDKGHKYLVFEANTGTEDGYQGEESLFNKAYYGKSTSFFRQESQKLLQSDKKRTAELANGALGMI
ELNDDYTLKKVMKPLIASNTVTDEIERANVFKMNGKWYLFTDSRGSKMTIDGITSNDIYMLGYVSNSLTGPYKPLNK
TGLVLKMDLDPNDVTFTYSHFAVPQAKGNNVVITSYMTNRGFYADKQSTFAPSFLLNIKGKKTSVVKDSILEQGQLT
VNK

FIGURE 11

ATGAAAGCCTTCACACTCGCTCTCTTCTTAGCTCTTTTCCTCTATCTCCTGCCCAATCCAGCCCATTCCACTATTAA
TGCAGACAATGTTAATGAAAATCAAACTGTAGAAGTAACTGCTAGTTCAGTAAACAATGAAAATAATAAGCAAGTAA
CTGAAAAAGATAGTGCAGATAAAAGTACTAGTGATGTGGCTGAAGATGCTAACACCAAGAAATCAAACGAAAATACA
GAAACTACAGAAAAGAATACTCAAACAGTTGTTACTAATGCGCCAGTAAGTGATGTGAAAAATACAAACACAGTTAC
CGCTGAAACACCTGTTGATAAAGTAGTAAATAATAGTGATCAAAAGACAACTAATGCTGCAACTACTGATACTAAAA
AAGATGATGTAAAACAAGTTGAAAAGAAAGACTCAGTAGATAAAACAAATGCTGAGGAAAATAAAGATAGTTCAGTA
AAGCCAGCTGAAAATGCTACTAAGGCTGAATTAAAGGGCCAAGTTAAAGATATCGTTGAAGAATCTGGTGTTGATAC
TAGCAAGTTAACTAATGATCAAATTAATGAATTAAATAAAATTAATTTCTCCAAAGAAGCAAAAAGTGGTACTCAGT
TAACTTACAACGACTTTAAAAAAATTGCTAAAACTTTAATTGAACAAGATGCTCGTTATGCTATTCCATTCTTCAAT
GCAAGTAAAATTAAAAATATGCCTGCTGCTAAAACACTTGATGCTCAAAGTGGAAAAGTAGAAGATTTGGAAATTTG
GGATTCATGGCCTGTTCAAGATGCAAAAACTGGTTACGTATCTAACTGGAATGGCTACCAATTAGTGATTGGTATGA
TGGGAGTTCCAAACGTCAATGATAACCACATTTATCTTCTTTACAACAAGTATGGTGATAATGACTTTAATCATTGG
AAGAATGCCGGTCCTATTTTCGGTCTAGGTACTCCAGTTATTCAACAATGGTCTGGATCAGCAACTTTAAATAAAGA
TGGCTCAATTCAACTTTACTACACTAAGGTTGATACTAGTGATAATAATACTAACCACCAAAAACTCGCTAGTGCAA
CTGTTTACTTAAATCTTGAAAAAGATCAAGATAAGATTTCTATTGCTCATGTTGACAACGACCATATTGTCTTTGAA
GGTGATGGTTACCACTACCAAACTTATGACCAATGGAAAGAAACTAACAAGGGTGCTGACAATATCGCAATGCGTGA
TGCACACGTGATTGATGATGATAATGGTAATCGTTACCTTGTGTTTGAAGCAAGTACTGGAACCGAAAATTATCAAG
GTGATGATCAAATTTATCAATGGTTAAATTACGGCGGTACTAACAAGGATAATTTAGGTGATTTCTTCCAAATTTTA
TCTAACTCCGATATTAAAGATAGAGCTAAATGGTCAAACGCTGCAATTGGTATCATTAAATTAAATGATGATGTTAA
GAATCCAAGTGTTGCAAAGGTCTACAGCCCACTTATTAGTGCACCAATGGTAAGTGATGAAATTGAACGCCCTGATG
TTGTTAAATTAGGTAATAAGTATTACTTATTTGCTGCTACTAGATTAAACCGTGGTAGTAACGATGATGCTTGGATG
GCAACTAACAAAGCAGTTGGTGATAACGTAGCTATGATTGGTTATGTTTCTGATAACTTAACTCATGGTTATGTTCC
ATTGAATGAATCTGGCGTTGTTTTAACTGCATCTGTACCGGCTAACTGGCGTACTGCAACTTATTCATACTATGCAG
TTCCAGTAGAAGGAAGAGATGATCAACTTTTAATTACTTCATACATCACTAATCGTGGTGAGGTTGCTGGAAAGGGT
ATGCATGCAACTTGGGCACCAAGTTTCTTGTTACAAATTAATCCAGATAACACTACTACTGTTTTAGCTAAAATGAC
TAACCAAGGGGATTGGATTTGGGATGATAGTAGTGAAAATCCAGATATGATGGGTGTACTTGAAAAAGATGCTCCAA
ATAGTGCTGCCCTTCCTGGAGAATGGGGAAAACCAGTTGATTGGGATTTAATTGGTGGATACAACTTGAAGCCACAC
CAACCTGTAACTCCTATTCCAAATGTACCAACTACTCCTGAAACCCCAACCACACCAGATAAGCCAGAGGTACCAAC
TACCCCTGAAGTTCCAACCACTCCAGAAACTCCAACTCCAGAAGCTCCAAAGAATCCAGTTAAGAAAACTAGTCAGT
CTAAACTTCCAAAGGCTGGAGATAAAAATAGCTTTGCAGCAGTTGTTTTAGGTGCTGTAAGTTCAATATTAGGTGCT
GTTGGTTTAACAGGTGTTTCAAAACGTAAACGTAATAATTAA

FIGURE 12

MKAFTLALFLALFLYLLPNPAHSTINADNVNENQTVEVTASSVNNENNKQVTEKDSADKSTSDVAEDANTKKSNENT
ETTEKNTQTVVTNAPVSDVKNTNTVTAETPVDKVVNNSDQKTTNAATTDTKKDDVKQVEKKDSVDKTNAEENKDSSV
KPAENATKAELKGQVKDIVEESGVDTSKLTNDQINELNKINFSKEAKSGTQLTYNDFKKIAKTLIEQDARYAIPFFN
ASKIKNMPAAKTLDAQSGKVEDLEIWDSWPVQDAKTGYVSNWNGYQLVIGMMGVPNVNDNHIYLLYNKYGDNDFNHW
KNAGPIFGLGTPVIQQWSGSATLNKDGSIQLYYTKVDTSDNNTNHQKLASATVYLNLEKDQDKISIAHVDNDHIVFE
GDGYHYQTYDQWKETNKGADNIAMRDAHVIDDDNGNRYLVFEASTGTENYQGDDQIYQWLNYGGTNKDNLGDFFQIL
SNSDIKDRAKWSNAAIGIIKLNDDVKNPSVAKVYSPLISAPMVSDEIERPDVVKLGNKYYLFAATRLNRGSNDDAWM
ATNKAVGDNVAMIGYVSDNLTHGYVPLNESGVVLTASVPANWRTATYSYYAVPVEGRDDQLLITSYITNRGEVAGKG
MHATWAPSFLLQINPDNTTTVLAKMTNQGDWIWDDSSENPDMMGVLEKDAPNSAALPGEWGKPVDWDLIGGYNLKPH
QPVTPIPNVPTTPETPTTPDKPEVPTTPEVPTTPETPTPEAPKNPVKKTSQSKLPKAGDKNSFAAVVLGAVSSILGA
VGLTGVSKRKRNN

1-SST

FIGURE 15

ATGCAACCAGGGAACGTCGTCCACCCCTTCCACATCCTGTATCAAATTAAGGAACGGGCGCTGAGCCTATGCCGAGA
CATATATAATGCGGCGACTCGGACATGGAGGGGCCTCAGGCATAGCCCAGCTAGTTATCTCATTCTCTCCTTAGCAA
TAATACTTAGCACCATGGCCCCGCGGTGGAATTCATGGAGTCCCCAAGCGCCGTCGTCCCCGGCACCACGGCGCCG
CTGCTTCCTTATGCGTACGCGCCGCTGCCGTCGTCCGCCGACGACGCCCGTCAAAACCGGAGTGGCGGGAGGTGGCG
CGCGTGCGCCGCCGTGCTGGCCGCATCGGCGTTGGCGGTGGTCGTCGTGGTCGGGCTCCTCGCGGGCGGCAGGGTGG
ATCGGGTCCCGGCCGGCGGAGACGTGGCGTCGGCCACGGTGCCGGCCGTGCCGATGGAGTTCCCGAGGAGCCGGGGC
AAGGACTTCGGCGTGTCGGAGAAGTCCTCCGGTGCCTACTCCACCGACGGCGGGTTCCCGTGGAGCAACGCCATGCT
GCAGTGGCAGCGCACCGGGTTCCATTTCCAGCCGGAGCAGCACTACATGAACGATCCCAACGGCCCCGTGTACTACG
GCGGATGGTACCACCTCTTCTACCAGCACAACCCCAAGGGCGACAGCTGGGGCAACATCGCGTGGGCCCACGCCGTC
TCCAAGGACATGGTCAACTGGCGCCACCTCCCTCTCGCCATGGTTCCCGACCAGTGGTACGACAGCAACGGCGTCCT
CACCGGCTCCATCACCGTGCTCCCCGACGGCCAGGTCATCCTGCTCTACACCGGCAACACCGACACCCTAGCCCAGG
TCCAGTGCCTCGCCACGCCCGCCGACCCGTCCGACCCGCTCCTCCGCGAGTGGGTCAAGCACCCCGCCAACCCCATC
CTCTACCCTCCCCCCGGCATCGGCCTCAAGGACTTCCGCGACCCCCTCACCGCCTGGTTCGACCACTCCGACCACAC
CTGGCGCACCGTCATCGGCTCCAAGGACGACGACGGCCACGCCGGCATCATCCTCAGCTACAAGACCAAGGACTTCG
TCAACTACGAGCTCATGCCGGGGAACATGCACCGCGGGCCCGACGGCACCGGAATGTACGAGTGCATCGACCTCTAC
CCCGTCGGCGGCAACTCGTCCGAGATGCTCGGCGGCGACGACTCGCCCGGCGTGCTCTTCGTGCTCAAGGAGAGCAG
CGACGACGAGCGCCACGACTACTACGCGCTCGGAAGGTTCGACGCCGTCGCCAACGTTTGGACGCCCATCGACCGGG
AGCTGGACCTTGGGATCGGGCTCAGATACGACTGGGGAAAGTACTACGCCTCCAAGTCCTTCTACGACCAGAAGAAG
AACCGCCGCATCGTATGGGCATACATCGGCGAGACCGACTCCGAGCAGGCCGACATCACCAAGGGATGGGCCAATCT
CATGACGATTCCAAGAACGGTGGAGCTTGACAGGAAGACCCGCACAAACCTCATCCAATGGCCAGTGGAGGAGGTCG
ACACCCTCCGCAGGAACTCCACGGACCTCGGTCGCATCACCGTCAACGCCGGCTCCGTCATTCGCCTCCCCCTCCAC
CAGGGCGCTCAACTCGACATCGAGGCCTCCTTCCAACTCAACTCTTCCGACGTGGATGCTATCAACGAGGCCGACGT
CGGCTACAACTGCAGCACCAGTGGTGCCGCCGTACGGGGGCGCTCGGCCCCTTTGGCCTCCTCGTCCTTGCCAACG
GCCGCACCGAACAGACGGCTGTGTACTTCTACGTGTCCAAGGGCGTCGACGGTGCCCTCCAGACCCACTTCTGCCAC
GACGAGTCACGGTCAACGCGGGCAAAGGATGTCGTGAATAGGATGATTGGCAGCATCGTGCCGGTGCTTGACGGTGA
GACCTTTTCGGTGAGGGTGCTAGTGGACCACTCCATCGTGCAGAGCTTCGCGATGGGCGGGAGGATCACGGCGACGT
CGCGGGCGTACCCGACGGAGGCCATCTACGCGGCCGCGGGGGTCTACCTCTTCAACAACGCCACGGGCGCCACCGTC
ACCGCCGAGAGGCTCGTCGTGCACGAGATGGCCTCAGCTGACAACCATATCTTCACGAACGACGACTTG

FIGURE 16

*MESPSAVVPGTTAPLLPYAYAPLPSSADDARQNRSGGRWRACAAVLAASALAVVVVVGLLAGGRVDRVPAGG*DVASA
TVPAVPMEFPRSRGKDFGVSEKSSGAYSTDGGFPWSNAMLQWQRTGFHFQPEQHYMNDPNGPVYYGGWYHLFYQHNP
KGDSWGNIAWAHAVSKDMVNWRHLPLAMVPDQWYDSNGVLTGSITVLPDGQVILLYTGNTDTLAQVQCLATPADPSD
PLLREWVKHPANPILYPPPGIGLKDFRDPLTAWFDHSDHTWRTVIGSKDDDGHAGIILSYKTKDFVNYELMPGNMHR
GPDGTGMYECIDLYPVGGNSSEMLGGDDSPGVLFVLKESSDDERHDYYALGRFDAVANVWTPIDRELDLGIGLRYDW
GKYYASKSFYDQKKNRRIVWAYIGETDSEQADITKGWANLMTIPRTVELDRKTRTNLIQWPVEEVDTLRRNSTDLGR
ITVNAGSVIRLPLHQGAQLDIEASFQLNSSDVDAINEADVGYNCSTSGAAVRGALGPFGLLVLANGRTEQTAVYFYV
SKGVDGALQTHFCHDESRSTRAKDVVNRMIGSIVPVLDGETFSVRVLVDHSIVQSFAMGGRITATSRAYPTEAIYAA
AGVYLFNNATGATVTAERLVVHEMASADNHIFTNDDL

FIGURE 17

ATGGAGTCCCCAAGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGGAGGTGGCGCGCGTGCGCCGCCGTGCTGGCCGCATCGGCG
TTGGCGGTGGTCGTCGTGGTCGGGCTCCTCGCGGGCGGCAGGGTGGATCGGGTCCCGGCCGGCGGAACGAACCAA
AAGCCATATAAGGAAACATACGGCATTTCCCATATTACACGCCATGATATGCTGCAAATCCCTGAACAGCAAAAA
AATGAAAAATATCAAGTTCCTGAATTCGATTCGTCCACAATTAAAAATATCTCTTCTGCAAAAGGCCTGGACGTT
TGGGACAGCTGGCCATTACAAAACGCTGACGGCACTGTCGCAAACTATCACGGCTACCACATCGTCTTTGCATTA
GCCGGAGATCCTAAAAATGCGGATGACACATCGATTTACATGTTCTATCAAAAGTCGGCGAAACTTCTATTGAC
AGCTGGAAAAACGCTGGCCGCGTCTTTAAAGACAGCGACAAATTCGATGCAAATGATTCTATCCTAAAAGACCAA
ACACAAGAATGGTCAGGTTCAGCCACATTTACATCTGACGGAAAAATCCGTTTATTCTACACTGATTTCTCCGGT
AAACATTACGGCAAACAAACACTGACAACTGCACAAGTTAACGTATCAGCATCAGACAGCTCTTTGAACATCAAC
GGTGTAGAGGATTATAAATCAATCTTTGACGGTGACGGAAAAACGTATCAAAATGTACAGCAGTTCATCGATGAA
GGCAACTACAGCTCAGGCGACAACCATACGCTGAGAGATCCTCACTACGTAGAAGATAAAGGCCACAAATACTTA
GTATTTGAAGCAAACACTGGAACTGAAGATGGCTACCAAGGCGAAGAATCTTTATTTAACAAAGCATACTATGGC
AAAAGCACATCATTCTTCCGTCAAGAAAGTCAAAAACTTCTGCAAAGCGATAAAAAACGCACGGCTGAGTTAGCA
AACGGCGCTCTCGGTATGATTGAGCTAAACGATGATTACACACTGAAAAAAGTGATGAAACCGCTGATTGCATCT
AACACAGTAACAGATGAAATTGAACGCGCGAACGTCTTTAAAATGAACGGCAAATGGTACCTGTTCACTGACTCC
CGCGGATCAAAAATGACGATTGACGGCATTACGTCTAACGATATTTACATGCTTGGTTATGTTTCTAATTCTTTA
ACTGGCCCATACAAGCCGCTGAACAAAACTGGCCTTGTGTTAAAAATGGATCTTGATCCTAACGATGTAACCTTT
ACTTACTCACACTTCGCTGTACCTCAAGCGAAAGGAAACAATGTCGTGATTACAAGCTATATGACAAACAGAGGA
TTCTACGCAGACAAACAATCAACGTTTGCGCCAAGCTTCCTGCTGAACATCAAAGGCAAGAAAACATCTGTTGTC
AAAGACAGCATCCTTGAACAAGGACAATTAACAGTTAACAAATAA

FIGURE 18

*MESPSAVVPGTTAPLLPYAYAPLPSSADDARQNRSGGRWRACAAVLAASALAVVVVVGLLAGGRVDRVPAGG*TNQ
KPYKETYGISHITRHDMLQIPEQQKNEKYQVPEFDSSTIKNISSAKGLDVWDSWPLQNADGTVANYHGYHIVFAL
AGDPKNADDTSIYMFYQKVGETSIDSWKNAGRVFKDSDKFDANDSILKDQTQEWSGSATFTSDGKIRLFYTDFSG
KHYGKQTLTTAQVNVSASDSSLNINGVEDYKSIFDGDGKTYQNVQQFIDEGNYSSGDNHTLRDPHYVEDKGHKYL
VFEANTGTEDGYQGEESLFNKAYYGKSTSFFRQESQKLLQSDKKRTAELANGALGMIELNDDYTLKKVMKPLIAS
NTVTDEIERANVFKMNGKWYLFTDSRGSKMTIDGITSNDIYMLGYVSNSLTGPYKPLNKTGLVLKMDLDPNDVTF
TYSHFAVPQAKGNNVVITSYMTNRGFYADKQSTFAPSFLLNIKGKKTSVVKDSILEQGQLTVNK

FIGURE 20

ATGGAGTCCCCAAGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGGAGGTGGCGCGCGTGCGCCGCCGTGCTGGCCGCATCGGCG
TTGGCGGTGGTCGTCGTGGTCGGGCTCCTCGCGGGCGGCAGGGTGGATCGGGTCCCGGCCGGCGGAACTATTAAT
GCAGACAATGTTAATGAAAATCAAACTGTAGAAGTAACTGCTAGTTCAGTAAACAATGAAAATAATAAGCAAGTA
ACTGAAAAGATAGTGCAGATAAAAGTACTAGTGATGTGGCTGAAGATGCTAACACCAAGAAATCAAACGAAAAT
ACAGAAACTACAGAAAAGAATACTCAAACAGTTGTTACTAATGCGCCAGTAAGTGATGTGAAAAATACAAACACA
GTTACCGCTGAAACACCTGTTGATAAAGTAGTAAATAATAGTGATCAAAAGACAACTAATGCTGCAACTACTGAT
ACTAAAAAAGATGATGTAAAACAAGTTGAAAAGAAAGACTCAGTAGATAAAACAAATGCTGAGGAAAATAAAGAT
AGTTCAGTAAAGCCAGCTGAAAATGCTACTAAGGCTGAATTAAAGGGCCAAGTTAAAGATATCGTTGAAGAATCT
GGTGTTGATACTAGCAAGTTAACTAATGATCAAATTAATGAATTAAATAAAATTAATTTCTCCAAAGAAGCAAAA
AGTGGTACTCAGTTAACTTACAACGACTTTAAAAAAATTGCTAAAACTTTAATTGAACAAGATGCTCGTTATGCT
ATTCCATTCTTCAATGCAAGTAAAATTAAAAATATGCCTGCTGCTAAAACACTTGATGCTCAAAGTGGAAAAGTA
GAAGATTTGGAAATTTGGGATTCATGGCCTGTTCAAGATGCAAAAACTGGTTACGTATCTAACTGGAATGGCTAC
CAATTAGTGATTGGTATGATGGGAGTTCCAAACGTCAATGATAACCACATTTATCTTCTTTACAACAAGTATGGT
GATAATGACTTTAATCATTGGAAGAATGCCGGTCCTATTTTCGGTCTAGGTACTCCAGTTATTCAACAATGGTCT
GGATCAGCAACTTTAAATAAAGATGGCTCAATTCAACTTTACTACACTAAGGTTGATACTAGTGATAATAATACT
AACCACCAAAAACTCGCTAGTGCAACTGTTTACTTAAATCTTGAAAAAGATCAAGATAAGATTTCTATTGCTCAT
GTTGACAACGACCATATTGTCTTTGAAGGTGATGGTTACCACTACCAAACTTATGACCAATGGAAAGAAACTAAC
AAGGGTGCTGACAATATCGCAATGCGTGATGCACACGTGATTGATGATGATAATGGTAATCGTTACCTTGTGTTT
GAAGCAAGTACTGGAACCGAAAATTATCAAGGTGATGATCAAATTTATCAATGGTTAAATTACGGCGGTACTAAC
AAGGATAATTTAGGTGATTTCTTCCAAATTTTATCTAACTCCGATATTAAAGATAGAGCTAAATGGTCAAACGCT
GCAATTGGTATCATTAAATTAAATGATGATGTTAAGAATCCAAGTGTTGCAAAGGTCTACAGCCCACTTATTAGT
GCACCAATGGTAAGTGATGAAATTGAACGCCCTGATGTTGTTAAATTAGGTAATAAGTATTACTTATTTGCTGCT
ACTAGATTAAACCGTGGTAGTAACGATGATGCTTGGATGGCAACTAACAAAGCAGTTGGTGATAACGTAGCTATG
ATTGGTTATGTTTCTGATAACTTAACTCATGGTTATGTTCCATTGAATGAATCTGGCGTTGTTTAACTGCATCT
GTACCGGCTAACTGGCGTACTGCAACTTATTCATACTATGCAGTTCCAGTAGAAGGAAGAGATGATCAACTTTTA
ATTACTTCATACATCACTAATCGTGGTGAGGTTGCTGGAAAGGGTATGCATGCAACTTGGGCACCAAGTTTCTTG
TTACAAATTAATCCAGATAACACTACTACTGTTTTAGCTAAAATGACTAACCAAGGGGATTGGATTTGGGATGAT
AGTAGTGAAAATCCAGATATGATGGGTGTACTTGAAAAAGATGCTCCAAATAGTGCTGCCCTTCCTGGAGAATGG
GGAAAACCAGTTGATTGGGATTTAATTGGTGGATACAACTTGAAGCCACACCAACCTGTAACTCCTATTCCAAAT
GTACCAACTACTCCTGAAACCCCAACCACACCAGATAAGCCAGAGGTACCAACTACCCCTGAAGTTCCAACCACT
CCAGAAACTCCAACTCCAGAAGCTCCAAAGAATCCAGTTAAGAAAACTAGTCAGTCTAAACTTCCAAAGGCTGGA
GATAAAAATAGCTTTGCAGCAGTTGTTTTAGGTGCTGTAAGTTCAATATTAGGTGCTGTTGGTTTAACAGGTGTT
TCAAAACGTAAACGTAATAATTAA

FIGURE 21

*MESPSAVVPGTTAPLLPYAYAPLPSSADDARQNRSGGRWRACAAVLAASALAVVVVVGLLAGGRVDRVPAGG*TINAD
NVNENQTVEVTASSVNNENNKQVTEKDSADKSTSDVAEDANTKKSNENTETTEKNTQTVVTNAPVSDVKNTNTVTAE
TPVDKVVNNSDQKTTNAATTDTKKDDVKQVEKKDSVDKTNAEENKDSSVKPAENATKAELKGQVKDIVEESGVDTSK
LTNDQINELNKINFSKEAKSGTQLTYNDFKKIAKTLIEQDARYAIPFFNASKIKNMPAAKTLDAQSGKVEDLEIWDS
WPVQDAKTGYVSNWNGYQLVIGMMGVPNVNDNHIYLLYNKYGDNDFNHWKNAGPIFGLGTPVIQQWSGSATLNKDGS
IQLYYTKVDTSDNNTNHQKLASATVYLNLEKDQDKISIAHVDNDHIVFEGDGYHYQTYDQWKETNKGADNIAMRDAH
VIDDDNGNRYLVFEASTGTENYQGDDQIYQWLNYGGTNKDNLGDFFQILSNSDIKDRAKWSNAAIGIIKLNDDVKNP
SVAKVYSPLISAPMVSDEIERPDVVKLGNKYYLFAATRLNRGSNDDAWMATNKAVGDNVAMIGYVSDNLTHGYVPLN
ESGVVLTASVPANWRTATYSYYAVPVEGRDDQLLITSYITNRGEVAGKGMHATWAPSFLLQINPDNTTTVLAKMTNQ
GDWIWDDSSENPDMMGVLEKDAPNSAALPGEWGKPVDWDLIGGYNLKPHQPVTPIPNVPTTPETPTTPDKPEVPTTP
EVPTTPETPTPEAPKNPVKKTSQSKLPKAGDKNSFAAVVLGAVSSILGAVGLTGVSKRKRNN

FIGURE 23 cgtggtcgagattgtgtattattctttagttattacaagacttttagctaaaatttgaaagaatttactttaagaaa
atcttaacatctgagataatttcagcaatagattatattttcattactctagcagtattttttgcagatcaatcgca
acatatatggttgttagaaaaaatgcactatatatatatatattatttttttcaattaaaagtgcatgatatataata
tatatatatatatatatgtgtgtgtgtatatggtcaaagaaattcttatacaaatatacacgaacacatatattt
gacaaaatcaaagtattacactaaacaatgagttggtgcatggccaaaacaaatatgtagattaaaaattccagcct
ccaaaaaaaaatccaagtgttgtaaagcattatatatatatagtagatcccaaattttttgtacaattccacactgat
cgaattttttaaagttgaatatctgacgtaggatttttttaatgtcttacctgaccatttactaataacattcatacg
ttttcatttgaaatatcctctataattatattgaatttggcacataataagaaacctaattggtgatttattttact
agtaaatttctggtgatgggctttctactagaaagctctcggaaaatcttggaccaaatccatattccatgacttcg
attgttaaccctattagttttcacaaacatactatcaatatcattgcaacggaaaagtacaagtaaaacattcaat
ccgatagggaagtgatgtaggaggttgggaagacaggcccagaaagagatttatctgacttgttttgtgtatagttt
tcaatgttcataaaggaagatggagacttgagaagttttttttggactttgtttagctttgttgggcgttttttttt
tttgatcaataactttgttgggcttatgatttgtaatattttcgtggactctttagtttatttagacgtgctaactt
tgttgggcttatgacttgttgtaacatattgtaacagatgacttgatgtgcgactaatctttacacattaaacatag
ttctgtttttttgaaagttcttattttcatttttatttgaatgttatatattttctatatttataattctagtaaaa
ggcaaattttgcttttaaatgaaaaaatatatattccacagtttcacctaatcttatgcatttagcagtacaaatt
caaaaatttcccatttttattcatgaatcataccattatatattaactaaatccaaggtaaaaaaaaggtatgaaag
ctctatagtaagtaaaatataaattccccataaggaaagggccaagtccaccaggcaagtaaaatgagcaagcacca
ctccaccatcacacaatttcactcatagataacgataagattcatggaattatcttccacgtggcattattccagcg
gttcaagccgataagggtctcaacacctctccttaggcctttgtggccgttaccaagtaaaattaacctcacacata
tccacactcaaaatccaacggtgtagatcctagtccacttgaatctcatgtatcctagaccctccgatcactccaaa
gcttgttctcattgttgttatcattatatatagatgaccaaagcactagaccaaacctcagtcacacaaagagtaaa
gaagaacaATGAAAGCCTTCACACTCGCTCTCTTCTTAGCTCTTTTCCTCTATCTCCTGCCCAATCCAGCCCATTCC
ACGAACCAAAAGCCATATAAGGAAACATACGGCATTTCCCATATTACACGCCATGATATGCTGCAAATCCCTGAACA
GCAAAAAAATGAAAAATATCAAGTTCCTGAATTCGATTCGTCCACAATTAAAAATATCTCTTCTGCAAAAGGCCTGG
ACGTTTGGGACAGCTGGCCATTACAAAACGCTGACGGCACTGTCGCAAACTATCACGGCTACCACATCGTCTTTGCA
TTAGCCGGAGATCCTAAAAATGCGGATGACACATCGATTTACATGTTCTATCAAAAAGTCGGCGAAACTTCTATTGA
CAGCTGGAAAAACGCTGGCCGCGTCTTTAAAGACAGCGACAAATTCGATGCAAATGATTCTATCCTAAAAGACCAAA
CACAAGAATGGTCAGGTTCAGCCACATTTACATCTGACGGAAAAATCCGTTTATTCTACACTGATTTCTCCGGTAAA
CATTACGGCAAACAAACACTGACAACTGCACAAGTTAACGTATCAGCATCAGACAGCTCTTTGAACATCAACGGTGT
AGAGGATTATAAATCAATCTTTGACGGTGACGGAAAAACGTATCAAAATGTACAGCAGTTCATCGATGAAGGCAACT
ACAGCTCAGGCGACAACCATACGCTGAGAGATCCTCACTACGTAGAAGATAAAGGCCACAAATACTTAGTATTTGAA
GCAAACACTGGAACTGAAGATGGCTACCAAGGCGAAGAATCTTTATTTAACAAAGCATACTATGGCAAAAGCACATC
ATTCTTCCGTCAAGAAAGTCAAAAACTTCTGCAAAGCGATAAAAAACGCACGGCTGAGTTAGCAAACGGCGCTCTCG
GTATGATTGAGCTAAACGATGATTACACACTGAAAAAAGTGATGAAACCGCTGATTGCATCTAACACAGTAACAGAT

FIGURE 23 (CONT'D)

```
GAAATTGAACGCGCGAACGTCTTTAAAATGAACGGCAAATGGTACCTGTTCACTGACTCCCGCGGATCAAAAATGAC
GATTGACGGCATTACGTCTAACGATATTTACATGCTTGGTTATGTTTCTAATTCTTTAACTGGCCCATACAAGCCGC
TGAACAAAACTGGCCTTGTGTTAAAAATGGATCTTGATCCTAACGATGTAACCTTTACTTACTCACACTTCGCTGTA
CCTCAAGCGAAAGGAAACAATGTCGTGATTACAAGCTATATGACAAACAGAGGATTCTACGCAGACAAACAATCAAC
GTTTGCGCCAAGCTTCCTGCTGAACATCAAAGGCAAGAAAACATCTGTTGTCAAAGACAGCATCCTTGAACAAGGAC
AATTAACAGTTAACAAATAAGatcgttcaaacatttggcaataaagtttcttaagaatgaatcctgttgccggtctt
gcgatgattatcatataatttctgttgaattacgttaagcatgaaataattaacatgtaatgcatgacgtaatttat
gagatgggtttttatgattagagtcccgcaattatacatttaatacgcgatagaaaacaaaatatagcgcgcaaact
aggataaattatcgcgcggtgtcatcaatgttactagatc
```

FIGURE 24 cgtggtcgagattgtgtattattctttagttattacaagacttttagctaaaatttgaaagaatttactttaagaaa
atcttaacatctgagataatttcagcaatagattatattttcattactctagcagtattttgcagatcaatcgca
acatatatggttgttagaaaaaatgcactatatatatatattattttttcaattaaaagtgcatgatatataata
tatatatatatatatatgtgtgtgtgtatatggtcaaagaaattcttatacaaatatacacgaacacatatattt
gacaaaatcaaagtattacactaaacaatgagttggtgcatggccaaaacaaatatgtagattaaaaattccagcct
ccaaaaaaaaatccaagtgttgtaaagcattatatatatagtagatcccaaattttgtacaattccacactgat
cgaatttttaaagttgaatatctgacgtaggattttttaatgtcttacctgaccatttactaataacattcatacg
ttttcatttgaaatatcctctataattatattgaatttggcacataataagaaacctaattggtgatttatttact
agtaaatttctggtgatgggctttctactagaaagctctcggaaaatcttggaccaaatccatattccatgacttcg
attgttaaccctattagttttcacaaacatactatcaatatcattgcaacggaaaaggtacaagtaaaacattcaat
ccgatagggaagtgatgtaggaggttgggaagacaggcccagaaagagatttatctgacttgttttgtgtatagttt
tcaatgttcataaaggaagatggagacttgagaagtttttttggactttgtttagctttgttgggcgttttttttt
tttgatcaataactttgttgggcttatgatttgtaatattttcgtggactctttagtttatttagacgtgctaactt
tgttgggcttatgacttgttgtaacatattgtaacagatgacttgatgtgcgactaatctttacacattaaacatag
ttctgtttttgaaagttcttattttcatttttatttgaatgttatatattttctatatttataattctagtaaaa
ggcaaatttgctttaaatgaaaaaatatatattccacagtttcacctaatcttatgcatttagcagtacaaatt
caaaaatttcccattttattcatgaatcataccattatatattaactaaatccaaggtaaaaaaaaggtatgaaag
ctctatagtaagtaaaatataaattccccataaggaaagggccaagtccaccaggcaagtaaaatgagcaagcacca
ctccaccatcacacaatttcactcatagataacgataagattcatggaattatcttccacgtggcattattccagcg
gttcaagccgataagggtctcaacacctctccttaggcctttgtggccgttaccaagtaaaattaacctcacacata
tccacactcaaaatccaacggtgtagatcctagtccacttgaatctcatgtatcctagaccctccgatcactccaaa
gcttgttctcattgttgttatcattatatatagatgaccaaagcactagaccaaacctcagtcacacaaagagtaaa
gaagaacaATGAAAGCCTTCACACTCGCTCTCTTCTTAGCTCTTTTCCTCTATCTCCTGCCCAATCCAGCCCATTCC
ACTATTAATGCAGACAATGTTAATGAAAATCAAACTGTAGAAGTAACTGCTAGTTCAGTAAACAATGAAAATAATAA
GCAAGTAACTGAAAAAGATAGTGCAGATAAAAGTACTAGTGATGTGGCTGAAGATGCTAACACCAAGAAATCAAACG
AAAATACAGAAACTACAGAAAAGAATACTCAAACAGTTGTTACTAATGCGCCAGTAAGTGATGTGAAAAATACAAAC
ACAGTTACCGCTGAAACACCTGTTGATAAAGTAGTAAATAATAGTGATCAAAAGACAACTAATGCTGCAACTACTGA
TACTAAAAAAGATGATGTAAAACAAGTTGAAAAGAAAGACTCAGTAGATAAAACAAATGCTGAGGAAAATAAAGATA
GTTCAGTAAAGCCAGCTGAAAATGCTACTAAGGCTGAATTAAAGGGCCAAGTTAAAGATATCGTTGAAGAATCTGGT
GTTGATACTAGCAAGTTAACTAATGATCAAATTAATGAATTAAATAAAATTAATTTCTCCAAAGAAGCAAAAAGTGG
TACTCAGTTAACTTACAACGACTTTAAAAAAATTGCTAAAACTTTAATTGAACAAGATGCTCGTTATGCTATTCCAT
TCTTCAATGCAAGTAAAATTAAAAATATGCCTGCTGCTAAAACACTTGATGCTCAAAGTGGAAAAGTAGAAGATTTG
GAAATTTGGGATTCATGGCCTGTTCAAGATGCAAAAACTGGTTACGTATCTAACTGGAATGGCTACCAATTAGTGAT
TGGTATGATGGGAGTTCCAAACGTCAATGATAACCACATTTATCTTCTTTACAACAAGTATGGTGATAATGACTTTA
ATCATTGGAAGAATGCCGGTCCTATTTTCGGTCTAGGTACTCCAGTTATTCAACAATGGTCTGGATCAGCAACTTTA
AATAAAGATGGCTCAATTCAACTTTACTACACTAAGGTTGATACTAGTGATAATAATACTAACCACCAAAAACTCGC

FIGURE 24 (CONT'D)

```
TAGTGCAACTGTTTACTTAAATCTTGAAAAAGATCAAGATAAGATTTCTATTGCTCATGTTGACAACGACCATATTG
TCTTTGAAGGTGATGGTTACCACTACCAAACTTATGACCAATGGAAAGAAACTAACAAGGGTGCTGACAATATCGCA
ATGCGTGATGCACACGTGATTGATGATGATAATGGTAATCGTTACCTTGTGTTTGAAGCAAGTACTGGAACCGAAAA
TTATCAAGGTGATGATCAAATTTATCAATGGTTAAATTACGGCGGTACTAACAAGGATAATTTAGGTGATTTCTTCC
AAATTTTATCTAACTCCGATATTAAAGATAGAGCTAAATGGTCAAACGCTGCAATTGGTATCATTAAATTAAATGAT
GATGTTAAGAATCCAAGTGTTGCAAAGGTCTACAGCCCACTTATTAGTGCACCAATGGTAAGTGATGAAATTGAACG
CCCTGATGTTGTTAAATTAGGTAATAAGTATTACTTATTTGCTGCTACTAGATTAAACCGTGGTAGTAACGATGATG
CTTGGATGGCAACTAACAAAGCAGTTGGTGATAACGTAGCTATGATTGGTTATGTTTCTGATAACTTAACTCATGGT
TATGTTCCATTGAATGAATCTGGCGTTGTTTTAACTGCATCTGTACCGGCTAACTGGCGTACTGCAACTTATTCATA
CTATGCAGTTCCAGTAGAAGGAAGAGATGATCAACTTTTAATTACTTCATACATCACTAATCGTGGTGAGGTTGCTG
GAAAGGGTATGCATGCAACTTGGGCACCAAGTTTCTTGTTACAAATTAATCCAGATAACACTACTACTGTTTTAGCT
AAAATGACTAACCAAGGGGATTGGATTTGGGATGATAGTAGTGAAAATCCAGATATGATGGGTGTACTTGAAAAAGA
TGCTCCAAATAGTGCTGCCCTTCCTGGAGAATGGGGAAAACCAGTTGATTGGGATTTAATTGGTGGATACAACTTGA
AGCCACACCAACCTGTAACTCCTATTCCAAATGTACCAACTACTCCTGAAACCCCAACCACACCAGATAAGCCAGAG
GTACCAACTACCCCTGAAGTTCCAACCACTCCAGAAACTCCAACTCCAGAAGCTCCAAAGAATCCAGTTAAGAAAAC
TAGTCAGTCTAAACTTCCAAAGGCTGGAGATAAAAATAGCTTTGCAGCAGTTGTTTTAGGTGCTGTAAGTTCAATAT
TAGGTGCTGTTGGTTTAACAGGTGTTTCAAAACGTAAACGTAATAATTAAgatcgttcaaacatttggcaataaagt
ttcttaagaatgaatcctgttgccggtcttgcgatgattatcataatttctgttgaattacgttaagcatgaaat
aattaacatgtaatgcatgacgtaatttatgagatgggttttttatgattagagtcccgcaattatacatttaatacg
cgatagaaaacaaaatatagcgcgcaaactaggataaattatcgcgcgcggtgtcatcaatgttactagatc
```

FIGURE 25 cgtggtcgagattgtgtattattctttagttattacaagacttttagctaaaatttgaaagaatttactttaagaaa
atcttaacatctgagataatttcagcaatagattatattttcattactctagcagtatttttgcagatcaatcgca
acatatatggttgttagaaaaaatgcactatatatatatattatttttttcaattaaaagtgcatgatatataata
tatatatatatatatatgtgtgtgtgtatatggtcaaagaaattcttatacaaatatacacgaacacatatattt
gacaaaatcaaagtattacactaaacaatgagttggtgcatggccaaaacaaatatgtagattaaaaattccagcct
ccaaaaaaaatccaagtgttgtaaagcattatatatatagtagatcccaattttgtacaattccacactgat
cgaatttttaaagttgaatatctgacgtaggatttttaatgtcttacctgaccatttactaataacattcatacg
ttttcatttgaaatatcctctataattatattgaatttggcacataataagaaacctaattggtgatttattttact
agtaaatttctggtgatgggctttctactagaaagctctcggaaaatcttggaccaaatccatattccatgacttcg
attgttaacctattagttttcacaaacatactatcaatatcattgcaacggaaaaggtacaagtaaaacattcaat
ccgataggggaagtgatgtaggaggttgggaagacaggcccagaaagagatttatctgacttgttttgtgtatagttt
tcaatgttcataaaggaagatggagacttgagaagtttttttggactttgtttagctttgttgggcgttttttttt
tttgatcaataactttgttgggcttatgatttgtaatattttcgtggactctttagtttatttagacgtgctaactt
tgttgggcttatgacttgttgtaacatattgtaacagatgacttgatgtgcgactaatctttacacattaaacatag
ttctgtttttgaaagttcttattttcattttatttgaatgttatatattttctatatttataattctagtaaaa
ggcaaattttgcttttaaatgaaaaaaatatatattccacagtttcacctaatcttatgcatttagcagtacaaatt
caaaaatttcccatttttattcatgaatcataccattatatattaactaaatccaaggtaaaaaaaaggtatgaaag
ctctatagtaagtaaaatataaattccccataaggaaagggccaagtccaccaggcaagtaaaatgagcaagcacca
ctccaccatcacacaatttcactcatagataacgataagattcatggaattatcttccacgtggcattattccagcg
gttcaagccgataagggtctcaacacctctccttaggcctttgtggccgttaccaagtaaaattaacctcacacata
tccacactcaaaatccaacggtgtagatcctagtccacttgaatctcatgtatcctagaccctccgatcactccaaa
gcttgttctcattgttgttatcattatatatagatgaccaaagcactagaccaaacctcagtcacacaaagagtaaa
gaagaaca**ATGGAGTCCCCAAGCGCCGTCGTCCCCGGCACCACGGCGCCGCTGCTTCCTTATGCGTACGCGCCGCTG
CCGTCGTCCGCCGACGACGCCCGTCAAAACCGGAGTGGCGGGAGGTGGCGCGCGTGCGCCGCCGTGCTGGCCGCATC
GGCGTTGGCGGTGGTCGTCGTGGTCGGGCTCCTCGCGGGCGGCAGGGTGGATCGGGTCCCGGCCGGCGGA**ACGAACC
AAAAGCCATATAAGGAAACATACGGCATTTCCCATATTACACGCCATGATATGCTGCAAATCCCTGAACAGCAAAAA
AATGAAAAATATCAAGTTCCTGAATTCGATTCGTCCACAATTAAAAATATCTCTTCTGCAAAAGGCCTGGACGTTTG
GGACAGCTGGCCATTACAAAACGCTGACGGCACTGTCGCAAACTATCACGGCTACCACATCGTCTTTGCATTAGCCG
GAGATCCTAAAAATGCGGATGACACATCGATTTACATGTTCTATCAAAAGTCGGCGAAACTTCTATTGACAGCTGG
AAAAACGCTGGCCGCGTCTTTAAAGACAGCGACAAATTCGATGCAAATGATTCTATCCTAAAAGACCAAACACAAGA
ATGGTCAGGTTCAGCCACATTTACATCTGACGGAAAAATCCGTTTATTCTACACTGATTTCTCCGGTAAACATTACG
GCAAACAAACACTGACAACTGCACAAGTTAACGTATCAGCATCAGACAGCTCTTTGAACATCAACGGTGTAGAGGAT
TATAAATCAATCTTTGACGGTGACGGAAAAACGTATCAAAATGTACAGCAGTTCATCGATGAAGGCAACTACAGCTC
AGGCGACAACCATACGCTGAGAGATCCTCACTACGTAGAAGATAAAGGCCACAAATACTTAGTATTTGAAGCAAACA
CTGGAACTGAAGATGGCTACCAAGGCGAAGAATCTTTATTTAACAAAGCATACTATGGCAAAAGCACATCATTCTTC
CGTCAAGAAAGTCAAAAACTTCTGCAAAGCGATAAAAAACGCACGGCTGAGTTAGCAAACGGCGCTCTCGGTATGAT

FIGURE 25 (CONT'D)

```
TGAGCTAAACGATGATTACACACTGAAAAAAGTGATGAAACCGCTGATTGCATCTAACACAGTAACAGATGAAATTG
AACGCGCGAACGTCTTTAAAATGAACGGCAAATGGTACCTGTTCACTGACTCCCGCGGATCAAAAATGACGATTGAC
GGCATTACGTCTAACGATATTTACATGCTTGGTTATGTTTCTAATTCTTTAACTGGCCCATACAAGCCGCTGAACAA
AACTGGCCTTGTGTTAAAAATGGATCTTGATCCTAACGATGTAACCTTTACTTACTCACACTTCGCTGTACCTCAAG
CGAAAGGAAACAATGTCGTGATTACAAGCTATATGACAAACAGAGGATTCTACGCAGACAAACAATCAACGTTTGCG
CCAAGCTTCCTGCTGAACATCAAAGGCAAGAAAACATCTGTTGTCAAAGACAGCATCCTTGAACAAGGACAATTAAC
AGTTAACAAATAAgatcgttcaaacatttggcaataaagtttcttaagaatgaatcctgttgccggtcttgcgatga
ttatcatataatttctgttgaattacgttaagcatgaaataattaacatgtaatgcatgacgtaatttatgagatgg
gttttatgattagagtcccgcaattatacatttaatacgcgatagaaaacaaaatatagcgcgcaaactaggataa
attatcgcgcgcggtgtcatcaatgttactagatc
```

FIGURE 26 cgtggtcgagattgtgtattattctttagttattacaagacttttagctaaaatttgaaagaatttactttaagaaa
atcttaacatctgagataatttcagcaatagattatattttcattactctagcagtattttgcagatcaatcgca
acatatatggttgttagaaaaaatgcactatatatatatattattttttcaattaaaagtgcatgatatataata
tatatatatatatatatgtgtgtgtgtatggtcaaagaaattcttatacaaatatacacgaacacatatattt
gacaaaatcaaagtattacactaaacaatgagttggtgcatggccaaaacaaatatgtagattaaaaattccagcct
ccaaaaaaaaatccaagtgttgtaaagcattatatatatagtagatcccaaatttttgtacaattccacactgat
cgaattttaaagttgaatatctgacgtaggatttttaatgtcttacctgaccatttactaataacattcatacg
ttttcatttgaaatatcctctaattatattgaatttggcacataataagaaacctaattggtgatttattttact
agtaaatttctggtgatgggctttctactagaaagctctcggaaaatcttggaccaaatccatattccatgacttcg
attgttaaccctattagttttcacaaacatactatcaatatcattgcaacggaaaaggtacaagtaaaacattcaat
ccgataggaagtgatgtaggaggttgggaagacaggcccagaaagagatttatctgacttgttttgtgtatagttt
tcaatgttcataaaggaagatggagacttgagaagtttttttggactttgtttagctttgttgggcgttttttttt
tttgatcaataactttgttgggcttatgatttgtaatattttcgtggactctttagtttatttagacgtgctaactt
tgttgggcttatgacttgttgtaacatattgtaacagatgacttgatgtgcgactaatctttacacattaaacatag
ttctgtttttgaaagttcttattttcattttatttgaatgttatatattttctatatttataattctagtaaaa
ggcaaattttgcttttaaatgaaaaaatatatattccacagtttcacctaatcttatgcatttagcagtacaaatt
caaaaatttcccatttttattcatgaatcataccattatatattaactaaatccaaggtaaaaaaaggtatgaaag
ctctatagtaagtaaaatataaattccccataaggaaagggccaagtccaccaggcaagtaaaatgagcaagcacca
ctccaccatcacacaatttcactcatagataacgataagattcatggaattatcttccacgtggcattattccagcg
gttcaagccgataagggtctcaacacctctccttaggcctttgtggccgttaccaagtaaaattaacctcacacata
tccacactcaaaatccaacggtgtagatcctagtccacttgaatctcatgtatcctagaccctccgatcactccaaa
gcttgttctcattgttgttatcattatatatagatgaccaaagcactagaccaaacctcagtcacacaaagagtaaa
gaagaaca**ATGGAGTCCCCAAGCGCCGTCGTCCCCGGCACCACGGCGCCGCTGCTTCCTTATGCGTACGCGCCGCTG
CCGTCGTCCGCCGACGACGCCCGTCAAAACCGGAGTGGCGGGAGGTGGCGCGCGTGCGCCGCCGTGCTGGCCGCATC
GGCGTTGGCGGTGGTCGTCGTGGTCGGGCTCCTCGCGGGCGGCAGGGTGGATCGGGTCCCGGCCGGCGGA**ACTATTA
ATGCAGACAATGTTAATGAAATCAAACTGTAGAAGTAACTGCTAGTTCAGTAAACAATGAAAATAATAAGCAAGTA
ACTGAAAAAGATAGTGCAGATAAAAGTACTAGTGATGTGGCTGAAGATGCTAACACCAAGAAATCAAACGAAAATAC
AGAAACTACAGAAAAGAATACTCAAACAGTTGTTACTAATGCGCCAGTAAGTGATGTGAAAAATACAAACACAGTTA
CCGCTGAAACACCTGTTGATAAAGTAGTAAATAATAGTGATCAAAAGACAACTAATGCTGCAACTACTGATACTAAA
AAAGATGATGTAAAACAAGTTGAAAAGAAAGACTCAGTAGATAAAACAAATGCTGAGGAAAATAAAGATAGTTCAGT
AAAGCCAGCTGAAAATGCTACTAAGGCTGAATTAAAGGGCCAAGTTAAAGATATCGTTGAAGAATCTGGTGTTGATA
CTAGCAAGTTAACTAATGATCAAATTAATGAATTAAATAAAATTAATTTCTCCAAAGAAGCAAAAGTGGTACTCAG
TTAACTTACAACGACTTTAAAAAAATTGCTAAAACTTTAATTGAACAAGATGCTCGTTATGCTATTCCATTCTTCAA
TGCAAGTAAAATTAAAAATATGCCTGCTGCTAAAACACTTGATGCTCAAAGTGGAAAAGTAGAAGATTTGGAAATTT
GGGATTCATGGCCTGTTCAAGATGCAAAAACTGGTTACGTATCTAACTGGAATGGCTACCAATTAGTGATTGGTATG
ATGGGAGTTCCAAACGTCAATGATAACCACATTTATCTTCTTTACAACAAGTATGGTGATAATGACTTTAATCATTG

FIGURE 26 (CONT'D)

```
GAAGAATGCCGGTCCTATTTTCGGTCTAGGTACTCCAGTTATTCAACAATGGTCTGGATCAGCAACTTTAAATAAAG
ATGGCTCAATTCAACTTTACTACACTAAGGTTGATACTAGTGATAATAATACTAACCACCAAAAACTCGCTAGTGCA
ACTGTTTACTTAAATCTTGAAAAAGATCAAGATAAGATTTCTATTGCTCATGTTGACAACGACCATATTGTCTTTGA
AGGTGATGGTTACCACTACCAAACTTATGACCAATGGAAAGAAACTAACAAGGGTGCTGACAATATCGCAATGCGTG
ATGCACACGTGATTGATGATGATAATGGTAATCGTTACCTTGTGTTTGAAGCAAGTACTGGAACCGAAAATTATCAA
GGTGATGATCAAATTTATCAATGGTTAAATTACGGCGGTACTAACAAGGATAATTTAGGTGATTTCTTCCAAATTTT
ATCTAACTCCGATATTAAAGATAGAGCTAAATGGTCAAACGCTGCAATTGGTATCATTAAATTAAATGATGATGTTA
AGAATCCAAGTGTTGCAAAGGTCTACAGCCCACTTATTAGTGCACCAATGGTAAGTGATGAAATTGAACGCCCTGAT
GTTGTTAAATTAGGTAATAAGTATTACTTATTTGCTGCTACTAGATTAAACCGTGGTAGTAACGATGATGCTTGGAT
GGCAACTAACAAAGCAGTTGGTGATAACGTAGCTATGATTGGTTATGTTTCTGATAACTTAACTCATGGTTATGTTC
CATTGAATGAATCTGGCGTTGTTTTAACTGCATCTGTACCGGCTAACTGGCGTACTGCAACTTATTCATACTATGCA
GTTCCAGTAGAAGGAAGAGATGATCAACTTTTAATTACTTCATACATCACTAATCGTGGTGAGGTTGCTGGAAAGGG
TATGCATGCAACTTGGGCACCAAGTTTCTTGTTACAAATTAATCCAGATAACACTACTACTGTTTTAGCTAAAATGA
CTAACCAAGGGGATTGGATTTGGGATGATAGTAGTGAAAATCCAGATATGATGGGTGTACTTGAAAAAGATGCTCCA
AATAGTGCTGCCCTTCCTGGAGAATGGGGAAAACCAGTTGATTGGGATTTAATTGGTGGATACAACTTGAAGCCACA
CCAACCTGTAACTCCTATTCCAAATGTACCAACTACTCCTGAAACCCCAACCACACCAGATAAGCCAGAGGTACCAA
CTACCCCTGAAGTTCCAACCACTCCAGAAACTCCAACTCCAGAAGCTCCAAAGAATCCAGTTAAGAAAACTAGTCAG
TCTAAACTTCCAAAGGCTGGAGATAAAAATAGCTTTGCAGCAGTTGTTTTAGGTGCTGTAAGTTCAATATTAGGTGC
TGTTGGTTTAACAGGTGTTTCAAAACGTAAACGTAATAATTAAgatcgttcaaacatttggcaataaagtttcttaa
gaatgaatcctgttgccggtcttgcgatgattatcatataatttctgttgaattacgttaagcatgaaataattaac
atgtaatgcatgacgtaatttatgagatgggtttttatgattagagtcccgcaattatacatttaatacgcgataga
aaacaaaatatagcgcgcaaactaggataaattatcgcgcggtgtcatcaatgttactagatc
```

FIGURE 29 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggagggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACGAAC
CAAAAGCCATATAAGGAAACATACGGCATTTCCCATATTACACGCCATGATATGCTGCAAATCCCTGAACAGCAAAA
AAATGAAAAATATCAAGTTCCTGAATTCGATTCGTCCACAATTAAAAATATCTCTTCTGCAAAAGGCCTGGACGTTT
GGGACAGCTGGCCATTACAAAACGCTGACGGCACTGTCGCAAACTATCACGGCTACCACATCGTCTTTGCATTAGCC
GGAGATCCTAAAAATGCGGATGACACATCGATTTACATGTTCTATCAAAAAGTCGGCGAAACTTCTATTGACAGCTG
GAAAAACGCTGGCCGCGTCTTTAAAGACAGCGACAAATTCGATGCAAATGATTCTATCCTAAAAGACCAAACACAAG
AATGGTCAGGTTCAGCCACATTTACATCTGACGGAAAAATCCGTTTATTCTACACTGATTTCTCCGGTAAACATTAC
GGCAAACAAACACTGACAACTGCACAAGTTAACGTATCAGCATCAGACAGCTCTTTGAACATCAACGGTGTAGAGGA
TTATAAATCAATCTTTGACGGTGACGGAAAAACGTATCAAAATGTACAGCAGTTCATCGATGAAGGCAACTACAGCT
CAGGCGACAACCATACGCTGAGAGATCCTCACTACGTAGAAGATAAAGGCCACAAATACTTAGTATTTGAAGCAAAC
ACTGGAACTGAAGATGGCTACCAAGGCGAAGAATCTTTATTTAACAAAGCATACTATGGCAAAAGCACATCATTCTT
CCGTCAAGAAAGTCAAAAACTTCTGCAAAGCGATAAAAAACGCACGGCTGAGTTAGCAAACGGCGCTCTCGGTATGA
TTGAGCTAAACGATGATTACACACTGAAAAAAGTGATGAAACCGCTGATTGCATCTAACACAGTAACAGATGAAATT
GAACGCGCGAACGTCTTTAAAATGAACGGCAAATGGTACCTGTTCACTGACTCCCGCGGATCAAAAATGACGATTGA
CGGCATTACGTCTAACGATATTTACATGCTTGGTTATGTTTCTAATTCTTTAACTGGCCCATACAAGCCGCTGAACA
AAACTGGCCTTGTGTTAAAAATGGATCTTGATCCTAACGATGTAACCTTTACTTACTCACACTTCGCTGTACCTCAA
GCGAAAGGAAACAATGTCGTGATTACAAGCTATATGACAAACAGAGGATTCTACGCAGACAAACAATCAACGTTTGC
GCCAAGCTTCCTGCTGAACATCAAAGGCAAGAAAACATCTGTTGTCAAAGACAGCATCCTTGAACAAGGACAATTAA
CAGTTAACAAATAAactatgagttgaaacaatggcctatctcatatgaagatcttttgtgaatttcacttttgtcca
cgacctctgttgcacgactctgctttccgaccggagcatacctttgttctatatgatttgtgtatgtatgtaggaa
cctatgttctcgagcatgcatacataattcctcataggtctatatacaccggctatccatatgcaaacctgtgtaa
tatttgttatatacaacacgcggaccattgtcttgctgttattaattcttttttcccgcaaaaaaggaaaagtttct
ttatttggcactgcaatggatatgcctcacagctagtgggtggagaattcagtatttgacattaagattccctgatt
tgcaattgcaaatttcagtttctttacttatatcactacaaaagtcttattgtttcttttccacgtcattaccatct
gctccattggtttttgctagtagaataggatgaagcatggacacagattaactgagctcgagctcatatgagctcgg
gtgaacaataaaatctgaaaatacttagaaagaattcaaaattttctgttttttgtggcaaaatttgacaaatgtta
taaatgcttgcaaagtttcatcatagaacgacattcgtggatgtcatggcaaaaaacaaattcagcactctgaaaat
aacttttttgaagtatcg

FIGURE 30 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggaggggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaatttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgaccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACGAAC
CAAAAGCCATATAAGGAAACATACGGCATTTCCCATATTACACGCCATGATATGCTGCAAATCCCTGAACAGCAAAA
AAATGAAAAATATCAAGTTCCTGAATTCGATTCGTCCACAATTAAAAATATCTCTTCTGCAAAAGGCCTGGACGTTT
GGGACAGCTGGCCATTACAAAACGCTGACGGCACTGTCGCAAACTATCACGGCTACCACATCGTCTTTGCATTAGCC
GGAGATCCTAAAAATGCGGATGACACATCGATTTACATGTTCTATCAAAAAGTCGGCGAAACTTCTATTGACAGCTG
GAAAAACGCTGGCCGCGTCTTTAAAGACAGCGACAAATTCGATGCAAATGATTCTATCCTAAAAGACCAAACACAAG
AATGGTCAGGTTCAGCCACATTTACATCTGACGGAAAAATCCGTTATTCTACACTGATTTCTCCGGTAAACATTAC
GGCAAACAAACACTGACAACTGCACAAGTTAACGTATCAGCATCAGACAGCTCTTTGAACATCAACGGTGTAGAGGA
TTATAAATCAATCTTTGACGGTGACGGAAAAACGTATCAAAATGTACAGCAGTTCATCGATGAAGGCAACTACAGCT
CAGGCGACAACCATACGCTGAGAGATCCTCACTACGTAGAAGATAAAGGCCACAAATACTTAGTATTTGAAGCAAAC
ACTGGAACTGAAGATGGCTACCAAGGCGAAGAATCTTTATTTAACAAAGCATACTATGGCAAAAGCACATCATTCTT
CCGTCAAGAAAGTCAAAAACTTCTGCAAAGCGATAAAAAACGCACGGCTGAGTTAGCAAACGGCGCTCTCGGTATGA
TTGAGCTAAACGATGATTACACACTGAAAAAAGTGATGAAACCGCTGATTGCATCTAACACAGTAACAGATGAAATT
GAACGCGCGAACGTCTTTAAAATGAACGGCAAATGGTACCTGTTCACTGACTCCCGCGGATCAAAAATGACGATTGA
CGGCATTACGTCTAACGATATTTACATGCTTGGTTATGTTTCTAATTCTTTAACTGGCCCATACAAGCCGCTGAACA
AAACTGGCCTTGTGTTAAAAATGGATCTTGATCCTAACGATGTAACCTTTACTTACTCACACTTCGCTGTACCTCAA
GCGAAAGGAAACAATGTCGTGATTACAAGCTATATGACAAACAGAGGATTCTACGCAGACAAACAATCAACGTTTGC
GCCAAGCTTCCTGCTGAACATCAAAGGCAAGAAAACATCTGTTGTCAAAGACAGCATCCTTGAACAAGGACAATTAA
CAGTTAACAAATA actatgagttgaaacaatggcctatctcatatgaagatcttttgtgaatttcacttttgtcca
cgacctctgttgcacgactctgctttccgaccggagcataccttttgttctatatgatttgtgtatgtatgtaggaa
cctatgttctcgagcatgcatacataattcctcataggtctatatacaccggctatccatatgcaaaacctgtgtaa
tatttgttatatacaacacgcggaccattgtcttgctgttattaattcttttttcccgcaaaaaaggaaaagtttct
ttatttggcactgcaatggatatgcctcacagctagtgggtggagaattcagtatttgacattaagattccctgatt
tgcaattgcaaatttcagtttctttacttatatcactacaaagtcttattgtttcttttccacgtcattaccatct
gctccattggttttgctagtagaataggatgaagcatggacacagattaactgagctcgagctcatatgagctcgg
gtgaacaataaatctgaaaatacttagaaagaattcaaattttctgttttttgtggcaaatttgacaaatgtta

FIGURE 30 (CONT'D)

taaatgcttgcaaagtttcatcatagaacgacattcgtggatgtcatggcaaaaaacaaattcagcactctgaaaat
aactttttgaagtatc*gtttgtgtcttctagattaatcctccaaacttttgattaaccaaaaaaattatcaaact*
*aacatgttctccttttttctttagaaattctaacgaatttatctttatactgatttgaatatacttaatttggtcat*
*ttggatgcccttacaacctccttaccaaactcactatggcaaatatatactattttccattgtaacataaatgtcc*
*ataatttgaattaaattcgttgcagtacgaaaccatccaactttgtccaaaaacaaaatccttataactatttactt*
*taatgtaaatatatcctctacttttgttttacaaccctagctcaaacaaatttattatttgcgataaaaaatcata*
*tcgaacaaactcgatgatttttttttcttacgttattaatgaaactaaaatatagaaaaaaacaagatgaaccaaa*
*ttttcacctatctaactacttaaatataatatgattaaatttggtaaagtttgaaaagtttctttaggaaatgtgaa*
*atattgatcacagtttctattgctaaaatcaccaacaaaacgcatgtcgccattcataattatggtttcacacctac*
*aactaggctaataagtaaataagtagacaactagactcaggtttgaaaaaaccataaaagccatatagcgttttctc*
*attgaaactgcgaacacgatcgtgtgaatgttgcagtttctagtttgatacaaacaaacaaaaacacaatttaatc*
*ttagattaaaaagaaaaaagagaacggagcccactagccactccttcaaacgtgtcttaccaactctcttctagaaa*
*caaattaggcttcaccttcctcttccaacctctctctctctctctctctcttctcaaaccatctctccataaag*
*ccctaatttcttcatcacaagaatcagaagaatactgcaaaaaact*tATGGACCTGCATCTAATTTTCGGTCCAACT
TGCACAGGAAAGACGACGACCGCGATAGCTCTTGCCCAGCAGACAGGGCTTCCAGTCCTTTCGCTTGATCGGGTCCA
ATGCTGTCCTCAACTATCAACCGGAAGCGGACGACCAACAGTGGAAGAACTGAAAGGAACGACGCGTCTCTACCTTG
ATGATCGGCCTCTGGTGGAGGGTATCATCGCAGCCAAGCAAGCTCATCATAGGCTGATCGAGGAGGTGTATAATCAT
GAGGCCAACGGCGGGCTTATTCTTGAGGGAGGATCCACCTCGTTGCTCAACTGCATGGCGCGAAACAGCTATTGGAG
TGCAGATTTTCGTTGGCATATTATTCGCCACAAGTTACCCGACCAAGAGACCTTCATGAAAGCGGCCAAGGCCAGAG
TTAAGCAGATGTTGCACCCCGCTGCAGGCCATTCTATTATTCAAGAGTTGGTTTATCTTTGGAATGAACCTCGGCTG
AGGCCCATTCTGAAAGAGATCGATGGATATCGATATGCCATGTTGTTTGCTAGCCAGAACCAGATCACGGCAGATAT
GCTATTGCAGCTTGACGCAAATATGGAAGGTAAGTTGATTAATGGGATCGCTCAGGAGTATTTCATCCATGCGCGCC
AACAGGAACAGAAATTCCCCCAAGTTAACGCAGCCGCTTTCGACGGATTCGAAGGTCATCCGTTCGGAATGTATTAG
GTAA*gtccgcaaaaatcaccagtctctctctacaaatctatctctctatttttctccagaataatgtgtgagtag*
*ttcccagataagggaattagggttcttatagggtttcgctcatgtgttgagcatataagaaacccttagtatgtatt*
*tgtatttgtaaaatacttctatcaataaaatttctaattcctaaaaccaaaatccagtgacct*

FIGURE 31

*gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggagggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgaccggcaatggggtcctcaactgtagccggcatcctcctctcctccgataatacaaata
cc*__ATGAAAGCCTTCACACTCGCTCTCTTCTTAGCTCTTTTCCTCTATCTCCTGCCCAATCCAGCCCATTCC__ACTATT
AATGCAGACAATGTTAATGAAAATCAAACTGTAGAAGTAACTGCTAGTTCAGTAAACAATGAAAATAATAAGCAAGT
AACTGAAAAAGATAGTGCAGATAAAAGTACTAGTGATGTGGCTGAAGATGCTAACACCAAGAAATCAAACGAAAATA
CAGAAACTACAGAAAAGAATACTCAAACAGTTGTTACTAATGCGCCAGTAAGTGATGTGAAAAATACAAACACAGTT
ACCGCTGAAACACCTGTTGATAAAGTAGTAAATAATAGTGATCAAAAGACAACTAATGCTGCAACTACTGATACTAA
AAAAGATGATGTAAAACAAGTTGAAAAGAAAGACTCAGTAGATAAAACAAATGCTGAGGAAAATAAAGATAGTTCAG
TAAAGCCAGCTGAAAATGCTACTAAGGCTGAATTAAAGGGCCAAGTTAAAGATATCGTTGAAGAATCTGGTGTTGAT
ACTAGCAAGTTAACTAATGATCAAATTAATGAATTAAATAAAATTAATTTCTCCAAAGAAGCAAAAAGTGGTACTCA
GTTAACTTACAACGACTTTAAAAAAATTGCTAAAACTTTAATTGAACAAGATGCTCGTTATGCTATTCCATTCTTCA
ATGCAAGTAAAATTAAAAATATGCCTGCTGCTAAAACACTTGATGCTCAAAGTGGAAAAGTAGAAGATTTGGAAATT
TGGGATTCATGGCCTGTTCAAGATGCAAAAACTGGTTACGTATCTAACTGGAATGGCTACCAATTAGTGATTGGTAT
GATGGGAGTTCCAAACGTCAATGATAACCACATTTATCTTCTTTACAACAAGTATGGTGATAATGACTTTAATCATT
GGAAGAATGCCGGTCCTATTTTCGGTCTAGGTACTCCAGTTATTCAACAATGGTCTGGATCAGCAACTTTAAATAAA
GATGGCTCAATTCAACTTTACTACACTAAGGTTGATACTAGTGATAATAATACTAACCACCAAAAACTCGCTAGTGC
AACTGTTTACTTAAATCTTGAAAAAGATCAAGATAAGATTTCTATTGCTCATGTTGACAACGACCATATTGTCTTTG
AAGGTGATGGTTACCACTACCAAACTTATGACCAATGGAAAGAAACTAACAAGGGTGCTGACAATATCGCAATGCGT
GATGCACACGTGATTGATGATGATAATGGTAATCGTTACCTTGTGTTTGAAGCAAGTACTGGAACCGAAAATTATCA
AGGTGATGATCAAATTTATCAATGGTTAAATTACGGCGGTACTAACAAGGATAATTTAGGTGATTTCTTCCAAATTT
TATCTAACTCCGATATTAAAGATAGAGCTAAATGGTCAAACGCTGCAATTGGTATCATTAAATTAAATGATGATGTT
AAGAATCCAAGTGTTGCAAAGGTCTACAGCCCACTTATTAGTGCACCAATGGTAAGTGATGAAATTGAACGCCCTGA
TGTTGTTAAATTAGGTAATAAGTATTACTTATTTGCTGCTACTAGATTAAACCGTGGTAGTAACGATGATGCTTGGA
TGGCAACTAACAAAGCAGTTGGTGATAACGTAGCTATGATTGGTTATGTTTCTGATAACTTAACTCATGGTTATGTT
CCATTGAATGAATCTGGCGTTGTTTTAACTGCATCTGTACCGGCTAACTGGCGTACTGCAACTTATTCATACTATGC
AGTTCCAGTAGAAGGAAGAGATGATCAACTTTTAATTACTTCATACATCACTAATCGTGGTGAGGTTGCTGGAAAGG
GTATGCATGCAACTTGGGCACCAAGTTTCTTGTTACAAATTAATCCAGATAACACTACTACTGTTTTAGCTAAAATG
ACTAACCAAGGGATTGGATTTGGGATGATAGTAGTGAAAATCCAGATATGATGGGTGTACTTGAAAAAGATGCTCC
AAATAGTGCTGCCCTTCCTGGAGAATGGGGAAAACCAGTTGATTGGGATTTAATTGGTGGATACAACTTGAAGCCAC
ACCAACCTGTAACTCCTATTCCAAATGTACCAACTACTCCTGAAACCCCAACCACACCAGATAAGCCAGAGGTACCA

FIGURE 31 (CONT'D)

```
ACTACCCCTGAAGTTCCAACCACTCCAGAAACTCCAACTCCAGAAGCTCCAAAGAATCCAGTTAAGAAAACTAGTCA
GTCTAAACTTCCAAAGGCTGGAGATAAAAATAGCTTTGCAGCAGTTGTTTTAGGTGCTGTAAGTTCAATATTAGGTG
CTGTTGGTTTAACAGGTGTTTCAAAACGTAAACGTAATAATTAAactatgagttgaaacaatggcctatctcatatg
aagatcttttgtgaatttcacttttgtccacgacctctgttgcacgactctgctttccgaccggagcatacctttttg
ttctatatgatttgtgtatgtatgtaggaacctatgttctcgagcatgcatacataattcctcataggtctatatac
accggctatccatatgcaaaacctgtgtaatatttgttatatacaacacgcggaccattgtcttgctgttattaatt
cttttttcccgcaaaaaaggaaaagtttctttatttggcactgcaatggatatgcctcacagctagtgggtggagaa
ttcagtatttgacattaagattccctgatttgcaattgcaaatttcagtttctttacttatatcactacaaaagtct
tattgtttcttttccacgtcattaccatctgctccattggttttttgctagtagaataggatgaagcatggacacaga
ttaactgagctcgagctcatatgagctcgggtgaacaataaaatctgaaaatacttagaaagaattcaaaattttct
gttttttgtggcaaaatttgacaaatgttataaatgcttgcaaagtttcatcatagaacgacattcgtggatgtcat
ggcaaaaaacaaattcagcactctgaaaataacttttttgaagtatcg
```

FIGURE 32 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggaggggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
ccATGAAAGCCTTCACACTCGCTCTCTTCTTAGCTCTTTTCCTCTATCTCCTGCCCAATCCAGCCCATTCCACTATT
AATGCAGACAATGTTAATGAAAATCAAACTGTAGAAGTAACTGCTAGTTCAGTAAACAATGAAAATAATAAGCAAGT
AACTGAAAAGATAGTGCAGATAAAAGTACTAGTGATGTGGCTGAAGATGCTAACACCAAGAAATCAAACGAAAATA
CAGAAACTACAGAAAAGAATACTCAAACAGTTGTTACTAATGCGCCAGTAAGTGATGTGAAAAATACAAACACAGTT
ACCGCTGAAACACCTGTTGATAAAGTAGTAAATAATAGTGATCAAAAGACAACTAATGCTGCAACTACTGATACTAA
AAAAGATGATGTAAAACAAGTTGAAAAGAAAGACTCAGTAGATAAAACAAATGCTGAGGAAAATAAAGATAGTTCAG
TAAAGCCAGCTGAAAATGCTACTAAGGCTGAATTAAAGGGCCAAGTTAAAGATATCGTTGAAGAATCTGGTGTTGAT
ACTAGCAAGTTAACTAATGATCAAATTAATGAATTAAATAAAATTAATTTCTCCAAAGAAGCAAAAAGTGGTACTCA
GTTAACTTACAACGACTTTAAAAAAATTGCTAAAACTTTAATTGAACAAGATGCTCGTTATGCTATTCCATTCTTCA
ATGCAAGTAAAATTAAAAATATGCCTGCTGCTAAAACACTTGATGCTCAAAGTGGAAAAGTAGAAGATTTGGAAATT
TGGGATTCATGGCCTGTTCAAGATGCAAAAACTGGTTACGTATCTAACTGGAATGGCTACCAATTAGTGATTGGTAT
GATGGGAGTTCCAAACGTCAATGATAACCACATTTATCTTCTTTACAACAAGTATGGTGATAATGACTTTAATCATT
GGAAGAATGCCGGTCCTATTTTCGGTCTAGGTACTCCAGTTATTCAACAATGGTCTGGATCAGCAACTTTAAATAAA
GATGGCTCAATTCAACTTTACTACACTAAGGTTGATACTAGTGATAATAATACTAACCACCAAAAACTCGCTAGTGC
AACTGTTTACTTAAATCTTGAAAAAGATCAAGATAAGATTTCTATTGCTCATGTTGACAACGACCATATTGTCTTTG
AAGGTGATGGTTACCACTACCAAACTTATGACCAATGGAAAGAAACTAACAAGGGTGCTGACAATATCGCAATGCGT
GATGCACACGTGATTGATGATGATAATGGTAATCGTTACCTTGTGTTTGAAGCAAGTACTGGAACCGAAAATTATCA
AGGTGATGATCAAATTTATCAATGGTTAAATTACGGCGGTACTAACAAGGATAATTTAGGTGATTTCTTCCAAATTT
TATCTAACTCCGATATTAAAGATAGAGCTAAATGGTCAAACGCTGCAATTGGTATCATTAAATTAAATGATGATGTT
AAGAATCCAAGTGTTGCAAAGGTCTACAGCCCACTTATTAGTGCACCAATGGTAAGTGATGAAATTGAACGCCCTGA
TGTTGTTAAATTAGGTAATAAGTATTACTTATTTGCTGCTACTAGATTAAACCGTGGTAGTAACGATGATGCTTGGA
TGGCAACTAACAAAGCAGTTGGTGATAACGTAGCTATGATTGGTTATGTTTCTGATAACTTAACTCATGGTTATGTT
CCATTGAATGAATCTGGCGTTGTTTTAACTGCATCTGTACCGGCTAACTGGCGTACTGCAACTTATTCATACTATGC
AGTTCCAGTAGAAGGAAGAGATGATCAACTTTTAATTACTTCATACATCACTAATCGTGGTGAGGTTGCTGGAAAGG
GTATGCATGCAACTTGGGCACCAAGTTTCTTGTTACAAATTAATCCAGATAACACTACTACTGTTTTAGCTAAAATG
ACTAACCAAGGGATTGGATTTGGGATGATAGTAGTGAAAATCCAGATATGATGGGTGTACTTGAAAAAGATGCTCC
AAATAGTGCTGCCCTTCCTGGAGAATGGGGAAAACCAGTTGATTGGGATTTAATTGGTGGATACAACTTGAAGCCAC
ACCAACCTGTAACTCCTATTCCAAATGTACCAACTACTCCTGAAACCCCAACCACACCAGATAAGCCAGAGGTACCA

FIGURE 32 (CONT'D)

ACTACCCCTGAAGTTCCAACCACTCCAGAAACTCCAACTCCAGAAGCTCCAAAGAATCCAGTTAAGAAAACTAGTCA
GTCTAAACTTCCAAAGGCTGGAGATAAAAATAGCTTTGCAGCAGTTGTTTTAGGTGCTGTAAGTTCAATATTAGGTG
CTGTTGGTTTAACAGGTGTTTCAAAACGTAAACGTAATAATTAAactatgagttgaaacaatggcctatctcatatg
aagatcttttgtgaatttcacttttgtccacgacctctgttgcacgactctgctttccgaccggagcatacctttg
ttctatatgatttgtgtatgtatgtaggaacctatgttctcgagcatgcatacataattcctcataggtctatatac
accggctatccatatgcaaaacctgtgtaatatttgttatatacaacacgcggaccattgtcttgctgttattaatt
cttttttcccgcaaaaaaggaaaagtttctttatttggcactgcaatggatatgcctcacagctagtgggtggagaa
ttcagtatttgacattaagattccctgatttgcaattgcaaatttcagtttctttacttatatcactacaaaagtct
tattgtttcttttccacgtcattaccatctgctccattggttttgctagtagaataggatgaagcatggacacaga
ttaactgagctcgagctcatatgagctcgggtgaacaataaaatctgaaaatacttagaaagaattcaaaattttct
gttttttgtggcaaaatttgacaaatgttataaatgcttgcaaagtttcatcatagaacgacattcgtggatgtcat
ggcaaaaaacaaattcagcactctgaaaataactttttgaagtatcg*gtttgtgtcttctagattaatcctccaaa*
*cttttgattaaccaaaaaattatcaaactaacatgttctccttttttctttagaaattctaacgaatttatcttta*
*tactgatttgaatatacttaatttggtcatttggatgccctttacaacctccttaccaaactcactatggcaaatat*
*atactattttccattgtaacataaatgtccataatttgaattaaattcgttgcagtacgaaaccatccaactttgtc*
*caaaaacaaatccttataactatttactttaatgtaaatatatcctctacttttgttttacaaccctagctcaaa*
*caaatttattatttgcgataaaaaatcatatcgaacaaactcgatgattttttttttcttacgttattaatgaaact*
*aaaatatagaaaaaacaagatgaaccaaattttcacctatctaactacttaaatataatatgattaaatttggtaa*
*agtttgaaaagtttctttaggaaatgtgaaatattgatcacagtttctattgctaaaatcaccaacaaaacgcatgt*
*cgccattcataattatggtttcacacctacaactaggctaataagtaaataagtagacaactagactcaggtttgaa*
*aaaaccataaaagccatatagcgttttctcattgaaactgcgaacacgatcgtgtgaatgttgcagtttctagtttt*
*gatacaaacaaacaaaaacacaatttaatcttagattaaaaagaaaaaagagaacggagcccactagccactccttc*
*aaacgtgtcttaccaactctcttctagaaacaaattaggcttcaccttcctcttccaacctctctctctctctctct*
*ctctctttctcaaaccatctctccataaagccctaatttcttcatcacaagaatcagaagaatactgcaaaaaactt*
ATGGACCTGCATCTAATTTTCGGTCCAACTTGCACAGGAAAGACGACGACCGCGATAGCTCTTGCCCAGCAGACAGG
GCTTCCAGTCCTTTCGCTTGATCGGGTCCAATGCTGTCCTCAACTATCAACCGGAAGCGGACGACCAACAGTGGAAG
AACTGAAAGGAACGACGCGTCTCTACCTTGATGATCGGCCTCTGGTGGAGGGTATCATCGCAGCCAAGCAAGCTCAT
CATAGGCTGATCGAGGAGGTGTATAATCATGAGGCCAACGGCGGGCTTATTCTTGAGGGAGGATCCACCTCGTTGCT
CAACTGCATGGCGCGAAACAGCTATTGGAGTGCAGATTTTCGTTGGCATATTATTCGCCACAAGTTACCCGACCAAG
AGACCTTCATGAAAGCGGCCAAGGCCAGAGTTAAGCAGATGTTGCACCCCGCTGCAGGCCATTCTATTATTCAAGAG
TTGGTTTATCTTTGGAATGAACCTCGGCTGAGGCCCATTCTGAAAGAGATCGATGGATATCGATATGCCATGTTGTT
TGCTAGCCAGAACCAGATCACGGCAGATATGCTATTGCAGCTTGACGCAAATATGGAAGGTAAGTTGATTAATGGGA
TCGCTCAGGAGTATTTCATCCATGCGCGCCAACAGGAACAGAAATTCCCCCAAGTTAACGCAGCCGCTTTCGACGGA
TTCGAAGGTCATCCGTTCGGAATGTATTAGGTAAgtccgcaaaaatcaccagtctctctctacaaatctatctctct
*ctattttctccagaataatgtgtgagtagttcccagataagggaattagggttcttataggtttcgctcatgtgt*
*tgagcatataagaaaccccttagtatgtatttgtatttgtaaaatacttctatcaataaaatttctaattcctaaaac*
*caaaatccagtgacct*

FIGURE 33

GATCCGGTGACTCAAAAAAGAAGAGCCGCCATCTGTCCAAGCGCCACTCCTACGAGAACTAAAATCCTATTCCCTCC
GTAAATAAATATAAGAGTGTTTAGATCACTACTTCTTTACAGAGAATTTCCTTCCCTCCAAGGGGAGGCGAATCCAT
AGGCACATCGACGGATATGGAGGGGGGAAACATATATTTTACTATGCTAGTTCAGTTAATTCTACCAAGAAAACATA
TATTTTATTTTGACAAACATTGTATAAATGTAGACATTCACATACACGTATGTACACCACCCTCTATGATTGCACAC
CCGCACACTATATGCCTATGAGCATACTTTCAAGAGTGAGCCAGCAAATTTTATGATAAAATGAAATATTTTGCCCA
GCCAACTCAGTCGCATCCTCGGACAATTTGTTATCAAGGAACTCACCCAAAAACAAGCAAAGCTAGAAAAAGGTTGT
GTGGCAGCCACCTAATGACATGAAGGACTGAAATTTCCAGCACACACAATGTATCCGACGGCAATGCTTCTTCCACT
GATCCGGAGAAGATAAGGAAACGAGGCAACCAGCGAACGTGAGCCATCCCAACCACATCTGTACCAAAGAAACGGGG
CTATATATACCGTGGTGACCCGGCAATGGGGTCCTCAACTGTAGCGGCATCCTCCTCTCCTCCGATAATACAAATA
CC*ATGGAGTCCCCAAGCGCCGTCGTCCCCGGCACCACGGCGCCGCTGCTTCCTTATGCGTACGCCGCTGCCGTCG*
*TCCGCCGACGACGCCCGTCAAAACCGGAGTGGCGGGAGGTGGCGCGCGTGCGCCGCCGTGCTGGCCGCATCGGCGTT*
*GGCGGTGGTCGTCGTGGTCGGGCTCCTCGCGGGCGGCAGGGTGGATCGGGTCCCGGCCGGCGGA*ACGAACCAAAAGC
CATATAAGGAAACATACGGCATTTCCCATATTACACGCCATGATATGCTGCAAATCCCTGAACAGCAAAAAATGAA
AAATATCAAGTTCCTGAATTCGATTCGTCCACAATTAAAAATATCTCTTCTGCAAAAGGCCTGGACGTTTGGGACAG
CTGGCCATTACAAAACGCTGACGGCACTGTCGCAAACTATCACGGCTACCACATCGTCTTTGCATTAGCCGGAGATC
CTAAAAATGCGGATGACACATCGATTTACATGTTCTATCAAAAAGTCGGCGAAACTTCTATTGACAGCTGGAAAAAC
GCTGGCCGCGTCTTTAAAGACAGCGACAAATTCGATGCAAATGATTCTATCCTAAAAGACCAAACACAAGAATGGTC
AGGTTCAGCCACATTTACATCTGACGGAAAAATCCGTTTATTCTACACTGATTTCTCCGGTAAACATTACGGCAAAC
AAACACTGACAACTGCACAAGTTAACGTATCAGCATCAGACAGCTCTTTGAACATCAACGGTGTAGAGGATTATAAA
TCAATCTTTGACGGTGACGGAAAAACGTATCAAAATGTACAGCAGTTCATCGATGAAGGCAACTACAGCTCAGGCGA
CAACCATACGCTGAGAGATCCTCACTACGTAGAAGATAAAGGCCACAAATACTTAGTATTTGAAGCAAACACTGGAA
CTGAAGATGGCTACCAAGGCGAAGAATCTTTATTTAACAAAGCATACTATGGCAAAAGCACATCATTCTTCCGTCAA
GAAAGTCAAAAACTTCTGCAAAGCGATAAAAAACGCACGGCTGAGTTAGCAAACGGCGCTCTCGGTATGATTGAGCT
AAACGATGATTACACACTGAAAAAAGTGATGAAACCGCTGATTGCATCTAACACAGTAACAGATGAAATTGAACGCG
CGAACGTCTTTAAAATGAACGGCAAATGGTACCTGTTCACTGACTCCGCGGATCAAAAATGACGATTGACGGCATT
ACGTCTAACGATATTTACATGCTTGGTTATGTTTCTAATTCTTTAACTGGCCCATACAAGCCGCTGAACAAAACTGG
CCTTGTGTTAAAAATGGATCTTGATCCTAACGATGTAACCTTTACTTACTCACACTTCGCTGTACCTCAAGCGAAAG
GAAACAATGTCGTGATTACAAGCTATATGACAAACAGAGGATTCTACGCAGACAAACAATCAACGTTTGCGCCAAGC
TTCCTGCTGAACATCAAAGGCAAGAAAACATCTGTTGTCAAAGACAGCATCCTTGAACAAGGACAATTAACAGTTAA
CAAATAAactatgagttgaaacaatggcctatctcatatgaagatcttttgtgaatttcacttttgtccacgacctc
tgttgcacgactctgctttccgaccggagcataccttttgttctatatgatttgtgtatgtatgtaggaacctatgt
tctcgagcatgcatacataattcctcataggtctatatacaccggctatccatatgcaaaacctgtgtaatatttgt
tatatacaacacgcggaccattgtcttgctgttattaattcttttttcccgcaaaaaaggaaaagtttctttatttg
gcactgcaatggatatgcctcacagctagtgggtggagaattcagtatttgacattaagattccctgatttgcaatt
gcaaatttcagtttctttacttatatcactacaaaagtcttattgtttcttttccacgtcattaccatctgctccat
tggttttgctagtagaataggatgaagcatggacacagattaactgagctcgagctcatatgagctcgggtgaaca
ataaaatctgaaaatacttagaaagaattcaaaattttctgttttttgtggcaaaatttgacaaatgttataaatgc

FIGURE 33 (CONT'D)

```
ttgcaaagtttcatcatagaacgacattcgtggatgtcatggcaaaaaacaaattcagcactctgaaaataactttt
ttgaagtatcg
```

FIGURE 34 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggaggggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
ccATGGAGTCCCCAAGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGGAGGTGGCGCGCGTGCGCCGCCGTGCTGGCCGCATCGGCGTT
GGCGGTGGTCGTCGTGGTCGGGCTCCTCGCGGGCGGCAGGGTGGATCGGGTCCCGGCCGGCGGAACGAACCAAAAGC
CATATAAGGAAACATACGGCATTTCCCATATTACACGCCATGATATGCTGCAAATCCCTGAACAGCAAAAAAATGAA
AAATATCAAGTTCCTGAATTCGATTCGTCCACAATTAAAAATATCTCTTCTGCAAAAGGCCTGGACGTTTGGGACAG
CTGGCCATTACAAAACGCTGACGGCACTGTCGCAAACTATCACGGCTACCACATCGTCTTTGCATTAGCCGGAGATC
CTAAAAATGCGGATGACACATCGATTTACATGTTCTATCAAAAGTCGGCGAAACTTCTATTGACAGCTGGAAAAAC
GCTGGCCGCGTCTTTAAAGACAGCGACAAATTCGATGCAAATGATTCTATCCTAAAAGACCAAACACAAGAATGGTC
AGGTTCAGCCACATTTACATCTGACGGAAAAATCCGTTTATTCTACACTGATTTCTCCGGTAAACATTACGGCAAAC
AAACACTGACAACTGCACAAGTTAACGTATCAGCATCAGACAGCTCTTTGAACATCAACGGTGTAGAGGATTATAAA
TCAATCTTTGACGGTGACGGAAAAACGTATCAAAATGTACAGCAGTTCATCGATGAAGGCAACTACAGCTCAGGCGA
CAACCATACGCTGAGAGATCCTCACTACGTAGAAGATAAAGGCCACAAATACTTAGTATTTGAAGCAAACACTGGAA
CTGAAGATGGCTACCAAGGCGAAGAATCTTTATTTAACAAAGCATACTATGGCAAAAGCACATCATTCTTCCGTCAA
GAAAGTCAAAAACTTCTGCAAAGCGATAAAAAACGCACGGCTGAGTTAGCAAACGGCGCTCTCGGTATGATTGAGCT
AAACGATGATTACACACTGAAAAAAGTGATGAAACCGCTGATTGCATCTAACACAGTAACAGATGAAATTGAACGCG
CGAACGTCTTTAAAATGAACGGCAAATGGTACCTGTTCACTGACTCCCGCGGATCAAAAATGACGATTGACGGCATT
ACGTCTAACGATATTTACATGCTTGGTTATGTTTCTAATTCTTTAACTGGCCCATACAAGCCGCTGAACAAAACTGG
CCTTGTGTTAAAAATGGATCTTGATCCTAACGATGTAACCTTTACTTACTCACACTTCGCTGTACCTCAAGCGAAAG
GAAACAATGTCGTGATTACAAGCTATATGACAAACAGAGGATTCTACGCAGACAAACAATCAACGTTTGCGCCAAGC
TTCCTGCTGAACATCAAAGGCAAGAAAACATCTGTTGTCAAAGACAGCATCCTTGAACAAGGACAATTAACAGTTAA
CAAATAActatgagttgaaacaatggcctatctcatatgaagatcttttgtgaatttcacttttgtccacgacctc
tgttgcacgactctgctttccgaccggagcatacctttgttctatatgatttgtgtatgtatgtaggaacctatgt
tctcgagcatgcatacataattcctcataggtctatatacaccggctatccatatgcaaaacctgtgtaatatttgt
tatatacaacacgcggaccattgtcttgctgttattaattcttttttcccgcaaaaaggaaaagtttctttatttg
gcactgcaatggatatgcctcacagctagtgggtggagaattcagtatttgacattaagattccctgatttgcaatt
gcaaatttcagtttctttacttatatcactacaaaagtcttattgtttcttttccacgtcattaccatctgctccat
tggttttgctagtagaataggatgaagcatggacacagattaactgagctcgagctcatatgagctcgggtgaaca
ataaaatctgaaaatacttagaaagaattcaaaattttctgttttttgtggcaaaatttgacaaatgttataaatgc

FIGURE 34 (CONT'D)

ttgcaaagtttcatcatagaacgacattcgtggatgtcatggcaaaaaacaaattcagcactctgaaaataacttttt
ttgaagtatcg*gtttgtgtcttctagattaatcctccaaacttttgattaaccaaaaaaattatcaaactaacatgt*
*tctccttttttctttagaaattctaacgaatttatctttatactgatttgaatatacttaatttggtcatttggatg*
*ccctttacaacctccttaccaaactcactatggcaaatatatactattttccattgtaacataaatgtccataattt*
*gaattaaattcgttgcagtacgaaaccatccaactttgtccaaaaacaaatccttataactatttactttaatgta*
*aatatatcctctacttttgtttttacaaccctagctcaaacaaatttattatttgcgataaaaaatcatatcgaaca*
*aactcgatgatttttttttcttacgttattaatgaaactaaaatatagaaaaaacaagatgaaccaaattttcac*
*ctatctaactacttaaatataatatgattaaatttggtaaagtttgaaaagtttctttaggaaatgtgaaatattga*
*tcacagtttctattgctaaaatcaccaacaaaacgcatgtcgccattcataattatggtttcacacctacaactagg*
*ctaataagtaaataagtagacaactagactcaggtttgaaaaaaccataaaagccatatagcgttttctcattgaaa*
*ctgcgaacacgatcgtgtgaatgttgcagtttctagttttgatacaaacaaacaaaaacacaatttaatcttagatt*
*aaaaagaaaaagagaacggagcccactagccactccttcaaacgtgtcttaccaactctcttctagaaacaaatta*
*ggcttcaccttcctcttccaacctctctctctctctctctctttctcaaaccatctctccataaagccctaat*
*ttcttcatcacaagaatcagaagaatactgcaaaaaact*tATGGACCTGCATCTAATTTTCGGTCCAACTTGCACAG
GAAAGACGACGACCGCGATAGCTCTTGCCCAGCAGACAGGGCTTCCAGTCCTTTCGCTTGATCGGGTCCAATGCTGT
CCTCAACTATCAACCGGAAGCGGACGACCAACAGTGGAAGAACTGAAAGGAACGACGCGTCTCTACCTTGATGATCG
GCCTCTGGTGGAGGGTATCATCGCAGCCAAGCAAGCTCATCATAGGCTGATCGAGGAGGTGTATAATCATGAGGCCA
ACGGCGGGCTTATTCTTGAGGGAGGATCCACCTCGTTGCTCAACTGCATGGCGCGAAACAGCTATTGGAGTGCAGAT
TTTCGTTGGCATATTATTCGCCACAAGTTACCCGACCAAGAGACCTTCATGAAAGCGGCCAAGGCCAGAGTTAAGCA
GATGTTGCACCCCGCTGCAGGCCATTCTATTATTCAAGAGTTGGTTTATCTTTGGAATGAACCTCGGCTGAGGCCCA
TTCTGAAAGAGATCGATGGATATCGATATGCCATGTTGTTTGCTAGCCAGAACCAGATCACGGCAGATATGCTATTG
CAGCTTGACGCAAATATGGAAGGTAAGTTGATTAATGGGATCGCTCAGGAGTATTTCATCCATGCGCGCCAACAGGA
ACAGAAATTCCCCCAAGTTAACGCAGCCGCTTTCGACGGATTCGAAGGTCATCCGTTCGGAATGTATTAGGTAa*gtc*
*cgcaaaaatcaccagtctctctctacaaatctatctctctctattttttctccagaataatgtgtgagtagttcccag*
*ataagggaattagggttcttatagggtttcgctcatgtgttgagcatataagaaacccttagtatgtatttgtattt*
*gtaaaatacttctatcaataaaatttctaattcctaaaaccaaaatccagtgacct*

FIGURE 35 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggagggggaaacatatattttactatgctagttcagttaattctaccaagaaaacata
tattttattttgacaaacattgtataaatgtagacattcacatacacgtatgtacaccaccctctatgattgcacac
ccgcacactatatgcctatgagcatactttcaagagtgagccagcaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
cc***ATGGAGTCCCCAAGCGCCGTCGTCCCCGGCACCACGGCGCCGCTGCTTCCTTATGCGTACGCGCCGCTGCCGTCG
TCCGCCGACGACGCCCGTCAAAACCGGAGTGGCGGGAGGTGGCGCGCGTGCGCCGCCGTGCTGGCCGCATCGGCGTT
GGCGGTGGTCGTCGTGGTCGGGCTCCTCGCGGGCGGCAGGGTGGATCGGGTCCCGGCCGGCGGA***ACTATTAATGCAG
ACAATGTTAATGAAAATCAAACTGTAGAAGTAACTGCTAGTTCAGTAAACAATGAAAATAATAAGCAAGTAACTGAA
AAAGATAGTGCAGATAAAAGTACTAGTGATGTGGCTGAAGATGCTAACACCAAGAAATCAAACGAAAATACAGAAAC
TACAGAAAAGAATACTCAAACAGTTGTTACTAATGCGCCAGTAAGTGATGTGAAAAATACAAACACAGTTACCGCTG
AAACACCTGTTGATAAAGTAGTAAATAATAGTGATCAAAAGACAACTAATGCTGCAACTACTGATACTAAAAAAGAT
GATGTAAAACAAGTTGAAAAGAAAGACTCAGTAGATAAAACAAATGCTGAGGAAAATAAAGATAGTTCAGTAAAGCC
AGCTGAAAATGCTACTAAGGCTGAATTAAAGGGCCAAGTTAAAGATATCGTTGAAGAATCTGGTGTTGATACTAGCA
AGTTAACTAATGATCAAATTAATGAATTAAATAAAATTAATTTCTCCAAAGAAGCAAAAAGTGGTACTCAGTTAACT
TACAACGACTTTAAAAAAATTGCTAAAACTTTAATTGAACAAGATGCTCGTTATGCTATTCCATTCTTCAATGCAAG
TAAAATTAAAAATATGCCTGCTGCTAAAACACTTGATGCTCAAAGTGGAAAAGTAGAAGATTTGGAAATTTGGGATT
CATGGCCTGTTCAAGATGCAAAAACTGGTTACGTATCTAACTGGAATGGCTACCAATTAGTGATTGGTATGATGGGA
GTTCCAAACGTCAATGATAACCACATTTATCTTCTTTACAACAAGTATGGTGATAATGACTTTAATCATTGGAAGAA
TGCCGGTCCTATTTTCGGTCTAGGTACTCCAGTTATTCAACAATGGTCTGGATCAGCAACTTTAAATAAAGATGGCT
CAATTCAACTTTACTACACTAAGGTTGATACTAGTGATAATAATACTAACCACCAAAAACTCGCTAGTGCAACTGTT
TACTTAAATCTTGAAAAAGATCAAGATAAGATTTCTATTGCTCATGTTGACAACGACCATATTGTCTTTGAAGGTGA
TGGTTACCACTACCAAACTTATGACCAATGGAAAGAAACTAACAAGGGTGCTGACAATATCGCAATGCGTGATGCAC
ACGTGATTGATGATGATAATGGTAATCGTTACCTTGTGTTTGAAGCAAGTACTGGAACCGAAAATTATCAAGGTGAT
GATCAAATTTATCAATGGTTAAATTACGGCGGTACTAACAAGGATAATTTAGGTGATTTCTTCCAAATTTTATCTAA
CTCCGATATTAAAGATAGAGCTAAATGGTCAAACGCTGCAATTGGTATCATTAAATTAAATGATGATGTTAAGAATC
CAAGTGTTGCAAAGGTCTACAGCCCACTTATTAGTGCACCAATGGTAAGTGATGAAATTGAACGCCCTGATGTTGTT
AAATTAGGTAATAAGTATTACTTATTTGCTGCTACTAGATTAAACCGTGGTAGTAACGATGATGCTTGGATGGCAAC
TAACAAAGCAGTTGGTGATAACGTAGCTATGATTGGTTATGTTTCTGATAACTTAACTCATGGTTATGTTCCATTGA
ATGAATCTGGCGTTGTTTTAACTGCATCTGTACCGGCTAACTGGCGTACTGCAACTTATTCATACTATGCAGTTCCA
GTAGAAGGAAGAGATGATCAACTTTTAATTACTTCATACATCACTAATCGTGGTGAGGTTGCTGGAAAGGGTATGCA
TGCAACTTGGGCACCAAGTTTCTTGTTACAAATTAATCCAGATAACACTACTACTGTTTTAGCTAAAATGACTAACC
AAGGGGATTGGATTTGGGATGATAGTAGTGAAAATCCAGATATGATGGGTGTACTTGAAAAGATGCTCCAAATAGT

FIGURE 35 (CONT'D)

```
GCTGCCCTTCCTGGAGAATGGGGAAAACCAGTTGATTGGGATTTAATTGGTGGATACAACTTGAAGCCACACCAACC
TGTAACTCCTATTCCAAATGTACCAACTACTCCTGAAACCCCAACCACACCAGATAAGCCAGAGGTACCAACTACCC
CTGAAGTTCCAACCACTCCAGAAACTCCAACTCCAGAAGCTCCAAAGAATCCAGTTAAGAAAACTAGTCAGTCTAAA
CTTCCAAAGGCTGGAGATAAAAATAGCTTTGCAGCAGTTGTTTTAGGTGCTGTAAGTTCAATATTAGGTGCTGTTGG
TTTAACAGGTGTTTCAAAACGTAAACGTAATAATTAAactatgagttgaaacaatggcctatctcatatgaagatct
tttgtgaatttcactttgtccacgacctctgttgcacgactctgctttccgaccggagcataccttttgttctata
tgatttgtgtatgtatgtaggaacctatgttctcgagcatgcatacataattcctcataggtctatatacaccggct
atccatatgcaaaacctgtgtaatatttgttatatacaacacgcggaccattgtcttgctgttattaattcttttttt
cccgcaaaaaaggaaaagtttctttatttggcactgcaatggatatgcctcacagctagtgggtggagaattcagta
tttgacattaagattccctgatttgcaattgcaaatttcagtttctttacttatatcactacaaaagtcttattgtt
tcttttccacgtcattaccatctgctccattggttttgctagtagaataggatgaagcatggacacagattaactg
agctcgagctcatatgagctcgggtgaacaataaaatctgaaaatacttagaaagaattcaaaattttctgtttttt
gtggcaaaatttgacaaatgttataaatgcttgcaaagtttcatcatagaacgacattcgtggatgtcatggcaaaa
aacaaattcagcactctgaaaataacttttttgaagtatcg
```

FIGURE 36 gatccggtgactcaaaaaagaagagccgccatctgtccaagcgccactcctacgagaactaaaatcctattccctcc
gtaaataaatataagagtgtttagatcactacttctttacagagaatttccttccctccaaggggaggcgaatccat
aggcacatcgacggatatggaggggggaaacatatattttactatgctagttcagttaattctaccaagaaaacata
tattttattttgacaaacattgtataaatgtagacattcacatacacgtatgtacaccacctctatgattgcacac
ccgcacactatatgcctatgagcatactttcaagagtgagccagcaaattttatgataaaatgaaatattttgccca
gccaactcagtcgcatcctcggacaatttgttatcaaggaactcacccaaaaacaagcaaagctagaaaaaggttgt
gtggcagccacctaatgacatgaaggactgaaatttccagcacacacaatgtatccgacggcaatgcttcttccact
gatccggagaagataaggaaacgaggcaaccagcgaacgtgagccatcccaaccacatctgtaccaaagaaacgggg
ctatatataccgtggtgacccggcaatggggtcctcaactgtagccggcatcctcctctcctccgataatacaaata
cc*ATGGAGTCCCCAAGCGCCGTCGTCCCCGGCACCACGGCGCCGCTGCTTCCTTATGCGTACGCGCCGCTGCCGTCG*
*TCCGCCGACGACGCCCGTCAAAACCGGAGTGGCGGGAGGTGGCGCGCGTGCGCCGCCGTGCTGGCCGCATCGGCGTT*
*GGCGGTGGTCGTCGTGGTCGGGCTCCTCGCGGGCGGCAGGGTGGATCGGGTCCCGGCCGGCGGA*ACTATTAATGCAG
ACAATGTTAATGAAAATCAAACTGTAGAAGTAACTGCTAGTTCAGTAAACAATGAAAATAATAAGCAAGTAACTGAA
AAAGATAGTGCAGATAAAAGTACTAGTGATGTGGCTGAAGATGCTAACACCAAGAAATCAAACGAAAATACAGAAAC
TACAGAAAAGAATACTCAAACAGTTGTTACTAATGCGCCAGTAAGTGATGTGAAAAATACAAACACAGTTACCGCTG
AAACACCTGTTGATAAAGTAGTAAATAATAGTGATCAAAAGACAACTAATGCTGCAACTACTGATACTAAAAAAGAT
GATGTAAAACAAGTTGAAAAGAAAGACTCAGTAGATAAAACAAATGCTGAGGAAAATAAAGATAGTTCAGTAAAGCC
AGCTGAAAATGCTACTAAGGCTGAATTAAAGGGCCAAGTTAAAGATATCGTTGAAGAATCTGGTGTTGATACTAGCA
AGTTAACTAATGATCAAATTAATGAATTAAATAAAATTAATTTCTCCAAAGAAGCAAAAAGTGGTACTCAGTTAACT
TACAACGACTTTAAAAAAATTGCTAAAACTTTAATTGAACAAGATGCTCGTTATGCTATTCCATTCTTCAATGCAAG
TAAAATTAAAAATATGCCTGCTGCTAAAACACTTGATGCTCAAAGTGGAAAAGTAGAAGATTTGGAAATTTGGGATT
CATGGCCTGTTCAAGATGCAAAAACTGGTTACGTATCTAACTGGAATGGCTACCAATTAGTGATTGGTATGATGGGA
GTTCCAAACGTCAATGATAACCACATTTATCTTCTTTACAACAAGTATGGTGATAATGACTTTAATCATTGGAAGAA
TGCCGGTCCTATTTTCGGTCTAGGTACTCCAGTTATTCAACAATGGTCTGGATCAGCAACTTTAAATAAAGATGGCT
CAATTCAACTTTACTACACTAAGGTTGATACTAGTGATAATAATACTAACCACCAAAAACTCGCTAGTGCAACTGTT
TACTTAAATCTTGAAAAAGATCAAGATAAGATTTCTATTGCTCATGTTGACAACGACCATATTGTCTTTGAAGGTGA
TGGTTACCACTACCAAACTTATGACCAATGGAAAGAAACTAACAAGGGTGCTGACAATATCGCAATGCGTGATGCAC
ACGTGATTGATGATGATAATGGTAATCGTTACCTTGTGTTTGAAGCAAGTACTGGAACCGAAAATTATCAAGGTGAT
GATCAAATTTATCAATGGTTAAATTACGGCGGTACTAACAAGGATAATTTAGGTGATTTCTTCCAAATTTTATCTAA
CTCCGATATTAAAGATAGAGCTAAATGGTCAAACGCTGCAATTGGTATCATTAAATTAAATGATGATGTTAAGAATC
CAAGTGTTGCAAAGGTCTACAGCCCACTTATTAGTGCACCAATGGTAAGTGATGAAATTGAACGCCCTGATGTTGTT
AAATTAGGTAATAAGTATTACTTATTTGCTGCTACTAGATTAAACCGTGGTAGTAACGATGATGCTTGGATGGCAAC
TAACAAAGCAGTTGGTGATAACGTAGCTATGATTGGTTATGTTTCTGATAACTTAACTCATGGTTATGTTCCATTGA
ATGAATCTGGCGTTGTTTTAACTGCATCTGTACCGGCTAACTGGCGTACTGCAACTTATTCATACTATGCAGTTCCA
GTAGAAGGAAGAGATGATCAACTTTTAATTACTTCATACATCACTAATCGTGGTGAGGTTGCTGGAAAGGGTATGCA
TGCAACTTGGGCACCAAGTTTCTTGTTACAAATTAATCCAGATAACACTACTACTGTTTTAGCTAAAATGACTAACC
AAGGGGATTGGATTTGGGATGATAGTAGTGAAAATCCAGATATGATGGGTGTACTTGAAAAGATGCTCCAAATAGT

FIGURE 36 (CONT'D)

```
GCTGCCCTTCCTGGAGAATGGGGAAAACCAGTTGATTGGGATTTAATTGGTGGATACAACTTGAAGCCACACCAACC
TGTAACTCCTATTCCAAATGTACCAACTACTCCTGAAACCCCAACCACACCAGATAAGCCAGAGGTACCAACTACCC
CTGAAGTTCCAACCACTCCAGAAACTCCAACTCCAGAAGCTCCAAAGAATCCAGTTAAGAAAACTAGTCAGTCTAAA
CTTCCAAAGGCTGGAGATAAAAATAGCTTTGCAGCAGTTGTTTTAGGTGCTGTAAGTTCAATATTAGGTGCTGTTGG
TTTAACAGGTGTTTCAAAACGTAAACGTAATAATTAAactatgagttgaaacaatggcctatctcatatgaagatct
tttgtgaatttcacttttgtccacgacctctgttgcacgactctgctttccgaccggagcataccttttgttctata
tgatttgtgtatgtatgtaggaacctatgttctcgagcatgcatacataattcctcataggtctatatacaccggct
atccatatgcaaaacctgtgtaatatttgttatatacaacacgcggaccattgtcttgctgttattaattctttttt
cccgcaaaaaaggaaaagtttctttatttggcactgcaatggatatgcctcacagctagtgggtggagaattcagta
tttgacattaagattccctgatttgcaattgcaaatttcagtttctttacttatatcactacaaaagtcttattgtt
tcttttccacgtcattaccatctgctccattggttttgctagtagaataggatgaagcatggacacagattaactg
agctcgagctcatatgagctcgggtgaacaataaaatctgaaaatacttagaaagaattcaaaattttctgttttt
gtggcaaaatttgacaaatgttataaatgcttgcaaagtttcatcatagaacgacattcgtggatgtcatggcaaaa
aacaaattcagcactctgaaataactttttttgaagtatcggtttgtgtcttctagattaatcctccaaacttttga
ttaaccaaaaaaattatcaaactaacatgttctccttttttctttagaaattctaacgaatttatctttatactgat
ttgaatatacttaatttggtcatttggatgccctttacaacctccttaccaaactcactatggcaaatatatactat
tttccattgtaacataaatgtccataatttgaattaaattcgttgcagtacgaaaccatccaactttgtccaaaaac
aaaatccttataactatttactttaatgtaaatatatcctctacttttgttttacaaccctagctcaaacaaattt
attatttgcgataaaaaatcatatcgaacaaactcgatgatttttttttttcttacgttattaatgaaactaaaatat
agaaaaaaacaagatgaaccaaattttcacctatctaactacttaaatataatatgattaaatttggtaaagtttga
aaagtttctttaggaaatgtgaaatattgatcacagtttctattgctaaaatcaccaacaaaacgcatgtcgccatt
cataattatggtttcacacctacaactaggctaataagtaaataagtagacaactagactcaggtttgaaaaaacca
taaaagccatatagcgttttctcattgaaactgcgaacacgatcgtgtgaatgttgcagtttctagttttgatacaa
acaaacaaaaacacaatttaatcttagattaaaaagaaaaaagagaacggagcccactagccactccttcaaacgtg
tcttaccaactctcttctagaaacaaattaggcttcaccttcctcttccaacctctctctctctctctctctctctt
tctcaaaccatctctccataaagccctaatttcttcatcacaagaatcagaagaatactgcaaaaaacttATGGACC
TGCATCTAATTTTCGGTCCAACTTGCACAGGAAAGACGACGACCGCGATAGCTCTTGCCCAGCAGACAGGGCTTCCA
GTCCTTTCGCTTGATCGGGTCCAATGCTGTCCTCAACTATCAACCGGAAGCGGACGACCAACAGTGGAAGAACTGAA
AGGAACGACGCGTCTCTACCTTGATGATCGGCCTCTGGTGGAGGGTATCATCGCAGCCAAGCAAGCTCATCATAGGC
TGATCGAGGAGGTGTATAATCATGAGGCAACGGCGGCTTATTCTTGAGGGAGGATCCACCTCGTTGCTCAACTGC
ATGGCGCGAAACAGCTATTGGAGTGCAGATTTTCGTTGGCATATTATTCGCCACAAGTTACCCGACCAAGAGACCTT
CATGAAAGCGGCCAAGGCCAGAGTTAAGCAGATGTTGCACCCCGCTGCAGGCCATTCTATTATTCAAGAGTTGGTTT
ATCTTTGGAATGAACCTCGGCTGAGGCCCATTCTGAAAGAGATCGATGGATATCGATATGCCATGTTGTTTGCTAGC
CAGAACCAGATCACGGCAGATATGCTATTGCAGCTTGACGCAAATATGGAAGGTAAGTTGATTAATGGGATCGCTCA
GGAGTATTTCATCCATGCGCGCCAACAGGAACAGAAATTCCCCAAGTTAACGCAGCCGCTTTCGACGGATTCGAAG
GTCATCCGTTCGGAATGTATTAGGTAAgtccgcaaaaatcaccagtctctctctacaaatctatctctctcttttt
tctccagaataatgtgtgagtagttcccagataagggaattaggttcttataggtttcgctcatgtgttgagcat
```

FIGURE 36 (CONT'D)

ataagaaacccttagtatgtatttgtatttgtaaaatacttctatcaataaaatttctaattcctaaaaccaaaatc
cagtgacct

PLANT TECHNOLOGY

STATEMENT OF RELATED APPLICATIONS

This application claims the benefit of U.S. Provisional Application 61/173,272 filed Apr. 28, 2009 which application is incorporated herein by reference in its entirety.

This application is related to U.S. Provisional Application No. 61/097,008 and the PCT application claiming priority therefrom, which applications are incorporated herein by reference in their entirety.

FIELD OF THE INVENTION

The present invention relates to the modification of fructan biosynthesis in plants and, more particularly, to methods of manipulating fructan biosynthesis in photosynthetic cells, and to related nucleic acids and constructs.

The present invention also relates to increasing plant biomass and, more particularly, to methods of enhancing biomass yield and/or yield stability, including shoot and/or root growth in a plant, and to related nucleic acids and constructs.

BACKGROUND OF THE INVENTION

Fructans are a type of water-soluble carbohydrate whose primary function is to provide a readily accessible energy reserve for plant growth. Fructans are associated with various advantageous characters in grasses, such as cold and drought tolerance, increased tiller survival, enhanced persistence, good regrowth after cutting or grazing, improved recovery from stress, early spring growth and increased nutritional quality.

Fructan synthesis and metabolism in grasses and cereals is complex. Fructans consist of linear or branched fructose chains attached to sucrose. The chain length of plant fructans ranges from three up to a few hundred fructose units. Different types of fructans can be distinguished based on the linkage types present. In perennial ryegrass three types of fructans have been identified: inulins, inulin neoseries and levan neoseries, with four fructosyltransferse (FT) enzymes involved in this fructan profile.

The enzyme 1-SST (sucrose:sucrose 1-fructosyltransferase) catalyses the first step in fructan biosynthesis while the remaining enzymes elongate the growing fructose chain (1-FFT: fructan:fructan 1-fructosyltransferase, 6G-FFT: 6-glucose fructosyltransferase, and 6-SFT: sucrose:fructose 6-fructosyltransferase). The enzymes 1-FEH or 6-FEH (fructoexohydrolase) reduce fructan chain length by releasing fructose molecules.

Bacteria use only one FT enzyme which contains both 1-SST and 1-FFT activities to synthesize high molecular weight fructan polymers. Most bacterial fructosyltransferases produce levan type fructan (levansucrases), which is characterized by β-2,6 linkages of fructose molecules, although inulosucrases that produce fructans of the inulin type (β-2,1 linkage) have been isolated from a few bacteria.

At least 3 bacterial levansucrases have been expressed in transgenic plants including, the SacB gene from *Bacillus subtilis*, the SacB gene from *Bacillus amyloliquefaciens*, and the FTF gene from *Streptococcus mutans*. Expression of these bacterial levansucrases in plants leads to the synthesis of very high molecular weight fructans of a DP of several thousands (for review see Cairns, 2003).

Fructans represent the major non-structural carbohydrate in 15% of plant species and play a key role in forage quality. Ruminant livestock grazing on high fructan diets show improved animal performance.

In grasses the level and composition of fructans has been increased in stems and leaf sheaths through the engineered expression of FT genes.

However, manipulating biochemical pathways by manipulating the activity of enzymes in the pathways may be difficult because of the ways in which the various enzymes and their substrates may interact.

Thus, it would be desirable to have improved methods of manipulating biochemical pathways, particularly in plants. For example, it would be desirable to have methods of manipulating fructan biosynthesis in plants, including forage grass species such as *Lolium*, *Festuca*, and *Brachiaria*; sugarcane and other grasses; and sorghum and other cereals such as wheat and maize; thereby facilitating the production of, for example:

forage grasses with improved herbage quality and/or yield, leading to improved pasture production, improved animal production and/or reduced environmental pollution;

bioenergy grasses and crops such as switchgrass, *Miscanthus*, sorghum (grain, forage and energy sorghum), sugarcane and energy cane with enhanced biomass yield, such as for bioethanol production; and cereals such as wheat, rice, maize, barley with increased grain and/or biomass yield.

Nucleic acid sequences encoding some of the enzymes involved in the fructan biosynthetic pathway have been isolated for certain species of plants. For example, PCT/AU01/00705 to the present applicants, describes fructosyltransferase homologues from *Lolium* and *Festuca*. However, there remains a need for materials useful in the modification of fructan biosynthesis in plants, and also to engineer fructan accumulation in different parts of the plant.

U.S. provisional patent application 61/097,008 describes constructs useful for modifying fructan biosynthesis in plants. However, those constructs preferably include a fusion gene encoding a translational fusion of two or more fructan biosynthetic enzymes, the genes making up the fusion preferably corresponding to plant fructan biosynthetic genes.

It is an object of the present invention to overcome, or at least alleviate, one or more of the difficulties or deficiencies associated with the prior art.

SUMMARY OF THE INVENTION

Applicants have found that it is possible to nutritionally enhance plants eg. forage grasses and/or to increase plant biomass by spatial reprogramming of the fructan-biosynthesis pathway in photosynthetic cells using a construct including a promoter or a functionally active fragment or variant thereof, operatively linked to a gene encoding a bacterial FT enzyme, or a functionally active fragment or variant thereof. Using this process it is possible to drive fructan accumulation in leaf blades, the plant organs that are primarily grazed by livestock, and which may not normally accumulate fructans. Thus, accumulation of fructans, especially those exhibiting a high degree of polymerization ('high DP fructans'), provides more accessible nutrition for grazing animals. Fructans accumulate in the stems and leaf sheaths, with leaf fructans only forming during periods where $CO_2$ assimilation outperforms growth. Forage grasses may be nutritionally enhanced by expressing fructan genes in photosynthetic cells where sucrose is synthesised, thus driving fructan accumulation preferentially in leaf blades and providing more energy to grazing livestock.

Thus, the present invention provides a method selected from of manipulating fructan biosynthesis in photosynthetic cells of a plant, and/or enhancing productivity of a biochemical pathway in a plant, said method comprising introducing into said plant an effective amount of a genetic construct comprising a promoter operatively linked to a nucleic acid encoding a bacterial fructosyltransferase (FT) enzyme.

BRIEF DESCRIPTION OF THE DRAWINGS

FIG. 2. Nucleotide sequence of SacB gene from *Bacillus subtilis* (Levansucrase) (SEQ ID NO: 5). Nucleotide sequence coding for the N-terminal signal peptide is in bold (SEQ ID NO: 6).

FIG. 3. Amino acid sequence SacB protein from *Bacillus subtilis* (Levansucrase). (SEQ ID NO: 7) The N-terminal signal peptide is in bold. (SEQ ID NO: 8)

FIG. 4. Nucleotide sequence of Lsc gene from *Lactobacillus johnsonii* NCC 533 (SEQ ID NO: 9) (Inulosucrase). Nucleotide sequence coding for the N-terminal signal peptide is in bold. (SEQ ID NO: 10)

FIG. 5. Amino acid sequence of Lsc protein from *Lactobacillus johnsonii* NCC 533 (Inulosucrase). (SEQ ID NO: 11) The N-terminal signal peptide is in bold. (SEQ ID NO: 12)

FIG. 6. Nucleotide sequence of SPOR531, Preprosporamin protein from *I. batatas*. (SEQ ID NO: 13) Vacuolar targeting signal sequence is shown in bold underlined. (SEQ ID NO: 14)

FIG. 7. Amino acid sequence of SPOR531, Preprosporamin protein from *I. batatas*. (SEQ ID NO: 15) Vacuolar targeting signal sequence is shown in bold underlined. (SEQ ID NO: 16)

FIG. 8. SPOR:SacB chimeric nucleotide sequence. (SEQ ID NO 17) The N-terminal signal sequence of SacB has been replaced by the vacuolar targeting signal of SPOR (indicated by bold underlined). (SEQ ID NO: 14)

FIG. 9. SPOR:SacB chimeric protein sequence. (SEQ ID NO: 18) The N-terminal signal sequence of SacB has been replaced by the vacuolar targeting signal of SPOR (indicated by bold underlined). (SEQ ID NO: 16)

FIG. 11. SPOR:Lsc chimeric nucleotide sequence. (SEQ ID NO: 19) The N-terminal signal sequence of Lsc has been replaced by the vacuolar targeting signal of SPOR (indicated by bold underlined). (SEQ ID NO: 14)

FIG. 12. SPOR:Lsc chimeric protein sequence. (SEQ ID NO: 20) The N-terminal signal sequence of Lsc has been replaced by the vacuolar targeting signal of SPOR (indicated by bold underlined). (SEQ ID NO: 16)

FIG. 15. Lp1-SST nucleotide sequence from *L. perenne*. (SEQ ID NO: 21) The Lp1-SST transmembrane domain coding sequence is shown in underline. (SEQ ID NO: 22)

FIG. 16. Lp1-SST protein sequence from *L. perenne*. (SEQ ID NO: 23) The Lp1-SST transmembrane domain is shown in bold italics. (SEQ ID NO: 24)

FIG. 17. Lp1-SST-SacB chimeric nucleotide sequence. (SEQ ID NO: 25) The N-terminal signal coding sequence of SacB has been replaced by the Lp1-SST transmembrane domain coding sequence (indicated by underline). (SEQ ID NO: 26)

FIG. 18. Lp1-SST-SacB chimeric protein sequence. (SEQ ID NO: 27) The N-terminal signal sequence of SacB has been replaced by the Lp1-SST transmembrane domain (indicated by bold italics). (SEQ ID NO: 24)

FIG. 20. Lp1-SST-Lsc chimeric nucleotide sequence. (SEQ ID NO: 28) The N-terminal signal coding sequence of Lsc has been replaced by the Lp1-SST transmembrane domain coding sequence (indicated by underline). (SEQ ID NO: 26)

FIG. 21. Lp1-SST-Lsc chimeric protein sequence. (SEQ ID NO: 29) The N-terminal signal sequence of Lsc has been replaced by the Lp1-SST transmembrane domain (indicated by bold italics). (SEQ ID NO: 24)

FIG. 23. Nucleotide sequences of the AtRbcS::SPOR-SacB::NOS expression cassette. (SEQ ID NO: 30)

FIG. 24. Nucleotide sequences of the AtRbcS::SPOR-Lsc::NOS expression cassette. (SEQ ID NO: 31)

FIG. 25. Nucleotide sequences of the AtRbcS::Lp1-SST-SacB::NOS expression cassette. (SEQ ID NO: 32)

FIG. 26. Nucleotide sequences of the AtRbcS::Lp1-SST-Lsc::NOS expression cassette. (SEQ ID NO: 33)

FIG. 29. Nucleotide sequences of the TaRbcSp::SPOR-SacB::TaRbcst expression cassette. (SEQ ID NO: 34)

FIG. 30. Nucleotide sequences of the TaRbcSp::SPOR-SacB::TaRbcst TaRbcst+AtMYB32::IPT::35S expression cassette. (SEQ ID NO: 35)

FIG. 31. Nucleotide sequences of the TaRbcSp::SPOR-Lsc::TaRbcst expression cassette. (SEQ ID NO: 36)

FIG. 32. Nucleotide sequences of the TaRbcSp::SPOR-Lsc::TaRbcst+AtMYB32::IPT::35S expression cassette. (SEQ ID NO: 37)

FIG. 33. Nucleotide sequences of the TaRbcSp::Lp1-SST-SacB::TaRbcst expression cassette. (SEQ ID NO: 38)

FIG. 34. Nucleotide sequences of the TaRbcSp::Lp1-SST-SacB::TaRbcst TaRbcst+AtMYB32::IPT::35S expression cassette. (SEQ ID NO: 39)

FIG. 35. Nucleotide sequences of the TaRbcSp::Lp1-SST-Lsc::TaRbcst expression cassette. (SEQ ID NO: 40)

FIG. 36. Nucleotide sequences of the TaRbcSp::SPOR-Lsc::TaRbcst+AtMYB32::IPT::35S expression cassette. (SEQ ID NO: 41)

DETAILED DESCRIPTION OF THE INVENTION

Figure 1:
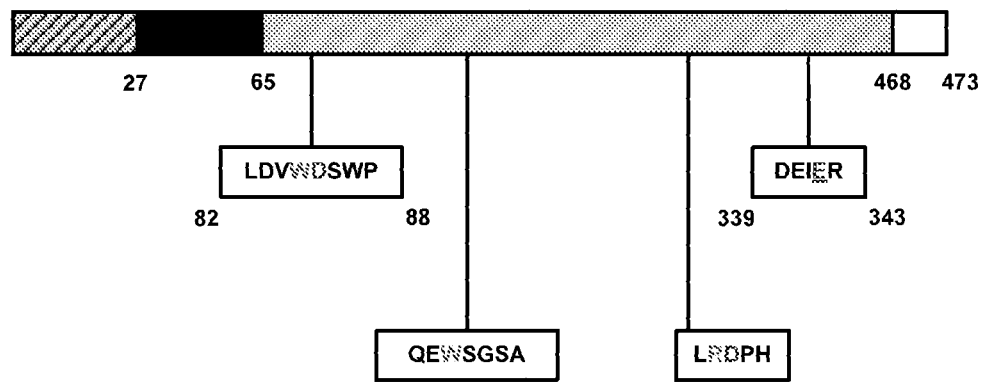
FIG. 1: Schematic representation of SacB protein from *Bacillus subtilis*, member of GH68 family. The four different regions shown are: N-terminal signal sequence; N-terminal variable region; catalytic core; and C-terminal variable region. Amino acid residues, including the catalytic triad (D86, D247 and E342) and sucrose binding (W85, W163 and R246). Also shown are SEQ ID No: 1 (LDVWDSWP), SEQ ID NO: 2 (QEWSGSA), SEQ ID NO: 3 (LRDPH) and SEQ ID NO: 4 (DEIER).
Figure 10:
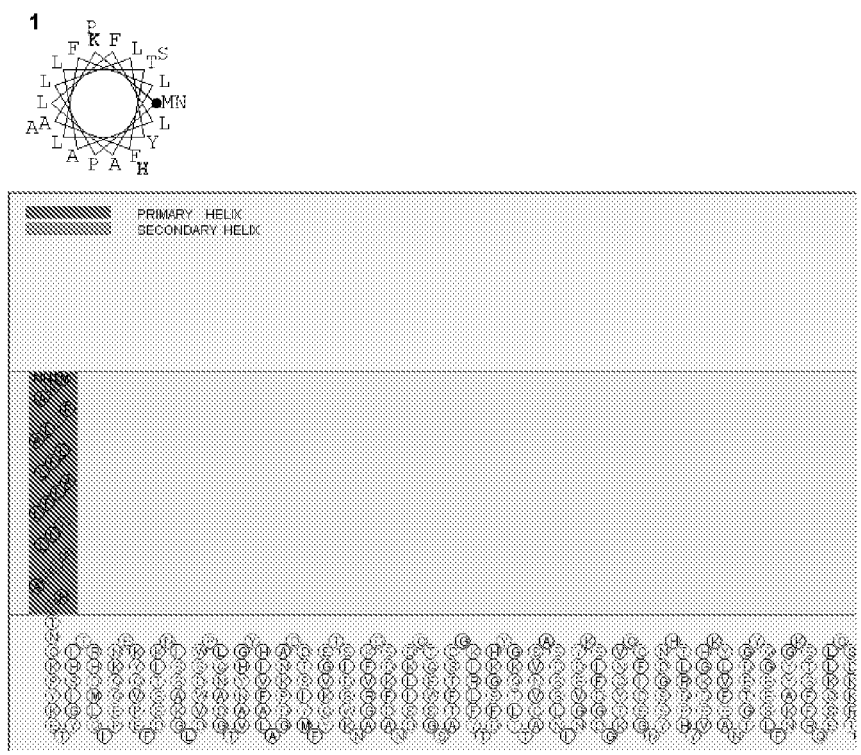
FIG. 10. Secondary Structure Prediction of SPOR-SacB fusion protein using Secondary Structure Prediction of Membrane Proteins software SOSUI http://bp.nuap.nagoya-u.ac.jp/sosui/

Fructans in forage grasses contribute significantly to the readily available energy in the feed for grazing ruminant animals. The fermentation processes in the rumen require considerable readily available energy. The improvement of the readily available energy in the rumen can increase the efficiency of rumen digestion. An increased efficiency in rumen digestion leads to an improved conversion of the forage protein fed to the ruminant animal into milk or meat, and to a reduction in nitrogenous waste.

Applicants have also found that the methods of the present invention may be facilitated by reprogramming photosynthetic cells for extended life, for example by delaying leaf senescence, to help increase plant biomass.

Applicants have found that a construct including a gene encoding a bacterial FT gene or functionally active fragment or variant thereof, may give superior results to a construct including a fusion gene encoding a translational fusion of two or more fructan biosynthetic enzymes. Use of a bacterial FT gene, for example containing both 1-SST and 1-FFT activities, may be technically less difficult than fusing separate genes, and may result in a construct that is more readily introduced into plants and/or performs better than a construct including fused genes.

For example, by expressing a bacterial FT gene, for example containing both 1-SST and 1-FFT activities, problems associated with differences in the expression patterns of these genes independently integrated into the plant genome may be alleviated, resulting in conversion of the sucrose molecules directly to fructans, those exhibiting a low degree of polymerisation ('low DP fructans') and a high degree of polymerization ('high DP fructans'). Furthermore, the FT protein may form a metabolic channel for the efficient biosynthesis of fructans.

Expression of FT genes in photosynthetic cells leading to the accumulation of low and high DP fructans in photosynthetic cells may lead to a release from inhibition mechanisms of photosynthesis, facilitating solar energy capture and increased $CO_2$ fixation.

Thus, applicants have found that reprogramming photosynthetic cells for extended life and enhanced fructan biosynthesis facilitates solar energy capture and increases plant biomass production including shoot and/or root growth.

Furthermore, since accumulation of low and high DP fructans has been associated with plant's tolerance to abiotic stress such as cold and drought; and since enhanced root growth and delayed leaf senescence has also been implicated in plant's tolerance of drought stress, reprogramming photosynthetic cells for extended life and enhanced fructan biosynthesis may facilitate yield stability and plants' tolerance of abiotic stresses.

Accordingly, in one aspect, the present invention provides a method of manipulating fructan biosynthesis in photosynthetic cells of a plant, said method including introducing into said plant an effective amount of a genetic construct including a promoter, or a functionally active fragment or variant thereof, operatively linked to a nucleic acid encoding a bacterial fructosyltransferase (FT) enzyme, or a functionally active fragment or variant thereof.

By 'manipulating fructan biosynthesis' is generally meant increasing fructan biosynthesis in a transformed plant relative to an untransformed control plant. However, for some applications it may be desirable to reduce or otherwise modify fructan biosynthesis in the transformed plant relative to the untransformed control plant. For example, it may be desirable to increase or decrease the activity of certain enzymes in the fructan biosynthetic pathway, in the transformed plant relative to the untransformed control plant.

By 'photosynthetic cells' is meant those cells of a plant in which photosynthesis takes place. Such cells generally contain the pigment chlorophyll and are otherwise known as green cells. Most photosynthetic cells are contained in the leaves of plants. Preferably, the genetic construct of the present invention is expressed in bundle sheath cells, more preferably in mesophyll and/or parenchymatous bundle sheath cells.

By 'an effective amount' is meant an amount sufficient to result in an identifiable phenotypic trait in said plant, or in a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

By 'genetic construct' is meant a recombinant nucleic acid molecule.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'->5' direction along the nucleic acid.

By 'nucleic acid' is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a bacterial fructosyltransferase (FT) enzyme' or 'bacterial fructosyl transferase gene' is meant a nucleic acid encoding an enzyme normally present in a bacterium which catalyses the synthesis of oligo- and/or polyfructans by transferring fructosyl moieties from sucrose-containing saccharides to acceptor molecules. The bacterial FT enzyme may include levansucrase activity and/or produce levan type fructan. The bacterial FT enzyme may include inulosucrase activity and/or produce inulin type fructan. A preferred bacterial FT includes both sucrose: sucrose 1-fructosyltransferase (1-SST) and fructan:fructan 1-fructosyltransferase (1-FFT) enzymatic activities. A SacB, Lsc or FTF gene may be used. A SacB or Lsc gene is particularly preferred.

By 'functionally active fragment or variant' in relation to a promoter is meant that the fragment or variant (such as an analogue, derivative or mutant) is capable of directing transcription of an operatively linked nucleic acid. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Preferably the fragment has a size of at least 20 nucleotides, more preferably at least 50 nucleotides, more preferably at least 100 nucleotides, more preferably at least 200 nucleotides, more preferably at least 300 nucleotides.

By 'functionally active' in relation to the nucleic acid encoding a bacterial FT enzyme is meant that the fragment or variant (such as an analogue, derivative or mutant) is capable of manipulating fructan biosynthesis in a plant by the method of the present invention, for example by being translated into an enzyme that is able to participate in the fructan biosynthetic pathway. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

By 'conservative nucleic acid changes' is meant nucleic acid substitutions that result in conservation of the amino acid in the encoded protein, due to the degeneracy of the genetic code and/or in conservative amino acid substitutions of one or more residues in the corresponding amino acid sequence.

By 'conservative amino acid substitutions' is meant the substitution of an amino acid by another one of the same class, the classes being as follows:

```
Nonpolar:        Ala, Val, Leu, Ile, Pro, Met Phe, Trp

Uncharged:       Gly, Ser, Thr, Cys, Tyr, Asn, Gln
polar:

Acidic:          Asp, Glu

Basic:           Lys, Arg, His
```

Other conservative amino acid substitutions may also be made as follows:

```
Aromatic:        Phe, Tyr, His

Proton Donor:    Asn, Gln, Lys, Arg, His, Trp

Proton:          Glu, Asp, Thr, Ser, Tyr, Asn, Gln
Acceptor:
```

Particularly preferred fragments and variants include one or more conserved sucrose binding/hydrolysis domains. Examples of such domains are shown in FIG. 1 and include LDVWDSWP (SEQ ID NO: 1), QEWSGSA (SEQ ID NO: 2), LRDPH (SEQ ID NO: 3) and DEIER (SEQ ID NO: 4).

Particularly preferred fragments and variants include a catalytic core. By a "catalytic core" is meant an internal region of the polypeptide excluding signal peptide and N- and C-terminal variable regions, which contains conserved sucrose binding and/or hydrolysis domains. An example of a catalytic core is shown in FIG. 1 and includes amino acid residues 65-468 of the SacB protein from *Bacillus subtilis*.

Particularly preferred fragments and variants include those lacking a signal peptide. By a "signal peptide" is meant an N-terminal signal sequence. An example of a signal peptide is shown in FIG. 1 and includes amino acids 1-27 of the SacB protein from *Bacillus subtilis*.

Particularly preferred fragments and variants have codon usage adapted for plants, including the start of translation for monocots and dicots.

Particularly preferred fragments and variants have cryptic splice sites and/or RNA destabilizing sequence elements inactivated or removed.

Preferably, the nucleic acid encoding a bacterial FT is isolated from or corresponds to a gene or genes from a bacterial species selected from the group consisting of *Bacillus*, *Lactobacillus* and *Streptococcus*, including *Bacillus subtilis*, *Bacillus amyloliquefaciens*, *Lactobacillus johnsonii* and *Streptococcus mutans*. Even more preferably, the nucleic acid encoding a bacterial FT enzyme is isolated from or corresponds to a SacB gene from *Bacillus subtilis* or *Bacillus amyloliquefaciens*, a Lsc gene from *Lactobacillus johnsonii* or a FTF gene from *Streptococcus mutans*.

In a particularly preferred embodiment the SacB gene includes a sequence selected from the group consisting of the sequence shown in FIG. 2 (SEQ ID NO: 5) and the nucleotide sequences encoding the polypeptide sequence shown in FIG. 3 (SEQ ID NO: 7); and functionally active fragments and variants thereof.

In a particularly preferred embodiment the Lsc gene includes a sequence selected from the group consisting of the sequence shown in FIG. 4 (SEQ ID NO: 9) and the nucleic acid sequences encoding the polypeptide sequence shown in FIG. 5 (SEQ ID NO: 10); and functionally active fragments and variants thereof.

Transgenic plants expressing bacterial levansucrases have been reported, in some instances, to display aberrant developmental phenotypes. While applicants do not wish to be restricted by theory, this may arise from inadequate compartmentalization of the levansucrase enzymes and fructan polymers. Cytosolic expression of a bacterial SacB gene in transgenic tobacco and potato plants was shown to be particularly disruptive to plant development (Caimi et al., 1997). However, plants expressing a bacterial fructosyl-transferase fused to vacuole-targeting signals accumulate fructans with no discernible effect on plant development (Ebskamp et al., 1994, Ye et al. 2001).

To reduce the possibility of aberrant developmental phenotypes the bacterial FT gene may be modified to alter its targeting signal sequence to direct the bacterial FT proteins to compartments where high fructan levels exist.

More particularly, a chimeric sequence may be created, whereby the N-signal peptide of the bacterial FT gene may be removed and replaced by a sub-cellular targeting sequence, preferably a vacuolar targeting sequence.

In a preferred embodiment, the vacuolar targeting sequence may be from or correspond to a gene encoding a preprosporamin protein, such as SPOR531 of sweet potato.

In a particularly preferred embodiment, the vacuolar targeting sequence may include a sequence selected from the group consisting of the sequence shown in bold underline in FIG. 6 (SEQ ID NO: 14) and the nucleic acid sequences encoding the polypeptide shown in bold underline in FIG. 7 (SEQ ID NO: 16); and functionally active fragments and variants thereof.

In a particularly preferred embodiment the nucleic acid encoding the bacterial FT enzyme may be a SPOR:SacB chimeric sequence. Preferably the SPOR:SacB chimeric sequence includes a sequence selected from the group consisting of the sequence shown in FIG. 8 (SEQ ID NO: 17) and the nucleic acid sequences encoding the polypeptide sequence shown in FIG. 9 (SEQ ID NO: 18); and functionally active fragments and variants thereof.

In a particularly preferred embodiment the nucleic acid encoding the bacterial FT enzyme may be a SPOR:Lsc chimeric sequence. Preferably, the SPOR:Lsc chimeric sequence includes a sequence selected from the group consisting of the sequence shown in FIG. 11 (SEQ ID NO: 19) and the nucleic acid sequences encoding the polypeptide sequence shown in FIG. 12 (SEQ ID NO: 20); and functionally active fragments and variants thereof.

In a particularly preferred embodiment, the genetic construct includes a sequence selected from the group consisting of the sequences shown in FIGS. 8 and 11 and the nucleic acid sequences encoding the polypeptides shown in FIGS. 9 and 12; and functionally active fragments and variants thereof.

In another preferred embodiment, a chimeric sequence may be is created, whereby the N-signal peptide of the bacterial FT gene may be removed and replaced by a transmembrane domain of a fructosyltransferase enzyme such as 1-SST.

In a particularly preferred embodiment, the transmembrane domain includes a sequence selected from the group consisting of the sequence shown in underline in FIG. 15 (SEQ ID NO: 21) and the nucleic acid sequences encoding the polypeptide shown in bold italics in FIG. 16 (SEQ ID NO: 23); and functionally active fragments and variants thereof.

In a particularly preferred embodiment, the genetic construct includes a sequence selected from the group consisting of the sequences shown in FIGS. 17 (SEQ ID NO: 25) and 20 (SEQ ID NO: 28) and the nucleic acid sequences encoding the polypeptides shown in FIGS. 18 (SEQ ID NO: 27) and 21 (SEQ ID NO: 29); and functionally active fragments and variants thereof.

By a 'chimeric sequence' is meant a hybrid produced recombinantly by expressing a fusion gene including two or more linked nucleic acids which originally encoded separate proteins, or functionally active fragments or variants thereof.

By a 'fusion gene' is meant that two or more nucleic acids are linked in such a way as to permit expression of the fusion protein, preferably as a translational fusion. This typically involves removing the stop codon from a nucleic acid sequence coding for a first protein, then appending the nucleic acid sequence of a second protein in frame. The fusion gene is then expressed by a cell as a single protein. The protein may be engineered to include the full sequence of both original proteins, or a functionally active fragment or variant of either or both.

The genetic construct may also include a nucleic acid sequence encoding a linker between the two linked nucleic acids. A 'linker' is any chemical, synthetic, carbohydrate, lipid, polypeptide molecule (or combination thereof) positioned between and joined to two adjacent active fragments in a fusion protein. A preferred linker of the invention is a flexible linker, such as a polypeptide chain consisting of one or more amino acid residues joined by amino acid bonds to the two active fragments. For example, a $(Gly_4 Ser)_3$ linker may be positioned between the two active fragments in the fusion protein.

The promoter used in the constructs and methods of the present invention may be a constitutive, tissue specific or inducible promoter. In a preferred embodiment, the promoter may be a light-regulated promoter, more preferably a photosynthetic promoter. By a 'light regulated promoter' is meant a promoter capable of mediating gene expression in response to light stimulus. By a 'photosynthetic promoter' is meant a promoter capable of mediating expression of a gene encoding a protein involved in a photosynthetic pathway in plants.

Less fructans accumulate in mature leaf blades than in leaf sheaths and stems. In order to specifically increase the level of fructans in leaf blades, a strategic approach has been devised that co-ordinately expresses fructan biosynthesis genes in photosynthetic cells. While applicants do not wish to be restricted by theory, the use of light-regulated or photosynthetic promoters may provide the following advantages:

Photosynthetic promoters are active in a large group of cells including leaf blades, the upper and outer stem (>55% cells);
They are active in sucrose producing cells (mesophyll and parenchymatous bundle sheath cells);
Their expression pattern temporally and spatially overlaps with sucrose accumulation;
Frutosyltransferase activity will remove sucrose from the source thereby preventing feedback suppression on photosynthesis, and may facilitate increases in $CO_2$ fixation;

Particularly preferred light-regulated promoters include a ribulose-1,5-bisphosphate carboxylase/oxygenase small subunit (RbcS) promoter and a chlorophyll a/b binding protein (CAB) promoter, and functionally active fragments and variants thereof.

The light-regulated promoter may be from any suitable plant species including monocotyledonous plants [such as maize, rice, wheat, barley, sorghum, sugarcane, energy cane, forage grasses (e.g. *Festuca, Lolium, Brachiaria, Paspalum, Pennisetum*), bioenergy grasses (e.g. switchgrass, *Miscanthus*)], dicotyledonous plants (such as *Arabidopsis*, soybean, canola, cotton, alfalfa and tobacco) and gymnosperms.

For transformation of monocots, preferably the light-regulated promoter is isolated from or corresponds to a promoter from a monocot species, more particularly a *Triticum* or *Lolium* species, even more particularly *Triticum aestivum* or *Lolium perenne*.

For transformation of dicots, preferably the light-regulated promoter is isolated from or corresponds to a promoter from a dicot species, more particularly an *Arabidopsis* species, even more particularly *Arabidopsis thaliana*.

In a particularly preferred embodiment, the RbcS promoter includes a sequence selected from the group consisting of the sequence shown in lower case italics in any one of FIGS. 23 to 26 (SEQ ID NO: 42), and functionally active fragments and variants thereof.

In another particularly preferred embodiment, the RbcS promoter includes a sequence selected from the group consisting of the sequence shown in lower case italics in any one of FIGS. 29 to 36 (SEQ ID NO: 43), and functionally active fragments and variants thereof.

The genetic constructs of the present invention may be introduced into the plants by any suitable technique. Techniques for incorporating the genetic constructs of the present invention into plant cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant to be transformed, and may be readily determined by an appropriately skilled person.

Cells incorporating the genetic constructs of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The methods of the present invention may be applied to a variety of plants, including monocotyledons [such as grasses (e.g. forage and bioenergy grasses including perennial ryegrass, tall fescue, Italian ryegrass, red fescue, reed canarygrass, big bluestem, cordgrass, napiergrass, wildrye, wild sugarcane, *Miscanthus*, switchgrass), corn or maize, rice, wheat, barley, sorghum, sugarcane, rye, oat) and energy crops (e.g. energy cane, energy sorghum)], dicotyledons [such as *Arabidopsis*, tobacco, soybean, canola, alfalfa, potato, cassava, clovers (e.g. white clover, red clover, subterranean clover), vegetable brassicas, lettuce, spinach] and gymnosperms.

In a further aspect of the present invention, there is provided a genetic construct capable of manipulating fructan biosynthesis in photosynthetic cells of a plant, said genetic construct including a light-regulated promoter, or functionally active fragment or variant thereof, operatively linked to a nucleic acid encoding a bacterial FT enzyme, or a functionally active fragment or variant thereof.

In a preferred embodiment, the genetic construct according to the present invention may be a vector.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

In a preferred embodiment of this aspect of the invention, the genetic construct may further include a terminator; said promoter, gene and terminator being operably linked.

The promoter, gene and terminator may be of any suitable type and may be endogenous to the target plant cell or may be exogenous, provided that they are functional in the target plant cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes (such as beta-glucuronidase (GUS) gene (gusA)]. The genetic construct may also contain a ribosome binding site for translation initiation. The genetic construct may also include appropriate sequences for amplifying expression.

In particular, the genetic construct may further include a nucleic acid sequence encoding a linker between the two linked nucleic acids, as hereinbefore described.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated. By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Applicant has also found that the methods of the present invention may result in enhanced biomass in the transformed plant relative to an untransformed control plant. This enhanced biomass may in turn be used as a selection tool for identifying transformed plants. This has the advantage that in some circumstances there may be no need to include an antibiotic resistance or other marker to select for transformants, where subsequent removal of such markers (and for the creation of marker-free plants) may present difficulties.

By 'enhancing biomass' or 'enhanced biomass' is meant enhancement of, increase in, or increased stability of biomass yield, including shoot and/or root growth, in a transformed plant relative to an untransformed control plant. For example, one or more growth characteristics selected from the group consisting of total leaf area, cumulative leaf area, leaf growth dynamics (ie. number of leaves over time), number of shoots, number of tillers, number of roots, root mass or weight, shoot mass or weight, root length, shoot length, stolon length, number of tubers, tuber weight, number of flowers, number of fruits, number of seeds, seed weight, fruit weight, percentage of flowering plants and seed yield per flower or per area sown; may be enhanced, increased or more stable in a transformed plant relative to an untransformed control plant.

This technique is particularly applicable to plants that are substantially genetically uniform or genetically identical or exhibit small phenotype differences in biomass prior to transformation.

Accordingly, in a further aspect of the present invention, there is provided a method of enhancing biomass in a plant, said method including introducing into said plant an effective amount of a genetic construct including a promoter, or a functionally active fragment or variant thereof, operatively liked to a nucleic acid encoding a bacterial FT-enzyme, or a functionally active fragment or variant thereof. Preferably, the promoter is a light regulated promoter.

In a still further aspect of the present invention, there is provided a method of enhancing biomass in a plant, said method including introducing into said plant effective amount of
(a) a genetic construct capable of manipulating fructan biosynthesis in photosynthetic cells of the plant, said genetic construct including a promoter, or a functionally active fragment or variant thereof, operatively linked to a nucleic acid encoding a bacterial FT enzyme, or a functionally active fragment or variant thereof; and (b) a genetic construct capable of manipulating senescence in the plant.

The genetic constructs may be introduced into the plant by any suitable technique, as hereinbefore described, and may be introduced concurrently, sequentially or separately.

Preferably the genetic construct capable of manipulating fructan biosynthesis is as hereinbefore described.

Preferably the genetic construct capable of manipulating senescence in the plant is capable of manipulating senescence in photosynthetic cells of the plant.

Preferably the genetic construct capable of manipulating senescence includes a myb gene promoter or modified myb gene promoter, or a functionally active fragment or variant thereof, operatively linked to a gene encoding an enzyme involved in biosynthesis of a cytokinin, or a functionally active fragment or variant thereof.

Suitable genetic constructs or vectors are described in International patent application PCT/AU01/01092 and U.S. patent application Ser. No. 11/789,526, the entire disclosures of which are incorporated herein by reference.

"Manipulating senescence" generally relates to delaying senescence in the transformed plant or cells or organs of the transformed plant, eg photosynthetic cells, relative to an untransformed control plant. However, for some applications it may be desirable to promote or otherwise modify senescence in the plant. Senescence may be promoted or otherwise modified for example, by utilizing an antisense gene.

The myb gene promoter may be of any suitable type. Preferably the myb gene promoter is a myb32 gene promoter. Preferably the myb gene promoter is from *Arabidopsis*, more preferably *Arabidopsis thaliana*. Most preferably the myb gene promoter includes a nucleotide sequence selected from the group consisting of the sequence shown in Sequence ID No: 1 of PCT/AU01/01092 (SEQ ID NO: 44) and functionally active fragments and variants thereof.

A suitable promoter is described in Li et al., Cloning of three MYB-like genes from *Arabidopsis* (PGR 99-138) Plant Physiology 121:313 (1999).

By a "modified myb gene promoter" is meant a promoter normally associated with a myb gene, which promoter is modified to delete or inactivate one or more root specific motifs and/or pollen specific motifs in said promoter.

Preferably the modified myb gene promoter is a modified myb32 gene promoter. Preferably the modified myb gene promoter is modified from the myb gene promoter from *Arabidopsis*, or more preferably *Arabidopsis thaliana*.

A suitable promoter which may be modified according to the present invention is described in Li et al., Cloning of three MYB-like genes from *Arabidopsis* (PER 99-138) Plant Physiology 121:313 (1999).

By a "root specific motif" is meant a sequence of 3-7 nucleotides, preferably 4-6 nucleotides, more preferably 5 nucleotides, which directs expression of any associated gene in the roots of a plant.

Preferably the root specific motif includes a consensus sequence ATATT or AATAT.

By a "pollen specific motif" is meant a sequence of 3-7 nucleotides, preferably 4-6 nucleotides, more preferably 4 or 5 nucleotides, which directs expression of an associated gene in the pollen of a plant.

Preferably the pollen specific motif includes a consensus sequence selected from the group consisting of TTTCT, AGAAA, TTCT and AGAA.

A root or pollen specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences show in Sequence ID Nos: 2, 3 and 4 of U.S. Ser. No. 11/789,526 (SEQ ID NOs: 45-47) and functionally active fragments and variants thereof. By a "gene encoding an enzyme involved in biosynthesis of a cytokinin" is meant a gene encoding an enzyme involved in the synthesis of cytokinins such kinetin, zeatin and benzyl adenine, for example a gene encoding isopentyl transferase (ipt), or ipt-like gene such as the sho gene (eg. from petunia). Preferably the gene is an isopentenyl transferase (ipt) gene or sho gene. In a preferred embodiment, the gene is from a species selected from the group consisting of *Agrobacterium*, more preferably *Agrobacterium tumefaciens*; *Lotus*, more preferably *Lotus japonicus*; and *Petunia*, more preferably *Petunia hybrida*.

Most preferably the gene includes a nucleotide sequence selected from the group consisting of the sequences shown in Sequence ID Nos: 5, 7 and 9 of U.S. Ser. No. 11/789,526 (SEQ ID NOs: 48-50), sequences encoding the polypeptides shown in Sequence ID Nos: 6, 8 and 10 of U.S. Ser. No. 11/789,526 (SEQ ID NOs: 51-53) and functionally active fragments and variants thereof.

The present invention also provides a method of selecting for transformed plants, said method including introducing into said plants an effective amount of a genetic construct including a promoter, or a functionally active fragment or variant thereof, operatively liked to a nucleic acid encoding a bacterial FT enzyme, or a functionally active fragment or variant thereof and selecting plants with enhanced biomass. Preferably the promoter is a light regulated promoter.

In a further aspect of the present invention there is provided a transgenic plant cell, plant, plant seed or other plant part with modified fructan biosynthetic characteristics or enhanced biomass relative to an untransformed control plant; said plant cell, plant, plant seed or other plant part including a genetic construct or vector according to the present invention.

By "modified fructan biosynthetic characteristics" is meant that the transformed plant exhibits increased fructan biosynthesis and/or contains increased levels of soluble carbohydrate relative to an untransformed control plant.

In a preferred embodiment the a transgenic plant cell, plant, plant seed or other plant part with enhanced biomass has an increase in biomass of at least approximately 15%, more preferably at least approximately 25%, more preferably at least approximately 35%, more preferably at least approximately 50% relative to an untransformed control plant.

For example, biomass may be increased by between approximately 15% and 500%, more preferably between approximately 25% and 300%, more preferably between approximately 35% and 200%, more preferably between approximately 50% and 100% relative to an untransformed control plant.

In a preferred embodiment, the transgenic plant cell, plant, plant seed or other plant part with modified fructan biosynthetic characteristics has an increase in soluble carbohydrate of least approximately 15%, more preferably at least approximately 25%, more preferably at least approximately 35%, more preferably at least approximately 50% relative to an untransformed control plant.

For example, soluble carbohydrates may be increased by between approximately 15% and 500%, more preferably between approximately 25% and 300%, more preferably between approximately 35% and 200%, more preferably between approximately 50% and 100% relative to an untransformed control plant.

Preferably the transgenic plant cell, plant, plant seed or other plant part is produced by a method according to the present invention.

The present invention also provides a transgenic plant, plant seed or other plant part derived from a plant cell of the present invention and including a genetic construct or vector of the present invention.

The present invention also provides a transgenic plant, plant seed or other plant part derived from a plant of the present invention and including a genetic construct or vector of the present invention.

Preferably, the transgenic plant cell, plant, plant seed or other plant part is a *Lolium* species, more preferably *Lolium perenne* or *Lolium arundinaceum*.

Preferably, the transgenic plant cell, plant, plant seed or other plant part is a cereal grain, more preferably a *Triticum* species, more preferably wheat (*Triticum aestivum*).

For example, the present invention enables the production of transgenic perennial ryegrass plants with increased fructans in leaf blades, vigorous growth and greater tolerance to abiotic stress, for improved nutrition for grazing animals.

The present invention also enables the production of transgenic wheat plants with increased fructans, vigorous growth, and tolerance to abiotic stress, for increased mass of usable carbohydrates, eg. for bio-fuel production or animal feed.

By 'plant cell' is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

By 'transgenic' is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into either the nuclear or plastidic genome.

The present invention will now be more fully described with reference to the accompanying examples and drawings. It should be understood, however, that the description following is illustrative only and should not be taken in any way as a restriction on the generality of the invention described above.

EXAMPLES

Example 1

Isolation of Bacterial Fructan Biosynthesis Genes

FIG. 1 presents a schematic representation of SacB protein from *Bacillus subtilis*. The four different regions shown are: N-terminal signal sequence; N-terminal variable region; catalytic core; and C-terminal variable region. Structurally, most of the bacterial inulosucrases and levansucrases share the N-terminal signal peptide, a catalytic triad. This sequence is removed during the sequence modification. The residues involved in sucrose binding are located inside the catalytic core sequences and remain untouched during the modification.

The bacterial levansucrase (SacB) and inulosucrase (Lsc) nucleotide and protein sequences are provided in FIGS. 2-5, respectively. However, for transformation into plants the bacterial levansucrase and inulosucrase sequences are also modified in the following manner:

Removal of the bacterial N-signal peptide;
Adaptation of codon usage, including the start of translation for monocots and dicots;
Removal of cryptic splice sites and RNA destabilizing sequence elements;
The coding sequence is further modified with putative sub-cellular targeting sequences including vacuolar targeting sequences for monocots and dicots as well as including plant 1-SST-specific transmembrane domains.

Outlines of these changes are indicated in the following example.

Example 2

Modification of Bacterial Fructan Biosynthesis Genes

Targeting of Bacterial Ft Genes to Specific Cellular Compartments

To direct the bacterial FT genes away from the cytosol and to compartment where both sucrose and fructan accumulate the coding sequences of SacB and Lsc are modified with a putative vacuolar targeting sequence from the pre-prosporamin protein (SPOR531) of sweet potato (*Ipomoea batatas*). The propeptide of a precursor to sporamin is required for targeting of sporamin to the vacuole (Hattori et al., 1985). The vacuolar targeting information of sporamin is encoded in an amino-terminal propeptide and is indicated in FIGS. 5 and 6.

Sequence modification involves the removal of the N-signal peptide from both the SacB and Lsc bacterial fuctan biosynthesis genes and the addition of SPOR531 vacuolar targeting signal (FIGS. 7-8 and 10-11, respectively).

Figure 13:
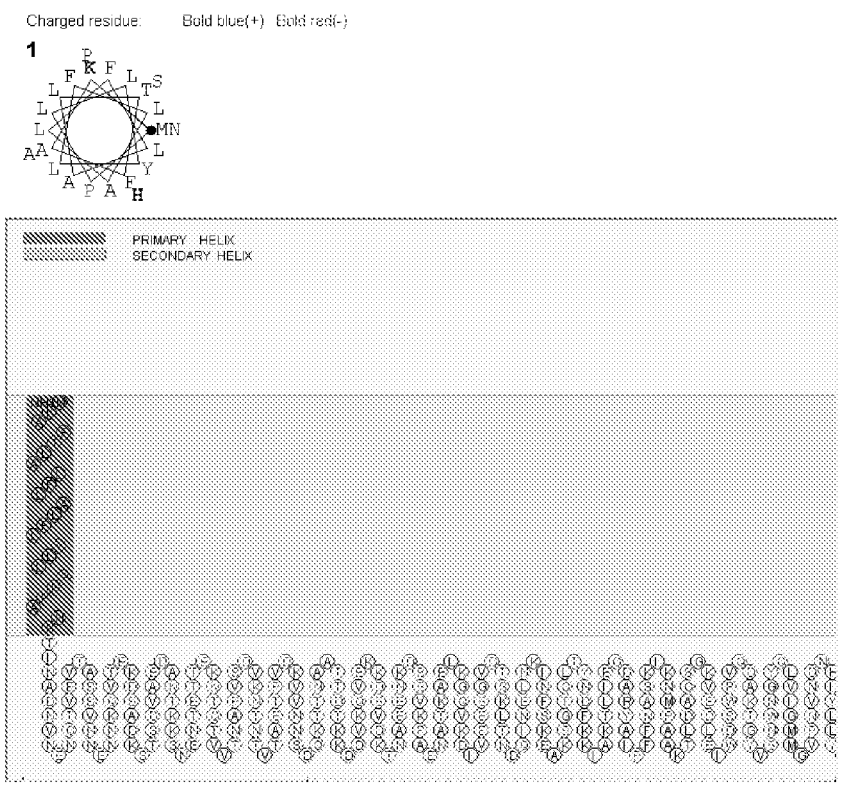
FIG. 13. Secondary Structure Prediction of SPOR-Lsc fusion protein using Secondary Structure Prediction of Membrane Proteins software SOSUI http://bp.nuap.nagoya-u.ac.jp/sosui/
Figure 14:
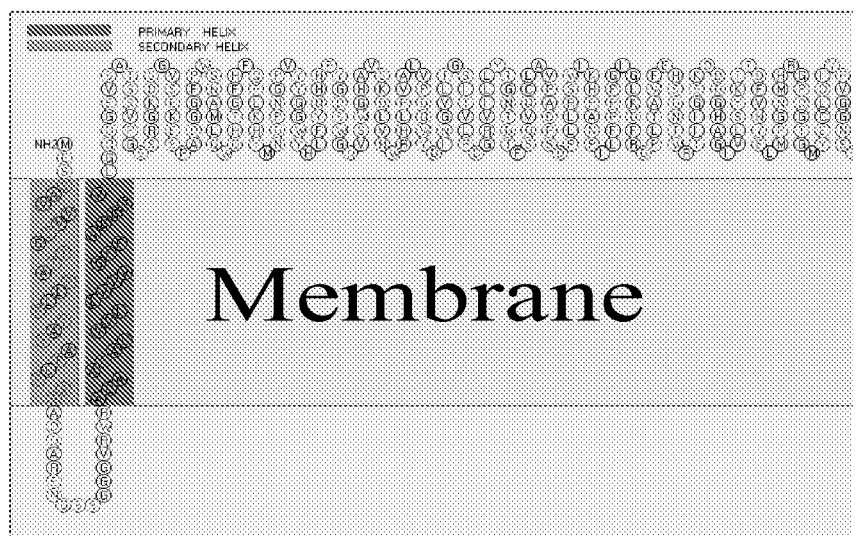
FIG. 14. Secondary Structure Prediction of Lp1-SST using Secondary Structure Prediction of Membrane Proteins software SOSUI http://bp.nuap.nagoya-u.ac.jp/sosui/
Figure 19:
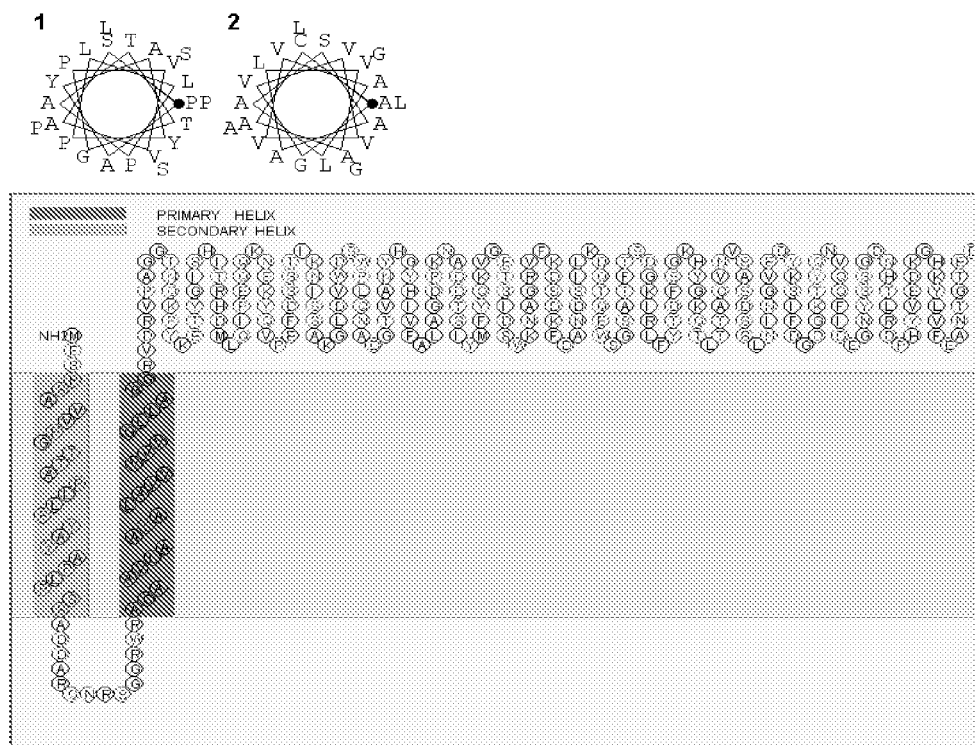
FIG. 19. Secondary Structure Prediction of Lp1-SST-SacB fusion protein using Secondary Structure Prediction of Membrane Proteins software SOSUI http://bp.nuap.nagoya-u.ac.jp/sosui/
Figure 22:
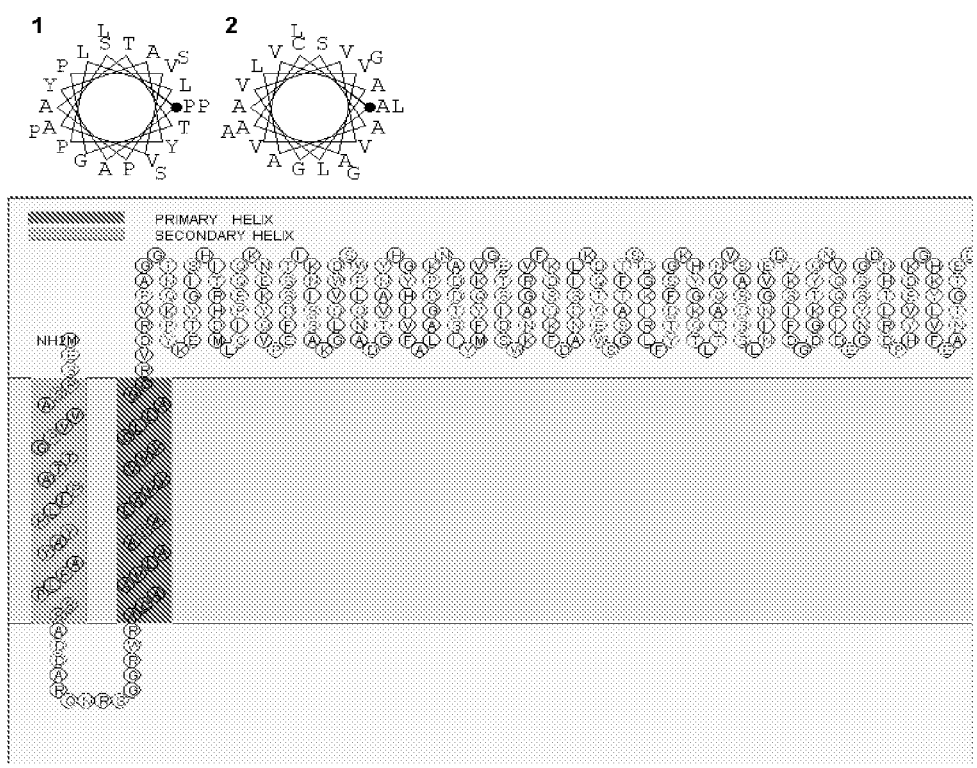
FIG. 22. Secondary Structure Prediction of Lp1-SST-Lsc fusion protein using Secondary Structure Prediction of Membrane Proteins software SOSUI http://bp.nuap.naqoya-u.ac.jp/sosui/

Prediction of subcellular localisation and topology of the modified proteins using the Secondary Structure Prediction of Membrane Proteins software SOSUI http://bp.nuap.nagoya-u.ac.jp/sosui/ indicates a transmembrane localization triggered by the vacuolar targeting signal (FIGS. 9 and 12). Addition of Transmembrane Domains from Lp1-SST Protein to Bacterial FT Genes The SOSUI software was also used to predict the secondary structure of the *Lolium perenne* 1-SST gene. This structure, indicating a transmembrane domain at the N terminus is indicated in FIG. 13. The transmembrane domain coding and protein sequences are indicated in FIGS. 14 and 15, respectively.

Sequence modification involves the removal of the N-signal peptide from both the SacB and Lsc bacterial fuctan biosynthesis genes and the addition of the Lp1-SST transmembrane domain (FIGS. 16-17 and 19-20, respectively). The modified sequences of SacB and Lsc were assessed using the Secondary Structure Prediction of Membrane Proteins software SOSUI for subsellular localization and protein topology and their predicted secondary structures are presented in FIGS. 18 and 21, respectively.

Example 3

Generating Vectors for Stable Transformation in Dicots

Synthesis of Expression Constructs

Expression constructs utlising photosyntheic promoters, the modified bacterial fructan biosynthesis genes indicated in Example 2 and the NOS terminator sequence for transformation into dicot plants is artificially synthesised.

The use of a photosynthetic promoter expresses the genes in tissues that accumulate fructans, while the modified sequences target the protein to specific plant cell compartments.

The Ribulose-1,5-bisphosphate carboxylase/oxygenase Small subunit (RbcS) is a well-characterised light-regulated gene in higher plants. A 1700 bp fragment of the *Arabidopsis thaliana* Ribulose-1,5-bisphosphate carboxylase/oxygenase Small subunit (AtRbcS) promoter sequence has previously been cloned. Primers are designed to amplify a smaller fragment containing the TATA signal from the AtRbcS promoter for use in expression vectors.

The newly predicted sequences for the modified bacterial fructan biosynthetic genes are be artificially synthesised altering codon usage for expression in plants, as well as removing cryptic splice sites and RNA destabilizing sequence elements, to optimise their performance in the plant cell.

FIGS. 23-26 represent the expression cassettes AtRbcS:: SPOR-SacB::NOS, (SEQ ID NO: 30) AtRbcS::SPOR-Lsc:: NOS (SEQ ID NO: 31), AtRbcS::Lp1-SST-SacB::NOS (SEQ ID NO: 32) and AtRbcS::Lp1-SST-Lsc::NOS (SEQ ID NO: 33), respectively, and have not yet had codon optimisation or removal of destabilising elements.
Generation of Constructs Containing Modified Bacterial FT Genes Driven by an *Arabidopsis* Photosynthetic Promoter for Transformation of Dicots Each synthesised expression cassette is placed in a Gateway enabled pDONOR vector for recombination into the final destination vector for transformation into plants.

Figure 27:
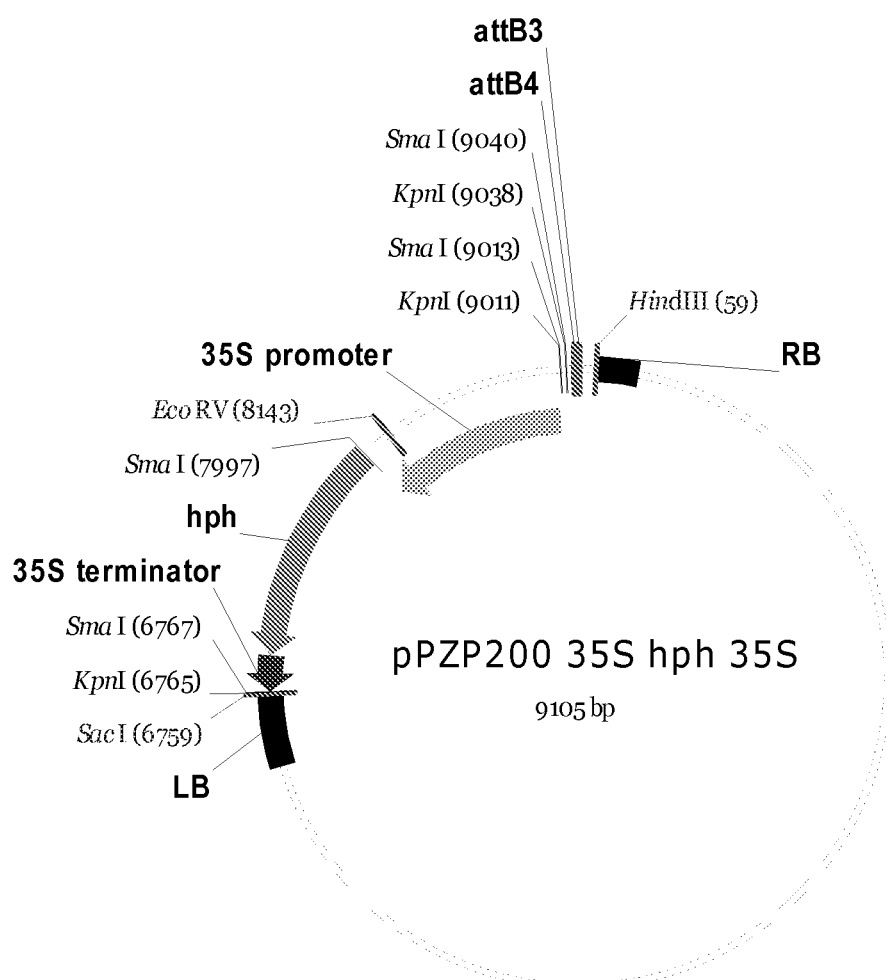
FIG. 27. Gateway pDestination vector

A Gateway enabled destination vector, containing the 35Sp:hph:35St selectable marker cassette has been generated, pPZP200_35Sp_hph_35St_R4/R3 (FIG. 27).

Figure 28A:
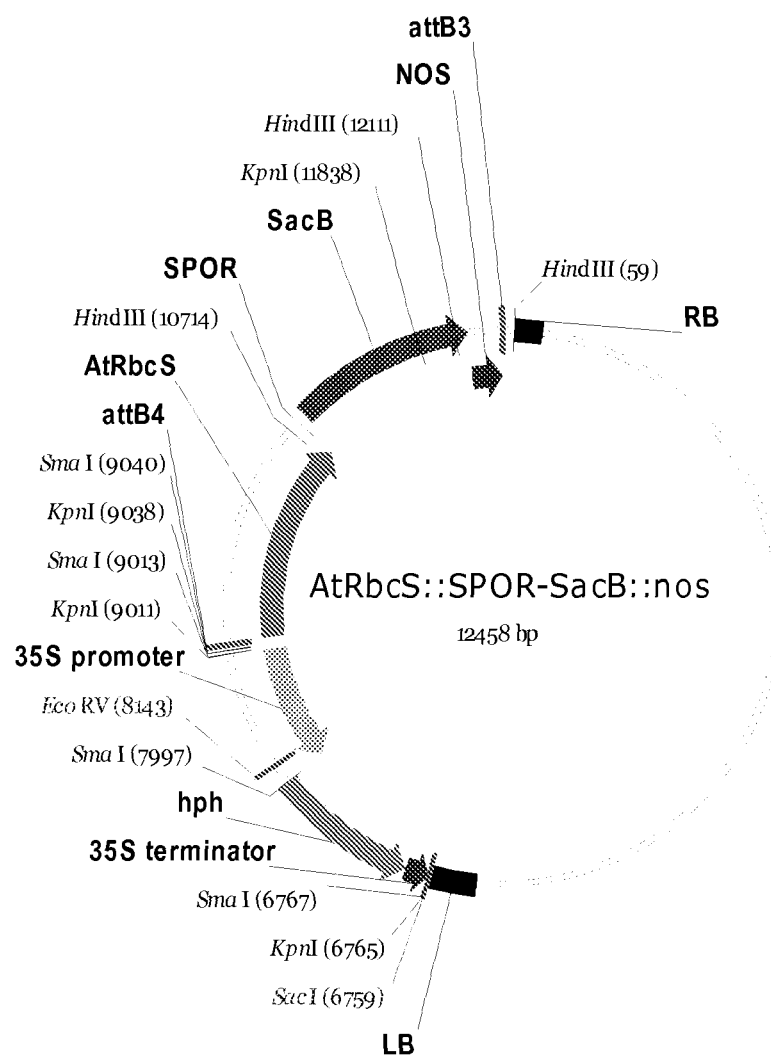
FIGS. 28A-D. Gateway pDestination vectors for transformation of dicots:
A. AtRbcS::SPOR-SacB::NOS; B. AtRbcS::SPOR-Lsc::NOS C. AtRbcS:Lp1-SST-SacB::NOS and D. AtRbcS::Lp1-SST-Lsc::NOS.
Figure 28B:
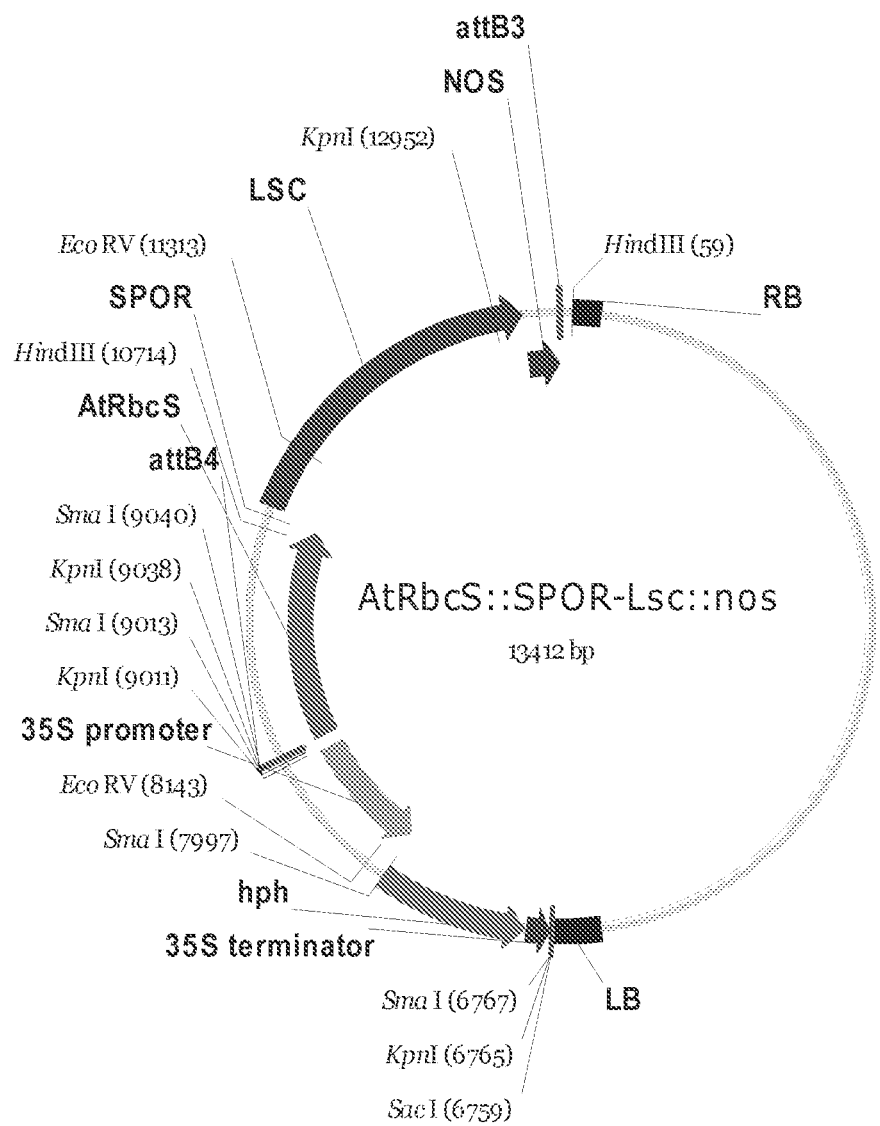
Figure 28C:
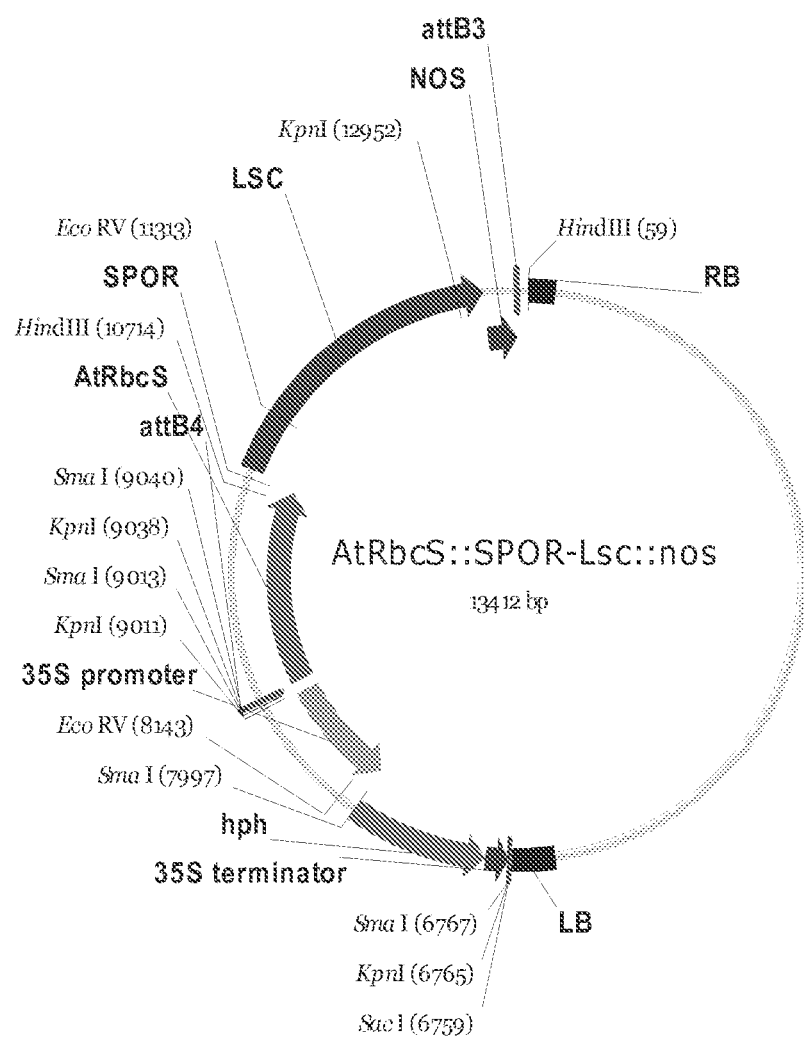
Figure 28D:
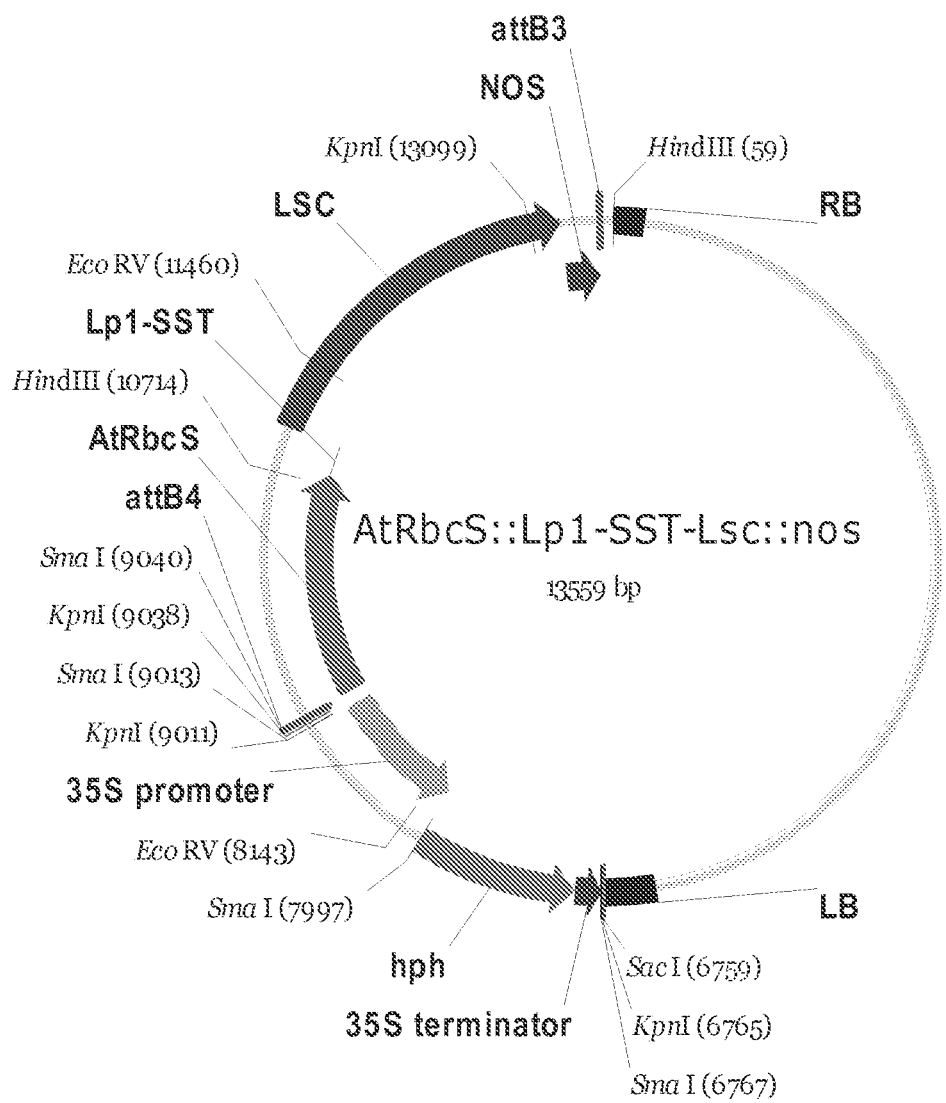
Figure 37:
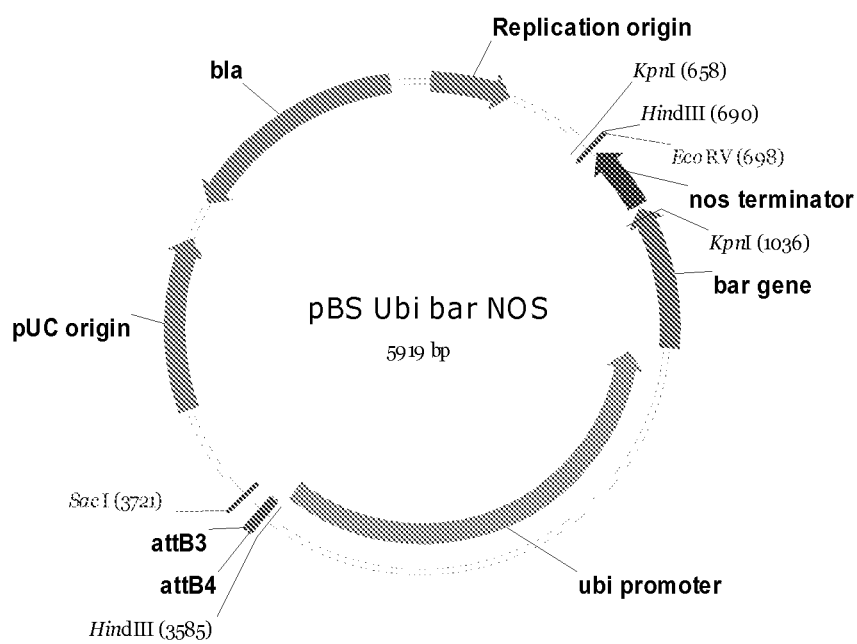
FIG. 37. Gateway pDestination vector pBS:ubi::bar::NOS
Figure 38A:
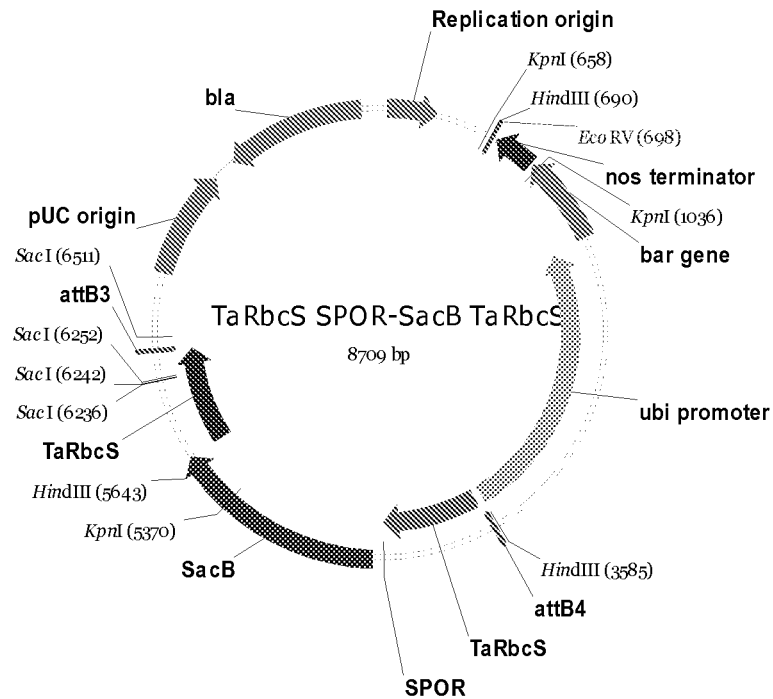
FIGS. 38A and B. Gateway pDestination vectors for transformation of monocots:
A. TaRbcS::SPOR-SacB::TaRbcS and B. TaRbcS::SPOR-SacB::TaRbcS+AtMYB32::IPT::35S FIGS. 39A and B. Gateway pDestination vectors for transformation of monocots:
A. TaRbcS::SPOR-Lsc::TaRbcS and B. TaRbcS::SPOR-Lsc::TaRbcS+AtMYB32::IPT::35S FIGS. 40A and B. Gateway pDestination vectors for transformation of monocots:
A. TaRbcS::Lp1-SST-SacB::TaRbcS and B. TaRbcS::Lp1-SST-SacB::TaRbcS+AtMYB32::IPT::35S FIGS. 41A and B. Gateway pDestination vectors for transformation of monocots:
A. TaRbcS::Lp1-SST-Lsc::TaRbcS and B. TaRbcS::Lp1-SST-Lsc::TaRbcS+AtMYB32::IPT::35S
Figure 38B:
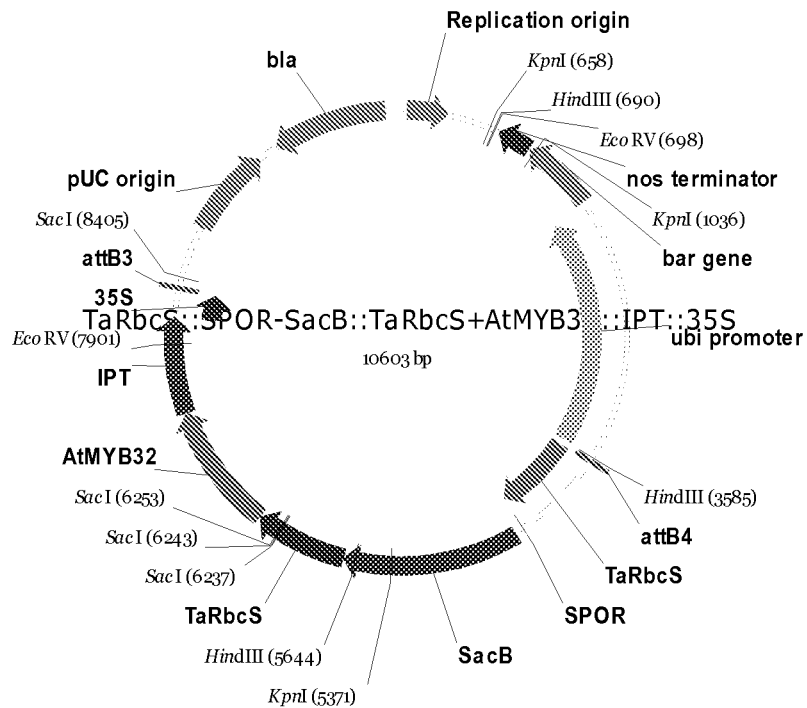
Figure 39A:
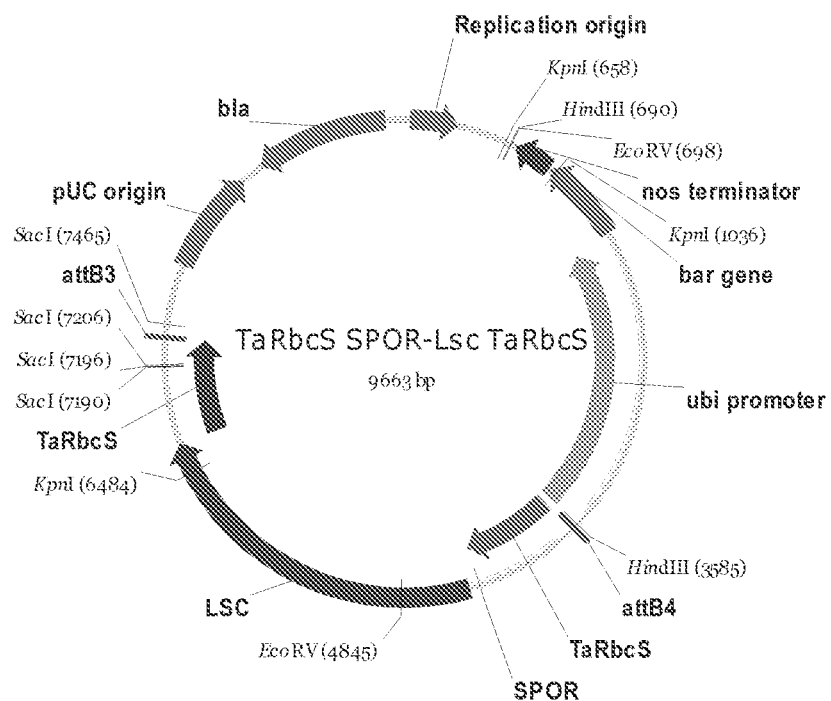
Figure 39B:
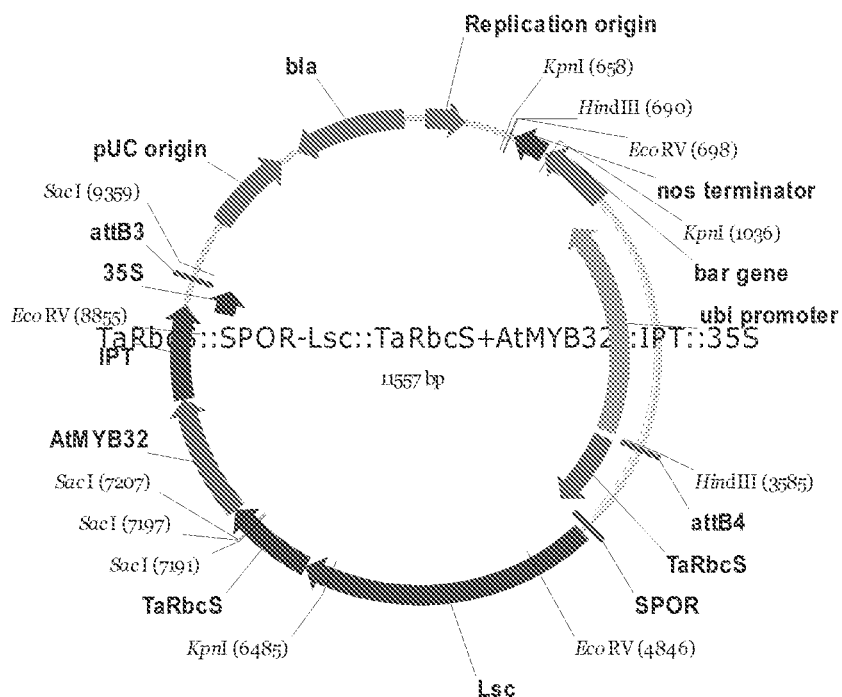
Figure 40A:
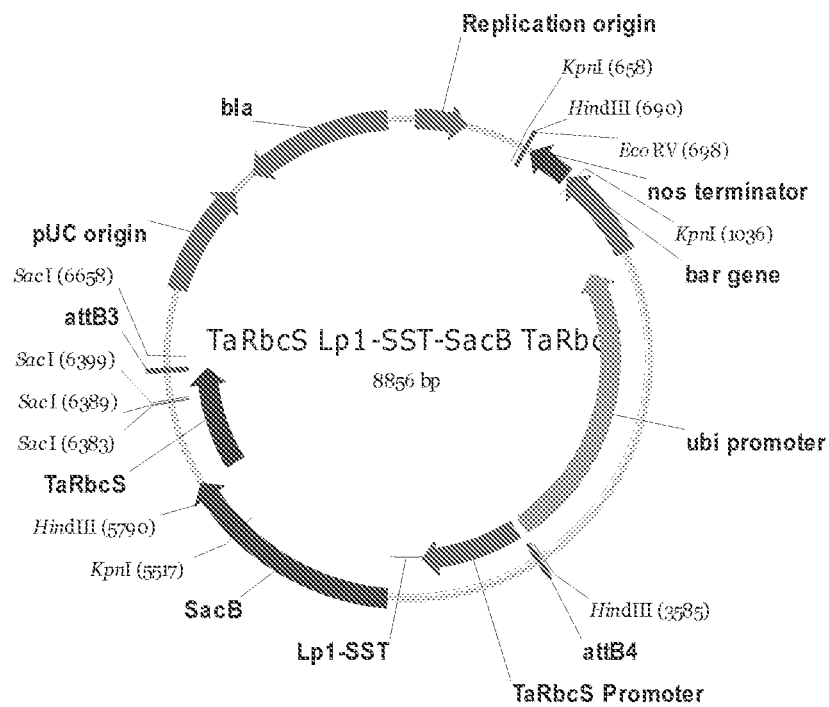
Figure 40B:
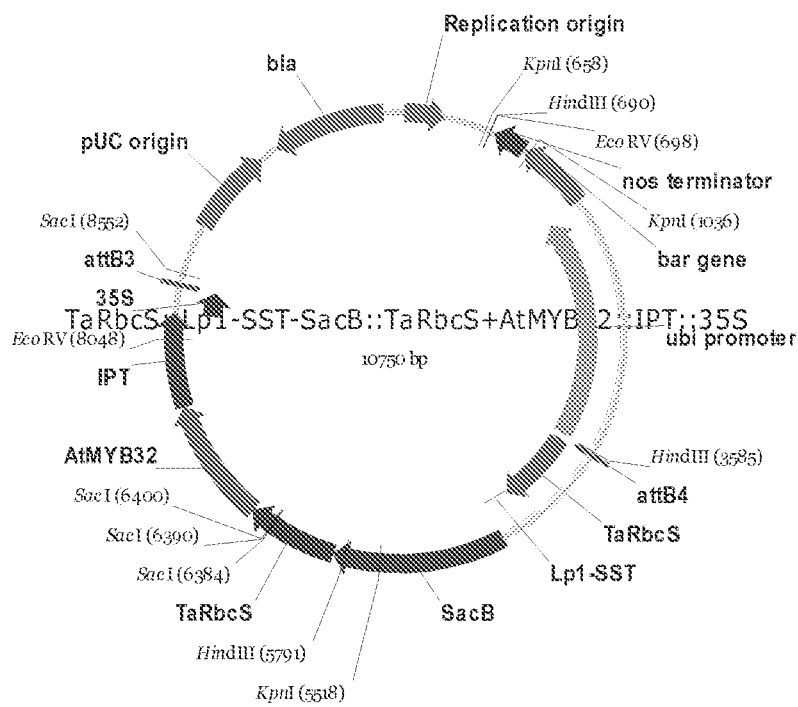
Figure 41A:
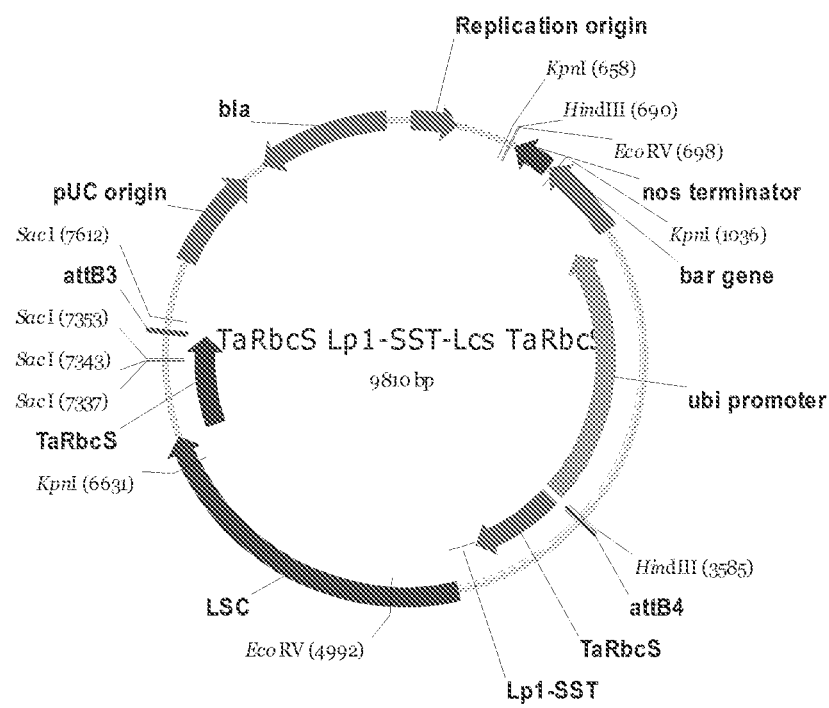
Figure 41B:
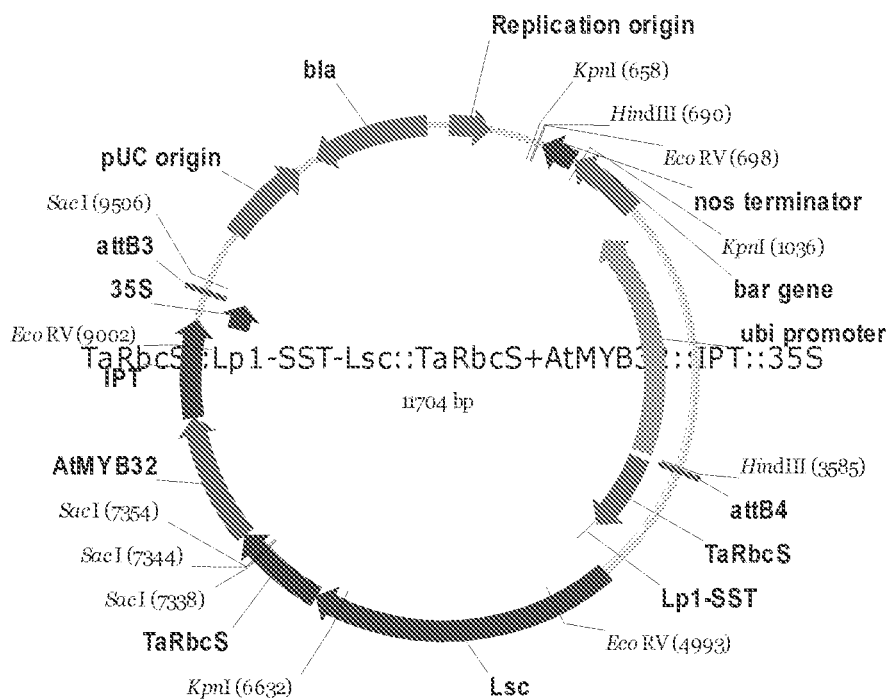

Gateway LR recombination reactions produce the following destination vectors for transformation into dicots:
AtRbcS::SPOR-SacB::NOS (FIG. 28A);
AtRbcS::SPOR-Lsc::NOS (FIG. 28B);
AtRbcS::Lp1-SST-SacB::NOS (FIG. 28*c*) and
AtRbcS::Lp1-SST-Lsc::NOS (FIG. 28*d*).

Example 4

Generating Vectors for Stable Transformation in Monocots

Synthesis of Expression Constructs

Expression constructs utilising the bread wheat photosyntheic promoter (TaRbcsp), the modified bacterial fructan biosynthesis genes, indicated in Example 2, and the TaRbcS terminator sequence for transformation into monocot plants are artificially synthesised. The use of a photosynthetic promoter expresses the genes in tissues that accumulate fructans, while the modified sequences target the protein to specific plant cell compartments.

The bread wheat (*Triticum aestivum*), TaRbcS regulatory sequences (promoter and terminator) have previously been cloned (Zeng, et al., 1995; Sasanuma, 2001). A 695 bp promoter fragment from sequence previously published containing the TATA signal from the TaRbcS gene (NCBI accession number AB042069) is amplified for use in expression vectors.

The newly predicted sequences for the modified bacterial fructan biosynthetic genes are artificially synthesised altering codon usage for expression in plants, as well as removing cryptic splice sites and RNA destabilizing sequence elements, to optimise their performance in the plant cell.

Using the methods outlined above expression cassettes are synthesised to generate transgenic plants that contain both fructan biosynthetic genes and the LXR™ technology. LXR™ technology is based on an expression cassette containing one candidate gene (IPT) for delayed leaf senescence under the control of the AtMYB32 gene promoter. The expression cassette AtMYB3p::IPT::35St is described in International patent application PCT/AU01/01092. The phenotype of transgenic LXR™ plants includes a decrease in leaf yellowing and chlorophyll loss associated with plant age leading to an increased photosynthetic ability resulting in improved tillering and vegetative biomass.

Integration of the two technologies leads to an increased expression of fructans via an extension of activation of the photosynthetic promoters and may have significant impact on the efficacy of a variety of applications by increasing the range of productivity in plants.

FIGS. 29-36 represent the expression cassettes, TaRbcS::SPOR-SacB::TaRbcS (SEQ ID NO: 34), TaRbcS::SPOR-SacB::TaRbcS+AtMYB32::IPT::35S (SEQ ID NO: 35), TaRbcS::SPOR-Lsc::TaRbcS (SEQ ID NO: 36), TaRbcS::SPOR-Lsc::TaRbcS+AtMYB32::IPT::35S (SEQ ID NO: 37), TaRbcS::Lp1-SST-SacB::TaRbcS (SEQ ID NO: 38), TaRbcS::Lp1-SST-SacB::TaRbcS+AtMYB32::IPT::35S (SEQ ID NO: 39), TaRbcS::Lp1-SST-Lsc::TaRbcS (SEQ ID NO: 40) and TaRbcS::Lp1-SST-Lsc::TaRbcS+AtMYB32::IPT::35S (SEQ ID NO: 41), respectively, and have not yet had codon optimisation or removal of destabilising elements.

Generation of Constructs Containing Modified Bacterial FT Genes Driven by a *Triticum* Photosynthetic Promoter for Transformation of Monocots Each synthesised expression cassette is placed in a Gateway enabled pDONOR vector for recombination into the final destination vector for transformation into plants.

A Gateway enabled destination vector, containing the Ubi::bar::NOS selectable marker cassette has been generated, pBS::Ubi::bar::NOS_R4/R3 (FIG. 37). Gateway LR recombination reactions produce the following destination vectors for transformation in to monocots:

TaRbcS::SPOR-SacB::TaRbcS (FIG. 38A);
TaRbcS::SPOR-SacB::TaRbcS+AtMYB32::IPT::35S (FIG. 38B);
TaRbcS::SPOR-Lsc::TaRbcS (FIG. 39A);
TaRbcS::SPOR-Lsc::TaRbcS+AtMYB32::IPT::35S (FIG. 39B);
TaRbcS::Lp1-SST-SacB::TaRbcS (FIG. 40A);
TaRbcS::Lp1-SST-SacB::TaRbcS+AtMYB32::IPT::35S (FIG. 40B);
TaRbcS::Lp1-SST-Lsc::TaRbcS (FIG. 41A) and
TaRbcS::Lp1-SST-Lsc::TaRbcS+AtMYB32::IPT::35S (FIG. 41B)

REFERENCES

Caimi P G, McCole L M, Klein T M, Hershey H P. 1997. Cytosolic expression of the *Bacillus amyloliquefaciens* SacB protein inhibits tissue development in transgenic tobacco and potato. New Phytologist 136, 19-28

Caimi P G, McCole L M, Klein T M, Kerr P S. 1996. Fructan accumulation and sucrose metabolism in transgenic maize endosperm expressing a *Bacillus amyloliquefaciens* sacB gene. Plant Physiology 110, 355-363

Cairns AJ. Fructan biosynthesis in transgenic plants. 2003. J Expt Biol 54: 549-67

Ebskamp MJM, van der Meer I M, Spronk B A, Weisbeek P J, Smeekens S C M. 1994. Accumulation of fructose polymers in transgenic tobacco. Bio/Technology 12, 272-275

Hattori T, Nakagawa T, Maeshima M, Nakamura K, Asahi T (1985) Molecular cloning and nucleotide sequence of cDNA for sporamin, the major soluble protein of sweet potato tuberous roots. Plant Mol Biol 5: 313-320

Sasanuma, T. (2001). Characterization of the rbcS multigene family in wheat: subfamily classification, determination of chromosomal location and evolutionary analysis. Mol Genetics Genomics 265(1): 161-171.

Ye X D, Wu X L, Zhao H, Frehner M, Noesberger J, Potrykus I, Spangenberg G. 2001. Altered fructan accumulation in transgenic *Lolium multiflorum* plants expressing a *Bacillus subtilis* sacB gene. Plant Cell Reports 20, 205-212

Zeng, W. K., et al. (1995). PCR Amplification and Sequencing of a Wheat rbcS Gene Promoter. Acta Bot Sinica 37, 496-500.

The invention claimed is:

1. A method for manipulating fructan biosynthesis in photosynthetic cells of a grass plant, said method comprising introducing into said grass plant an effective amount of a genetic construct comprising a promoter operatively linked to a nucleic acid encoding a bacterial fructosyltransferase (FT) enzyme, wherein said promoter is a light-regulated promoter.

2. The method according to claim 1 wherein said bacterial FT enzyme comprises both sucrose:sucrose 1-fructosyltransferase (1-SST) and fructan:fructan 1-fructosyltransferase (1-FFT) enzymatic activities.

3. The method according to claim 2 wherein said nucleic acid encoding the bacterial FT enzyme is a nucleic acid selected from the group consisting of SacB, Lsc and FTF genes.

4. The method according to claim 1, wherein the nucleic acid encoding a bacterial FT enzyme is one from which a sequence encoding an N-terminal signal peptide has been removed and replaced by
   a sub-cellular targeting sequence, or
   a sequence encoding a transmembrane domain of a fructosyltransferase enzyme.

5. The method according to claim 4, wherein the nucleic acid encoding a bacterial FT enzyme comprises a sub-cellular targeting sequence that includes a vacuolar targeting sequence.

6. The method according to claim 5, wherein the vacuolar targeting sequence is from or corresponds to a gene encoding a preprosporamin.

7. A method of enhancing biomass in a grass plant, said method comprising introducing into said grass plant an effective amount of a genetic construct comprising a promoter, operatively linked to a nucleic acid encoding a bacterial fructosyltransferase (FT) enzyme, wherein the promoter is a light-regulated promoter.

8. The method according to claim 7, wherein said method further comprises introducing into said grass plant an effective amount of a genetic construct capable of manipulating senescence in the plant, wherein the genetic construct capable of manipulating senescence comprises a myb gene promoter or modified myb gene promoter, operatively linked to a gene encoding an enzyme involved in biosynthesis of a cytokinin.

9. A method of selecting for transformed grass plants, said method comprising introducing into said grass plants an effective amount of a genetic construct comprising a promoter operatively linked to a nucleic acid encoding bacterial fructosysltransferase enzyme, and selecting grass plants with enhanced biomass.

10. A method for manipulating fructan biosynthesis in photosynthetic cells of a grass plant, said method comprising introducing into said grass plant an effective amount of a genetic construct comprising a promoter operatively linked to a nucleic acid encoding a bacterial fructosyltransferase (FT) enzyme, wherein said promoter is a light-regulated promoter wherein the nucleic acid encoding a bacterial FT enzyme is one from which a sequence encoding an N-terminal signal peptide has been removed and replaced by a sequence encoding a transmembrane domain of a fructosyltransferase enzyme.

11. The method according to claim 10, wherein said fructosyltransferase enzyme is sucrose:sucrose 1-fructosyltransferase (1-SST).

12. A transgenic grass plant cell, grass plant, grass plant seed or other grass plant part with modified fructan biosynthetic characteristics or enhanced biomass relative to an untransformed control plant; said grass plant cell, grass plant, grass plant seed or other grass plant part comprising a genetic construct comprising a promoter, operatively linked to a nucleic acid encoding a bacterial FT enzyme, wherein said promoter is a light regulated promoter.

13. The transgenic grass plant cell, grass plant, grass plant seed or other grass plant part according to claim 12 wherein said bacterial FT enzyme comprises both sucrose:sucrose 1-fructosyltransferase (1-SST) and fructan:fructan 1-fructosyltransferase (1-FFT) enzymatic activities.

14. The transgenic grass plant cell, grass plant, grass plant seed or other grass plant part according to claim 12 wherein said nucleic acid encoding a bacterial FT enzyme is a nucleic acid selected from the group consisting of SacB, Lsc and FTF genes.

15. The transgenic grass plant cell, grass plant, grass plant seed or other grass plant part according to claim 12, wherein the nucleic acid encoding a bacterial FT enzyme is one from which a sequence encoding an N-terminal signal peptide has been removed and replaced by
   a sub-cellular targeting sequence, or
   a sequence encoding a transmembrane domain of a fructosyltransferase enzyme.

* * * * *

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: Conserved domain

<400> SEQUENCE: 1

Leu Asp Val Trp Asp Ser Trp Pro
1               5

<210> SEQ ID NO 2
<211> LENGTH: 7
<212> TYPE: PRT
```

<213> ORGANISM: Artificial Sequence
<220> FEATURE:
<223> OTHER INFORMATION: Conserved domain

<400> SEQUENCE: 2

Gln Glu Trp Ser Gly Ser Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Conserved domain

<400> SEQUENCE: 3

Leu Arg Asp Pro His
1               5

<210> SEQ ID NO 4
<211> LENGTH: 5
<212> TYPE: PRT
<213> ORGANISM: Artificial Sequence
<220> FEATURE:
<223> OTHER INFORMATION: Conserved domain

<400> SEQUENCE: 4

Asp Glu Ile Glu Arg
1               5

<210> SEQ ID NO 5
<211> LENGTH: 1422
<212> TYPE: DNA
<213> ORGANISM: Bacillus subtilis

<400> SEQUENCE: 5

```
atgaacatca aaaagtttgc aaaacaagca acagtattaa cctttactac cgcactgctg      60
gcaggaggcg caactcaagc gtttgcgaaa gaaacgaacc aaaagccata taggaaaaca     120
tacggcattt cccatattac acgccatgat atgctgcaaa tccctgaaca gcaaaaaaat     180
gaaaaatatc aagttcctga attcgattcg tccacaatta aaaatatctc ttctgcaaaa     240
ggcctggacg tttgggacag ctggccatta caaaacgctg acggcactgt cgcaaactat     300
cacggctacc acatcgtctt tgcattagcc ggagatccta aaaatgcgga tgacacatcg     360
atttacatgt ctatcaaaa agtcggcgaa acttctattg acagctggaa aaacgctggc     420
cgcgtcttta aagacagcga caattcgat gcaaatgatt ctatcctaaa agaccaaaca     480
caagaatggt caggttcagc cacatttaca tctgacggaa aaatccgttt attctacact     540
gatttctccg gtaaacatta cggcaaacaa acactgacaa ctgcacaagt taacgtatca     600
gcatcagaca gctcttttga catcaacggt gtagaggatt ataaatcaat ctttgacggt     660
gacggaaaaa cgtatcaaaa tgtacagcag ttcatcgatg aaggcaacta cagctcaggc     720
gacaaccata cgctgagaga tcctcactac gtagaagata aaggccacaa atacttagta     780
tttgaagcaa acactggaac tgaagatggc taccaaggcg aagaatcttt atttaacaaa     840
gcatactatg gcaaaagcac atcattcttc cgtcaagaaa gtcaaaaact ctgcaaagc     900
gataaaaaac gcacggctga gttagcaaac ggcgctctcg gtatgattga gctaaacgat     960
gattacacac tgaaaaaagt gatgaaaccg ctgattgcat ctaacacagt aacagatgaa    1020
attgaacgcg cgaacgtctt taaaatgaac ggcaaatggt acctgttcac tgactcccgc    1080
```

-continued

```
ggatcaaaaa tgacgattga cggcattacg tctaacgata tttacatgct tggttatgtt      1140
tctaattctt taactggccc atacaagccg ctgaacaaaa ctggccttgt gttaaaaatg      1200
gatcttgatc ctaacgatgt aacctttact tactcacact tcgctgtacc tcaagcgaaa      1260
ggaaacaatg tcgtgattac aagctatatg acaaacagag gattctacgc agacaaacaa      1320
tcaacgtttg cgccaagctt cctgctgaac atcaaaggca agaaaacatc tgttgtcaaa      1380
gacagcatcc ttgaacaagg acaattaaca gttaacaaat aa                        1422
```

<210> SEQ ID NO 6
<211> LENGTH: 93
<212> TYPE: DNA
<213> ORGANISM: Bacillus subtilis

<400> SEQUENCE: 6

```
atgaacatca aaagtttgc aaaacaagca acagtattaa cctttactac cgcactgctg       60
gcaggaggcg caactcaagc gtttgcgaaa gaa                                   93
```

<210> SEQ ID NO 7
<211> LENGTH: 473
<212> TYPE: PRT
<213> ORGANISM: Bacillus subtilis

<400> SEQUENCE: 7

```
Met Asn Ile Lys Lys Phe Ala Lys Gln Ala Thr Val Leu Thr Phe Thr
 1               5                   10                  15

Thr Ala Leu Leu Ala Gly Gly Ala Thr Gln Ala Phe Ala Lys Glu Thr
            20                  25                  30

Asn Gln Lys Pro Tyr Lys Glu Thr Tyr Gly Ile Ser His Ile Thr Arg
        35                  40                  45

His Asp Met Leu Gln Ile Pro Glu Gln Gln Lys Asn Glu Lys Tyr Gln
    50                  55                  60

Val Pro Glu Phe Asp Ser Ser Thr Ile Lys Asn Ile Ser Ser Ala Lys
65                  70                  75                  80

Gly Leu Asp Val Trp Asp Ser Trp Pro Leu Gln Asn Ala Asp Gly Thr
                85                  90                  95

Val Ala Asn Tyr His Gly Tyr His Ile Val Phe Ala Leu Ala Gly Asp
            100                 105                 110

Pro Lys Asn Ala Asp Asp Thr Ser Ile Tyr Met Phe Tyr Gln Lys Val
        115                 120                 125

Gly Glu Thr Ser Ile Asp Ser Trp Lys Asn Ala Gly Arg Val Phe Lys
    130                 135                 140

Asp Ser Asp Lys Phe Asp Ala Asn Asp Ser Ile Leu Lys Asp Gln Thr
145                 150                 155                 160

Gln Glu Trp Ser Gly Ser Ala Thr Phe Thr Ser Asp Gly Lys Ile Arg
                165                 170                 175

Leu Phe Tyr Thr Asp Phe Ser Gly Lys His Tyr Gly Lys Gln Thr Leu
            180                 185                 190

Thr Thr Ala Gln Val Asn Val Ser Ala Ser Asp Ser Ser Leu Asn Ile
        195                 200                 205

Asn Gly Val Glu Asp Tyr Lys Ser Ile Phe Asp Gly Asp Gly Lys Thr
    210                 215                 220

Tyr Gln Asn Val Gln Gln Phe Ile Asp Glu Gly Asn Tyr Ser Ser Gly
225                 230                 235                 240

Asp Asn His Thr Leu Arg Asp Pro His Tyr Val Glu Asp Lys Gly His
                245                 250                 255
```

Lys Tyr Leu Val Phe Glu Ala Asn Thr Gly Thr Glu Asp Gly Tyr Gln
            260                 265                 270

Gly Glu Glu Ser Leu Phe Asn Lys Ala Tyr Tyr Gly Lys Ser Thr Ser
        275                 280                 285

Phe Phe Arg Gln Glu Ser Gln Lys Leu Leu Gln Ser Asp Lys Lys Arg
    290                 295                 300

Thr Ala Glu Leu Ala Asn Gly Ala Leu Gly Met Ile Glu Leu Asn Asp
305                 310                 315                 320

Asp Tyr Thr Leu Lys Lys Val Met Lys Pro Leu Ile Ala Ser Asn Thr
                325                 330                 335

Val Thr Asp Glu Ile Glu Arg Ala Asn Val Phe Lys Met Asn Gly Lys
            340                 345                 350

Trp Tyr Leu Phe Thr Asp Ser Arg Gly Ser Lys Met Thr Ile Asp Gly
        355                 360                 365

Ile Thr Ser Asn Asp Ile Tyr Met Leu Gly Tyr Val Ser Asn Ser Leu
    370                 375                 380

Thr Gly Pro Tyr Lys Pro Leu Asn Lys Thr Gly Leu Val Leu Lys Met
385                 390                 395                 400

Asp Leu Asp Pro Asn Asp Val Thr Phe Thr Tyr Ser His Phe Ala Val
                405                 410                 415

Pro Gln Ala Lys Gly Asn Asn Val Val Ile Thr Ser Tyr Met Thr Asn
            420                 425                 430

Arg Gly Phe Tyr Ala Asp Lys Gln Ser Thr Phe Ala Pro Ser Phe Leu
        435                 440                 445

Leu Asn Ile Lys Gly Lys Lys Thr Ser Val Val Lys Asp Ser Ile Leu
    450                 455                 460

Glu Gln Gly Gln Leu Thr Val Asn Lys
465                 470

<210> SEQ ID NO 8
<211> LENGTH: 31
<212> TYPE: PRT
<213> ORGANISM: Bacillus subtilis

<400> SEQUENCE: 8

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Lys Glu
            20                  25                  30

<210> SEQ ID NO 9
<211> LENGTH: 2394
<212> TYPE: DNA
<213> ORGANISM: Lactobacillus johnsonii

<400> SEQUENCE: 9
atgttggaaa ataaaaatca taaaaagata tctttaagcg gaaaatcttt gttaatggga      60
accttgtcaa cagcagcaat tgtattaagt gcatcaactg caaatgctgc gactattaat    120
gcagacaatg ttaatgaaaa tcaaactgta gaagtaactg ctagttcagt aaacaatgaa    180
aataataagc aagtaactga aaagatagt gcagataaaa gtactagtga tgtggctgaa    240
gatgctaaca ccaagaaatc aaacgaaaat acagaaacta cagaaaagaa tactcaaaca    300
gttgttacta atgcgccagt aagtgatgtg aaaaatacaa acacagttac cgctgaaaca    360
cctgttgata agtagtaaa taatagtgat caaaagacaa ctaatgctgc aactactgat    420

```
actaaaaaag atgatgtaaa acaagttgaa aagaaagact cagtagataa aacaaatgct    480
gaggaaaata aagatagttc agtaaagcca gctgaaaatg ctactaaggc tgaattaaag    540
ggccaagtta aagatatcgt tgaagaatct ggtgttgata ctagcaagtt aactaatgat    600
caaattaatg aattaaataa aattaatttc tccaaagaag caaaaagtgg tactcagtta    660
acttacaacg actttaaaaa aattgctaaa actttaattg aacaagatgc tcgttatgct    720
attccattct tcaatgcaag taaaattaaa aatatgcctg ctgctaaaac acttgatgct    780
caaagtggaa aagtagaaga tttggaaatt tgggattcat ggcctgttca agatgcaaaa    840
actggttacg tatctaactg gaatggctac caattagtga ttggtatgat gggagttcca    900
aacgtcaatg ataaccacat ttatcttctt tacaacaagt atggtgataa tgactttaat    960
cattggaaga atgccggtcc tattttcggt ctaggtactc cagttattca acaatggtct   1020
ggatcagcaa ctttaaataa agatggctca attcaacttt actacactaa ggttgatact   1080
agtgataata atactaacca ccaaaaaactc gctagtgcaa ctgtttactt aaatcttgaa   1140
aaagatcaag ataagatttc tattgctcat gttgacaacg accatattgt ctttgaaggt   1200
gatggttacc actaccaaac ttatgaccaa tggaagaaa ctaacaaggg tgctgacaat   1260
atcgcaatgc gtgatgcaca cgtgattgat gatgataatg gtaatcgtta ccttgtgttt   1320
gaagcaagta ctggaaccga aaattatcaa ggtgatgatc aaatttatca atggttaaat   1380
tacggcggta ctaacaagga taatttaggt gatttcttcc aaattttatc taactccgat   1440
attaaagata gagctaaatg gtcaaacgct gcaattggta tcattaaatt aaatgatgat   1500
gttaagaatc caagtgttgc aaaggtctac agcccactta ttagtgcacc aatggtaagt   1560
gatgaaattg aacgccctga tgttgttaaa ttaggtaata agtattactt atttgctgct   1620
actagattaa accgtggtag taacgatgat gcttggatgg caactaacaa agcagttggt   1680
gataacgtag ctatgattgg ttatgtttct gataacttaa ctcatggtta tgttccattg   1740
aatgaatctg gcgttgtttt aactgcatct gtaccggcta actggcgtac tgcaacttat   1800
tcatactatg cagttccagt agaaggaaga gatgatcaac ttttaattac ttcatacatc   1860
actaatcgtg gtgaggttgc tggaaagggt atgcatgcaa cttgggcacc aagtttcttg   1920
ttacaaatta atccagataa cactactact gttttagcta aaatgactaa ccaaggggat   1980
tggatttggg atgatagtag tgaaaatcca gatatgatgg gtgtacttga aaagatgct    2040 ccaaatagtg ctgcccttcc tggagaatgg ggaaaaccag ttgattggga tttaattggt   2100
ggatacaact tgaagccaca ccaacctgta actcctattc caaatgtacc aactactcct   2160
gaaaccccaa ccacaccaga taagccagag gtaccaacta cccctgaagt tccaaccact   2220
ccagaaactc caactccaga agctccaaag aatccagtta agaaaactag tcagtctaaa   2280
cttccaaagg ctggagataa aaatagcttt gcagcagttg ttttaggtgc tgtaagttca   2340
atattaggtg ctgttggttt aacaggtgtt tcaaaacgta acgtaataa ttaa           2394
```

<210> SEQ ID NO 10
<211> LENGTH: 112
<212> TYPE: DNA
<213> ORGANISM: Lactobacillus johnsonii

<400> SEQUENCE: 10

```
atgttggaaa ataaaaatca taaaaagata tctttaagcg aaaatctttt gttaatggga    60
accttgtcaa cagcagcaat tgtattaagt gcatcaactg caaatgctgc ga           112
```

```
<210> SEQ ID NO 11
<211> LENGTH: 797
<212> TYPE: PRT
<213> ORGANISM: Lactobacillus johnsonii

<400> SEQUENCE: 11
```

| | | | | | | | | | | | | | | |
|---|---|---|---|---|---|---|---|---|---|---|---|---|---|---|
| Met | Leu | Glu | Asn | Lys | Asn | His | Lys | Lys | Ile | Ser | Leu | Ser | Gly | Lys | Ser |
| 1 | | | | 5 | | | | | 10 | | | | | 15 | |
| Leu | Leu | Met | Gly | Thr | Leu | Ser | Thr | Ala | Ala | Ile | Val | Leu | Ser | Ala | Ser |
| | | | 20 | | | | | 25 | | | | | 30 | | |
| Thr | Ala | Asn | Ala | Ala | Thr | Ile | Asn | Ala | Asp | Asn | Val | Asn | Glu | Asn | Gln |
| | | 35 | | | | | 40 | | | | | 45 | | | |
| Thr | Val | Glu | Val | Thr | Ala | Ser | Ser | Val | Asn | Asn | Glu | Asn | Asn | Lys | Gln |
| | 50 | | | | | 55 | | | | | 60 | | | | |
| Val | Thr | Glu | Lys | Asp | Ser | Ala | Asp | Lys | Ser | Thr | Ser | Asp | Val | Ala | Glu |
| 65 | | | | | 70 | | | | | 75 | | | | | 80 |
| Asp | Ala | Asn | Thr | Lys | Lys | Ser | Asn | Glu | Asn | Thr | Glu | Thr | Thr | Glu | Lys |
| | | | | 85 | | | | | 90 | | | | | 95 | |
| Asn | Thr | Gln | Thr | Val | Val | Thr | Asn | Ala | Pro | Val | Ser | Asp | Val | Lys | Asn |
| | | | 100 | | | | | 105 | | | | | 110 | | |
| Thr | Asn | Thr | Val | Thr | Ala | Glu | Thr | Pro | Val | Asp | Lys | Val | Val | Asn | Asn |
| | | 115 | | | | | 120 | | | | | 125 | | | |
| Ser | Asp | Gln | Lys | Thr | Thr | Asn | Ala | Ala | Thr | Thr | Asp | Thr | Lys | Lys | Asp |
| 130 | | | | | 135 | | | | | 140 | | | | | |
| Asp | Val | Lys | Gln | Val | Glu | Lys | Lys | Asp | Ser | Val | Asp | Lys | Thr | Asn | Ala |
| 145 | | | | | 150 | | | | | 155 | | | | | 160 |
| Glu | Glu | Asn | Lys | Asp | Ser | Ser | Val | Lys | Pro | Ala | Glu | Asn | Ala | Thr | Lys |
| | | | | 165 | | | | | 170 | | | | | 175 | |
| Ala | Glu | Leu | Lys | Gly | Gln | Val | Lys | Asp | Ile | Val | Glu | Glu | Ser | Gly | Val |
| | | | 180 | | | | | 185 | | | | | 190 | | |
| Asp | Thr | Ser | Lys | Leu | Thr | Asn | Asp | Gln | Ile | Asn | Glu | Leu | Asn | Lys | Ile |
| | | 195 | | | | | 200 | | | | | 205 | | | |
| Asn | Phe | Ser | Lys | Glu | Ala | Lys | Ser | Gly | Thr | Gln | Leu | Thr | Tyr | Asn | Asp |
| | 210 | | | | | 215 | | | | | 220 | | | | |
| Phe | Lys | Lys | Ile | Ala | Lys | Thr | Leu | Ile | Glu | Gln | Asp | Ala | Arg | Tyr | Ala |
| 225 | | | | | 230 | | | | | 235 | | | | | 240 |
| Ile | Pro | Phe | Phe | Asn | Ala | Ser | Lys | Ile | Lys | Asn | Met | Pro | Ala | Ala | Lys |
| | | | | 245 | | | | | 250 | | | | | 255 | |
| Thr | Leu | Asp | Ala | Gln | Ser | Gly | Lys | Val | Glu | Asp | Leu | Glu | Ile | Trp | Asp |
| | | | 260 | | | | | 265 | | | | | 270 | | |
| Ser | Trp | Pro | Val | Gln | Asp | Ala | Lys | Thr | Gly | Tyr | Val | Ser | Asn | Trp | Asn |
| | | 275 | | | | | 280 | | | | | 285 | | | |
| Gly | Tyr | Gln | Leu | Val | Ile | Gly | Met | Met | Gly | Val | Pro | Asn | Val | Asn | Asp |
| | 290 | | | | | 295 | | | | | 300 | | | | |
| Asn | His | Ile | Tyr | Leu | Leu | Tyr | Asn | Lys | Tyr | Gly | Asp | Asn | Asp | Phe | Asn |
| 305 | | | | | 310 | | | | | 315 | | | | | 320 |
| His | Trp | Lys | Asn | Ala | Gly | Pro | Ile | Phe | Gly | Leu | Gly | Thr | Pro | Val | Ile |
| | | | | 325 | | | | | 330 | | | | | 335 | |
| Gln | Gln | Trp | Ser | Gly | Ser | Ala | Thr | Leu | Asn | Lys | Asp | Gly | Ser | Ile | Gln |
| | | | 340 | | | | | 345 | | | | | 350 | | |
| Leu | Tyr | Tyr | Thr | Lys | Val | Asp | Thr | Ser | Asp | Asn | Asn | Thr | Asn | His | Gln |
| | | 355 | | | | | 360 | | | | | 365 | | | |
| Lys | Leu | Ala | Ser | Ala | Thr | Val | Tyr | Leu | Asn | Leu | Glu | Lys | Asp | Gln | Asp |
| | 370 | | | | | 375 | | | | | 380 | | | | |

```
Lys Ile Ser Ile Ala His Val Asp Asn Asp His Ile Val Phe Glu Gly
385                 390                 395                 400

Asp Gly Tyr His Tyr Gln Thr Tyr Asp Gln Trp Lys Glu Thr Asn Lys
            405                 410                 415

Gly Ala Asp Asn Ile Ala Met Arg Asp Ala His Val Ile Asp Asp Asp
        420                 425                 430

Asn Gly Asn Arg Tyr Leu Val Phe Glu Ala Ser Thr Gly Thr Glu Asn
    435                 440                 445

Tyr Gln Gly Asp Asp Gln Ile Tyr Gln Trp Leu Asn Tyr Gly Gly Thr
        450                 455                 460

Asn Lys Asp Asn Leu Gly Asp Phe Phe Gln Ile Leu Ser Asn Ser Asp
465                 470                 475                 480

Ile Lys Asp Arg Ala Lys Trp Ser Asn Ala Ala Ile Gly Ile Ile Lys
            485                 490                 495

Leu Asn Asp Asp Val Lys Asn Pro Ser Val Ala Lys Val Tyr Ser Pro
                500                 505                 510

Leu Ile Ser Ala Pro Met Val Ser Asp Glu Ile Glu Arg Pro Asp Val
            515                 520                 525

Val Lys Leu Gly Asn Lys Tyr Tyr Leu Phe Ala Ala Thr Arg Leu Asn
    530                 535                 540

Arg Gly Ser Asn Asp Asp Ala Trp Met Ala Thr Asn Lys Ala Val Gly
545                 550                 555                 560

Asp Asn Val Ala Met Ile Gly Tyr Val Ser Asp Asn Leu Thr His Gly
                565                 570                 575

Tyr Val Pro Leu Asn Glu Ser Gly Val Val Leu Thr Ala Ser Val Pro
            580                 585                 590

Ala Asn Trp Arg Thr Ala Thr Tyr Ser Tyr Tyr Ala Val Pro Val Glu
        595                 600                 605

Gly Arg Asp Asp Gln Leu Leu Ile Thr Ser Tyr Ile Thr Asn Arg Gly
    610                 615                 620

Glu Val Ala Gly Lys Gly Met His Ala Thr Trp Ala Pro Ser Phe Leu
625                 630                 635                 640

Leu Gln Ile Asn Pro Asp Asn Thr Thr Thr Val Leu Ala Lys Met Thr
            645                 650                 655

Asn Gln Gly Asp Trp Ile Trp Asp Asp Ser Ser Glu Asn Pro Asp Met
                660                 665                 670

Met Gly Val Leu Glu Lys Asp Ala Pro Asn Ser Ala Ala Leu Pro Gly
            675                 680                 685

Glu Trp Gly Lys Pro Val Asp Trp Asp Leu Ile Gly Gly Tyr Asn Leu
        690                 695                 700

Lys Pro His Gln Pro Val Thr Pro Ile Pro Asn Val Pro Thr Thr Pro
705                 710                 715                 720

Glu Thr Pro Thr Thr Pro Asp Lys Pro Glu Val Pro Thr Thr Pro Glu
            725                 730                 735

Val Pro Thr Thr Pro Glu Thr Pro Thr Pro Glu Ala Pro Lys Asn Pro
                740                 745                 750

Val Lys Lys Thr Ser Gln Ser Lys Leu Pro Lys Ala Gly Asp Lys Asn
            755                 760                 765

Ser Phe Ala Ala Val Val Leu Gly Ala Val Ser Ile Leu Gly Ala
        770                 775                 780

Val Gly Leu Thr Gly Val Ser Lys Arg Lys Arg Asn Asn
785                 790                 795
```

<210> SEQ ID NO 12
<211> LENGTH: 37
<212> TYPE: PRT
<213> ORGANISM: Lactobacillus johnsonii

<400> SEQUENCE: 12

Met Leu Glu Asn Lys Asn His Lys Lys Ile Ser Leu Ser Gly Lys Ser
1               5                   10                  15

Leu Leu Met Gly Thr Leu Ser Thr Ala Ala Ile Val Leu Ser Ala Ser
            20                  25                  30

Thr Ala Asn Ala Ala
        35

<210> SEQ ID NO 13
<211> LENGTH: 657
<212> TYPE: DNA
<213> ORGANISM: Ipomoea batatas

<400> SEQUENCE: 13
atgaaagcct tcacactcgc tctcttctta gctctttttcc tctatctcct gcccaatcca      60
gcccattcca ggttcaatcc catccgcctc cccaccacac acgaacccgc ctcctctgaa     120
actccagtac tcgacatcaa cggcgacgag gtccgcgccg gcgggaacta ctacatggtc     180
tccgccatat ggggagccgg cggggggaggg ctaagactcg cccacttgga cacgatgtcc     240
aaatgcgcca gcgacgtcat cgtatccccc aacgacttag acaacggcga ccccatcacc     300
atcacgccgg cgacggccga cccggaatcc accgtggtca tggcgtcgac ctaccagact     360
ttccggttca atatcgccaa caacaaactg tgcgtgaaga acgtgaactg ggggaatccag    420 cacgacagcg cgtccgggca gtatttcctg aaagacggcg agtttgtctc cgacaatagc     480
aaccagttca agattgaggt ggtggatgcc aaccttaact tctacaaact cacttactgt     540
cagttcggct ccgacaaatg ctacaactgc ggcagattcc acgaccccat gttgaggacc     600
acgcgcttgg ctctctccaa ttctcccttc gttttttgtca tcaaacctac cgatgtg        657

<210> SEQ ID NO 14
<211> LENGTH: 69
<212> TYPE: DNA
<213> ORGANISM: Ipomoea batatas

<400> SEQUENCE: 14
atgaaagcct tcacactcgc tctcttctta gctctttttcc tctatctcct gcccaatcca      60
gcccattcc                                                              69

<210> SEQ ID NO 15
<211> LENGTH: 219
<212> TYPE: PRT
<213> ORGANISM: Ipomoea batatas

<400> SEQUENCE: 15

Met Lys Ala Phe Thr Leu Ala Leu Phe Leu Ala Leu Phe Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala Ser Ser Glu Thr Pro Val Leu Asp Ile Asn Gly
        35                  40                  45

Asp Glu Val Arg Ala Gly Gly Asn Tyr Tyr Met Val Ser Ala Ile Trp
    50                  55                  60

Gly Ala Gly Gly Gly Gly Leu Arg Leu Ala His Leu Asp Thr Met Ser

```
                65                  70                  75                  80
Lys Cys Ala Ser Asp Val Ile Val Ser Pro Asn Asp Leu Asp Asn Gly
                    85                  90                  95

Asp Pro Ile Thr Ile Thr Pro Ala Thr Ala Asp Pro Glu Ser Thr Val
                100                 105                 110

Val Met Ala Ser Thr Tyr Gln Thr Phe Arg Phe Asn Ile Ala Asn Asn
                115                 120                 125

Lys Leu Cys Val Lys Asn Val Asn Trp Gly Ile Gln His Asp Ser Ala
                130                 135                 140

Ser Gly Gln Tyr Phe Leu Lys Asp Gly Glu Phe Val Ser Asp Asn Ser
145                 150                 155                 160

Asn Gln Phe Lys Ile Glu Val Val Asp Ala Asn Leu Asn Phe Tyr Lys
                165                 170                 175

Leu Thr Tyr Cys Gln Phe Gly Ser Asp Lys Cys Tyr Asn Cys Gly Arg
                180                 185                 190

Phe His Asp Pro Met Leu Arg Thr Thr Arg Leu Ala Leu Ser Asn Ser
                195                 200                 205

Pro Phe Val Phe Val Ile Lys Pro Thr Asp Val
    210                 215
```

<210> SEQ ID NO 16
<211> LENGTH: 23
<212> TYPE: PRT
<213> ORGANISM: Ipomoea batatas

<400> SEQUENCE: 16

```
Met Lys Ala Phe Thr Leu Ala Leu Phe Leu Ala Leu Phe Leu Tyr Leu
1               5                   10                  15

Leu Pro Asn Pro Ala His Ser
            20
```

<210> SEQ ID NO 17
<211> LENGTH: 1398
<212> TYPE: DNA
<213> ORGANISM: Artificial Sequence
<220> FEATURE:
<223> OTHER INFORMATION: Chimeric sequence

<400> SEQUENCE: 17

```
atgaaagcct tcacactcgc tctcttctta gctcttttcc tctatctcct gcccaatcca      60
gcccattcca cgaaccaaaa gccatataag gaaacatacg gcatttccca tattacacgc     120
catgatatgc tgcaaatccc tgaacagcaa aaaatgaaa aatatcaagt tcctgaattc     180
gattcgtcca caattaaaaa tatctcttct gcaaaaggcc tggacgtttg gacagctgg      240
ccattacaaa acgctgacgg cactgtcgca aactatcacg ctaccacat cgtctttgca     300
ttagccggag atcctaaaaa tgcggatgac acatcgattt acatgttcta tcaaaaagtc     360
ggcgaaactt ctattgacag ctggaaaaac gctggccgcg tctttaaaga cagcgacaaa     420
ttcgatgcaa atgattctat cctaaaagac caaacacaag aatggtcagg ttcagccaca     480
tttacatctg acggaaaaat ccgtttattc tacactgatt ctccggtaa acattacggc     540
aaacaaacac tgacaactgc acaagttaac gtatcagcat cagacagctc tttgaacatc     600
aacggtgtag aggattataa atcaatcttt gacggtgacg gaaaaacgta tcaaaatgta     660
cagcagttca tcgatgaagg caactacagc tcaggcgaca accatacgct gagagatcct     720
cactacgtag aagataaagg ccacaaatac ttagtatttg aagcaaacac tggaactgaa     780
```

```
gatggctacc aaggcgaaga atctttattt aacaaagcat actatggcaa aagcacatca    840
ttcttccgtc aagaaagtca aaaacttctg caaagcgata aaaaacgcac ggctgagtta    900
gcaaacggcg ctctcggtat gattgagcta acgatgatt acacactgaa aaaagtgatg     960
aaaccgctga ttgcatctaa cacagtaaca gatgaaattg aacgcgcgaa cgtctttaaa   1020
atgaacggca atggtacct gttcactgac tcccgcggat caaaaatgac gattgacggc   1080
attacgtcta acgatattta catgcttggt tatgtttcta attctttaac tggcccatac   1140
aagccgctga acaaaactgg ccttgtgtta aaaatggatc ttgatcctaa cgatgtaacc   1200
tttacttact cacacttcgc tgtacctcaa gcgaaaggaa acaatgtcgt gattacaagc   1260
tatatgacaa acagaggatt ctacgcagac aaacaatcaa cgtttgcgcc aagcttcctg   1320
ctgaacatca aaggcaagaa aacatctgtt gtcaaagaca gcatccttga caaggacaa    1380 ttaacagtta acaaataa                                                 1398
```

<210> SEQ ID NO 18
<211> LENGTH: 465
<212> TYPE: PRT
<213> ORGANISM: Artificial Sequence
<220> FEATURE:
<223> OTHER INFORMATION: Chimeric sequence

<400> SEQUENCE: 18

```
Met Lys Ala Phe Thr Leu Ala Leu Phe Leu Ala Leu Phe Leu Tyr Leu
1               5                   10                  15

Leu Pro Asn Pro Ala His Ser Thr Asn Gln Lys Pro Tyr Lys Glu Thr
            20                  25                  30

Tyr Gly Ile Ser His Ile Thr Arg His Asp Met Leu Gln Ile Pro Glu
        35                  40                  45

Gln Gln Lys Asn Glu Lys Tyr Gln Val Pro Glu Phe Asp Ser Ser Thr
    50                  55                  60

Ile Lys Asn Ile Ser Ser Ala Lys Gly Leu Asp Val Trp Asp Ser Trp
65                  70                  75                  80

Pro Leu Gln Asn Ala Asp Gly Thr Val Ala Asn Tyr His Gly Tyr His
                85                  90                  95

Ile Val Phe Ala Leu Ala Gly Asp Pro Lys Asn Ala Asp Asp Thr Ser
            100                 105                 110

Ile Tyr Met Phe Tyr Gln Lys Val Gly Glu Thr Ser Ile Asp Ser Trp
        115                 120                 125

Lys Asn Ala Gly Arg Val Phe Lys Asp Ser Asp Lys Phe Asp Ala Asn
    130                 135                 140

Asp Ser Ile Leu Lys Asp Gln Thr Gln Glu Trp Ser Gly Ser Ala Thr
145                 150                 155                 160

Phe Thr Ser Asp Gly Lys Ile Arg Leu Phe Tyr Thr Asp Phe Ser Gly
                165                 170                 175

Lys His Tyr Gly Lys Gln Thr Leu Thr Thr Ala Gln Val Asn Val Ser
            180                 185                 190

Ala Ser Asp Ser Ser Leu Asn Ile Asn Gly Val Glu Asp Tyr Lys Ser
        195                 200                 205

Ile Phe Asp Gly Asp Gly Lys Thr Tyr Gln Asn Val Gln Gln Phe Ile
    210                 215                 220

Asp Glu Gly Asn Tyr Ser Ser Gly Asp Asn His Thr Leu Arg Asp Pro
225                 230                 235                 240

His Tyr Val Glu Asp Lys Gly His Lys Tyr Leu Val Phe Glu Ala Asn
                245                 250                 255
```

Thr Gly Thr Glu Asp Gly Tyr Gln Gly Glu Glu Ser Leu Phe Asn Lys
            260                 265                 270

Ala Tyr Tyr Gly Lys Ser Thr Ser Phe Phe Arg Gln Glu Ser Gln Lys
        275                 280                 285

Leu Leu Gln Ser Asp Lys Lys Arg Thr Ala Glu Leu Ala Asn Gly Ala
    290                 295                 300

Leu Gly Met Ile Glu Leu Asn Asp Asp Tyr Thr Leu Lys Lys Val Met
305                 310                 315                 320

Lys Pro Leu Ile Ala Ser Asn Thr Val Thr Asp Glu Ile Glu Arg Ala
                325                 330                 335

Asn Val Phe Lys Met Asn Gly Lys Trp Tyr Leu Phe Thr Asp Ser Arg
            340                 345                 350

Gly Ser Lys Met Thr Ile Asp Gly Ile Thr Ser Asn Asp Ile Tyr Met
        355                 360                 365

Leu Gly Tyr Val Ser Asn Ser Leu Thr Gly Pro Tyr Lys Pro Leu Asn
    370                 375                 380

Lys Thr Gly Leu Val Leu Lys Met Asp Leu Asp Pro Asn Asp Val Thr
385                 390                 395                 400

Phe Thr Tyr Ser His Phe Ala Val Pro Gln Ala Lys Gly Asn Asn Val
                405                 410                 415

Val Ile Thr Ser Tyr Met Thr Asn Arg Gly Phe Tyr Ala Asp Lys Gln
            420                 425                 430

Ser Thr Phe Ala Pro Ser Phe Leu Leu Asn Ile Lys Gly Lys Lys Thr
        435                 440                 445

Ser Val Val Lys Asp Ser Ile Leu Glu Gln Gly Gln Leu Thr Val Asn
    450                 455                 460

Lys
465

<210> SEQ ID NO 19
<211> LENGTH: 2352
<212> TYPE: DNA
<213> ORGANISM: Artificial Sequence
<220> FEATURE:
<223> OTHER INFORMATION: Chimeric sequence

<400> SEQUENCE: 19
atgaaagcct tcacactcgc tctcttctta gctcttttcc tctatctcct gcccaatcca      60
gcccattcca ctattaatgc agacaatgtt aatgaaaatc aaactgtaga agtaactgct     120
agttcagtaa caatgaaaaa taataagcaa gtaactgaaa agatagtgc agataaaagt     180 actagtgatg tggctgaaga tgctaacacc aagaaatcaa acgaaaatac agaaactaca     240
gaaaagaata ctcaaacagt tgttactaat gcgccagtaa gtgatgtgaa aaatacaaac     300
acagttaccg ctgaaacacc tgttgataaa gtagtaaata tagtgatca aaagacaact     360 aatgctgcaa ctactgatac taaaaaagat gatgtaaaac aagttgaaaa gaaagactca     420
gtagataaaa caaatgctga ggaaaataaa gatagttcag taaagccagc tgaaaatgct     480
actaaggctg aattaaaggg ccaagttaaa gatatcgttg aagaatctgg tgttgatact     540
agcaagttaa ctaatgatca aattaatgaa ttaaataaaa ttaatttctc caagaagca     600 aaaagtggta ctcagttaac ttacaacgac tttaaaaaaa ttgctaaaac tttaattgaa     660
caagatgctc gttatgctat tccattcttc aatgcaagta aaattaaaaa tatgcctgct     720
gctaaaacac ttgatgctca agtggaaaaa gtagaagatt tggaaatttg ggattcatgg     780

```
cctgttcaag atgcaaaaac tggttacgta tctaactgga atggctacca attagtgatt    840
ggtatgatgg gagttccaaa cgtcaatgat aaccacattt atcttcttta caacaagtat    900
ggtgataatg actttaatca ttggaagaat gccggtccta ttttcggtct aggtactcca    960
gttattcaac aatggtctgg atcagcaact ttaaataaag atggctcaat tcaactttac   1020
tacactaagg ttgatactag tgataataat actaaccacc aaaaactcgc tagtgcaact   1080
gtttacttaa atcttgaaaa agatcaagat aagatttcta ttgctcatgt tgacaacgac   1140
catattgtct ttgaaggtga tggttaccac taccaaactt atgaccaatg aaagaaact   1200 aacaagggtg ctgacaatat cgcaatgcgt gatgcacacg tgattgatga tgataatggt   1260
aatcgttacc ttgtgtttga agcaagtact ggaaccgaaa attatcaagg tgatgatcaa   1320
atttatcaat ggttaaatta cggcggtact aacaaggata atttaggtga tttcttccaa   1380 atttatcta actccgatat taagatagag ctaaatggt caaacgctgc aattggtatc   1440
attaaattaa atgatgatgt taagaatcca agtgttgcaa aggtctacag cccacttatt   1500
agtgcaccaa tggtaagtga tgaaattgaa cgccctgatg ttgttaaatt aggtaataag   1560
tattacttat ttgctgctac tagattaaac cgtggtagta acgatgatgc ttggatggca   1620
actaacaaag cagttggtga taacgtagct atgattggtt atgtttctga taacttaact   1680
catggttatg ttccattgaa tgaatctggc gttgttttaa ctgcatctgt accggctaac   1740
tggcgtactg caacttattc atactatgca gttccagtag aaggaagaga tgatcaactt   1800
ttaattactt catacatcac taatcgtggt gaggttgctg gaaagggtat gcatgcaact   1860
tgggcaccaa gtttcttgtt acaaattaat ccagataaca ctactactgt tttagctaaa   1920
atgactaacc aaggggattg gatttgggat gatagtagtg aaaatccaga tatgatgggt   1980
gtacttgaaa aagatgctcc aaatagtgct gcccttcctg gagaatgggg aaaaccagtt   2040
gattgggatt taattggtgg atacaacttg aagccacacc aacctgtaac tcctattcca   2100
aatgtaccaa ctactcctga acccaacc acaccagata gccagaggt accaactacc   2160 cctgaagttc caaccactcc agaaactcca actccagaag ctccaaagaa tccagttaag   2220
aaaactagtc agtctaaact tccaaaggct ggagataaaa atagctttgc agcagttgtt   2280
ttaggtgctg taagttcaat attaggtgct gttggtttaa caggtgtttc aaaacgtaaa   2340
cgtaataatt aa                                                      2352
```

<210> SEQ ID NO 20
<211> LENGTH: 783
<212> TYPE: PRT
<213> ORGANISM: Artificial Sequence
<220> FEATURE:
<223> OTHER INFORMATION: Chimeric sequence

<400> SEQUENCE: 20

```
Met Lys Ala Phe Thr Leu Ala Leu Phe Leu Ala Leu Phe Leu Tyr Leu
1               5                   10                  15

Leu Pro Asn Pro Ala His Ser Thr Ile Asn Ala Asp Asn Val Asn Glu
            20                  25                  30

Asn Gln Thr Val Glu Val Thr Ala Ser Ser Val Asn Asn Glu Asn Asn
        35                  40                  45

Lys Gln Val Thr Glu Lys Asp Ser Ala Asp Lys Ser Thr Ser Asp Val
    50                  55                  60

Ala Glu Asp Ala Asn Thr Lys Lys Ser Asn Glu Asn Thr Glu Thr Thr
65                  70                  75                  80
```

-continued

Glu Lys Asn Thr Gln Thr Val Val Thr Asn Ala Pro Val Ser Asp Val
                85                  90                  95

Lys Asn Thr Asn Thr Val Thr Ala Glu Thr Pro Val Asp Lys Val Val
            100                 105                 110

Asn Asn Ser Asp Gln Lys Thr Thr Asn Ala Ala Thr Thr Asp Thr Lys
            115                 120                 125

Lys Asp Asp Val Lys Gln Val Glu Lys Lys Asp Ser Val Asp Lys Thr
            130                 135                 140

Asn Ala Glu Glu Asn Lys Asp Ser Ser Val Lys Pro Ala Glu Asn Ala
145                 150                 155                 160

Thr Lys Ala Glu Leu Lys Gly Gln Val Lys Asp Ile Val Glu Glu Ser
                165                 170                 175

Gly Val Asp Thr Ser Lys Leu Thr Asn Asp Gln Ile Asn Glu Leu Asn
            180                 185                 190

Lys Ile Asn Phe Ser Lys Glu Ala Lys Ser Gly Thr Gln Leu Thr Tyr
            195                 200                 205

Asn Asp Phe Lys Lys Ile Ala Lys Thr Leu Ile Glu Gln Asp Ala Arg
210                 215                 220

Tyr Ala Ile Pro Phe Phe Asn Ala Ser Lys Ile Lys Asn Met Pro Ala
225                 230                 235                 240

Ala Lys Thr Leu Asp Ala Gln Ser Gly Lys Val Glu Asp Leu Glu Ile
                245                 250                 255

Trp Asp Ser Trp Pro Val Gln Asp Ala Lys Thr Gly Tyr Val Ser Asn
            260                 265                 270

Trp Asn Gly Tyr Gln Leu Val Ile Gly Met Met Gly Val Pro Asn Val
            275                 280                 285

Asn Asp Asn His Ile Tyr Leu Leu Tyr Asn Lys Tyr Gly Asp Asn Asp
290                 295                 300

Phe Asn His Trp Lys Asn Ala Gly Pro Ile Phe Gly Leu Gly Thr Pro
305                 310                 315                 320

Val Ile Gln Gln Trp Ser Gly Ser Ala Thr Leu Asn Lys Asp Gly Ser
                325                 330                 335

Ile Gln Leu Tyr Tyr Thr Lys Val Asp Thr Ser Asp Asn Asn Thr Asn
            340                 345                 350

His Gln Lys Leu Ala Ser Ala Thr Val Tyr Leu Asn Leu Glu Lys Asp
            355                 360                 365

Gln Asp Lys Ile Ser Ile Ala His Val Asp Asn Asp His Ile Val Phe
            370                 375                 380

Glu Gly Asp Gly Tyr His Tyr Gln Thr Tyr Asp Gln Trp Lys Glu Thr
385                 390                 395                 400

Asn Lys Gly Ala Asp Asn Ile Ala Met Arg Asp Ala His Val Ile Asp
                405                 410                 415

Asp Asp Asn Gly Asn Arg Tyr Leu Val Phe Glu Ala Ser Thr Gly Thr
            420                 425                 430

Glu Asn Tyr Gln Gly Asp Asp Gln Ile Tyr Gln Trp Leu Asn Tyr Gly
            435                 440                 445

Gly Thr Asn Lys Asp Asn Leu Gly Asp Phe Phe Gln Ile Leu Ser Asn
450                 455                 460

Ser Asp Ile Lys Asp Arg Ala Lys Trp Ser Asn Ala Ala Ile Gly Ile
465                 470                 475                 480

Ile Lys Leu Asn Asp Asp Val Lys Asn Pro Ser Val Ala Lys Val Tyr
                485                 490                 495

Ser Pro Leu Ile Ser Ala Pro Met Val Ser Asp Glu Ile Glu Arg Pro

|     |     |     |     | 500 |     |     |     | 505 |     |     |     | 510 |     |     |
| --- | --- | --- | --- | --- | --- | --- | --- | --- | --- | --- | --- | --- | --- | --- |
| Asp | Val | Val | Lys | Leu | Gly | Asn | Lys | Tyr | Tyr | Leu | Phe | Ala | Ala | Thr | Arg |
|     |     |     | 515 |     |     |     |     | 520 |     |     |     |     | 525 |     |     |
| Leu | Asn | Arg | Gly | Ser | Asn | Asp | Asp | Ala | Trp | Met | Ala | Thr | Asn | Lys | Ala |
|     |     |     | 530 |     |     |     |     | 535 |     |     |     |     | 540 |     |     |
| Val | Gly | Asp | Asn | Val | Ala | Met | Ile | Gly | Tyr | Val | Ser | Asp | Asn | Leu | Thr |
| 545 |     |     |     |     | 550 |     |     |     |     | 555 |     |     |     |     | 560 |
| His | Gly | Tyr | Val | Pro | Leu | Asn | Glu | Ser | Gly | Val | Val | Leu | Thr | Ala | Ser |
|     |     |     |     | 565 |     |     |     |     | 570 |     |     |     |     | 575 |     |
| Val | Pro | Ala | Asn | Trp | Arg | Thr | Ala | Thr | Tyr | Ser | Tyr | Tyr | Ala | Val | Pro |
|     |     |     | 580 |     |     |     |     | 585 |     |     |     |     | 590 |     |     |
| Val | Glu | Gly | Arg | Asp | Asp | Gln | Leu | Leu | Ile | Thr | Ser | Tyr | Ile | Thr | Asn |
|     |     |     | 595 |     |     |     |     | 600 |     |     |     |     | 605 |     |     |
| Arg | Gly | Glu | Val | Ala | Gly | Lys | Gly | Met | His | Ala | Thr | Trp | Ala | Pro | Ser |
|     |     |     | 610 |     |     |     |     | 615 |     |     |     |     | 620 |     |     |
| Phe | Leu | Leu | Gln | Ile | Asn | Pro | Asp | Asn | Thr | Thr | Thr | Val | Leu | Ala | Lys |
| 625 |     |     |     |     | 630 |     |     |     |     | 635 |     |     |     |     | 640 |
| Met | Thr | Asn | Gln | Gly | Asp | Trp | Ile | Trp | Asp | Asp | Ser | Ser | Glu | Asn | Pro |
|     |     |     |     | 645 |     |     |     |     | 650 |     |     |     |     | 655 |     |
| Asp | Met | Met | Gly | Val | Leu | Glu | Lys | Asp | Ala | Pro | Asn | Ser | Ala | Ala | Leu |
|     |     |     || 660 |     |     |     |     | 665 |     |     |     |     | 670 |     |     |
| Pro | Gly | Glu | Trp | Gly | Lys | Pro | Val | Asp | Trp | Asp | Leu | Ile | Gly | Gly | Tyr |
|     |     |     | 675 |     |     |     |     | 680 |     |     |     |     | 685 |     |     |
| Asn | Leu | Lys | Pro | His | Gln | Pro | Val | Thr | Pro | Ile | Pro | Asn | Val | Pro | Thr |
|     |     |     | 690 |     |     |     |     | 695 |     |     |     |     | 700 |     |     |
| Thr | Pro | Glu | Thr | Pro | Thr | Thr | Pro | Asp | Lys | Pro | Glu | Val | Pro | Thr | Thr |
| 705 |     |     |     |     | 710 |     |     |     |     | 715 |     |     |     |     | 720 |
| Pro | Glu | Val | Pro | Thr | Thr | Pro | Glu | Thr | Pro | Thr | Pro | Glu | Ala | Pro | Lys |
|     |     |     |     | 725 |     |     |     |     | 730 |     |     |     |     | 735 |     |
| Asn | Pro | Val | Lys | Lys | Thr | Ser | Gln | Ser | Lys | Leu | Pro | Lys | Ala | Gly | Asp |
|     |     |     | 740 |     |     |     |     | 745 |     |     |     |     | 750 |     |     |
| Lys | Asn | Ser | Phe | Ala | Ala | Val | Val | Leu | Gly | Ala | Val | Ser | Ser | Ile | Leu |
|     |     |     | 755 |     |     |     |     | 760 |     |     |     |     | 765 |     |     |
| Gly | Ala | Val | Gly | Leu | Thr | Gly | Val | Ser | Lys | Arg | Lys | Arg | Asn | Asn |     |
|     |     |     | 770 |     |     |     |     | 775 |     |     |     |     | 780 |     |     |

<210> SEQ ID NO 21
<211> LENGTH: 2148
<212> TYPE: DNA
<213> ORGANISM: Lolium perenne

<400> SEQUENCE: 21

| atgcaaccag | ggaacgtcgt | ccaccccttc | cacatcctgt | atcaaattaa | ggaacgggcg | 60 |
| ctgagcctat | gccgagacat | atataatgcg | gcgactcgga | catggagggg | cctcaggcat | 120 |
| agcccagcta | gttatctcat | tctctcctta | gcaataatac | ttagcaccat | ggcccccgcg | 180 |
| gtggaattca | tggagtcccc | aagcgccgtc | gtccccggca | ccacggcgcc | gctgcttcct | 240 |
| tatgcgtacg | cgccgctgcc | gtcgtccgcc | gacgacgccc | gtcaaaaccg | gagtggcggg | 300 |
| aggtggcgcg | cgtgcgccgc | cgtgctggcc | gcatcggcgt | tggcggtggt | cgtcgtggtc | 360 |
| gggctcctcg | cgggcggcag | ggtggatcgg | gtcccggccg | gcggagacgt | ggcgtcggcc | 420 |
| acggtgccgg | ccgtgccgat | ggagttcccg | aggagccggg | gcaaggactt | cggcgtgtcg | 480 |
| gagaagtcct | ccggtgccta | ctccaccgac | ggcgggttcc | cgtggagcaa | cgccatgctg | 540 |

-continued

```
cagtggcagc gcaccgggtt ccatttccag ccggagcagc actacatgaa cgatcccaac    600
ggccccgtgt actacggcgg atggtaccac ctcttctacc agcacaaccc caagggcgac    660
agctggggca acatcgcgtg ggcccacgcc gtctccaagg acatggtcaa ctggcgccac    720
ctccctctcg ccatggttcc cgaccagtgg tacgacagca acggcgtcct caccggctcc    780
atcaccgtgc tccccgacgg ccaggtcatc ctgctctaca ccggcaacac cgacacccta    840
gcccaggtcc agtgcctcgc cacgcccgcc gacccgtccg accgctcct ccgcgagtgg     900
gtcaagcacc ccgccaaccc catcctctac cctccccccg gcatcggcct caaggacttc    960
cgcgacccc tcaccgcctg gttcgaccac tccgaccaca cctggcgcac cgtcatcggc    1020
tccaaggacg acgacggcca cgccggcatc atcctcagct acaagaccaa ggacttcgtc   1080
aactacgagc tcatgccggg gaacatgcac cgcgggcccg acggcaccgg aatgtacgag   1140
tgcatcgacc tctaccccgt cggcggcaac tcgtccgaga tgctcggcgg cgacgactcg   1200
cccggcgtgc tcttcgtgct caaggagagc agcgacgacg agcgccacga ctactacgcg   1260
ctcggaaggt tcgacgccgt cgccaacgtt tggacgccca tcgaccggga gctggacctt   1320
gggatcgggc tcagatacga ctggggaaag tactacgcct ccaagtcctt ctacgaccag   1380
aagaagaacc gccgcatcgt atgggcatac atcggcgaga ccgactccga gcaggccgac   1440
atcaccaagg gatgggccaa tctcatgacg attccaagaa cggtggagct tgacaggaag   1500
acccgcacaa acctcatcca atggccagtg agaggtcg acaccctccg caggaactcc    1560
acggacctcg gtcgcatcac cgtcaacgcc ggctccgtca ttcgcctccc cctccaccag   1620
ggcgctcaac tcgacatcga ggcctccttc caactcaact cttccgacgt ggatgctatc   1680
aacgaggccg acgtcggcta caactgcagc accagtggtg ccgccgtacg ggggggcgctc   1740
ggcccctttg gcctcctcgt ccttgccaac ggccgcaccg aacagacggc tgtgtacttc   1800
tacgtgtcca agggcgtcga cggtgccctc cagacccact tctgccacga cgagtcacgg   1860
tcaacgcggg caaaggatgt cgtgaatagg atgattggca gcatcgtgcc ggtgcttgac   1920
ggtgagacct tttcggtgag ggtgctagtg gaccactcca tcgtgcagag cttcgcgatg   1980
ggcgggagga tcacggcgac gtcgcgggcg tacccgacgg aggccatcta cgcggccgcg   2040
ggggtctacc tcttcaacaa cgccacgggc gccaccgtca ccgccgagag gctcgtcgtg   2100
cacgagatgg cctcagctga caaccatatc ttcacgaacg acgacttg               2148
```

<210> SEQ ID NO 22
<211> LENGTH: 405
<212> TYPE: DNA
<213> ORGANISM: Lolium perenne

<400> SEQUENCE: 22

```
atgcaaccag ggaacgtcgt ccaccccttc cacatcctgt atcaaattaa ggaacgggcg     60
ctgagcctat gccagacat atataatgcg gcgactcgga catggagggg cctcaggcat    120
agcccagcta gttatctcat tctctcctta gcaataatac ttagcaccat ggcccccgcg    180
gtggaattca tggagtcccc aagcgccgtc gtccccggca ccacggcgcc gctgcttcct    240
tatgcgtacg cgccgctgcc gtcgtccgcc gacgacgccc gtcaaaaccg gagtggcggg    300
aggtggcgcg cgtcgccgc cgtgctggcc gcatcggcgt tggcggtggt cgtcgtggtc    360
gggctcctcg cgggcggcag ggtggatcgg gtcccggccg gcgga                   405
```

<210> SEQ ID NO 23
<211> LENGTH: 653

<212> TYPE: PRT
<213> ORGANISM: Lolium perenne

<400> SEQUENCE: 23

Met Glu Ser Pro Ser Ala Val Val Pro Gly Thr Thr Ala Pro Leu Leu
1               5                   10                  15

Pro Tyr Ala Tyr Ala Pro Leu Pro Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Gly Leu Leu Ala Gly Gly Arg
50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Gly His Ala Gly Ile Ile
        275                 280                 285

Leu Ser Tyr Lys Thr Lys Asp Phe Val Asn Tyr Glu Leu Met Pro Gly
290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
370                 375                 380

Trp Gly Lys Tyr Tyr Ala Ser Lys Ser Phe Tyr Asp Gln Lys Lys Asn
385                 390                 395                 400

```
Arg Arg Ile Val Trp Ala Tyr Ile Gly Glu Thr Asp Ser Glu Gln Ala
            405                 410                 415

Asp Ile Thr Lys Gly Trp Ala Asn Leu Met Thr Ile Pro Arg Thr Val
        420                 425                 430

Glu Leu Asp Arg Lys Thr Arg Thr Asn Leu Ile Gln Trp Pro Val Glu
            435                 440                 445

Glu Val Asp Thr Leu Arg Arg Asn Ser Thr Asp Leu Gly Arg Ile Thr
        450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Asp Val Asp Ala
            485                 490                 495

Ile Asn Glu Ala Asp Val Gly Tyr Asn Cys Ser Thr Ser Gly Ala Ala
        500                 505                 510

Val Arg Gly Ala Leu Gly Pro Phe Gly Leu Leu Val Leu Ala Asn Gly
            515                 520                 525

Arg Thr Glu Gln Thr Ala Val Tyr Phe Tyr Val Ser Lys Gly Val Asp
        530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Pro Val Leu
            565                 570                 575

Asp Gly Glu Thr Phe Ser Val Arg Val Leu Asp His Ser Ile Val
        580                 585                 590

Gln Ser Phe Ala Met Gly Gly Arg Ile Thr Ala Thr Ser Arg Ala Tyr
            595                 600                 605

Pro Thr Glu Ala Ile Tyr Ala Ala Gly Val Tyr Leu Phe Asn Asn
        610                 615                 620

Ala Thr Gly Ala Thr Val Thr Ala Glu Arg Leu Val Val His Glu Met
625                 630                 635                 640

Ala Ser Ala Asp Asn His Ile Phe Thr Asn Asp Leu
            645                 650

<210> SEQ ID NO 24
<211> LENGTH: 72
<212> TYPE: PRT
<213> ORGANISM: Lolium perenne

<400> SEQUENCE: 24

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Gly Leu Leu Ala Gly Gly Arg
    50                  55                  60

Val Asp Arg Val Pro Ala Gly Gly
65                  70

<210> SEQ ID NO 25
<211> LENGTH: 1545
<212> TYPE: DNA
<213> ORGANISM: Artificial Sequence
<220> FEATURE:
<223> OTHER INFORMATION: Chimeric sequence
```

<400> SEQUENCE: 25

```
atggagtccc caagcgccgt cgtccccggc accacggcgc cgctgcttcc ttatgcgtac     60
gcgccgctgc cgtcgtccgc cgacgacgcc cgtcaaaacc ggagtggcgg gaggtggcgc    120
gcgtgcgccg ccgtgctggc cgcatcggcg ttggcggtgg tcgtcgtggt cgggctcctc    180
gcgggcggca gggtggatcg ggtcccggcc ggcggaacga accaaaagcc atataaggaa    240
acatacggca tttcccatat tacacgccat gatatgctgc aaatccctga cagcaaaaa    300
aatgaaaaat atcaagttcc tgaattcgat tcgtccacaa ttaaaaatat ctcttctgca    360
aaaggcctgg acgtttggga cagctggcca ttacaaaacg ctgacggcac tgtcgcaaac    420
tatcacggct accacatcgt ctttgcatta gccggagatc ctaaaaatgc ggatgacaca    480
tcgatttaca tgttctatca aaagtcggc gaaacttcta ttgacagctg aaaaacgct     540
ggccgcgtct ttaaagacag cgacaaattc gatgcaaatg attctatcct aaaagaccaa    600
acacaagaat ggtcaggttc agccacattt acatctgacg gaaaaatccg tttattctac    660
actgatttct ccggtaaaca ttacggcaaa caaacactga caactgcaca gttaacgta    720
tcagcatcag acagctcttt gaacatcaac ggtgtagagg attataaatc aatctttgac    780
ggtgacggaa aaacgtatca aaatgtacag cagttcatcg atgaaggcaa ctacagctca    840
ggcgacaacc atacgctgag agatcctcac tacgtagaag ataaaggcca caaatactta    900
gtatttgaag caaacactgg aactgaagat ggctaccaag cgaagaatc tttatttaac    960
aaagcatact atggcaaaag cacatcattc ttccgtcaag aaagtcaaaa acttctgcaa   1020
agcgataaaa aacgcacggc tgagttagca acggcgctc tcggtatgat tgagctaaac   1080
gatgattaca cactgaaaaa agtgatgaaa ccgctgattg catctaacac agtaacagat   1140
gaaattgaac gcgcgaacgt ctttaaaatg aacggcaaat ggtacctgtt cactgactcc   1200
cgcggatcaa aaatgacgat tgacggcatt acgtctaacg atatttacat gcttggttat   1260
gtttctaatt ctttaactgg cccatacaag ccgctgaaca aaactggcct tgtgttaaaa   1320
atggatcttg atcctaacga tgtaaccttt acttactcac acttcgctgt acctcaagcg   1380
aaaggaaaca atgtcgtgat tacaagctat atgacaaaca gaggattcta cgcagacaaa   1440
caatcaacgt ttgcgccaag cttcctgctg aacatcaaag gcaagaaaac atctgttgtc   1500
aaagacagca tccttgaaca aggacaatta acagttaaca aataa                    1545
```

<210> SEQ ID NO 26
<211> LENGTH: 216
<212> TYPE: DNA
<213> ORGANISM: Lolium perenne

<400> SEQUENCE: 26

```
atggagtccc caagcgccgt cgtccccggc accacggcgc cgctgcttcc ttatgcgtac     60
gcgccgctgc cgtcgtccgc cgacgacgcc cgtcaaaacc ggagtggcgg gaggtggcgc    120
gcgtgcgccg ccgtgctggc cgcatcggcg ttggcggtgg tcgtcgtggt cgggctcctc    180
gcgggcggca gggtggatcg ggtcccggcc ggcgga                              216
```

<210> SEQ ID NO 27
<211> LENGTH: 514
<212> TYPE: PRT
<213> ORGANISM: Artificial Sequence
<220> FEATURE:
<223> OTHER INFORMATION: Chimeric sequence

<400> SEQUENCE: 27

```
Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Gly Leu Leu Ala Gly Gly Arg
    50                  55                  60

Val Asp Arg Val Pro Ala Gly Gly Thr Asn Gln Lys Pro Tyr Lys Glu
65              70                  75                  80

Thr Tyr Gly Ile Ser His Ile Thr Arg His Asp Met Leu Gln Ile Pro
                85                  90                  95

Glu Gln Gln Lys Asn Glu Lys Tyr Gln Val Pro Glu Phe Asp Ser Ser
            100                 105                 110

Thr Ile Lys Asn Ile Ser Ser Ala Lys Gly Leu Asp Val Trp Asp Ser
        115                 120                 125

Trp Pro Leu Gln Asn Ala Asp Gly Thr Val Ala Asn Tyr His Gly Tyr
    130                 135                 140

His Ile Val Phe Ala Leu Ala Gly Asp Pro Lys Asn Ala Asp Asp Thr
145                 150                 155                 160

Ser Ile Tyr Met Phe Tyr Gln Lys Val Gly Glu Thr Ser Ile Asp Ser
                165                 170                 175

Trp Lys Asn Ala Gly Arg Val Phe Lys Asp Ser Asp Lys Phe Asp Ala
            180                 185                 190

Asn Asp Ser Ile Leu Lys Asp Gln Thr Gln Glu Trp Ser Gly Ser Ala
        195                 200                 205

Thr Phe Thr Ser Asp Gly Lys Ile Arg Leu Phe Tyr Thr Asp Phe Ser
    210                 215                 220

Gly Lys His Tyr Gly Lys Gln Thr Leu Thr Thr Ala Gln Val Asn Val
225                 230                 235                 240

Ser Ala Ser Asp Ser Ser Leu Asn Ile Asn Gly Val Glu Asp Tyr Lys
                245                 250                 255

Ser Ile Phe Asp Gly Asp Gly Lys Thr Tyr Gln Asn Val Gln Gln Phe
            260                 265                 270

Ile Asp Glu Gly Asn Tyr Ser Ser Gly Asp Asn His Thr Leu Arg Asp
        275                 280                 285

Pro His Tyr Val Glu Asp Lys Gly His Lys Tyr Leu Val Phe Glu Ala
    290                 295                 300

Asn Thr Gly Thr Glu Asp Gly Tyr Gln Gly Glu Glu Ser Leu Phe Asn
305                 310                 315                 320

Lys Ala Tyr Tyr Gly Lys Ser Thr Ser Phe Phe Arg Gln Glu Ser Gln
                325                 330                 335

Lys Leu Leu Gln Ser Asp Lys Lys Arg Thr Ala Glu Leu Ala Asn Gly
            340                 345                 350

Ala Leu Gly Met Ile Glu Leu Asn Asp Asp Tyr Thr Leu Lys Lys Val
        355                 360                 365

Met Lys Pro Leu Ile Ala Ser Asn Thr Val Thr Asp Glu Ile Glu Arg
    370                 375                 380

Ala Asn Val Phe Lys Met Asn Gly Lys Trp Tyr Leu Phe Thr Asp Ser
385                 390                 395                 400

Arg Gly Ser Lys Met Thr Ile Asp Gly Ile Thr Ser Asn Asp Ile Tyr
                405                 410                 415
```

```
Met Leu Gly Tyr Val Ser Asn Ser Leu Thr Gly Pro Tyr Lys Pro Leu
            420                 425                 430
Asn Lys Thr Gly Leu Val Leu Lys Met Asp Leu Asp Pro Asn Asp Val
        435                 440                 445
Thr Phe Thr Tyr Ser His Phe Ala Val Pro Gln Ala Lys Gly Asn Asn
    450                 455                 460
Val Val Ile Thr Ser Tyr Met Thr Asn Arg Gly Phe Tyr Ala Asp Lys
465                 470                 475                 480
Gln Ser Thr Phe Ala Pro Ser Phe Leu Leu Asn Ile Lys Gly Lys Lys
            485                 490                 495
Thr Ser Val Val Lys Asp Ser Ile Leu Glu Gln Gly Gln Leu Thr Val
        500                 505                 510
Asn Lys

<210> SEQ ID NO 28
<211> LENGTH: 2499
<212> TYPE: DNA
<213> ORGANISM: Artificial Sequence
<220> FEATURE:
<223> OTHER INFORMATION: Chimeric sequence

<400> SEQUENCE: 28
atggagtccc caagcgccgt cgtccccggc accacggcgc cgctgcttcc ttatgcgtac      60
gcgccgctgc cgtcgtccgc cgacgacgcc cgtcaaaacc ggagtggcgg gaggtggcgc     120
gcgtgcgccg ccgtgctggc cgcatcggcg ttggcggtgg tcgtcgtggt cgggctcctc     180
gcgggcggca gggtggatcg ggtcccggcc ggcggaacta ttaatgcaga caatgttaat     240
gaaaatcaaa ctgtagaagt aactgctagt tcagtaaaca atgaaaataa taagcaagta     300
actgaaaaag atagtgcaga taaagtact agtgatgtgg ctgaagatgc taacaccaag     360
aaatcaaacg aaaatacaga aactacagaa agaatactc aaacagttgt tactaatgcg     420
ccagtaagtg atgtgaaaaa tacaaacaca gttaccgctg aaacacctgt tgataaagta     480
gtaaataata gtgatcaaaa gacaactaat gctgcaacta ctgatactaa aaaagatgat     540
gtaaaacaag ttgaaaagaa agactcagta gataaaacaa atgctgagga aaataaagat     600
agttcagtaa agccagctga aaatgctact aaggctgaat taagggcca agttaaagat     660
atcgttgaag aatctggtgt tgatactagc aagttaacta tgatcaaat taatgaatta     720
aataaaatta atttctccaa agaagcaaaa agtggtactc agttaactta caacgacttt     780
aaaaaaattg ctaaaacttt aattgaacaa gatgctcgtt atgctattcc attcttcaat     840
gcaagtaaaa ttaaaaatat gcctgctgct aaaacacttg atgctcaaag tggaaaagta     900
gaagatttgg aaatttggga ttcatggcct gttcaagatg caaaaactgg ttacgtatct     960
aactggaatg ctaccaatt agtgattggt atgatgggag ttccaaacgt caatgataac    1020
cacatttatc ttcttacaa caagtatggt gataatgact ttaatcattg aagaatgcc    1080
ggtcctattt tcggtctagg tactccagtt attcaacaat ggtctggatc agcaacttta    1140
aataaagatg gctcaattca actttactac actaaggttg atactagtga ataataact    1200
aaccaccaaa aactcgctag tgcaactgtt tacttaaatc ttgaaaaaga tcaagataag    1260
atttctattg ctcatgttga caacgaccat attgtctttg aaggtgatgg ttaccactac    1320
caaacttatg accaatggaa agaaactaac aagggtgctg acaatatcgc aatgcgtgat    1380
gcacacgtga ttgatgatga taatggtaat cgttaccttg tgtttgaagc aagtactgga    1440
```

```
accgaaaatt atcaaggtga tgatcaaatt tatcaatggt taaattacgg cggtactaac    1500
aaggataatt taggtgattt cttccaaatt ttatctaact ccgatattaa agatagagct    1560
aaatggtcaa acgctgcaat tggtatcatt aaattaaatg atgatgttaa gaatccaagt    1620
gttgcaaagg tctacagccc acttattagt gcaccaatgg taagtgatga atttgaacgc    1680
cctgatgttg ttaaattagg taataagtat tacttatttg ctgctactag attaaaccgt    1740
ggtagtaacg atgatgcttg gatggcaact aacaaagcag ttggtgataa cgtagctatg    1800
attggttatg tttctgataa cttaactcat ggttatgttc cattgaatga atctggcgtt    1860
gttttaactg catctgtacc ggctaactgg cgtactgcaa cttattcata ctatgcagtt    1920
ccagtagaag gaagagatga tcaacttta attacttcat acatcactaa tcgtggtgag    1980
gttgctggaa agggtatgca tgcaacttgg gcaccaagtt tcttgttaca aattaatcca    2040
gataacacta ctactgtttt agctaaaatg actaaccaag gggattggat ttgggatgat    2100
agtagtgaaa atccagatat gatgggtgta cttgaaaaag atgctccaaa tagtgctgcc    2160
cttcctggag aatggggaaa accagttgat tgggatttaa ttggtggata caacttgaag    2220
ccacaccaac ctgtaactcc tattccaaat gtaccaacta ctcctgaaac cccaaccaca    2280
ccagataagc cagaggtacc aactacccct gaagttccaa ccactccaga aactccaact    2340
ccagaagctc caaagaatcc agttaagaaa actagtcagt ctaaacttcc aaaggctgga    2400
gataaaaata gctttgcagc agttgtttta ggtgctgtaa gttcaatatt aggtgctgtt    2460
ggtttaacag gtgtttcaaa acgtaaacgt aataattaa                          2499
```

<210> SEQ ID NO 29
<211> LENGTH: 832
<212> TYPE: PRT
<213> ORGANISM: Artificial Sequence
<220> FEATURE:
<223> OTHER INFORMATION: Chimeric sequence

<400> SEQUENCE: 29

```
Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Gly Leu Leu Ala Gly Gly Arg
    50                  55                  60

Val Asp Arg Val Pro Ala Gly Gly Thr Ile Asn Ala Asp Asn Val Asn
65                  70                  75                  80

Glu Asn Gln Thr Val Glu Val Thr Ala Ser Ser Val Asn Asn Glu Asn
                85                  90                  95

Asn Lys Gln Val Thr Glu Lys Asp Ser Ala Asp Lys Ser Thr Ser Asp
            100                 105                 110

Val Ala Glu Asp Ala Asn Thr Lys Lys Ser Asn Glu Asn Thr Glu Thr
        115                 120                 125

Thr Glu Lys Asn Thr Gln Thr Val Val Thr Asn Ala Pro Val Ser Asp
    130                 135                 140

Val Lys Asn Thr Asn Thr Val Thr Ala Glu Thr Pro Val Asp Lys Val
145                 150                 155                 160

Val Asn Asn Ser Asp Gln Lys Thr Thr Asn Ala Ala Thr Thr Asp Thr
                165                 170                 175
```

-continued

```
Lys Lys Asp Asp Val Lys Gln Val Glu Lys Lys Asp Ser Val Asp Lys
                180                 185                 190

Thr Asn Ala Glu Glu Asn Lys Asp Ser Ser Val Lys Pro Ala Glu Asn
        195                 200                 205

Ala Thr Lys Ala Glu Leu Lys Gly Gln Val Lys Asp Ile Val Glu Glu
        210                 215                 220

Ser Gly Val Asp Thr Ser Lys Leu Thr Asn Asp Gln Ile Asn Glu Leu
225                 230                 235                 240

Asn Lys Ile Asn Phe Ser Lys Glu Ala Lys Ser Gly Thr Gln Leu Thr
                245                 250                 255

Tyr Asn Asp Phe Lys Lys Ile Ala Lys Thr Leu Ile Glu Gln Asp Ala
                260                 265                 270

Arg Tyr Ala Ile Pro Phe Phe Asn Ala Ser Lys Ile Lys Asn Met Pro
            275                 280                 285

Ala Ala Lys Thr Leu Asp Ala Gln Ser Gly Lys Val Glu Asp Leu Glu
        290                 295                 300

Ile Trp Asp Ser Trp Pro Val Gln Asp Ala Lys Thr Gly Tyr Val Ser
305                 310                 315                 320

Asn Trp Asn Gly Tyr Gln Leu Val Ile Gly Met Met Gly Val Pro Asn
                325                 330                 335

Val Asn Asp Asn His Ile Tyr Leu Leu Tyr Asn Lys Tyr Gly Asp Asn
            340                 345                 350

Asp Phe Asn His Trp Lys Asn Ala Gly Pro Ile Phe Gly Leu Gly Thr
        355                 360                 365

Pro Val Ile Gln Gln Trp Ser Gly Ser Ala Thr Leu Asn Lys Asp Gly
        370                 375                 380

Ser Ile Gln Leu Tyr Tyr Thr Lys Val Asp Thr Ser Asp Asn Asn Thr
385                 390                 395                 400

Asn His Gln Lys Leu Ala Ser Ala Thr Val Tyr Leu Asn Leu Glu Lys
                405                 410                 415

Asp Gln Asp Lys Ile Ser Ile Ala His Val Asp Asn Asp His Ile Val
            420                 425                 430

Phe Glu Gly Asp Gly Tyr His Tyr Gln Thr Tyr Asp Gln Trp Lys Glu
        435                 440                 445

Thr Asn Lys Gly Ala Asp Asn Ile Ala Met Arg Asp Ala His Val Ile
        450                 455                 460

Asp Asp Asp Asn Gly Asn Arg Tyr Leu Val Phe Glu Ala Ser Thr Gly
465                 470                 475                 480

Thr Glu Asn Tyr Gln Gly Asp Asp Gln Ile Tyr Gln Trp Leu Asn Tyr
                485                 490                 495

Gly Gly Thr Asn Lys Asp Asn Leu Gly Asp Phe Phe Gln Ile Leu Ser
            500                 505                 510

Asn Ser Asp Ile Lys Asp Arg Ala Lys Trp Ser Asn Ala Ala Ile Gly
        515                 520                 525

Ile Ile Lys Leu Asn Asp Asp Val Lys Asn Pro Ser Val Ala Lys Val
        530                 535                 540

Tyr Ser Pro Leu Ile Ser Ala Pro Met Val Ser Asp Glu Ile Glu Arg
545                 550                 555                 560

Pro Asp Val Val Lys Leu Gly Asn Lys Tyr Tyr Leu Phe Ala Ala Thr
                565                 570                 575

Arg Leu Asn Arg Gly Ser Asn Asp Asp Ala Trp Met Ala Thr Asn Lys
            580                 585                 590

Ala Val Gly Asp Asn Val Ala Met Ile Gly Tyr Val Ser Asp Asn Leu
```

```
                595                 600                 605
Thr His Gly Tyr Val Pro Leu Asn Glu Ser Gly Val Val Leu Thr Ala
        610                 615                 620

Ser Val Pro Ala Asn Trp Arg Thr Ala Thr Tyr Ser Tyr Tyr Ala Val
625                 630                 635                 640

Pro Val Glu Gly Arg Asp Asp Gln Leu Leu Ile Thr Ser Tyr Ile Thr
                645                 650                 655

Asn Arg Gly Glu Val Ala Gly Lys Gly Met His Ala Thr Trp Ala Pro
            660                 665                 670

Ser Phe Leu Leu Gln Ile Asn Pro Asp Asn Thr Thr Val Leu Ala
            675                 680                 685

Lys Met Thr Asn Gln Gly Asp Trp Ile Trp Asp Ser Ser Glu Asn
690                 695                 700

Pro Asp Met Met Gly Val Leu Glu Lys Asp Ala Pro Asn Ser Ala Ala
705                 710                 715                 720

Leu Pro Gly Glu Trp Gly Lys Pro Val Asp Trp Asp Leu Ile Gly Gly
                725                 730                 735

Tyr Asn Leu Lys Pro His Gln Pro Val Thr Pro Ile Pro Asn Val Pro
            740                 745                 750

Thr Thr Pro Glu Thr Pro Thr Thr Pro Asp Lys Pro Glu Val Pro Thr
            755                 760                 765

Thr Pro Glu Val Pro Thr Thr Pro Glu Thr Pro Thr Pro Glu Ala Pro
770                 775                 780

Lys Asn Pro Val Lys Lys Thr Ser Gln Ser Lys Leu Pro Lys Ala Gly
785                 790                 795                 800

Asp Lys Asn Ser Phe Ala Ala Val Leu Gly Ala Val Ser Ser Ile
                805                 810                 815

Leu Gly Ala Val Gly Leu Thr Gly Val Ser Lys Arg Lys Arg Asn Asn
            820                 825                 830

<210> SEQ ID NO 30
<211> LENGTH: 3353
<212> TYPE: DNA
<213> ORGANISM: Artificial Sequence
<220> FEATURE:
<223> OTHER INFORMATION: Chimeric sequence

<400> SEQUENCE: 30
cgtggtcgag attgtgtatt attctttagt tattacaaga cttttagcta aaatttgaaa      60
gaatttactt taagaaaatc ttaacatctg agataaattc agcaatagat tatatttttc     120
attactctag cagtattttt gcagatcaat cgcaacatat atggttgtta gaaaaaatgc     180
actatatata tatatattat tttttcaatt aaaagtgcat gatatataat atatatatat     240
atatatatat gtgtgtgtgt atatggtcaa agaaattctt atacaaatat acacgaacac     300
atatatttga caaatcaaa gtattacact aaacaatgag ttggtgcatg gccaaaacaa     360
atatgtagat taaaaattcc agcctccaaa aaaaaatcca gtgttgtaa agcattatat     420 atatatagta gatcccaaat ttttgtacaa ttccacactg atcgaattt taaagttgaa     480 tatctgacgt aggattttt taatgtctta cctgaccatt tactaataac attcatacgt     540
tttcatttga aatatcctct ataattatat tgaatttggc acataataag aaacctaatt     600
ggtgatttat tttactagta aatttctggt gatgggcttt ctactagaaa gctctcggaa     660
aatcttggac caaatccata ttccatgact tcgattgtta accctattag ttttcacaaa     720
catactatca atatcattgc aacggaaaag gtacaagtaa acattcaat ccgatagggaa     780
```

```
agtgatgtag gaggttggga agacaggccc agaaagagat ttatctgact tgttttgtgt      840
atagttttca atgttcataa aggaagatgg agacttgaga agttttttt ggactttgtt      900
tagctttgtt gggcgttttt ttttttgat caataacttt gttgggctta tgatttgtaa      960
tattttcgtg gactctttag tttatttaga cgtgctaact tgttgggct tatgacttgt     1020
tgtaacatat tgtaacagat gacttgatgt gcgactaatc tttacacatt aaacatagtt     1080
ctgtttttg aaagttctta ttttcatttt tatttgaatg ttatatattt ttctatattt     1140
ataattctag taaaaggcaa attttgcttt taaatgaaaa aaatatatat tccacagttt     1200
cacctaatct tatgcattta gcagtacaaa ttcaaaaatt tcccatttt attcatgaat     1260
cataccatta tatattaact aaatccaagg taaaaaaag gtatgaaagc tctatagtaa     1320
gtaaaatata aattccccat aaggaaaggg ccaagtccac caggcaagta aaatgagcaa     1380
gcaccactcc accatcacac aatttcactc atagataacg ataagattca tggaattatc     1440
ttccacgtgg cattattcca gcggttcaag ccgataaggg tctcaacacc tctccttagg     1500
cctttgtggc cgttaccaag taaaattaac ctcacacata tccacactca aaatccaacg     1560
gtgtagatcc tagtccactt gaatctcatg tatcctagac cctccgatca ctccaaagct     1620
tgttctcatt gttgttatca ttatatatag atgaccaaag cactagacca aacctcagtc     1680
acacaaagag taaagaagaa caatgaaagc cttcacactc gctctcttct tagctctttt     1740
cctctatctc ctgcccaatc cagcccattc cacgaaccaa aagccatata aggaaacata     1800
cggcatttcc catattacac gccatgatat gctgcaaatc cctgaacagc aaaaaaatga     1860
aaaatatcaa gttcctgaat tcgattcgtc cacaattaaa aatatctctt ctgcaaaagg     1920
cctggacgtt tgggacagct ggccattaca aaacgctgac ggcactgtcg caaactatca     1980
cggctaccac atcgtctttg cattagccgg agatcctaaa aatgcggatg acacatcgat     2040
ttacatgttc tatcaaaaag tcggcgaaac ttctattgac agctggaaaa acgctggccg     2100
cgtctttaaa gacagcgaca aattcgatgc aaatgattct atcctaaaag accaaacaca     2160
agaatggtca ggttcagcca catttacatc tgacggaaaa atccgtttat tctacactga     2220
tttctccggt aaacattacg gcaaacaaac actgacaact gcacaagtta acgtatcagc     2280
atcagacagc tctttgaaca tcaacggtgt agaggattat aaatcaatct ttgacggtga     2340
cggaaaaacg tatcaaaatg tacagcagtt catcgatgaa ggcaactaca gctcaggcga     2400
caaccatacg ctgagagatc ctcactacgt agaagataaa ggccacaaat acttagtatt     2460
tgaagcaaac actggaactg aagatggcta ccaaggcgaa gaatctttat ttaacaaagc     2520
atactatggc aaaagcacat cattcttccg tcaagaaagt caaaaacttc tgcaaagcga     2580
taaaaaacgc acggctgagt tagcaaacgg cgctctcggt atgattgagc taaacgatga     2640
ttacacactg aaaaagtga tgaaaccgct gattgcatct aacacagtaa cagatgaaat     2700
tgaacgcgcg aacgtcttta aaatgaacgg caaatggtac ctgttcactg actcccgcgg     2760
atcaaaaatg acgattgacg gcattacgtc taacgatatt tacatgcttg gttatgtttc     2820
taattctttta actgggccat acaagccgct gaacaaaact ggccttgtgt taaaaatgga     2880
tcttgatcct aacgatgtaa cctttactta ctccacacttc gctgtacctc aagcgaaagg     2940
aaacaatgtc gtgattacaa gctatatgac aaacagagga ttctacgcag acaaacaatc     3000
aacgtttgcg ccaagcttcc tgctgaacat caaaggcaag aaaacatctg ttgtcaaaga     3060
cagcatcctt gaacaaggac aattaacagt taacaaataa gatcgttcaa acatttggca     3120
```

-continued

| | |
|---|---|
| ataaagtttc ttaagaatga atcctgttgc cggtcttgcg atgattatca tataatttct | 3180 |
| gttgaattac gttaagcatg aaataattaa catgtaatgc atgacgtaat ttatgagatg | 3240 |
| ggtttttatg attagagtcc cgcaattata catttaatac gcgatagaaa acaaaatata | 3300 |
| gcgcgcaaac taggataaat tatcgcgcgc ggtgtcatca atgttactag atc | 3353 |

<210> SEQ ID NO 31
<211> LENGTH: 4307
<212> TYPE: DNA
<213> ORGANISM: Artificial Sequence
<220> FEATURE:
<223> OTHER INFORMATION: Chimeric sequence

<400> SEQUENCE: 31

| | |
|---|---|
| cgtggtcgag attgtgtatt attctttagt tattacaaga cttttagcta aaatttgaaa | 60 |
| gaatttactt taagaaaatc ttaacatctg agataatttc agcaatagat tatattttc | 120 |
| attactctag cagtattttt gcagatcaat cgcaacatat atggttgtta gaaaaaatgc | 180 |
| actatatata tatatattat tttttcaatt aaaagtgcat gatatataat atatatatat | 240 |
| atatatatat gtgtgtgtgt atatggtcaa agaaattctt atacaaatat acacgaacac | 300 |
| atatatttga caaaatcaaa gtattacact aaacaatgag ttggtgcatg gccaaaacaa | 360 |
| atatgtagat taaaaattcc agcctccaaa aaaaaatcca agtgttgtaa agcattatat | 420 |
| atatatagta gatcccaaat ttttgtacaa ttccacactg atcgaatttt taagttgaa | 480 |
| tatctgacgt aggatttttt taatgtctta cctgaccatt tactaataac attcatacgt | 540 |
| tttcatttga aatatcctct ataattatat tgaatttggc acataataag aaacctaatt | 600 |
| ggtgatttat tttactagta aatttctggt gatgggcttt ctactagaaa gctctcggaa | 660 |
| aatcttggac caaatccata ttccatgact tcgattgtta accctattag ttttcacaaa | 720 |
| catactatca atatcattgc aacggaaaag gtacaagtaa acattcaat ccgatagga | 780 |
| agtgatgtag gaggttggga agacaggccc agaaagagat ttatctgact tgttttgtgt | 840 |
| atagttttca atgttcataa aggaagatgg agacttgaga agttttttt ggactttgtt | 900 |
| tagcttgtt gggcgttttt tttttttgat caataacttt gttgggctta tgatttgtaa | 960 |
| tattttcgtg gactctttag tttatttaga cgtgctaact ttgttgggct tatgacttgt | 1020 |
| tgtaacatat tgtaacagat gacttgatgt gcgactaatc tttacacatt aaacatagtt | 1080 |
| ctgtttttg aaagttctta ttttcatttt tatttgaatg ttatatattt ttctatattt | 1140 |
| ataattctag taaaaggcaa attttgcttt taaatgaaaa aatatatat tccacagttt | 1200 |
| cacctaatct tatgcattta gcagtacaaa ttcaaaaatt tcccattttt attcatgaat | 1260 |
| cataccatta tatattaact aaatccaagg taaaaaaaag gtatgaaagc tctatagtaa | 1320 |
| gtaaaatata aattccccat aaggaaaggg ccaagtccac caggcaagta aaatgagcaa | 1380 |
| gcaccactcc accatcacac aatttccactc atagataacg ataagattca tggaattatc | 1440 |
| ttccacgtgg cattattcca gcggttcaag ccgataaggg tctcaacacc tctccttagg | 1500 |
| cctttgtggc cgttaccaag taaaattaac ctcacacata tccacactca aaatccaacg | 1560 |
| gtgtagatcc tagtccactt gaatctcatg tatcctagac cctccgatca ctccaaagct | 1620 |
| tgttctcatt gttgttatca ttatatatag atgaccaaag cactagacca aacctcagtc | 1680 |
| acacaaagag taaagaagaa caatgaaagc cttcacactc gctctcttct tagctctttt | 1740 |
| cctctatctc ctgcccaatc cagcccattc cactattaat gcagacaatg ttaatgaaaa | 1800 |
| tcaaactgta gaagtaactg ctagttcagt aaacaatgaa aataataagc aagtaactga | 1860 |

```
aaaagatagt gcagataaaa gtactagtga tgtggctgaa gatgctaaca ccaagaaatc    1920
aaacgaaaat acagaaacta cagaaaagaa tactcaaaca gttgttacta atgcgccagt    1980
aagtgatgtg aaaaatacaa acacagttac cgctgaaaca cctgttgata aagtagtaaa    2040
taatagtgat caaaagacaa ctaatgctgc aactactgat actaaaaaag atgatgtaaa    2100
acaagttgaa aagaaagact cagtagataa aacaaatgct gaggaaaata aagatagttc    2160
agtaaagcca gctgaaaatg ctactaaggc tgaattaaag ggccaagtta agatatcgt     2220 tgaagaatct ggtgttgata ctagcaagtt aactaatgat caaattaatg aattaaataa    2280
aattaatttc tccaaagaag caaaaagtgg tactcagtta acttacaacg actttaaaaa    2340
aattgctaaa actttaattg aacaagatgc tcgttatgct attccattct tcaatgcaag    2400
taaaattaaa aatatgcctg ctgctaaaac acttgatgct caaagtggaa aagtagaaga    2460
tttggaaatt tgggattcat ggcctgttca agatgcaaaa actggttacg tatctaactg    2520
gaatggctac caattagtga ttggtatgat gggagttcca aacgtcaatg ataaccacat    2580
ttatcttctt tacaacaagt atggtgataa tgactttaat cattggaaga atgccggtcc    2640
tattttcggt ctaggtactc cagttattca acaatggtct ggatcagcaa ctttaaataa    2700
agatggctca attcaacttt actacactaa ggttgatact agtgataata atactaacca    2760
ccaaaaactc gctagtgcaa ctgtttactt aaatcttgaa aaagatcaag ataagatttc    2820
tattgctcat gttgacaacg accatattgt ctttgaaggt gatggttacc actaccaaac    2880
ttatgaccaa tggaaagaaa ctaacaaggg tgctgacaat atcgcaatgc gtgatgcaca    2940
cgtgattgat gatgataatg gtaatcgtta ccttgtgttt gaagcaagta ctggaaccga    3000
aaattatcaa ggtgatgatc aaatttatca atggttaaat tacggcggta ctaacaagga    3060
taatttaggt gatttcttcc aaattttatc taactccgat attaaagata gagctaaatg    3120
gtcaaacgct gcaattggta tcattaaatt aaatgatgat gttaagaatc caagtgttgc    3180
aaaggtctac agcccactta ttagtgcacc aatggtaagt gatgaaattg aacgccctga    3240
tgttgttaaa ttaggtaata agtattactt atttgctgct actagattaa accgtggtag    3300
taacgatgat gcttggatgg caactaacaa agcagttggt gataacgtag ctatgattgg    3360
ttatgtttct gataacttaa ctcatggtta tgttccattg aatgaatctg gcgttgtttt    3420
aactgcatct gtaccggcta actggcgtac tgcaacttat tcatactatg cagttccagt    3480
agaaggaaga gatgatcaac tttttaattac ttcatacatc actaatcgtg gtgaggttgc    3540
tggaaagggt atgcatgcaa cttgggcacc aagtttcttg ttacaaatta atccagataa    3600
cactactact gttttagcta aaatgactaa ccaagggat tggatttggg atgatagtag    3660
tgaaaatcca gatatgatgg gtgtacttga aaaagatgct ccaaatagtg ctgcccttcc    3720
tggagaatgg ggaaaaccag ttgattggga tttaattggt ggatacaact tgaagccaca    3780
ccaacctgta actcctattc caaatgtacc aactactcct gaaacccaa ccacaccaga     3840 taagccagag gtaccaacta cccctgaagt tccaaccact ccagaaactc caactccaga    3900
agctccaaag aatccagtta agaaaactag tcagtctaaa cttccaaagg ctggagataa    3960
aaatagcttt gcagcagttg ttttaggtgc tgtaagttca atattaggtg ctgttggttt    4020
aacaggtgtt tcaaaacgta aacgtaataa ttaagatcgt tcaaacattt ggcaataaag    4080
tttcttaaga atgaatcctg ttgccggtct tgcgatgatt atcatataat ttctgttgaa    4140
ttacgttaag catgaaataa ttaacatgta atgcatgacg taatttatga gatgggtttt    4200
```

```
tatgattaga gtcccgcaat tatacattta atacgcgata gaaaacaaaa tatagcgcgc    4260
aaactaggat aaattatcgc gcgcggtgtc atcaatgtta ctagatc                  4307

<210> SEQ ID NO 32
<211> LENGTH: 3500
<212> TYPE: DNA
<213> ORGANISM: Artificial Sequence
<220> FEATURE:
<223> OTHER INFORMATION: Chimeric sequence

<400> SEQUENCE: 32
cgtggtcgag attgtgtatt attctttagt tattacaaga cttttagcta aaatttgaaa      60
gaatttactt taagaaaatc ttaacatctg agataaattc agcaatagat tatattttc     120 attactctag cagtattttt gcagatcaat cgcaacatat atggttgtta gaaaaaatgc    180
actatatata tatatattat tttttcaatt aaaagtgcat gatatataat atatatatat    240
atatatatat gtgtgtgtgt atatggtcaa agaaattctt atacaaatat acacgaacac    300
atatatttga caaaatcaaa gtattacact aaacaatgag ttggtgcatg gccaaaacaa    360
atatgtagat taaaaattcc agcctccaaa aaaaaatcca agtgttgtaa agcattatat    420
atatatagta gatcccaaat ttttgtacaa ttccacactg atcgaatttt taagttgaa     480 tatctgacgt aggatttttt taatgtctta cctgaccatt tactaataac attcatacgt    540
tttcatttga aatatcctct ataattatat tgaatttggc acataataag aaacctaatt    600
ggtgatttat tttactagta aatttctggt gatgggcttt ctactagaaa gctctcggaa    660
aatcttggac caaatccata ttccatgact tcgattgtta accctattag ttttcacaaa    720
catactatca atatcattgc aacggaaaag gtacaagtaa acattcaat ccgatagga     780 agtgatgtag gaggttggga agacaggccc agaaagagat ttatctgact tgttttgtgt    840
atagttttca atgttcataa aggaagatgg agacttgaga agtttttttt ggactttgtt    900
tagctttgtt gggcgttttt tttttttgat caataacttt gttgggctta tgatttgtaa    960
tattttcgtg gactctttag tttatttaga cgtgctaact ttgttgggct tatgacttgt   1020
tgtaacatat tgtaacagat gacttgatgt gcgactaatc tttacacatt aaacatagtt   1080
ctgttttttg aaagttctta ttttcatttt tatttgaatg ttatatattt ttctatattt   1140
ataattctag taaaaggcaa attttgcttt taaatgaaaa aatatatat tccacagttt    1200 cacctaatct tatgcattta gcagtacaaa ttcaaaaatt tcccatttttt attcatgaat   1260 cataccatta tatattaact aaatccaagg taaaaaaag gtatgaaagc tctatagtaa    1320
gtaaaatata aattccccat aaggaaaggg ccaagtccac caggcaagta aaatgagcaa    1380
gcaccactcc accatcacac aatttcactc atagataacg ataagattca tggaattatc    1440
ttccacgtgg cattattcca gcggttcaag ccgataaggg tctcaacacc tctccttagg   1500
cctttgtggc cgttaccaag taaaattaac ctcacacata tccacactca aaatccaacg    1560
gtgtagatcc tagtccactt gaatctcatg tatcctagac cctccgatca ctccaaagct   1620
tgttctcatt gttgttatca ttatatatag atgaccaaag cactagacca aacctcagtc    1680
acacaaagag taaagaagaa caatggagtc cccaagcgcc gtcgtcccg gcaccacggc    1740 gccgctgctt cctatgcgt acgcgccgct gccgtcgtcc gccgacgacg cccgtcaaaa    1800
ccggagtggc gggaggtggc gcgcgtgcgc cgccgtgctg gccgcatcgg cgttggcggt    1860
ggtcgtcgtg gtcgggctcc tcgcgggcgg cagggtggat cgggtcccgg ccggcggaac    1920
gaaccaaaag ccatataagg aaacatacgg catttcccat attacacgcc atgatatgct    1980
```

```
gcaaatccct gaacagcaaa aaaatgaaaa atatcaagtt cctgaattcg attcgtccac    2040
aattaaaaat atctcttctg caaaaggcct ggacgtttgg gacagctggc cattacaaaa    2100
cgctgacggc actgtcgcaa actatcacgg ctaccacatc gtctttgcat tagccggaga    2160
tcctaaaaat gcggatgaca catcgattta catgttctat caaaaagtcg gcgaaacttc    2220
tattgacagc tggaaaaacg ctggccgcgt ctttaaagac agcgacaaat tcgatgcaaa    2280
tgattctatc ctaaaagacc aaacacaaga atggtcaggt tcagccacat ttacatctga    2340
cggaaaaatc cgtttattct acactgattt ctccggtaaa cattacggca aacaaacact    2400
gacaactgca caagttaacg tatcagcatc agacagctct ttgaacatca acggtgtaga    2460
ggattataaa tcaatctttg acggtgacgg aaaaacgtat caaaatgtac agcagttcat    2520
cgatgaaggc aactcagct caggcgacaa ccatacgctg agagatcctc actacgtaga    2580
agataaaggc cacaaatact tagtatttga agcaaacact ggaactgaag atggctacca    2640
aggcgaagaa tctttattta acaaagcata ctatggcaaa agcacatcat tcttccgtca    2700
agaaagtcaa aaacttctgc aaagcgataa aaaacgcacg gctgagttag caaacggcgc    2760
tctcggtatg attgagctaa acgatgatta cacactgaaa aaagtgatga accgctgat    2820 tgcatctaac acagtaacag atgaaattga acgcgcgaac gtctttaaaa tgaacggcaa    2880
atggtacctg ttcactgact cccgcggatc aaaaatgacg attgacggca ttacgtctaa    2940
cgatatttac atgcttggtt atgtttctaa ttctttaact ggcccataca gccgctgaa    3000 caaaactggc cttgtgttaa aaatggatct tgatcctaac gatgtaacct ttacttactc    3060
acacttcgct gtacctcaag cgaaaggaaa caatgtcgtg attacaagct atatgacaaa    3120
cagaggattc tacgcagaca acaatcaac gtttgcgcca agcttcctgc tgaacatcaa    3180
aggcaagaaa acatctgttg tcaaagacag catccttgaa caaggacaat taacagttaa    3240
caaataagat cgttcaaaca tttggcaata aagtttctta agaatgaatc ctgttgccgg    3300
tcttgcgatg attatcatat aatttctgtt gaattacgtt aagcatgaaa taattaacat    3360
gtaatgcatg acgtaattta tgagatgggt ttttatgatt agagtcccgc aattatacat    3420
ttaatacgcg atagaaaaca aaatatagcg cgcaaactag gataaattat cgcgcgcggt    3480
gtcatcaatg ttactagatc                                               3500
```

<210> SEQ ID NO 33
<211> LENGTH: 5234
<212> TYPE: DNA
<213> ORGANISM: Artificial Sequence
<220> FEATURE:
<223> OTHER INFORMATION: Chimeric sequence

<400> SEQUENCE: 33

```
cgtggtcgag attgtgtatt attctttagt tattacaaga cttttagcta aaatttgaaa     60
gaatttactt taagaaaatc ttaacatctg agataaattc agcaatagat tatattttc    120 attactctag cagtattttt gcagatcaat cgcaacatat atggttgtta gaaaaaatgc    180
actatatata tatatattat tttttcaatt aaaagtgcat gatatataat atatatatat    240
atatatatat gtgtgtgtgt atatggtcaa agaaattctt atacaaatat acacgaacac    300
atatatttga caaatcaaa gtattacact aaacaatgag ttggtgcatg gccaaaacaa    360
atatgtagat taaaaattcc agcctccaaa aaaaaatcca agtgttgtaa agcattatat    420
atatatagta gatcccaaat ttttgtacaa ttccacactg atcgaatttt taagttgaa    480
```

```
tatctgacgt aggattttttt taatgtctta cctgaccatt tactaataac attcatacgt    540
tttcatttga aatatcctct ataattatat tgaatttggc acataataag aaacctaatt    600
ggtgatttat tttactagta aatttctggt gatgggcttt ctactagaaa gctctcggaa    660
aatcttggac caaatccata ttccatgact tcgattgtta accctattag ttttcacaaa    720
catactatca atatcattgc aacggaaaag gtacaagtaa acattcaat ccgataggga     780 cgtggtcgag attgtgtatt attctttagt tattacaaga cttttagcta aaatttgaaa    840
gaatttactt taagaaaatc ttaacatctg agataatttc agcaatagat tatattttc    900 attactctag cagtattttt gcagatcaat cgcaacatat atggttgtta gaaaaaatgc    960
actatatata tatatattat tttttcaatt aaaagtgcat gatatataat atatatatat    1020
atatatatat gtgtgtgtgt atatggtcaa agaaattctt atacaaatat acacgaacac    1080
atatatttga caaaatcaaa gtattacact aaacaatgag ttggtgcatg gccaaaacaa    1140
atatgtagat taaaaattcc agcctccaaa aaaaaatcca agtgttgtaa agcattatat    1200
atatatagta gatcccaaat ttttgtacaa ttccacactg atcgaatttt taaagttgaa    1260
tatctgacgt aggattttttt taatgtctta cctgaccatt tactaataac attcatacgt    1320
tttcatttga aatatcctct ataattatat tgaatttggc acataataag aaacctaatt    1380
ggtgatttat tttactagta aatttctggt gatgggcttt ctactagaaa gctctcggaa    1440
aatcttggac caaatccata ttccatgact tcgattgtta accctattag ttttcacaaa    1500
catactatca atatcattgc aacggaaaag gtacaagtaa acattcaat ccgataggga     1560 agtgatgtag gaggttggga agacaggccc agaaagagat ttatctgact tgttttgtgt    1620
atagttttca atgttcataa aggaagatgg agacttgaga agttttttt ggactttgtt    1680 tagctttgtt gggcgttttt ttttttttgat caataacttt gttgggctta tgatttgtaa    1740
tattttcgtg gactctttag tttatttaga cgtgctaact ttgttgggct tatgacttgt    1800
tgtaacatat tgtaacagat gacttgatgt gcgactaatc tttacacatt aaacatagtt    1860
ctgttttttg aaagttctta ttttcatttt tatttgaatg ttatatattt ttctatattt    1920
ataattctag taaaaggcaa atttttgcttt taaatgaaaa aatatatat tccacagttt    1980 cacctaatct tatgcattta gcagtacaaa ttcaaaaatt tcccattttt attcatgaat    2040
cataccatta tatattaact aaatccaagg taaaaaaaag gtatgaaagc tctatagtaa    2100
gtaaaatata aattccccat aaggaaaggg ccaagtccac caggcaagta aaatgagcaa    2160
gcaccactcc accatcacac aatttcactc atagataacg ataagattca tggaattatc    2220
ttccacgtgg cattattcca gcggttcaag ccgataaggg tctcaacacc tctccttagg    2280
cctttgtggc cgttaccaag taaaattaac ctcacacata tccacactca aaatccaacg    2340
gtgtagatcc tagtccactt gaatctcatg tatcctagac cctccgatca ctccaaagct    2400
tgttctcatt gttgttatca ttatatatag atgaccaaag cactagacca aacctcagtc    2460
acacaaagag taaagaagaa caatggagtc cccaagcgcc gtcgtcccg gcaccacggc     2520 gccgctgctt ccttatgcgt acgcgccgct gccgtcgtcc gccgacgacg cccgtcaaaa    2580
ccggagtggc gggaggtggc gcgcgtgcgc cgccgtgctg gccgcatcgg cgttggcggt    2640
ggtcgtcgtg gtcgggctcc tcgcgggcgg cagggtggat cgggtcccgg ccggcggaac    2700
tattaatgca gacaatgtta atgaaaatca aactgtagaa gtaactgcta gttcagtaaa    2760
caatgaaaat aataagcaag taactgaaaa agatagtgca gataaaagta ctagtgatgt    2820
ggctgaagat gctaacacca agaaatcaaa cgaaaataca gaaactacag aaaagaatac    2880
```

```
tcaaacagtt gttactaatg cgccagtaag tgatgtgaaa aatacaaaca cagttaccgc    2940
tgaaacacct gttgataaag tagtaaataa tagtgatcaa aagacaacta atgctgcaac    3000
tactgatact aaaaaagatg atgtaaaaca agttgaaaag aaagactcag tagataaaac    3060
aaatgctgag gaaaataaag atagttcagt aaagccagct gaaaatgcta ctaaggctga    3120
attaaagggc caagttaaag atatcgttga agaatctggt gttgatacta gcaagttaac    3180
taatgatcaa attaatgaat taaataaaat taatttctcc aaagaagcaa aaagtggtac    3240
tcagttaact tacaacgact ttaaaaaaat tgctaaaact ttaattgaac aagatgctcg    3300
ttatgctatt ccattcttca atgcaagtaa aattaaaaat atgcctgctg ctaaaacact    3360
tgatgctcaa agtggaaaag tagaagattt ggaaatttgg gattcatggc ctgttcaaga    3420
tgcaaaaact ggttacgtat ctaactggaa tggctaccaa ttagtgattg gtatgatggg    3480
agttccaaac gtcaatgata accacattta tcttctttac aacaagtatg gtgataatga    3540
ctttaatcat tggaagaatg ccggtcctat tttcggtcta ggtactccag ttattcaaca    3600
atggtctgga tcagcaactt taaataaaga tggctcaatt caactttact acactaaggt    3660
tgatactagt gataataata ctaaccacca aaaactcgct agtgcaactg tttacttaaa    3720
tcttgaaaaa gatcaagata agatttctat tgctcatgtt gacaacgacc atattgtctt    3780
tgaaggtgat ggttaccact accaaactta tgaccaatgg aaagaaacta caagggtgc    3840 tgacaatatc gcaatgcgtg atgcacacgt gattgatgat gataatggta atcgttacct    3900
tgtgtttgaa gcaagtactg gaaccgaaaa ttatcaaggt gatgatcaaa tttatcaatg    3960
gttaaattac ggcggtacta caaggataa tttaggtgat ttcttccaaa ttttatctaa    4020
ctccgatatt aaagatagag ctaaatggtc aaacgctgca attggtatca ttaaattaaa    4080
tgatgatgtt aagaatccaa gtgttgcaaa ggtctacagc ccacttatta gtgcaccaat    4140
ggtaagtgat gaaattgaac gccctgatgt tgttaaatta ggtaataagt attacttatt    4200
tgctgctact agattaaacc gtggtagtaa cgatgatgct tggatggcaa ctaacaaagc    4260
agttggtgat aacgtagcta tgattggtta tgtttctgat aacttaactc atggttatgt    4320
tccattgaat gaatctggcg ttgttttaac tgcatctgta ccggctaact ggcgtactgc    4380
aacttattca tactatgcag ttccagtaga aggaagagat gatcaacttt taattacttc    4440
atacatcact aatcgtggtg aggttgctgg aaagggtatg catgcaactt gggcaccaag    4500
tttcttgtta caaattaatc cagataacac tactactgtt ttagctaaaa tgactaacca    4560
aggggattgg atttgggatg atagtagtga aaatccagat atgatgggtg tacttgaaaa    4620
agatgctcca aatagtgctg ccccttcctgg agaatgggga aaaccagttg attgggattt    4680
aattggtgga tacaacttga agccacacca acctgtaact cctattccaa atgtaccaac    4740
tactcctgaa accccaacca caccagataa gccagaggta ccaactaccc ctgaagttcc    4800
aaccactcca gaaactccaa ctccagaagc tccaaagaat ccagttaaga aaactagtca    4860
gtctaaactt ccaaaggctg gagataaaaa tagctttgca gcagttgttt taggtgctgt    4920
aagttcaata ttaggtgctg ttggtttaac aggtgtttca aaacgtaaac gtaataatta    4980
agatcgttca acatttggc aataaagttt cttaagaatg aatcctgttg ccggtcttgc    5040
gatgattatc atataatttc tgttgaatta cgttaagcat gaaataatta acatgtaatg    5100
catgacgtaa tttatgagat gggttttat gattagagtc ccgcaattat acatttaata    5160
cgcgatagaa aacaaaatat agcgcgcaaa ctaggataaa ttatcgcgcg cggtgtcatc    5220
```
aatgttacta gatc                                                       5234

<210> SEQ ID NO 34
<211> LENGTH: 2790
<212> TYPE: DNA
<213> ORGANISM: Artificial Sequence
<220> FEATURE:
<223> OTHER INFORMATION: Chimeric sequence

<400> SEQUENCE: 34

| | |
|---|---|
| gatccggtga ctcaaaaaag aagagccgcc atctgtccaa gcgccactcc tacgagaact | 60 |
| aaaatcctat tccctccgta aataaatata agagtgttta gatcactact tctttacaga | 120 |
| gaatttcctt ccctccaagg ggaggcgaat ccataggcac atcgacggat atggaggggg | 180 |
| gaaacatata ttttactatg ctagttcagt taattctacc aagaaaacat atattttatt | 240 |
| ttgacaaaca ttgtataaat gtagacattc acatacacgt atgtacacca ccctctatga | 300 |
| ttgcacaccc gcacactata tgcctatgag catactttca agagtgagcc agcaaatttt | 360 |
| atgataaaat gaaatatttt gcccagccaa ctcagtcgca tcctcggaca atttgttatc | 420 |
| aaggaactca cccaaaaaca agcaaagcta gaaaaaggtt gtgtggcagc cacctaatga | 480 |
| catgaaggac tgaaatttcc agcacacaca atgtatccga cggcaatgct tcttccactg | 540 |
| atccggagaa gataaggaaa cgaggcaacc agcgaacgtg agccatccca accacatctg | 600 |
| taccaaagaa acggggctat atataccgtg gtgacccggc aatggggtcc tcaactgtag | 660 |
| ccggcatcct cctctcctcc gataatacaa ataccatgaa agccttcaca ctcgctctct | 720 |
| tcttagctct tttcctctat ctcctgccca atccagccca ttccacgaac caaaagccat | 780 |
| ataaggaaac atacggcatt tcccatatta cacgccatga tatgctgcaa atccctgaac | 840 |
| agcaaaaaaa tgaaaaatat caagttcctg aattcgattc gtccacaatt aaaaatatct | 900 |
| cttctgcaaa aggcctggac gtttgggaca gctggccatt acaaaacgct gacggcactg | 960 |
| tcgcaaacta tcacggctac cacatcgtct ttgcattagc cggagatcct aaaaatgcgg | 1020 |
| atgacacatc gatttacatg ttctatcaaa aagtcggcga aacttctatt gacagctgga | 1080 |
| aaaacgctgg ccgcgtcttt aaagacagcg acaaattcga tgcaaatgat tctatcctaa | 1140 |
| aagaccaaac acaagaatgg tcaggttcag ccacatttac atctgacgga aaaatccgtt | 1200 |
| tattctacac tgatttctcc ggtaaacatt acggcaaaca aacactgaca actgcacaag | 1260 |
| ttaacgtatc agcatcagac agctctttga acatcaacgg tgtagaggat tataaatcaa | 1320 |
| tctttgacgg tgacggaaaa acgtatcaaa atgtacagca gttcatcgat gaaggcaact | 1380 |
| acagctcagg cgacaaccat acgctgagag atcctcacta cgtagaagat aaaggccaca | 1440 |
| aatacttagt atttgaagca aacactggaa ctgaagatgg ctaccaaggc gaagaatctt | 1500 |
| tatttaacaa agcatactat ggcaaaagca catcattctt ccgtcaagaa agtcaaaaac | 1560 |
| ttctgcaaag cgataaaaaa cgcacggctg agttagcaaa cggcgctctc ggtatgattg | 1620 |
| agctaaacga tgattacaca ctgaaaaaag tgatgaaacc gctgattgca tctaacacag | 1680 |
| taacagatga aattgaacgc gcgaacgtct ttaaaatgaa cggcaaatgg tacctgttca | 1740 |
| ctgactcccg cggatcaaaa atgacgattg acggcattac gtctaacgat atttacatgc | 1800 |
| ttggttatgt ttctaattct ttaactggcc catacaagcc gctgaacaaa actggccttg | 1860 |
| tgttaaaaat ggatcttgat cctaacgatg taacctttac ttactcacac ttcgctgtac | 1920 |
| ctcaagcgaa aggaaacaat gtcgtgatta caagctatat gacaaacaga ggattctacg | 1980 |
| cagacaaaca atcaacgttt gcgccaagct tcctgctgaa catcaaaggc aagaaaacat | 2040 |

```
ctgttgtcaa agacagcatc cttgaacaag acaattaac agttaacaaa taaactatga   2100
gttgaaacaa tggcctatct catatgaaga tcttttgtga atttcactt tgtccacgac    2160 ctctgttgca cgactctgct ttccgaccgg agcataccttt tgttctata tgatttgtgt   2220 atgtatgtag gaacctatgt tctcgagcat gcatacataa ttcctcatag gtctatatac   2280
accggctatc catatgcaaa acctgtgtaa tatttgttat atacaacacg cggaccattg    2340
tcttgctgtt attaattctt ttttcccgca aaaaggaaa agtttcttta tttggcactg     2400
caatggatat gcctcacagc tagtgggtgg agaattcagt atttgacatt aagattccct    2460
gatttgcaat tgcaaatttc agtttcttta cttatatcac tacaaaagtc ttattgtttc    2520
ttttccacgt cattaccatc tgctccattg ttttttgcta gtagaatagg atgaagcatg    2580
gacacagatt aactgagctc gagctcatat gagctcgggt gaacaataaa atctgaaaat    2640
acttagaaag aattcaaaat tttctgtttt ttgtggcaaa atttgacaaa tgttataaat    2700
gcttgcaaag tttcatcata gaacgacatt cgtggatgtc atggcaaaaa acaaattcag    2760
cactctgaaa ataactttt tgaagtatcg                                     2790
```

<210> SEQ ID NO 35
<211> LENGTH: 4683
<212> TYPE: DNA
<213> ORGANISM: Artificial Sequence
<220> FEATURE:
<223> OTHER INFORMATION: Chimeric sequence

<400> SEQUENCE: 35

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atatttatt     240 ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acgggctat atataccgtg gtgacccggc aatggggtcc tcaactgtag     660
ccggcatcct cctctcctcc gataatacaa ataccatgaa agccttcaca ctcgctctct    720
tcttagctct tttcctctat ctcctgccca atccagccca ttcacgaac caaaagccat     780 ataaggaaac atacggcatt tcccatatta cacgccatga tgctgcaa atccctgaac      840 agcaaaaaaa tgaaaatat caagttcctg aattcgattc gtccacaatt aaaaatatct     900
cttctgcaaa aggcctggac gtttgggaca gctggccatt acaaaacgct gacggcactg    960
tcgcaaacta tcacggctac cacatcgtct ttgcattagc cggagatcct aaaaatgcgg   1020
atgacacatc gatttacatg ttctatcaaa aagtcggcga aacttctatt gacagctgga   1080
aaaacgctgg ccgcgtcttt aaagacagcg acaaattcga tgcaaatgat tctatcctaa    1140
aagaccaaac acaagaatgg tcaggttcag ccacatttac atctgacgga aaaatccgtt    1200
tattctacac tgatttctcc ggtaaacatt acggcaaaca aacactgaca actgcacaag    1260
```

-continued

| | |
|---|---|
| ttaacgtatc agcatcagac agctctttga acatcaacgg tgtagaggat tataaatcaa | 1320 |
| tctttgacgg tgacggaaaa acgtatcaaa atgtacagca gttcatcgat gaaggcaact | 1380 |
| acagctcagg cgacaaccat acgctgagag atcctcacta cgtagaagat aaaggccaca | 1440 |
| aatacttagt atttgaagca aacactggaa ctgaagatgg ctaccaaggc gaagaatctt | 1500 |
| tatttaacaa agcatactat ggcaaaagca catcattctt ccgtcaagaa agtcaaaaac | 1560 |
| ttctgcaaag cgataaaaaa cgcacggctg agttagcaaa cggcgctctc ggtatgattg | 1620 |
| agctaaacga tgattacaca ctgaaaaaag tgatgaaacc gctgattgca tctaacacag | 1680 |
| taacagatga aattgaacgc gcgaacgtct ttaaaatgaa cggcaaatgg tacctgttca | 1740 |
| ctgactcccg cggatcaaaa atgacgattg acggcattac gtctaacgat atttacatgc | 1800 |
| ttggttatgt ttctaattct taactggcc catacaagcc gctgaacaaa actggccttg | 1860 |
| tgttaaaaat ggatcttgat cctaacgatg taaccttttac ttactcacac ttcgctgtac | 1920 |
| ctcaagcgaa aggaaacaat gtcgtgatta caagctatat gacaaacaga ggattctacg | 1980 |
| cagacaaaca atcaacgttt gcgccaagct tcctgctgaa catcaaaggc aagaaaacat | 2040 |
| ctgttgtcaa agacagcatc cttgaacaag acaattaaac agttaacaaa taaactatga | 2100 |
| gttgaaacaa tggcctatct catatgaaga tcttttgtga atttcacttt tgtccacgac | 2160 |
| ctctgttgca cgactctgct ttccgaccgg agcataacctt tgttctata tgatttgtgt | 2220 |
| atgtatgtag gaacctatgt tctcgagcat gcatacataa ttcctcatag gtctatatac | 2280 |
| accggctatc catatgcaaa acctgtgtaa tatttgttat atacaacacg cggaccattg | 2340 |
| tcttgctgtt attaattctt ttttcccgca aaaaggaaa agtttcttta tttggcactg | 2400 |
| caatggatat gcctcacagc tagtgggtgg agaattcagt atttgacatt aagattccct | 2460 |
| gatttgcaat tgcaaatttc agtttcttta cttatatcac tacaaaagtc ttattgtttc | 2520 |
| ttttccacgt cattaccatc tgctccattg gttttttgcta gtagaatagg atgaagcatg | 2580 |
| gacacagatt aactgagctc gagctcatat gagctcgggt gaacaataaa atctgaaaat | 2640 |
| acttagaaag aattcaaaat tttctgtttt ttgtggcaaa atttgacaaa tgttataaat | 2700 |
| gcttgcaaag tttcatcata gaacgacatt cgtggatgtc atggcaaaaa acaaattcag | 2760 |
| cactctgaaa ataactttttt tgaagtatcg gtttgtgtct tctagattaa tcctccaaac | 2820 |
| ttttgattaa ccaaaaaaat tatcaaacta acatgttctc cttttttctt tagaaattct | 2880 |
| aacgaattta tctttatact gatttgaata tacttaattt ggtcatttgg atgcccttta | 2940 |
| caacctcctt accaaactca ctatggcaaa tatatactat tttccattgt aacataaatg | 3000 |
| tccataattt gaattaaatt cgttgcagta cgaaaccatc caactttgtc caaaaacaaa | 3060 |
| atccttataa ctatttactt taatgtaaat atatcctcta cttttgtttt tacaacccta | 3120 |
| gctcaaacaa atttattatt tgcgataaaa aatcatatcg aacaaactcg atgatttttt | 3180 |
| ttttcttacg ttattaatga aactaaaata tagaaaaaaa caagatgaac caaattttca | 3240 |
| cctatctaac tacttaaata taatatgatt aaatttggta agtttgaaa agtttcttta | 3300 |
| ggaaatgtga atattgatc acagtttcta ttgctaaaat caccaacaaa acgcatgtcg | 3360 |
| ccattcataa ttatggtttc acacctacaa ctaggctaat aagtaaataa gtagacaact | 3420 |
| agactcaggt ttgaaaaaac cataaaagcc atatagcgtt ttctcattga aactgcgaac | 3480 |
| acgatcgtgt gaatgttgca gtttctagtt ttgatacaaa caaacaaaaa cacaatttaa | 3540 |
| tcttagatta aaaagaaaaa agagaacgga gcccactagc cactccttca aacgtgtctt | 3600 |
| accaactctc ttctagaaac aaattaggct tcaccttcct cttccaacct ctctctctct | 3660 |

```
ctctctctct ctttctcaaa ccatctctcc ataaagccct aatttcttca tcacaagaat    3720
cagaagaata ctgcaaaaaa cttatggacc tgcatctaat tttcggtcca acttgcacag    3780
gaaagacgac gaccgcgata gctcttgccc agcagacagg gcttccagtc ctttcgcttg    3840
atcgggtcca atgctgtcct caactatcaa ccggaagcgg acgaccaaca gtggaagaac    3900
tgaaaggaac gacgcgtctc taccttgatg atcggcctct ggtggagggt atcatcgcag    3960
ccaagcaagc tcatcatagg ctgatcgagg aggtgtataa tcatgaggcc aacggcgggc    4020
ttattcttga gggaggatcc acctcgttgc tcaactgcat ggcgcgaaac agctattgga    4080
gtgcagattt tcgttggcat attattcgcc acaagttacc cgaccaagag accttcatga    4140
aagcggccaa ggccagagtt aagcagatgt tgcaccccgc tgcaggccat tctattattc    4200
aagagttggt ttatctttgg aatgaacctc ggctgaggcc cattctgaaa gagatcgatg    4260
gatatcgata tgccatgttg tttgctagcc agaaccagat cacggcagat atgctattgc    4320
agcttgacgc aaatatggaa ggtaagttga ttaatgggat cgctcaggag tatttcatcc    4380
atgcgcgcca acaggaacag aaattccccc aagttaacgc agccgctttc gacggattcg    4440
aaggtcatcc gttcggaatg tattaggtaa gtccgcaaaa atcaccagtc tctctctaca    4500
aatctatctc tctctatttt tctccagaat aatgtgtgag tagttcccag ataagggaat    4560
tagggttctt atagggtttc gctcatgtgt tgagcatata agaaacccct agtatgtatt    4620
tgtatttgta aaatacttct atcaataaaa tttctaattc ctaaaaccaa aatccagtga    4680
cct                                                                  4683

<210> SEQ ID NO 36
<211> LENGTH: 3744
<212> TYPE: DNA
<213> ORGANISM: Artificial Sequence
<220> FEATURE:
<223> OTHER INFORMATION: Chimeric sequence

<400> SEQUENCE: 36
gatccggtga ctcaaaaaag aagagccgcc atctgtccaa gcgccactcc tacgagaact      60
aaaatcctat tccctccgta aataaatata agagtgttta gatcactact tctttacaga     120
gaatttcctt ccctccaagg ggaggcgaat ccataggcac atcgacggat atggaggggg     180
gaaacatata ttttactatg ctagttcagt taattctacc aagaaaacat atattttatt     240
ttgacaaaca ttgtataaat gtagacattc acatacacgt atgtacacca ccctctatga     300
ttgcacaccc gcacactata tgcctatgag catactttca agagtgagcc agcaaatttt     360
atgataaaat gaaatatttt gcccagccaa ctcagtcgca tcctcggaca atttgttatc     420
aaggaactca cccaaaaaca agcaaagcta gaaaaaggtt gtgtggcagc cacctaatga     480
catgaaggac tgaaatttcc agcacacaca atgtatccga cggcaatgct tcttccactg     540
atccggagaa gataaggaaa cgaggcaacc agcgaacgtg agccatccca accacatctg     600
taccaaagaa acggggctat atataccgtg gtgacccggc aatggggtcc tcaactgtag     660
ccggcatcct cctctcctcc gataatacaa ataccatgaa agccttcaca ctcgctctct     720
tcttagctct tttcctctat ctcctgccca atccagccca ttccactatt aatgcagaca     780
atgttaatga aaatcaaact gtagaagtaa ctgctagttc agtaaacaat gaaaataata     840
agcaagtaac tgaaaaagat agtgcagata aagtactagt gatgtggct gaagatgcta     900
acaccaagaa atcaaacgaa aatacagaaa ctacagaaaa gaatactcaa acagttgtta     960
```

```
ctaatgcgcc agtaagtgat gtgaaaaata caaacacagt taccgctgaa acacctgttg   1020
ataaagtagt aaataatagt gatcaaaaga caactaatgc tgcaactact gatactaaaa   1080
aagatgatgt aaaacaagtt gaaaagaaag actcagtaga taaaacaaat gctgaggaaa   1140
ataaagatag ttcagtaaag ccagctgaaa atgctactaa ggctgaatta aagggccaag   1200
ttaaagatat cgttgaagaa tctggtgttg atactagcaa gttaactaat gatcaaatta   1260
atgaattaaa taaaattaat ttctccaaag aagcaaaaag tggtactcag ttaacttaca   1320
acgactttaa aaaaattgct aaaactttaa ttgaacaaga tgctcgttat gctattccat   1380
tcttcaatgc aagtaaaatt aaaaatatgc ctgctgctaa aacacttgat gctcaaagtg   1440
gaaaagtaga agatttggaa atttgggatt catggcctgt tcaagatgca aaaactggtt   1500
acgtatctaa ctggaatggc taccaattag tgattggtat gatgggagtt ccaaacgtca   1560
atgataacca catttatctt ctttacaaca agtatggtga taatgacttt aatcattgga   1620
agaatgccgg tcctattttc ggtctaggta ctccagttat tcaacaatgg tctggatcag   1680
caactttaaa taaagatggc tcaattcaac tttactacac taaggttgat actagtgata   1740
ataatactaa ccaccaaaaa ctcgctagtg caactgttta cttaaatctt gaaaaagatc   1800
aagataagat ttctattgct catgttgaca acgaccatat tgtctttgaa ggtgatggtt   1860
accactacca aacttatgac caatggaaag aaactaacaa gggtgctgac aatatcgcaa   1920
tgcgtgatgc acacgtgatt gatgatgata atggtaatcg ttaccttgtg tttgaagcaa   1980
gtactggaac cgaaaattat caaggtgatg atcaaattta tcaatggtta aattacggcg   2040
gtactaacaa ggataattta ggtgatttct tccaaatttt atctaactcc gatattaaag   2100
atagagctaa atggtcaaac gctgcaattg gtatcattaa attaaatgat gatgttaaga   2160
atccaagtgt tgcaaaggtc tacagcccac ttattagtgc accaatggta agtgatgaaa   2220
ttgaacgccc tgatgttgtt aaattaggta ataagtatta cttatttgct gctactagat   2280
taaaccgtgg tagtaacgat gatgcttgga tggcaactaa caaagcagtt ggtgataacg   2340
tagctatgat tggttatgtt tctgataact taactcatgg ttatgttcca ttgaatgaat   2400
ctggcgttgt tttaactgca tctgtaccgg ctaactggcg tactgcaact tattcatact   2460
atgcagttcc agtagaagga agagatgatc aacttttaat tacttcatac atcactaatc   2520
gtggtgaggt tgctggaaag ggtatgcatg caacttgggc accaagtttc ttgttacaaa   2580
ttaatccaga taacactact actgttttag ctaaaatgac taaccaaggg gattggattt   2640
gggatgatag tagtgaaaat ccagatatga tgggtgtact tgaaaaagat gctccaaata   2700
gtgctgccct tcctggagaa tggggaaaac cagttgattg ggatttaatt ggtggataca   2760
acttgaagcc acaccaacct gtaactccta ttccaaatgt accaactact cctgaaaccc   2820
caaccacacc agataagcca gaggtaccaa ctacccctga agttccaacc actccagaaa   2880
ctccaactcc agaagctcca aagaatccag ttaagaaaac tagtcagtct aaacttccaa   2940
aggctggaga taaaaatagc tttgcagcag ttgttttagg tgctgtaagt tcaatattag   3000
gtgctgttgg tttaacaggt gtttcaaaac gtaaacgtaa taattaaact atgagttgaa   3060
acaatggcct atctcatatg aagatctttt gtgaatttca cttttgtcca cgacctctgt   3120
tgcacgactc tgctttccga ccggagcata ccttttgttc tatatgattt gtgtatgtat   3180
gtaggaacct atgttctcga gcatgcatac ataattcctc ataggtctat atacaccggc   3240
tatccatatg caaaacctgt gtaatatttg ttatatacaa cacgcggacc attgtcttgc   3300
tgttattaat tcttttttcc cgcaaaaaag gaaaagtttc tttatttggc actgcaatgg   3360
```

```
atatgcctca cagctagtgg gtggagaatt cagtatttga cattaagatt ccctgatttg   3420
caattgcaaa tttcagtttc tttacttata tcactacaaa agtcttattg tttcttttcc   3480
acgtcattac catctgctcc attggttttt gctagtagaa taggatgaag catggacaca   3540
gattaactga gctcgagctc atatgagctc gggtgaacaa taaaatctga aaatacttag   3600
aaagaattca aaattttctg ttttttgtgg caaaatttga caaatgttat aaatgcttgc   3660
aaagtttcat catagaacga cattcgtgga tgtcatggca aaaacaaat tcagcactct   3720 gaaaataact tttttgaagt atcg                                         3744
```

<210> SEQ ID NO 37
<211> LENGTH: 5637
<212> TYPE: DNA
<213> ORGANISM: Artificial Sequence
<220> FEATURE:
<223> OTHER INFORMATION: Chimeric sequence

<400> SEQUENCE: 37

```
gatccggtga ctcaaaaaag aagagccgcc atctgtccaa gcgccactcc tacgagaact     60
aaaatcctat tccctccgta ataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgaa agccttcaca ctcgctctct    720
tcttagctct tttcctctat ctcctgccca atccagccca ttccactatt aatgcagaca    780
atgttaatga aaatcaaact gtagaagtaa ctgctagttc agtaaacaat gaaaataata    840
agcaagtaac tgaaaaagat agtgcagata aagtactag tgatgtggct gaagatgcta    900
acaccaagaa atcaaacgaa aatacagaaa ctacagaaaa gaatactcaa acagttgtta    960
ctaatgcgcc agtaagtgat gtgaaaaata caaacacagt taccgctgaa acacctgttg   1020
ataaagtagt aaataatagt gatcaaaaga caactaatgc tgcaactact gatactaaaa   1080
aagatgatgt aaaacaagtt gaaaagaaag actcagtaga taaacaaat gctgaggaaa   1140 ataaagatag ttcagtaaag ccagctgaaa atgctactaa ggctgaatta aagggccaag   1200
ttaaagatat cgttgaagaa tctggtgttg atactagcaa gttaactaat gatcaaatta   1260
atgaattaaa taaaattaat ttctccaaag aagcaaaaag tggtactcag ttaacttaca   1320
acgactttaa aaaaattgct aaactttaa ttgaacaaga tgctcgttat gctattccat   1380
tcttcaatgc aagtaaaatt aaaaatatgc ctgctgctaa aacacttgat gctcaaagtg   1440
gaaaagtaga agatttggaa atttgggatt catggcctgt tcaagatgca aaaactggtt   1500
acgtatctaa ctggaatggc taccaattag tgattggtat gatgggagtt ccaaacgtca   1560
atgataacca catttatctt ctttacaaca agtatggtga taatgacttt aatcattgga   1620
```

```
agaatgccgg tcctatttc ggtctaggta ctccagttat tcaacaatgg tctggatcag    1680
caactttaaa taaagatggc tcaattcaac tttactacac taaggttgat actagtgata    1740
ataatactaa ccaccaaaaa ctcgctagtg caactgttta cttaaatctt gaaaaagatc    1800
aagataagat ttctattgct catgttgaca acgaccatat tgtctttgaa ggtgatggtt    1860
accactacca aacttatgac caatggaaag aaactaacaa gggtgctgac aatatcgcaa    1920
tgcgtgatgc acacgtgatt gatgatgata atggtaatcg ttaccttgtg tttgaagcaa    1980
gtactggaac cgaaaattat caaggtgatg atcaaattta tcaatggtta aattacggcg    2040
gtactaacaa ggataattta ggtgatttct tccaaatttt atctaactcc gatattaaag    2100
atagagctaa atggtcaaac gctgcaattg gtatcattaa attaaatgat gatgttaaga    2160
atccaagtgt tgcaaaggtc tacagcccac ttattagtgc accaatggta agtgatgaaa    2220
ttgaacgccc tgatgttgtt aaattaggta ataagtatta cttatttgct gctactagat    2280
taaaccgtgg tagtaacgat gatgcttgga tggcaactaa caaagcagtt ggtgataacg    2340
tagctatgat tggttatgtt tctgataact taactcatgg ttatgttcca ttgaatgaat    2400
ctggcgttgt tttaactgca tctgtaccgg ctaactggcg tactgcaact tattcatact    2460
atgcagttcc agtagaagga agagatgatc aacttttaat tacttcatac atcactaatc    2520
gtggtgaggt tgctggaaag ggtatgcatg caacttgggc accaagtttc ttgttacaaa    2580
ttaatccaga taacactact actgttttag ctaaaatgac taaccaaggg gattggattt    2640
gggatgatag tagtgaaaat ccagatatga tgggtgtact tgaaaaagat gctccaaata    2700
gtgctgccct tcctggagaa tggggaaaac cagttgattg ggatttaatt ggtggataca    2760
acttgaagcc acaccaacct gtaactccta ttccaaatgt accaactact cctgaaaccc    2820
caaccacacc agataagcca gaggtaccaa ctaccctga agttccaacc actccagaaa    2880
ctccaactcc agaagctcca aagaatccag ttaagaaaac tagtcagtct aaacttccaa    2940
aggctggaga taaaaatagc tttgcagcag ttgtttttagg tgctgtaagt tcaatattag    3000
gtgctgttgg tttaacaggt gtttcaaaac gtaaacgtaa taattaaact atgagttgaa    3060
acaatggcct atctcatatg aagatctttt gtgaatttca cttttgtcca cgacctctgt    3120
tgcacgactc tgctttccga ccggagcata ccttttgttc tatatgattt gtgtatgtat    3180
gtaggaacct atgttctcga gcatgcatac ataattcctc ataggtctat atacaccggc    3240
tatccatatg caaaacctgt gtaatatttg ttatatacaa cacgcggacc attgtcttgc    3300
tgttattaat tctttttcc cgcaaaaaag gaaaagtttc tttatttggc actgcaatgg    3360
atatgcctca cagctagtgg gtggagaatt cagtatttga cattaagatt ccctgatttg    3420
caattgcaaa tttcagtttc tttacttata tcactacaaa agtcttattg tttcttttcc    3480
acgtcattac catctgctcc attggttttt gctagtagaa taggatgaag catggacaca    3540
gattaactga gctcgagctc atatgagctc gggtgaacaa taaaatctga aaatacttag    3600
aaagaattca aaatttctg ttttttgtgg caaaatttga caaatgttat aaatgcttgc    3660
aaagtttcat catagaacga cattcgtgga tgtcatggca aaaaacaaat tcagcactct    3720
gaaaataact tttttgaagt atcggtttgt gtcttctaga ttaatcctcc aaactttga    3780 ttaaccaaaa aaattatcaa actaacatgt tctcctttt tctttagaaa ttctaacgaa    3840
tttatcttta tactgatttg aatatactta atttggtcat ttggatgccc tttacaacct    3900
ccttaccaaa ctcactatgg caaatatata ctattttcca ttgtaacata aatgtccata    3960
atttgaatta aattcgttgc agtacgaaac catccaactt tgtccaaaaa caaaatcctt    4020
```

```
ataactattt actttaatgt aaatatatcc tctacttttg ttttacaac cctagctcaa    4080 acaaatttat tatttgcgat aaaaaatcat atcgaacaaa ctcgatgatt tttttttttct   4140 tacgttatta atgaaactaa aatatagaaa aaaacaagat gaaccaaatt ttcacctatc    4200
taactactta aatataatat gattaaattt ggtaaagttt gaaaagtttc tttaggaaat    4260
gtgaaatatt gatcacagtt tctattgcta aaatcaccaa caaaacgcat gtcgccattc    4320
ataattatgg tttcacacct acaactaggc taataagtaa ataagtagac aactagactc    4380
aggtttgaaa aaccataaa agccatatag cgttttctca ttgaaactgc gaacacgatc     4440
gtgtgaatgt tgcagtttct agttttgata caaacaaaca aaaacacaat ttaatcttag    4500
attaaaaaga aaaagagaaa cggagcccac tagccactcc ttcaaacgtg tcttaccaac    4560
tctcttctag aaacaaatta ggcttcacct tcctcttcca acctctctct ctctctctct    4620
ctctctttct caaaccatct ctccataaag ccctaatttc ttcatcacaa gaatcagaag    4680
aatactgcaa aaaacttatg gacctgcatc taattttcgg tccaacttgc acaggaaaga    4740
cgacgaccgc gatagctctt gcccagcaga cagggcttcc agtcctttcg cttgatcggg    4800
tccaatgctg tcctcaacta tcaaccggaa gcggacgacc aacagtggaa gaactgaaag    4860
gaacgacgcg tctctacctt gatgatcggc ctctggtgga gggtatcatc gcagccaagc    4920
aagctcatca taggctgatc gaggaggtgt ataatcatga ggccaacggc gggcttattc    4980
ttgagggagg atccacctcg ttgctcaact gcatggcgcg aaacagctat tggagtgcag    5040
attttcgttg gcatattatt cgccacaagt tacccgacca agagaccttc atgaaagcgg    5100
ccaaggccag agttaagcag atgttgcacc ccgctgcagg ccattctatt attcaagagt    5160
tggtttatct ttggaatgaa cctcggctga ggcccattct gaaagagatc gatggatatc    5220
gatatgccat gttgtttgct agccagaacc agatcacggc agatatgcta ttgcagcttg    5280
acgcaaatat ggaaggtaag ttgattaatg ggatcgctca ggagtatttc atccatgcgc    5340
gccaacagga acagaaattc ccccaagtta acgcagccgc tttcgacgga ttcgaaggtc    5400
atccgttcgg aatgtattag gtaagtccgc aaaaatcacc agtctctctc tacaaatcta    5460
tctctctcta tttttctcca gaataatgtg tgagtagttc ccagataagg gaattagggt    5520
tcttataggg tttcgctcat gtgttgagca tataagaaac ccttagtatg tatttgtatt    5580
tgtaaaatac ttctatcaat aaaatttcta attcctaaaa ccaaaatcca gtgacct       5637
```

<210> SEQ ID NO 38
<211> LENGTH: 2937
<212> TYPE: DNA
<213> ORGANISM: Artificial Sequence
<220> FEATURE:
<223> OTHER INFORMATION: Chimeric sequence

<400> SEQUENCE: 38

```
gatccggtga ctcaaaaaag aagagccgcc atctgtccaa gcgccactcc tacgagaact      60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atatttatt     240 ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
```

```
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaaccggagt ggcgggaggt ggcgcgcgtg cgccgccgtg ctggccgcat    840
cggcgttggc ggtggtcgtc gtggtcgggc tcctcgcggg cggcagggtg gatcgggtcc    900
cggccggcgg aacgaaccaa agccatata aggaaacata cggcatttcc catattacac    960
gccatgatat gctgcaaatc cctgaacagc aaaaaaatga aaatatcaa gttcctgaat    1020 tcgattcgtc cacaattaaa aatatctctt ctgcaaaagg cctggacgtt tgggacagct    1080
ggccattaca aaacgctgac ggcactgtcg caaactatca cggctaccac atcgtctttg    1140
cattagccgg agatcctaaa aatgcggatg acacatcgat ttacatgttc tatcaaaaag    1200
tcggcgaaac ttctattgac agctggaaaa acgctggccg cgtcttttaaa gacagcgaca    1260 aattcgatgc aaatgattct atcctaaaag accaaacaca agaatggtca ggttcagcca    1320
catttacatc tgacggaaaa atccgttttat tctacactga tttctccggt aaacattacg    1380
gcaaacaaac actgacaact gcacaagtta acgtatcagc atcagacagc tctttgaaca    1440
tcaacggtgt agaggattat aaatcaatct ttgacggtga cggaaaaacg tatcaaaatg    1500
tacagcagtt catcgatgaa ggcaactaca gctcaggcga caaccatacg ctgagagatc    1560
ctcactacgt agaagataaa ggccacaaat acttagtatt tgaagcaaac actggaactg    1620
aagatggcta ccaaggcgaa gaatctttat ttaacaaagc atactatggc aaaagcacat    1680
cattcttccg tcaagaaagt caaaaacttc tgcaaagcga taaaaaacgc acggctgagt    1740
tagcaaacgg cgctctcggt atgattgagc taaacgatga ttacacactg aaaaaagtga    1800
tgaaaccgct gattgcatct aacacagtaa cagatgaaat tgaacgcgcg aacgtcttta    1860
aaatgaacgg caaatggtac ctgttcactg actcccgcgg atcaaaaatg acgattgacg    1920
gcattacgtc taacgatatt tacatgcttg gttatgtttc taattcttta actggcccat    1980
acaagccgct gaacaaaact ggccttgtgt taaaaatgga tcttgatcct aacgatgtaa    2040
cctttactta ctcacacttc gctgtacctc aagcgaaagg aaacaatgtc gtgattacaa    2100
gctatatgac aaaacagagga ttctacgcag acaaacaatc aacgtttgcg ccaagcttcc    2160
tgctgaacat caaaggcaag aaaacatctg ttgtcaaaga cagcatcctt gaacaaggac    2220
aattaacagt taacaaataa actatgagtt gaaacaatgg cctatctcat atgaagatct    2280
tttgtgaatt tcactttttgt ccacgacctc tgttgcacga ctctgctttc cgaccggagc    2340
ataccttttg ttctatatga tttgtgtatg tatgtaggaa cctatgttct cgagcatgca    2400
tacataattc ctcataggtc tatatacacc ggctatccat atgcaaaacc tgtgtaatat    2460
ttgttatata caacacgcgg accattgtct tgctgttatt aattcttttt tcccgcaaaa    2520
aaggaaaagt ttctttattt ggcactgcaa tggatatgcc tcacagctag tgggtggaga    2580
attcagtatt tgacattaag attccctgat ttgcaattgc aaatttcagt ttctttactt    2640
atatcactac aaaagtctta ttgtttcttt tccacgtcat taccatctgc tccattggtt    2700
tttgctagta gaataggatg aagcatggac acagattaac tgagctcgag ctcatatgag    2760
ctcgggtgaa caataaaatc tgaaaatact tagaaagaat tcaaaatttt ctgtttttg    2820
```

```
tggcaaaatt tgacaaatgt tataaatgct tgcaaagttt catcatagaa cgacattcgt    2880
ggatgtcatg gcaaaaaaca aattcagcac tctgaaaata acttttttga agtatcg      2937

<210> SEQ ID NO 39
<211> LENGTH: 4830
<212> TYPE: DNA
<213> ORGANISM: Artificial Sequence
<220> FEATURE:
<223> OTHER INFORMATION: Chimeric sequence

<400> SEQUENCE: 39
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa cgggggctat atataccgtg gtgacccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaccggagt ggcgggaggt ggcgcgcgtg cgccgccgtg ctggccgcat     840
cggcgttggc ggtggtcgtc gtggtcgggc tcctcgcggg cggcagggtg gatcgggtcc    900
cggccggcgg aacgaaccaa aagccatata aggaaacata cggcatttcc catattacac    960
gccatgatat gctgcaaatc cctgaacagc aaaaaaatga aaatatcaa gttcctgaat    1020 tcgattcgtc cacaattaaa aatatctctt ctgcaaaagg cctggacgtt tgggacagct   1080
ggccattaca aaacgctgac ggcactgtcg caaactatca cggctaccac atcgtctttg   1140
cattagccgg agatcctaaa aatgcggatg acacatcgat ttacatgttc tatcaaaaag   1200
tcggcgaaac ttctattgac agctggaaaa acgctggccg cgtctttaaa gacagcgaca   1260
aattcgatgc aaatgattct atcctaaaag accaaacaca agaatggtca ggttcagcca   1320
catttacatc tgacggaaaa atccgtttat tctacactga tttctccggt aaacattacg   1380
gcaaacaaac actgacaact gcacaagtta acgtatcagc atcagacagc tctttgaaca   1440
tcaacggtgt agaggattat aaatcaatct ttgacggtga cggaaaaacg tatcaaaatg   1500
tacagcagtt catcgatgaa ggcaactaca gctcaggcga caaccatacg ctgagagatc   1560
ctcactacgt agaagataaa ggccacaaat acttagtatt tgaagcaaac actggaactg   1620
aagatggcta ccaaggcgaa gaatctttat ttaacaaagc atactatggc aaaagcacat   1680
cattcttccg tcaagaaagt caaaaacttc tgcaaagcga taaaaaacgc acggctgagt   1740
tagcaaacgg cgctctcggt atgattgagc taaacgatga ttacacactg aaaaaagtga   1800
tgaaaccgct gattgcatct aacacagtaa cagatgaaat tgaacgcgcg aacgtctttta   1860 aaatgaacgg caaatggtac ctgttcactg actcccgcgg atcaaaaatg acgattgacg   1920
```

```
gcattacgtc taacgatatt tacatgcttg gttatgtttc taattcttta actggcccat    1980
acaagccgct gaacaaaact ggccttgtgt taaaaatgga tcttgatcct aacgatgtaa    2040
cctttactta ctcacacttc gctgtacctc aagcgaaagg aaacaatgtc gtgattacaa    2100
gctatatgac aaacagagga ttctacgcag acaaacaatc aacgtttgcg ccaagcttcc    2160
tgctgaacat caaaggcaag aaaacatctg ttgtcaaaga cagcatcctt gaacaaggac    2220
aattaacagt taacaaataa actatgagtt gaaacaatgg cctatctcat atgaagatct    2280
tttgtgaatt tcacttttgt ccacgacctc tgttgcacga ctctgctttc cgaccggagc    2340 atacctttttg ttctatatga tttgtgtatg tatgtaggaa cctatgttct cgagcatgca    2400
tacataattc ctcataggtc tatatacacc ggctatccat atgcaaaacc tgtgtaatat    2460 tgttatata caacacgcgg accattgtct tgctgttatt aattcttttt tcccgcaaaa    2520
aaggaaaagt ttctttattt ggcactgcaa tggatatgcc tcacagctag tgggtggaga    2580
attcagtatt tgacattaag attccctgat ttgcaattgc aaatttcagt ttctttactt    2640
atatcactac aaaagtctta ttgtttcttt tccacgtcat taccatctgc tccattggtt    2700
tttgctagta gaataggatg aagcatggac acagattaac tgagctcgag ctcatatgag    2760
ctcgggtgaa caataaaatc tgaaaatact tagaaagaat tcaaaatttt ctgtttttttg    2820 tggcaaaatt tgacaaatgt tataaatgct tgcaaagttt catcatagaa cgacattcgt    2880
ggatgtcatg gcaaaaaaca aattcagcac tctgaaaata actttttttga agtatcggtt    2940 tgtgtcttct agattaatcc tccaaacttt tgattaacca aaaaaattat caaactaaca    3000
tgttctcctt ttttctttag aaattctaac gaattttatct ttatactgat ttgaatatac    3060
ttaatttggt catttggatg ccctttacaa cctccttacc aaactcacta tggcaaatat    3120
atactatttt ccattgtaac ataaatgtcc ataatttgaa ttaaattcgt tgcagtacga    3180
aaccatccaa ctttgtccaa aaacaaaatc cttataacta tttactttaa tgtaaatata    3240
tcctctactt ttgtttttac aaccctagct caaacaaatt tattatttgc gataaaaaat    3300
catatcgaac aaactcgatg attttttttt tcttacgtta ttaatgaaac taaaatatag    3360
aaaaaaacaa gatgaaccaa attttcacct atctaactac ttaaatataa tatgattaaa    3420
tttggtaaag tttgaaaagt ttctttagga aatgtgaaat attgatcaca gtttctattg    3480
ctaaaatcac caacaaaacg catgtcgcca ttcataatta tggtttcaca cctacaacta    3540
ggctaataag taaataagta gacaactaga ctcaggtttg aaaaaaccat aaaagccata    3600
tagcgttttc tcattgaaac tgcgaacacg atcgtgtgaa tgttcagtt tctagttttg     3660 atacaaacaa acaaaaacac aatttaatct tagattaaaa agaaaaaaga gaacggagcc    3720
cactagccac tccttcaaac gtgtcttacc aactctcttc tagaaacaaa ttaggcttca    3780
ccttcctctt ccaacctctc tctctctctc tctctctctt tctcaaacca tctctccata    3840
aagccctaat ttcttcatca caagaatcag aagaatactg caaaaaactt atggacctgc    3900
atctaatttt cggtccaact tgcacaggaa agacgacgac cgcgatagct cttgcccagc    3960
agacagggct tccagtcctt tcgcttgatc gggtccaatg ctgtcctcaa ctatcaaccg    4020
gaagcggacg accaacagtg gaagaactga aggaacgac gcgtctctac cttgatgatc      4080
ggcctctggt ggagggtatc atcgcagcca agcaagctca tcataggctg atcgaggagg    4140
tgtataatca tgaggccaac ggcgggctta ttcttgaggg aggatccacc tcgttgctca    4200
actgcatggc gcgaaacagc tattggagtg cagattttcg ttggcatatt attcgccaca    4260
agttacccga ccaagagacc ttcatgaaag cggccaaggc cagagttaag cagatgttgc    4320
```

| | |
|---|---|
| accccgctgc aggccattct attattcaag agttggttta tctttggaat gaacctcggc | 4380 |
| tgaggcccat tctgaaagag atcgatggat atcgatatgc catgttgttt gctagccaga | 4440 |
| accagatcac ggcagatatg ctattgcagc ttgacgcaaa tatggaaggt aagttgatta | 4500 |
| atgggatcgc tcaggagtat ttcatccatg cgcgccaaca ggaacagaaa ttcccccaag | 4560 |
| ttaacgcagc cgctttcgac ggattcgaag gtcatccgtt cggaatgtat taggtaagtc | 4620 |
| cgcaaaaatc accagtctct ctctacaaat ctatctctct ctattttct ccagaataat | 4680 |
| gtgtgagtag ttcccagata agggaattag ggttcttata gggtttcgct catgtgttga | 4740 |
| gcatataaga aaccccttagt atgtatttgt atttgtaaaa tacttctatc aataaaattt | 4800 |
| ctaattccta aaaccaaaat ccagtgacct | 4830 |

<210> SEQ ID NO 40
<211> LENGTH: 3891
<212> TYPE: DNA
<213> ORGANISM: Artificial Sequence
<220> FEATURE:
<223> OTHER INFORMATION: Chimeric sequence

<400> SEQUENCE: 40

| | |
|---|---|
| gatccggtga ctcaaaaaag aagagccgcc atctgtccaa gcgccactcc tacgagaact | 60 |
| aaaatcctat tccctccgta aataaatata agagtgttta gatcactact tctttacaga | 120 |
| gaatttcctt ccctccaagg ggaggcgaat ccataggcac atcgacggat atggaggggg | 180 |
| gaaacatata ttttactatg ctagttcagt taattctacc aagaaaacat atattttatt | 240 |
| ttgacaaaca ttgtataaat gtagacattc acatacacgt atgtacacca ccctctatga | 300 |
| ttgcacaccc gcacactata tgcctatgag catactttca agagtgagcc agcaaatttt | 360 |
| atgataaaat gaaatatttt gcccagccaa ctcagtcgca tcctcggaca atttgttatc | 420 |
| aaggaactca cccaaaaaca agcaaagcta gaaaaaggtt gtgtggcagc cacctaatga | 480 |
| catgaaggac tgaaatttcc agcacacaca atgtatccga cggcaatgct tcttccactg | 540 |
| atccggagaa gataaggaaa cgaggcaacc agcgaacgtg agccatccca accacatctg | 600 |
| taccaaagaa acggggctat atataccgtg gtgacccggc aatggggtcc tcaactgtag | 660 |
| ccggcatcct cctctcctcc gataatacaa ataccatgga gtcccaagc gccgtcgtcc | 720 |
| ccggcaccac ggcgccgctg cttccttatg cgtacgcgcc gctgccgtcg tccgccgacg | 780 |
| acgcccgtca aaaccggagt ggcgggaggt ggcgcgcgtg cgccgccgtg ctggccgcat | 840 |
| cggcgttggc ggtggtcgtc gtggtcgggc tcctcgcggg cggcagggtg gatcgggtcc | 900 |
| cggccggcgg aactattaat gcagacaatg ttaatgaaaa tcaaactgta gaagtaactg | 960 |
| ctagttcagt aaacaatgaa aataataagc aagtaactga aaagatagt gcagataaaa | 1020 |
| gtactagtga tgtggctgaa gatgctaaca ccaagaaatc aaacgaaaat acagaaacta | 1080 |
| cagaaaagaa tactcaaaca gttgttacta atgcgccagt aagtgatgtg aaaaatacaa | 1140 |
| acacagttac cgctgaaaca cctgttgata agtagtaaa taatagtgat caaaagacaa | 1200 |
| ctaatgctgc aactactgat actaaaaaag atgatgtaaa acaagttgaa agaaagact | 1260 |
| cagtagataa aacaaatgct gaggaaaata agatagttc agtaaagcca gctgaaaatg | 1320 |
| ctactaaggc tgaattaaag ggccaagtta agatatcgt tgaagaatct ggtgttgata | 1380 |
| ctagcaagtt aactaatgat caaattaatg aattaaataa aattaattc tccaagaag | 1440 |
| caaaaagtgg tactcagtta acttacaacg actttaaaaa aattgctaaa actttaattg | 1500 |

-continued

```
aacaagatgc tcgttatgct attccattct tcaatgcaag taaaattaaa aatatgcctg    1560
ctgctaaaac acttgatgct caaagtggaa aagtagaaga tttggaaatt tgggattcat    1620
ggcctgttca agatgcaaaa actggttacg tatctaactg gaatggctac caattagtga    1680
ttggtatgat gggagttcca aacgtcaatg ataaccacat ttatcttctt tacaacaagt    1740
atggtgataa tgactttaat cattggaaga atgccggtcc tattttcggt ctaggtactc    1800
cagttattca acaatggtct ggatcagcaa ctttaaataa agatggctca attcaacttt    1860
actacactaa ggttgatact agtgataata atactaacca ccaaaaactc gctagtgcaa    1920
ctgtttactt aaatcttgaa aaagatcaag ataagatttc tattgctcat gttgacaacg    1980
accatattgt ctttgaaggt gatggttacc actaccaaac ttatgaccaa tggaaagaaa    2040
ctaacaaggg tgctgacaat atcgcaatgc gtgatgcaca cgtgattgat gatgataatg    2100
gtaatcgtta ccttgtgttt gaagcaagta ctggaaccga aaattatcaa ggtgatgatc    2160
aaatttatca atggttaaat tacggcggta ctaacaagga taatttaggt gatttcttcc    2220
aaattttatc taactccgat attaaagata gagctaaatg gtcaaacgct gcaattggta    2280
tcattaaatt aaatgatgat gttaagaatc caagtgttgc aaaggtctac agcccactta    2340
ttagtgcacc aatggtaagt gatgaaattg aacgccctga tgttgttaaa ttaggtaata    2400
agtattactt atttgctgct actagattaa accgtggtag taacgatgat gcttggatgg    2460
caactaacaa agcagttggt gataacgtag ctatgattgg ttatgtttct gataacttaa    2520
ctcatggtta tgttccattg aatgaatctg gcgttgtttt aactgcatct gtaccggcta    2580
actggcgtac tgcaacttat tcatactatg cagttccagt agaaggaaga gatgatcaac    2640
ttttaattac ttcatacatc actaatcgtg gtgaggttgc tggaaagggt atgcatgcaa    2700
cttgggcacc aagtttcttg ttacaaatta atccagataa cactactact gttttagcta    2760
aaatgactaa ccaaggggat tggatttggg atgatagtag tgaaaatcca gatatgatgg    2820
gtgtacttga aaaagatgct ccaaatagtg ctgcccttcc tggagaatgg ggaaaaccag    2880
ttgattggga tttaattggt ggatacaact tgaagccaca ccaacctgta actcctattc    2940
caaatgtacc aactactcct gaaaccccaa ccacaccaga taagccagag gtaccaacta    3000
cccctgaagt tccaaccact ccagaaactc caactccaga agctccaaag aatccagtta    3060
agaaaactag tcagtctaaa cttccaaagg ctggagataa aaatagcttt gcagcagttg    3120
ttttaggtgc tgtaagttca atattaggtg ctgttggttt aacaggtgtt tcaaaacgta    3180
aacgtaataa ttaaactatg agttgaaaca atggcctatc tcatatgaag atcttttgtg    3240
aatttcactt ttgtccacga cctctgttgc acgactctgc tttccgaccg gagcataacct    3300
tttgttctat atgatttgtg tatgtatgta ggaacctatg ttctcgagca tgcatacata    3360
attcctcata ggtctatata caccggctat ccatatgcaa aacctgtgta atatttgtta    3420
tatacaacac gcggaccatt gtcttgctgt tattaattct tttttcccgc aaaaaaggaa    3480
aagtttcttt atttggcact gcaatggata tgcctcacag ctagtgggtg gagaaattcag   3540
tatttgacat taagattccc tgatttgcaa ttgcaaattt cagtttcttt acttatatca    3600
ctacaaaagt cttattgttt cttttccacg tcattaccat ctgctccatt ggttttgct    3660
agtagaatag gatgaagcat ggacacagat taactgagct cgagctcata tgagctcggg    3720
tgaacaataa aatctgaaaa tacttagaaa gaattcaaaa ttttctgttt tttgtggcaa    3780
aatttgacaa atgttataaa tgcttgcaaa gtttcatcat agaacgacat tcgtggatgt    3840
catggcaaaa aacaaattca gcactctgaa aataactttt ttgaagtatc g             3891
```

<210> SEQ ID NO 41
<211> LENGTH: 5784
<212> TYPE: DNA
<213> ORGANISM: Artificial Sequence
<220> FEATURE:
<223> OTHER INFORMATION: Chimeric sequence

<400> SEQUENCE: 41

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgaccggc aatggggtcc tcaactgtag    660
ccggcatcct cctctcctcc gataatacaa ataccatgga gtccccaagc gccgtcgtcc    720
ccggcaccac ggcgccgctg cttccttatg cgtacgcgcc gctgccgtcg tccgccgacg    780
acgcccgtca aaaccggagt ggcgggaggt ggcgcgcgtg cgccgccgtg ctggccgcat    840
cggcgttggc ggtggtcgtc gtggtcgggc tcctcgcggg cggcagggtg gatcgggtcc    900
cggccggcgg aactattaat gcagacaatg ttaatgaaaa tcaaactgta gaagtaactg    960
ctagttcagt aaacaatgaa aataataagc aagtaactga aaagatagt gcagataaaa   1020
gtactagtga tgtggctgaa gatgctaaca ccaagaaatc aaacgaaaat acagaaacta   1080
cagaaaagaa tactcaaaca gttgttacta atgcgccagt aagtgatgtg aaaaatacaa   1140
acacagttac cgctgaaaca cctgttgata agtagtaaa taatagtgat caaaagacaa   1200
ctaatgctgc aactactgat actaaaaaag atgatgtaaa acaagttgaa agaaaagact   1260
cagtagataa aacaaatgct gaggaaaata agatagttc agtaaagcca gctgaaaatg   1320
ctactaaggc tgaattaaag ggccaagtta agatatcgt tgaagaatct ggtgttgata   1380
ctagcaagtt aactaatgat caaattaatg aattaaataa aattaatttc tccaaagaag   1440
caaaaagtgg tactcagtta acttacaacg actttaaaaa aattgctaaa actttaattg   1500
aacaagatgc tcgttatgct attccattct tcaatgcaag taaattaaa aatatgcctg   1560
ctgctaaaac acttgatgct caaagtggaa aagtagaaga tttggaaatt tgggattcat   1620
ggcctgttca agatgcaaaa actggttacg tatctaactg gaatggctac caattagtga   1680
ttggtatgat gggagttcca acgtcaatg ataaccacat ttatcttctt tacaacaagt   1740
atggtgataa tgactttaat cattggaaga atgccggtcc tattttcggt ctaggtactc   1800
cagttattca acaatggtct ggatcagcaa ctttaaataa agatggctca attcaacttt   1860
actacactaa ggttgatact agtgataata atactaacca ccaaaaactc gctagtgcaa   1920
ctgtttactt aaatcttgaa aaagatcaag ataagatttc tattgctcat gttgacaacg   1980
accatattgt ctttgaaggt gatggttacc actaccaaac ttatgaccaa tggaaagaaa   2040
```

```
ctaacaaggg tgctgacaat atcgcaatgc gtgatgcaca cgtgattgat gatgataatg    2100
gtaatcgtta ccttgtgttt gaagcaagta ctggaaccga aaattatcaa ggtgatgatc    2160
aaatttatca atggttaaat tacggcggta ctaacaagga taatttaggt gatttcttcc    2220
aaattttatc taactccgat attaaagata gagctaaatg gtcaaacgct gcaattggta    2280
tcattaaatt aaatgatgat gttaagaatc caagtgttgc aaaggtctac agcccactta    2340
ttagtgcacc aatggtaagt gatgaaattg aacgccctga tgttgttaaa ttaggtaata    2400
agtattactt atttgctgct actagattaa accgtggtag taacgatgat gcttggatgg    2460
caactaacaa agcagttggt gataacgtag ctatgattgg ttatgtttct gataacttaa    2520
ctcatggtta tgttccattg aatgaatctg gcgttgtttt aactgcatct gtaccggcta    2580
actggcgtac tgcaacttat tcatactatg cagttccagt agaaggaaga gatgatcaac    2640
ttttaattac ttcatacatc actaatcgtg gtgaggttgc tggaaagggt atgcatgcaa    2700
cttgggcacc aagtttcttg ttacaaatta atccagataa cactactact gttttagcta    2760
aaatgactaa ccaaggggat tggatttggg atgatagtag tgaaaatcca gatatgatgg    2820
gtgtacttga aaaagatgct ccaaatagtg ctgcccttcc tggagaatgg ggaaaaccag    2880
ttgattggga tttaattggt ggatacaact tgaagccaca ccaacctgta actcctattc    2940
caaatgtacc aactactcct gaaaccccaa ccacaccaga taagccagag gtaccaacta    3000
cccctgaagt tccaaccact ccagaaactc caactccaga agctcaaaag aatccagtta    3060
agaaaactag tcagtctaaa cttccaaagg ctggagataa aaatagcttt gcagcagttg    3120
ttttaggtgc tgtaagttca atattaggtg ctgttggttt aacaggtgtt tcaaaacgta    3180
aacgtaataa ttaaactatg agttgaaaca atggcctatc tcatatgaag atcttttgtg    3240
aatttcactt ttgtccacga cctctgttgc acgactctgc tttccgaccg gagcataacct    3300
tttgttctat atgatttgtg tatgtatgta ggaacctatg ttctcgagca tgcatacata    3360
attcctcata ggtctatata caccggctat ccatatgcaa aacctgtgta atatttgtta    3420
tatacaacac gcggaccatt gtcttgctgt tattaattct tttttcccgc aaaaaaggaa    3480
aagtttcttt atttggcact gcaatggata tgcctcacag ctagtgggtg gagaattcag    3540
tatttgacat taagattccc tgatttgcaa ttgcaaatttt cagtttcttt acttatatca    3600
ctacaaaagt cttattgttt cttttccacg tcattaccat ctgctccatt ggttttttgct    3660
agtagaatag gatgaagcat ggacacagat taactgagct cgagctcata tgagctcggg    3720
tgaacaataa aatctgaaaa tacttagaaa gaattcaaaa ttttctgttt tttgtggcaa    3780
aatttgacaa atgttataaa tgcttgcaaa gtttcatcat agaacgacat tcgtggatgt    3840
catggcaaaa aacaaattca gcactctgaa ataactttt ttgaagtatc ggtttgtgtc    3900
ttctagatta atcctccaaa cttttgatta accaaaaaaa ttatcaaact aacatgttct    3960
cctttttttct ttagaaattc taacgaattt atctttatac tgatttgaat atacttaatt    4020
tggtcatttg gatgcccttt acaacctcct taccaaactc actatggcaa atatatacta    4080
ttttccattg taacataaat gtccataatt tgaattaaat tcgttgcagt acgaaaccat    4140
ccaactttgt ccaaaaacaa aatccttata actatttact ttaatgtaaa tatatcctct    4200
acttttgttt ttacaaccct agctcaaaca aatttattat ttgcgataaa aaatcatatc    4260
gaacaaactc gatgattttt ttttcttac gttattaatg aaactaaaat atagaaaaaa    4320
acaagatgaa ccaaatttc acctatctaa ctacttaaat ataatgat taaatttggt    4380
aaagtttgaa aagtttcttt aggaaatgtg aaatattgat cacagtttct attgctaaaa    4440
```

```
tcaccaacaa acgcatgtc gccattcata attatggttt cacacctaca actaggctaa      4500
taagtaaata agtagacaac tagactcagg tttgaaaaaa ccataaaagc catatagcgt      4560
tttctcattg aaactgcgaa cacgatcgtg tgaatgttgc agtttctagt tttgatacaa      4620
acaaacaaaa acacaattta atcttagatt aaaaagaaaa aagagaacgg agcccactag      4680
ccactccttc aaacgtgtct taccaactct cttctagaaa caaattaggc ttcaccttcc      4740
tcttccaacc tctctctctc tctctctctc tctttctcaa accatctctc cataaagccc      4800
taatttcttc atcacaagaa tcagaagaat actgcaaaaa acttatggac ctgcatctaa      4860
ttttcggtcc aacttgcaca ggaaagacga cgaccgcgat agctcttgcc cagcagacag      4920
ggcttccagt cctttcgctt gatcgggtcc aatgctgtcc tcaactatca accggaagcg      4980
gacgaccaac agtggaagaa ctgaaaggaa cgacgcgtct taccttgat gatcggcctc      5040 tggtggaggg tatcatcgca gccaagcaag ctcatcatag gctgatcgag gaggtgtata      5100
atcatgaggc caacggcggg cttattcttg agggaggatc cacctcgttg ctcaactgca      5160
tggcgcgaaa cagctattgg agtgcagatt tcgttggca tattattcgc cacaagttac      5220
ccgaccaaga gaccttcatg aaagcggcca aggccagagt taagcagatg ttgcacccccg      5280 ctgcaggcca ttctattatt caagagttgg tttatctttg gaatgaacct cggctgaggc      5340
ccattctgaa agagatcgat ggatatcgat atgccatgtt gtttgctagc cagaaccaga      5400
tcacggcaga tatgctattg cagcttgacg caaatatgga aggtaagttg attaatggga      5460
tcgctcagga gtatttcatc catgcgcgcc aacaggaaca gaaattcccc caagttaacg      5520
cagccgcttt cgacggattc gaaggtcatc cgttcggaat gtattaggta agtccgcaaa      5580
aatcaccagt ctctctctac aaatctatct ctctctattt ttctccagaa taatgtgtga      5640
gtagttccca gataagggaa ttagggttct tatagggttt cgctcatgtg ttgagcatat      5700
aagaaaccct tagtatgtat ttgtatttgt aaaatacttc tatcaataaa atttctaatt      5760
cctaaaacca aaatccagtg acct                                            5784

<210> SEQ ID NO 42
<211> LENGTH: 1702
<212> TYPE: DNA
<213> ORGANISM: Arabidopsis thaliana

<400> SEQUENCE: 42
cgtggtcgag attgtgtatt attctttagt tattacaaga cttttagcta aaatttgaaa        60
gaatttactt taagaaaatc ttaacatctg agataaattc agcaatagat tatattttc        120 attactctag cagtattttt gcagatcaat cgcaacatat atggttgtta gaaaaaatgc       180
actatatata tatatattat tttttcaatt aaaagtgcat gatatataat atatatatat       240
atatatatat gtgtgtgtgt atatggtcaa agaaattctt atacaaatat acacgaacac       300
atatatttga caaatcaaa gtattacact aaacaatgag ttggtgcatg ccaaaacaa         360 atatgtagat taaaaattcc agcctccaaa aaaaaatcca agtgttgtaa agcattatat       420
atatatagta gatcccaaat ttttgtacaa ttccacactg atcgaattt taaagttgaa        480 tatctgacgt aggatttttt taatgtctta cctgaccatt tactaataac attcatacgt       540
tttcatttga aatatcctct ataattatat tgaatttggc acataataag aaacctaatt       600
ggtgatttat tttactagta aatttctggt gatgggcttt ctactagaaa gctctcggaa       660
aatcttggac caaatccata ttccatgact tcgattgtta accctattag ttttcacaaa      720
```

| | |
|---|---|
| catactatca atatcattgc aacggaaaag gtacaagtaa aacattcaat ccgataggga | 780 |
| agtgatgtag gaggttggga agacaggccc agaaagagat ttatctgact tgttttgtgt | 840 |
| atagttttca atgttcataa aggaagatgg agacttgaga agttttttt ggactttgtt | 900 |
| tagctttgtt gggcgttttt tttttttgat caataacttt gttgggctta tgatttgtaa | 960 |
| tattttcgtg gactctttag tttatttaga cgtgctaact ttgttgggct tatgacttgt | 1020 |
| tgtaacatat tgtaacagat gacttgatgt gcgactaatc tttacacatt aaacatagtt | 1080 |
| ctgttttttg aaagttctta ttttcattt tatttgaatg ttatatattt ttctatattt | 1140 |
| ataattctag taaaaggcaa atttgcttt taaatgaaaa aatatatat tccacagttt | 1200 |
| cacctaatct tatgcattta gcagtacaaa ttcaaaaatt tcccattttt attcatgaat | 1260 |
| cataccatta tatattaact aaatccaagg taaaaaaag gtatgaaagc tctatagtaa | 1320 |
| gtaaaatata aattccccat aaggaaaggg ccaagtccac caggcaagta aaatgagcaa | 1380 |
| gcaccactcc accatcacac aatttcactc atagataacg ataagattca tggaattatc | 1440 |
| ttccacgtgg cattattcca gcggttcaag ccgataaggg tctcaacacc tctccttagg | 1500 |
| cctttgtggc cgttaccaag taaaattaac ctcacacata tccacactca aaatccaacg | 1560 |
| gtgtagatcc tagtccactt gaatctcatg tatcctagac cctccgatca ctccaaagct | 1620 |
| tgttctcatt gttgttatca ttatatatag atgaccaaag cactagacca aacctcagtc | 1680 |
| acacaaagag taaagaagaa ca | 1702 |

<210> SEQ ID NO 43
<211> LENGTH: 695
<212> TYPE: DNA
<213> ORGANISM: Triticum aestivum

<400> SEQUENCE: 43

| | |
|---|---|
| gatccggtga ctcaaaaaag aagagccgcc atctgtccaa gcgccactcc tacgagaact | 60 |
| aaaatcctat tccctccgta aataaatata agagtgttta gatcactact tctttacaga | 120 |
| gaatttcctt ccctccaagg ggaggcgaat ccataggcac atcgacggat atggagggg | 180 |
| gaaacatata ttttactatg ctagttcagt taattctacc aagaaaacat atattttat | 240 |
| ttgacaaaca ttgtataaat gtagacattc acatacacgt atgtacacca ccctctatga | 300 |
| ttgcacaccc gcacactata tgcctatgag catactttca agagtgagcc agcaaatttt | 360 |
| atgataaaat gaaatatttt gcccagccaa ctcagtcgca tcctcggaca atttgttatc | 420 |
| aaggaactca cccaaaaaca agcaaagcta gaaaaaggtt gtgtggcagc cacctaatga | 480 |
| catgaaggac tgaaatttcc agcacacaca atgtatccga cggcaatgct tcttccactg | 540 |
| atccggagaa gataaggaaa cgaggcaacc agcgaacgtg agccatccca accacatctg | 600 |
| taccaaagaa acggggctat atataccgtg gtgacccggc aatggggtcc tcaactgtag | 660 |
| ccggcatcct cctctcctcc gataatacaa atacc | 695 |

<210> SEQ ID NO 44
<211> LENGTH: 941
<212> TYPE: DNA
<213> ORGANISM: Arabidopsis thaliana

<400> SEQUENCE: 44

| | |
|---|---|
| gtttgtgtct tctagattaa tcctccaaac ttttgattaa ccaaaaaaat tatcaaacta | 60 |
| acatgttctc cttttttctt tagaaattct aacgaattta tctttatact gatttgaata | 120 |
| tacttaattt ggtcatttgg atgccctta caacctcctt accaaactca ctatggcaaa | 180 |

```
tatatactat tttccattgt aacataaatg tccataattt gaattaaatt cgttgcagta      240
cgaaaccatc caactttgtc caaaaacaaa atccttataa ctatttactt taatgtaaat      300
atatcctcta cttttgtttt tacaacccta gctcaaacaa atttattatt tgcgataaaa      360
aatcatatcg aacaaactcg atgattttt ttttcttacg ttattaatga aactaaaata       420
tagaaaaaaa caagatgaac caaattttca cctatctaac tacttaaata taatatgatt      480
aaatttggta agtttgaaa agtttcttta gaaatgtgaa atattgatca cagttttctat      540 tgctaaaatc accaacaaaa cgcatgtcgc cattcataat tatggtttca cctacaac       600 taggctaata agtaaataag tagacaacta gactcaggtt tgaaaaaacc ataaagcca       660 tatagcgttt tctcattgaa actgcgaaca cgatcgtgtg aatgttgcag tttctagttt      720
tgatacaaac aaacaaaaac acaatttaat cttagattaa aagaaaaaa gagaacggag       780 cccactagcc actccttcaa acgtgtctta ccaactctct tctagaaaca aattaggctt      840
caccttcctc ttccaacctc tctctctctc tctctctctt tttctcaaac catctctcca     900
taaagcccta atttcttcat cacaagaatc agaagaagaa a                          941

<210> SEQ ID NO 45
<211> LENGTH: 588
<212> TYPE: DNA
<213> ORGANISM: Arabidopsis thaliana

<400> SEQUENCE: 45
gtttgtgtct tctagattaa tcctccaaac tttgattaa ccaaaaaaat tatcaaacta       60
acatgttctc cttttttctt tagaaattct aacgaattta tctttatact gatttgaata     120
tacttaattt ggtcatttgg atgccctta caacctcctt accaaactca ttgatcacag      180
tttctattgc taaaatcacc aacaaaacgc atgtcgccat tcataattat ggtttcacac     240
ctacaactag gctaataagt aaataagtag acaactagac tcaggtttga aaaaaccata     300
aaagccatat agcgttttct cattgaaact gcgaacacga tcgtgtgaat gttgcagttt     360
ctagttttga tacaaacaaa caaaacaca atttaatctt agattaaaaa gaaaaaagag       420
aacggagccc actagccact ccttcaaacg tgtcttacca actctcttct agaaacaaat     480
taggcttcac cttcctcttc caacctctct ctctctctct ctctcttttt ctcaaaccat     540
ctctccataa agccctaatt tcttcatcac aagaatcaga agaagaaa                   588

<210> SEQ ID NO 46
<211> LENGTH: 468
<212> TYPE: DNA
<213> ORGANISM: Arabidopsis thaliana

<400> SEQUENCE: 46
tacttaattt ggtcatttgg atgccctta caacctcctt accaaactca ttgatcacag       60
tttctattgc taaaatcacc aacaaaacgc atgtcgccat tcataattat ggtttcacac     120
ctacaactag gctaataagt aaataagtag acaactagac tcaggtttga aaaaaccata     180
aaagccatat agcgttttct cattgaaact gcgaacacga tcgtgtgaat gttgcagttt     240
ctagttttga tacaaacaaa caaaacaca atttaatctt agattaaaaa gaaaaaagag       300
aacggagccc actagccact ccttcaaacg tgtcttacca actctcttct agaaacaaat     360
taggcttcac cttcctcttc caacctctct ctctctctct ctctcttttt ctcaaaccat     420
ctctccataa agccctaatt tcttcatcac aagaatcaga agaagaaa                   468
```

<210> SEQ ID NO 47
<211> LENGTH: 419
<212> TYPE: DNA
<213> ORGANISM: Arabidopsis thaliana

<400> SEQUENCE: 47

| | | |
|---|---|---|
| attgatcaca gtttctattg ctaaaatcac caacaaaacg catgtcgcca ttcataatta | 60 |
| tggtttcaca cctacaacta ggctaataag taaataagta dacaactaga ctcaggtttg | 120 |
| aaaaaaccat aaaagccata tagcgttttc tcattgaaac tgcgaacacg atcgtgtgaa | 180 |
| tgttgcagtt tctagttttg atacaaacaa acaaaaacac aatttaatct tagattaaaa | 240 |
| agaaaaaaga gaacggagcc cactagccac tccttcaaac gtgtcttacc aactctcttc | 300 |
| tagaaacaaa ttaggcttca ccttcctctt ccaacctctc tctctctctc tctctcttt | 360 |
| tctcaaacca tctctccata aagccctaat ttcttcatca caagaatcag aagaagaaa | 419 |

<210> SEQ ID NO 48
<211> LENGTH: 723
<212> TYPE: DNA
<213> ORGANISM: Agrobacterium tumefaciens

<400> SEQUENCE: 48

| | | |
|---|---|---|
| atggacctgc atctaatttt cggtccaact tgcacaggaa agacgacgac cgcgatagct | 60 |
| cttgcccagc agacagggct tccagtcctt tcgcttgatc gggtccaatg ctgtcctcaa | 120 |
| ctatcaaccg gaagcggacg accaacagtg gaagaactga aggaacgac gcgtctctac | 180 |
| cttgatgatc ggcctctggt ggagggtatc atcgcagcca agcaagctca tcataggctg | 240 |
| atcgaggagg tgtataatca tgaggccaac ggcgggctta ttcttgaggg aggatccacc | 300 |
| tcgttgctca actgcatggc gcgaaacagc tattggagtg cagattttcg ttggcatatt | 360 |
| attcgccaca agttacccga ccaagagacc ttcatgaaag cggccaaggc cagagttaag | 420 |
| cagatgttgc accccgctgc aggccattct attattcaag agttggttta tctttggaat | 480 |
| gaacctcggc tgaggcccat tctgaaagag atcgatggat atcgatatgc catgttgttt | 540 |
| gctagccaga accagatcac ggcagatatg ctattgcagc ttgacgcaaa tatggaaggt | 600 |
| aagttgatta atgggatcgc tcaggagtat ttcatccatg cgcgccaaca ggaacagaaa | 660 |
| ttcccccaag ttaacgcagc cgctttcgac ggattcgaag gtcatccgtt cggaatgtat | 720 |
| tag | 723 |

<210> SEQ ID NO 49
<211> LENGTH: 975
<212> TYPE: DNA
<213> ORGANISM: Lotus japonicus

<400> SEQUENCE: 49

| | | |
|---|---|---|
| atgtccatct caatgctaat gtgcagacta agacaaccct aataaacgt tccctgcagt | 60 |
| ggcaaaaaac tgagcatgag gcagattcaa aaggagaagg tagtgttggt gatgggagct | 120 |
| acagggacag gaaagtcaaa gctctccatt gacctcgcca cctgttccc ctcagaaatc | 180 |
| atcaactccg acaagattca aatctacgac ggcctcgaca tcgtcaccaa caaaatctcc | 240 |
| aaggaagaac aacgtggaat ccccaccac ctcctcggaa ctcaaaaccc taacacagac | 300 |
| ttcaccgccg gcgatttcag tgactgttcc accgccgcca ttgacgcaat cacaagccgc | 360 |
| gaccaccttc cgatcatcgc cggaggttcg aactcctacc tggaggcgtt aatcgacgac | 420 |
| gacgactaca aattccgatc gaggtacgac ttctgctgcc tctgggtcga cgtgcaatg | 480 |
| ccggtgctgg actcatacgt ggcggcgcgt gtggatcaga tgctccggag cggaatggtg | 540 |

```
gaggagctga gaccgttttt caacgcgaac ggcgactact cgagaggaat cagaagagcg      600
attggggttc ctgaattcga cgagtatttc cggcgggaag ggttcgccga tgaggaaacg      660
aggaaattgt tactggagcg agcggtgagg gagatgaagg tgaacacgtg caagctcgcg      720
aggaggcaat tggggaagat tcagaggctg aggaatgtga agaggtggga gattcaccgt      780
gttgatgcga cgccggtgtt ttggaagcgt ggggaggagg ctgatgaggc gtggcggaag      840
gtggtggcag agcctagtgc tatgatcgta gcgcagtttc tgtataaggc aaagagtgat      900
gtgaatgttg tttctggcgg tttcagagtg ccggcgggtt caacggagag tgttatggcg      960
gcggcgacgt gttag                                                       975

<210> SEQ ID NO 50
<211> LENGTH: 1053
<212> TYPE: DNA
<213> ORGANISM: Petunia x hybrida

<400> SEQUENCE: 50
atgttaattg tagtacatat tattagcatc acacgcatca tattcatcac cttaacccat       60
aatcatctcc atttccttat gtttagatca ttatcataca atcacaagca cctcaaattc      120
cttacaaacc cgaccacacg ggtactccga agaaacatgt cgtcatccac tgtagtaaca      180
atacccggcc ccacacaaaa aaacaaaaac aaaatcatag taataatggg tgcaacaggt      240
tcaggaaaat caaaactctc aatagacctc gtcacacgtc actatccttt ttccgaaatc      300
attaactccg acaaaatcca aattaccaaa ggtttaaaca taaccacaaa caaaatcact      360
gtacccgacc gacgtggcgt agttcatcat ttactcggcg agattgaccc cgactttaac      420
ttttctcctt ctcatttccg gtcaattgct ggtcaacgca ttaactccat tattaatcgc      480
cataaactcc cattcctcgt tggtgggtcc aactcatata tctacgcttt attaacaaac      540
cggttcgacc cggattttaa ccctgattca aacccggttc attttatatc caacgagtta      600
cgctacaact gttgttttat ttgggtcgat gtattaaacc cggttttgaa tgagtatttg      660
gataaacggg tcgatgagat gatgaactcg ggtatgtatg aagaactgga acagtttttt      720
aaagaaaaca ggttttcgga tccgggtttg gaacccggtc gggccaccgg ttgaggaaa      780 gcgataggg taccggaaat ggagaggtat tttaagaaga gctgtacgta tgaggaagca      840
gtgagggaaa taaagaaaa cacgtggcgg ttagcgaaga agcagatgtg gaagatccaa      900
cggttgagag aagcagggtg ggacctacaa agagtagatg ccacggaggc atttgtggag      960
gcgatgagta ataagaagga aaagggaatt atttgggaaa acaagtagt ggaaccaagt     1020 gtcaagattg tgaaccgttt tttgttggac tga                                 1053

<210> SEQ ID NO 51
<211> LENGTH: 240
<212> TYPE: PRT
<213> ORGANISM: Agrobacterium tumefaciens

<400> SEQUENCE: 51

Met Asp Leu His Leu Ile Phe Gly Pro Thr Cys Thr Gly Lys Thr Thr
1               5                   10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Asp Asp Arg
    50                  55                  60
```

-continued

Pro Leu Val Glu Gly Ile Ala Ala Lys Gln Ala His His Arg Leu
65                  70                  75                  80

Ile Glu Glu Val Tyr Asn His Glu Ala Asn Gly Gly Leu Ile Leu Glu
                85                  90                  95

Gly Gly Ser Thr Ser Leu Leu Asn Cys Met Ala Arg Asn Ser Tyr Trp
            100                 105                 110

Ser Ala Asp Phe Arg Trp His Ile Ile Arg His Lys Leu Pro Asp Gln
        115                 120                 125

Glu Thr Phe Met Lys Ala Ala Lys Ala Arg Val Lys Gln Met Leu His
    130                 135                 140

Pro Ala Ala Gly His Ser Ile Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ala Asp Met Leu Leu
            180                 185                 190

Gln Leu Asp Ala Asn Met Glu Gly Lys Leu Ile Asn Gly Ile Ala Gln
        195                 200                 205

Glu Tyr Phe Ile His Ala Arg Gln Gln Glu Gln Lys Phe Pro Gln Val
    210                 215                 220

Asn Ala Ala Ala Phe Asp Gly Phe Glu Gly His Pro Phe Gly Met Tyr
225                 230                 235                 240

<210> SEQ ID NO 52
<211> LENGTH: 324
<212> TYPE: PRT
<213> ORGANISM: Lotus japonicus

<400> SEQUENCE: 52

Met Ser Ile Ser Met Leu Met Cys Arg Leu Arg Gln Pro Leu Ile Asn
1               5                   10                  15

Val Pro Cys Ser Gly Lys Lys Leu Ser Met Arg Gln Ile Gln Lys Glu
            20                  25                  30

Lys Val Val Leu Val Met Gly Ala Thr Gly Thr Gly Lys Ser Lys Leu
        35                  40                  45

Ser Ile Asp Leu Ala Thr Cys Phe Pro Ser Glu Ile Ile Asn Ser Asp
    50                  55                  60

Lys Ile Gln Ile Tyr Asp Gly Leu Asp Ile Val Thr Asn Lys Ile Ser
65                  70                  75                  80

Lys Glu Glu Gln Arg Gly Ile Pro His His Leu Leu Gly Thr Gln Asn
                85                  90                  95

Pro Asn Thr Asp Phe Thr Ala Gly Asp Phe Ser Asp Cys Ser Thr Ala
            100                 105                 110

Ala Ile Asp Ala Ile Thr Ser Arg Asp His Leu Pro Ile Ile Ala Gly
        115                 120                 125

Gly Ser Asn Ser Tyr Leu Glu Ala Leu Ile Asp Asp Asp Tyr Lys
    130                 135                 140

Phe Arg Ser Arg Tyr Asp Phe Cys Cys Leu Trp Val Asp Val Ala Met
145                 150                 155                 160

Pro Val Leu Asp Ser Tyr Val Ala Ala Arg Val Asp Gln Met Leu Arg
                165                 170                 175

Ser Gly Met Val Glu Glu Leu Arg Pro Phe Phe Asn Ala Asn Gly Asp
            180                 185                 190

Tyr Ser Arg Gly Ile Arg Arg Ala Ile Gly Val Pro Glu Phe Asp Glu
        195                 200                 205

```
Tyr Phe Arg Arg Glu Gly Phe Ala Asp Glu Glu Thr Arg Lys Leu Leu
    210                 215                 220

Leu Glu Arg Ala Val Arg Glu Met Lys Val Asn Thr Cys Lys Leu Ala
225                 230                 235                 240

Arg Arg Gln Leu Gly Lys Ile Gln Arg Leu Arg Asn Val Lys Arg Trp
                245                 250                 255

Glu Ile His Arg Val Asp Ala Thr Pro Val Phe Trp Lys Arg Gly Glu
            260                 265                 270

Glu Ala Asp Glu Ala Trp Arg Lys Val Val Ala Glu Pro Ser Ala Met
        275                 280                 285

Ile Val Ala Gln Phe Leu Tyr Lys Ala Lys Ser Asp Val Asn Val Val
290                 295                 300

Ser Gly Gly Phe Arg Val Pro Ala Gly Ser Thr Glu Ser Val Met Ala
305                 310                 315                 320

Ala Ala Thr Cys

<210> SEQ ID NO 53
<211> LENGTH: 350
<212> TYPE: PRT
<213> ORGANISM: Petunia x hybrida

<400> SEQUENCE: 53

Met Leu Ile Val Val His Ile Ile Ser Ile Thr Arg Ile Ile Phe Ile
1               5                   10                  15

Thr Leu Thr His Asn His Leu His Phe Leu Met Phe Arg Ser Leu Ser
            20                  25                  30

Tyr Asn His Lys His Leu Lys Phe Leu Thr Asn Pro Thr Thr Arg Val
        35                  40                  45

Leu Arg Arg Asn Met Ser Ser Ser Thr Val Val Thr Ile Pro Gly Pro
    50                  55                  60

Thr Gln Lys Asn Lys Asn Lys Ile Ile Val Ile Met Gly Ala Thr Gly
65                  70                  75                  80

Ser Gly Lys Ser Lys Leu Ser Ile Asp Leu Val Thr Arg His Tyr Pro
                85                  90                  95

Phe Ser Glu Ile Ile Asn Ser Asp Lys Ile Gln Ile Thr Lys Gly Leu
            100                 105                 110

Asn Ile Thr Thr Asn Lys Ile Thr Val Pro Asp Arg Arg Gly Val Val
        115                 120                 125

His His Leu Leu Gly Glu Ile Asp Pro Asp Phe Asn Phe Ser Pro Ser
    130                 135                 140

His Phe Arg Ser Ile Ala Gly Gln Arg Ile Asn Ser Ile Ile Asn Arg
145                 150                 155                 160

His Lys Leu Pro Phe Leu Val Gly Gly Ser Asn Ser Tyr Ile Tyr Ala
                165                 170                 175

Leu Leu Thr Asn Arg Phe Asp Pro Asp Phe Asn Pro Asp Ser Asn Pro
            180                 185                 190

Val His Phe Ile Ser Asn Glu Leu Arg Tyr Asn Cys Cys Phe Ile Trp
        195                 200                 205

Val Asp Val Leu Asn Pro Val Leu Asn Glu Tyr Leu Asp Lys Arg Val
    210                 215                 220

Asp Glu Met Met Asn Ser Gly Met Tyr Glu Glu Leu Glu Gln Phe Phe
225                 230                 235                 240

Lys Glu Asn Arg Phe Ser Asp Pro Gly Leu Glu Pro Gly Arg Ala Thr
                245                 250                 255
```

-continued

```
Gly Leu Arg Lys Ala Ile Gly Val Pro Glu Met Glu Arg Tyr Phe Lys
            260                 265                 270

Lys Ser Cys Thr Tyr Glu Glu Ala Val Arg Glu Ile Lys Glu Asn Thr
        275                 280                 285

Trp Arg Leu Ala Lys Lys Gln Met Trp Lys Ile Gln Arg Leu Arg Glu
    290                 295                 300

Ala Gly Trp Asp Leu Gln Arg Val Asp Ala Thr Glu Ala Phe Val Glu
305                 310                 315                 320

Ala Met Ser Asn Lys Lys Glu Lys Gly Ile Ile Trp Glu Lys Gln Val
                325                 330                 335

Val Glu Pro Ser Val Lys Ile Val Asn Arg Phe Leu Leu Asp
                340                 345                 350
```

UNITED STATES PATENT AND TRADEMARK OFFICE
CERTIFICATE OF CORRECTION

PATENT NO. : 9,840,695 B2
APPLICATION NO. : 12/722878
DATED : December 12, 2017
INVENTOR(S) : Spangenberg et al.

It is certified that error appears in the above-identified patent and that said Letters Patent is hereby corrected as shown below:

In the Claims

Column 123, Line(s) 30-31, Claim 2 should read -- ...transferase (1-SST) and fructan:fructan 1-fructosyltransferase (1-FFT) enzymatic activities. --

Column 124, Line(s) 21, Claim 9 should read -- ...fructosyltransferase enzyme, and selecting grass plants... --

Signed and Sealed this
First Day of May, 2018

Andrei Iancu
*Director of the United States Patent and Trademark Office*